US009469690B2

(12) United States Patent
Rother et al.

(10) Patent No.: US 9,469,690 B2
(45) Date of Patent: *Oct. 18, 2016

(54) METHODS OF TREATING COMPLEMENT-ASSOCIATED DISORDERS WITH ANTI-C5A ANTIBODIES

(71) Applicant: Alexion Pharmaceuticals, Inc., New Haven, CT (US)

(72) Inventors: Russell P. Rother, Oklahoma City, OK (US); Douglas L. Sheridan, Branford, CT (US); Paul P. Tamburini, Kensington, CT (US); Yuchun Zhang, Cheshire, CT (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/088,421

(22) Filed: Apr. 1, 2016

(65) Prior Publication Data

US 2016/0207997 A1     Jul. 21, 2016

Related U.S. Application Data

(60) Division of application No. 15/040,258, filed on Feb. 10, 2016, now Pat. No. 9,371,378, which is a continuation of application No. 14/933,368, filed on Nov. 5, 2015, now Pat. No. 9,309,310, which is a division of application No. 14/657,176, filed on Mar. 13, 2015, now Pat. No. 9,221,901, which is a division of application No. 13/695,277, filed as application No. PCT/US2011/349672 on Apr. 29, 2011, now Pat. No. 9,011,852.

(60) Provisional application No. 61/471,465, filed on Apr. 4, 2011, provisional application No. 61/330,260, filed on Apr. 30, 2010.

(51) Int. Cl.

| A61K 39/395 | (2006.01) |
| C07K 16/28 | (2006.01) |
| C07K 16/18 | (2006.01) |
| C07K 16/46 | (2006.01) |
| A61K 39/00 | (2006.01) |

(52) U.S. Cl.
CPC ............. *C07K 16/28* (2013.01); *C07K 16/18* (2013.01); *C07K 16/461* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,485,045 A | 11/1984 | Regen |
| 4,544,545 A | 10/1985 | Ryan et al. |
| 4,634,666 A | 1/1987 | Engleman et al. |
| 4,676,980 A | 6/1987 | Segal et al. |
| 4,686,100 A | 8/1987 | Raffin et al. |
| 4,816,567 A | 3/1989 | Cabilly et al. |
| 4,863,457 A | 9/1989 | Lee |
| 4,868,116 A | 9/1989 | Morgan et al. |
| 4,946,778 A | 8/1990 | Ladner et al. |
| 4,980,286 A | 12/1990 | Morgan et al. |
| 5,013,556 A | 5/1991 | Woodle et al. |
| 5,223,409 A | 6/1993 | Ladner et al. |
| 5,258,498 A | 11/1993 | Huston et al. |
| 5,308,341 A | 5/1994 | Chanoch |
| 5,403,484 A | 4/1995 | Ladner et al. |
| 5,427,908 A | 6/1995 | Dower et al. |
| 5,443,505 A | 8/1995 | Wong et al. |
| 5,447,150 A | 9/1995 | Bacon |
| 5,501,856 A | 3/1996 | Ohtori et al. |
| 5,516,637 A | 5/1996 | Huang et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,591,669 A | 1/1997 | Krimpenfort et al. |
| 5,612,205 A | 3/1997 | Kay et al. |
| 5,624,821 A | 4/1997 | Winter et al. |
| 5,625,126 A | 4/1997 | Lonberg et al. |
| 5,625,825 A | 4/1997 | Rostoker et al. |

(Continued)

FOREIGN PATENT DOCUMENTS

| EP | 0245993 B1 | 11/1987 |
| EP | 0430539 A2 | 6/1991 |

(Continued)

OTHER PUBLICATIONS

Engberg et al., Methods Mol Biol 51:355-376 (1995).
Etz et al., J Bacteriol 183:6924-6935 (2001).
European Office Action for Application No. 11775670.0, 4 pages, dated Sep. 3, 2013.
Fang, C. et al., Blood, 114 (5):1005-1015 (2009).
Ferry et al., Proc Natl Acad Sci USA 88:8377-8381 (1991).
Fischetti, F. et al., Blood, 106(7): 2340-2346 (2006).
Fishwild et al., Nature Biotechnol 14:845-851 (1996).
Fivash et al., Curr Opin Biotechnol 9:97-101 (1998).
Flotte et al., Am J Respir Cell Mol Biol 7:349-356 (1992).

(Continued)

*Primary Examiner* — Phillip Gambel
(74) *Attorney, Agent, or Firm* — Tara Rahemba, Esq.; Jane E. Remillard, Esq.; Jill Gorny Sloper, Esq.

(57) ABSTRACT

The present disclosure relates to, inter alia, antibodies, or antigen-binding fragments thereof, that bind to C5a and to use of the antibodies in methods for treating or preventing complement-associated disorders such as, but not limited to, atypical hemolytic uremic syndrome, age-related macular degeneration, rheumatoid arthritis, sepsis, severe burn, antiphospholipid syndrome, asthma, lupus nephritis, Goodpasture's syndrome, and chronic obstructive pulmonary disease.

14 Claims, 20 Drawing Sheets

(56) References Cited

U.S. PATENT DOCUMENTS

| | | |
|---|---|---|
| 5,633,425 A | 5/1997 | Lonberg et al. |
| 5,643,763 A | 7/1997 | Dunn et al. |
| 5,648,260 A | 7/1997 | Winter et al. |
| 5,658,727 A | 8/1997 | Barbas et al. |
| 5,661,016 A | 8/1997 | Lonberg et al. |
| 5,698,426 A | 12/1997 | Huse |
| 5,721,367 A | 2/1998 | Kay et al. |
| 5,733,743 A | 3/1998 | Johnson et al. |
| 5,750,753 A | 5/1998 | Kimae et al. |
| 5,759,808 A | 6/1998 | Casterman et al. |
| 5,770,429 A | 6/1998 | Lonberg et al. |
| 5,773,019 A | 6/1998 | Ashton et al. |
| 5,780,225 A | 7/1998 | Wigler et al. |
| 5,789,215 A | 8/1998 | Berns et al. |
| 5,789,650 A | 8/1998 | Lonberg et al. |
| 5,807,824 A | 9/1998 | van Oostrum et al. |
| 5,814,318 A | 9/1998 | Lonberg et al. |
| 5,821,047 A | 10/1998 | Garrard et al. |
| 5,837,499 A | 11/1998 | van Oostrum et al. |
| 5,874,299 A | 2/1999 | Lonberg et al. |
| 5,877,397 A | 3/1999 | Lonberg et al. |
| 5,939,598 A | 8/1999 | Kucherlapati et al. |
| 5,969,108 A | 10/1999 | McCafferty et al. |
| 5,997,848 A | 12/1999 | Patton et al. |
| 6,001,329 A | 12/1999 | Buchsbaum et al. |
| 6,001,386 A | 12/1999 | Ashton et al. |
| 6,019,968 A | 2/2000 | Platz et al. |
| 6,065,645 A | 5/2000 | Sawhney et al. |
| 6,075,181 A | 6/2000 | Kucherlapati et al. |
| 6,095,141 A | 8/2000 | Armer et al. |
| 6,114,598 A | 9/2000 | Kucherlapati et al. |
| 6,146,361 A | 11/2000 | DiBiasi et al. |
| 6,150,584 A | 11/2000 | Kucherlapati et al. |
| 6,162,963 A | 12/2000 | Kucherlapati et al. |
| 6,170,717 B1 | 1/2001 | Di Giovanni et al. |
| 6,192,891 B1 | 2/2001 | Gravel et al. |
| 6,194,551 B1 | 2/2001 | Idusogie et al. |
| 6,200,296 B1 | 3/2001 | Dibiasi et al. |
| 6,255,458 B1 | 7/2001 | Lonberg et al. |
| 6,277,099 B1 | 8/2001 | Strowe et al. |
| 6,300,064 B1 | 10/2001 | Knappik et al. |
| 6,300,129 B1 | 10/2001 | Lonberg et al. |
| 6,302,855 B1 | 10/2001 | Lav et al. |
| 6,355,245 B1 | 3/2002 | Evans et al. |
| 6,657,103 B1 | 12/2003 | Kucherlapati et al. |
| 6,673,346 B1 | 1/2004 | Ward et al. |
| 6,673,986 B1 | 1/2004 | Kucherlapati et al. |
| 6,680,209 B1 | 1/2004 | Buechler et al. |
| 6,698,622 B2 | 3/2004 | Sawhney et al. |
| 6,713,610 B1 | 3/2004 | Kucherlapati et al. |
| 6,794,132 B2 | 9/2004 | Buechler et al. |
| 6,866,845 B1 | 3/2005 | Ward et al. |
| 6,933,368 B2 | 8/2005 | Co et al. |
| 6,987,166 B2 | 1/2006 | Ward et al. |
| 6,995,259 B1 | 2/2006 | Vargeese et al. |
| 7,041,871 B1 | 5/2006 | Lonberg et al. |
| 7,112,341 B1 | 9/2006 | Nagarajan et al. |
| 7,393,648 B2 | 7/2008 | Rother et al. |
| 7,432,356 B2 | 10/2008 | Fung et al. |
| 7,455,837 B2 | 11/2008 | Guo et al. |
| 7,556,615 B2 | 7/2009 | Pettis et al. |
| 7,595,430 B2 | 9/2009 | Jayakrishna |
| 7,704,497 B2 | 4/2010 | Dall'Acqua et al. |
| 7,816,497 B2 | 10/2010 | Ambati |
| 7,928,284 B2 | 4/2011 | Ambati |
| 8,206,716 B2 | 6/2012 | Fung et al. |
| 8,372,404 B2 | 2/2013 | Fung et al. |
| 8,753,625 B2 | 6/2014 | Fung et al. |
| 8,802,096 B2 | 8/2014 | Guo et al. |
| 9,011,852 B2 | 4/2015 | Rother et al. |
| 9,221,901 B2 | 12/2015 | Rother et al. |
| 9,309,310 B2 | 4/2016 | Rother et al. |
| 9,371,378 B1 | 6/2016 | Rother et al. |
| 2002/0026176 A1 | 2/2002 | Varner et al. |
| 2003/0229905 A1 | 12/2003 | Kucherlapati et al. |
| 2004/0010810 A1 | 1/2004 | Kucherlapati et al. |
| 2004/0093622 A1 | 5/2004 | Kucherlapati et al. |
| 2005/0054055 A1 | 3/2005 | Kucherlapati et al. |
| 2005/0076395 A1 | 4/2005 | Kucherlapati et al. |
| 2005/0271660 A1 | 12/2005 | Wang |
| 2005/0287630 A1 | 12/2005 | Kucherlapati et al. |
| 2006/0040363 A1 | 2/2006 | Kucherlapati et al. |
| 2006/0052294 A1 | 3/2006 | Otto |
| 2006/0153836 A1 | 7/2006 | Bailly et al. |
| 2006/0159684 A1 | 7/2006 | Ward et al. |
| 2006/0160726 A1 | 7/2006 | Fairlie et al. |
| 2007/0172483 A1 | 7/2007 | Schwaeble et al. |
| 2007/0235029 A1 | 10/2007 | Zhu et al. |
| 2008/0071063 A1 | 3/2008 | Allan et al. |
| 2008/0202513 A1 | 8/2008 | Birchall et al. |
| 2008/0241223 A1 | 10/2008 | Nivaggioli et al. |
| 2009/0017031 A1 | 1/2009 | Fung |
| 2009/0041764 A1 | 2/2009 | Spuler et al. |
| 2009/0110679 A1 | 4/2009 | Li et al. |
| 2009/0130716 A1 | 5/2009 | Bowdish et al. |
| 2009/0186036 A1 | 7/2009 | Violette et al. |
| 2009/0214538 A1 | 8/2009 | Fung et al. |
| 2010/0297117 A1 | 11/2010 | Sloey et al. |
| 2013/0224187 A1 | 8/2013 | Rother et al. |
| 2014/0110226 A1 | 4/2014 | Findley et al. |
| 2014/0206849 A1 | 7/2014 | Rother et al. |
| 2015/0183859 A1 | 7/2015 | Rother et al. |
| 2016/0053004 A1 | 2/2016 | Rother et al. |

FOREIGN PATENT DOCUMENTS

| | | |
|---|---|---|
| EP | 0463151 A1 | 1/1992 |
| EP | 0488401 A1 | 6/1992 |
| EP | 0519596 A1 | 12/1992 |
| EP | 0546073 A1 | 6/1993 |
| EP | 1878441 A2 | 1/2008 |
| EP | 2055777 B1 | 5/2009 |
| EP | 2130552 A1 | 12/2009 |
| EP | 2153848 A2 | 2/2010 |
| WO | 8902468 A1 | 3/1989 |
| WO | 8905345 A1 | 6/1989 |
| WO | 8907136 A2 | 8/1989 |
| WO | 90/02809 A1 | 3/1990 |
| WO | 9110737 A1 | 7/1991 |
| WO | 92/01047 | 1/1992 |
| WO | 92/03918 A1 | 3/1992 |
| WO | 9207573 A1 | 5/1992 |
| WO | 9218619 A1 | 10/1992 |
| WO | 92/22324 A1 | 12/1992 |
| WO | 92/22645 A1 | 12/1992 |
| WO | 9222647 A1 | 12/1992 |
| WO | 9222670 A1 | 12/1992 |
| WO | 93/12227 A1 | 6/1993 |
| WO | 9311236 A1 | 6/1993 |
| WO | 9311237 A1 | 6/1993 |
| WO | 9400569 A1 | 1/1994 |
| WO | 94/02602 A1 | 2/1994 |
| WO | 94/25585 A1 | 11/1994 |
| WO | 94/28027 A1 | 12/1994 |
| WO | 94/29351 A2 | 12/1994 |
| WO | 9515982 A2 | 6/1995 |
| WO | 9520401 A1 | 8/1995 |
| WO | 95/29697 A1 | 11/1995 |
| WO | 9614436 A1 | 5/1996 |
| WO | 96/27011 A1 | 9/1996 |
| WO | 96/34096 A1 | 10/1996 |
| WO | 97/13852 A1 | 4/1997 |
| WO | 98/24884 A1 | 6/1998 |
| WO | 98/24893 A2 | 6/1998 |
| WO | 98/47531 A2 | 10/1998 |
| WO | 99/51642 A1 | 10/1999 |
| WO | 00/34317 A2 | 6/2000 |
| WO | 0061178 A1 | 10/2000 |
| WO | 0069887 A2 | 11/2000 |
| WO | 0115731 A1 | 3/2001 |
| WO | 0178693 A2 | 10/2001 |
| WO | 02/43478 A2 | 6/2002 |
| WO | 02069232 A2 | 9/2002 |
| WO | 03015819 A1 | 2/2003 |

(56) References Cited

FOREIGN PATENT DOCUMENTS

| | | |
|---|---|---|
| WO | 2004024156 A1 | 3/2004 |
| WO | 2004026380 A2 | 4/2004 |
| WO | 2004043223 A2 | 5/2004 |
| WO | 2004060407 A1 | 7/2004 |
| WO | 2004073551 A2 | 9/2004 |
| WO | 2004/103294 A2 | 12/2004 |
| WO | 2004108158 A1 | 12/2004 |
| WO | 2005011735 A1 | 2/2005 |
| WO | 2005023193 A2 | 3/2005 |
| WO | 2006/053301 A2 | 5/2006 |
| WO | 2006/122257 A2 | 11/2006 |
| WO | 2007/024715 A9 | 3/2007 |
| WO | 2007/094754 A2 | 8/2007 |
| WO | 2008009062 A1 | 1/2008 |
| WO | 2008022390 A1 | 2/2008 |
| WO | 2008024188 A2 | 2/2008 |
| WO | 2009014633 A1 | 1/2009 |
| WO | 2009015087 A2 | 1/2009 |
| WO | 2009/072598 A1 | 6/2009 |
| WO | 2009105217 A2 | 8/2009 |
| WO | 2009108931 A2 | 9/2009 |
| WO | 2009111701 A2 | 9/2009 |
| WO | 2009151634 A1 | 12/2009 |
| WO | 2010/006059 A1 | 1/2010 |
| WO | 2010054403 A1 | 5/2010 |
| WO | 2011063980 A1 | 6/2011 |

OTHER PUBLICATIONS

Forastiero, R. et al., Lupus, 14, 129-136 (2005).
Gerard et al., J Immunology 149(8):2600-2606 (1992).
Giannakopoulos, B. et al., Blood, 109(2): 422-430 (2007).
Giannini et al., J Biol Chem 270(32):19166-19172 (1995).
Girardi, G. et al., The Journal of Clinical Investigation, 112(11), 1644-1654 (2003).
Glaser et al., J Immunol 149:3903-3913 (1992).
Grabherr et al., Comb Chem & High Throughput Screen, 4:185-192 (2001).
Green and Jakobovits, J Exp Med 188:483-495 (1998).
Gruber et al., J Immunol 152:5368-5374 (1994).
Gulsen and Chauhan, Opthalmol Vis Sci 45:No. 7, 2342-2347 (2004).
Gupta et al., Vaccine 13(14):1263-1276 (1995).
Haeney et al., Clin Exp Immunol 40:16-24 (1980).
Hanauske et al., Clin Cancer Res 13(2, part 1):523-531 (2007).
Hanes et al., Nat Biotechnol 18:1287-1292 (2000).
Hartmann, Herbert et al., "Rapid quantification of C3a and C5a using a combination of chromatographic and Immunoassay procedures," Journal of Immunological Methods, vol. 166:35-44 (1993).
Haviland et al., J Immunol, vol. 146, No. 1, 362-368 (1991).
Hetherington et al., Antimicrobial Agents and Chemotherapy 50(10):3499-3500 (2006).
Hezareh et al., J Virol 75:12161-12168 (2001).
Hill et al., Clin Adv Hematol Oncol 3(11):849-50 (2005).
Hillmen et al., N Engl J Med 350(6):552-559 (2004).
Holers and Thurman, Molecular Immunology 41:147-152 (2004).
Holers,V., Immunological Reviews 223:300-316 (2008).
Hollinger et al., Proc Natl Acad Sci USA 90:6444-6448 (1993).
Holt et al., Trends Biotechnol 21(11):484-490 (2003).
Honnegger and Pluckthun, J Mol Biol 309:657-670 (2001).
Hoogenboom et al., J Mol Biol 227:381-388 (1992).
Hoogenboom et al., Trends in Biotechnology 15:62-70 (1997).
Hou et al., Cytokine 10:319-330 (1998).
Houdebine, Curr Opin Biotechnol 13(6):625-629 (2002).
http://blast.ncbi.nlm.nih.gov/Blast.cgi, NCBI Accession No. AAA52985.
http://blast.ncbi.nlm.nih.gov/Blast.cgi, NCBI Accession No. CAA51145.1.
Huber et al., Proc Natl Acad Sci USA 88:8039-8043 (1991).
Hudson et al., J Immunol Methods 231(1-2):177-189 (1999).
Huston et al., Hum Antibodies 10(3-4):127-142 (2001).
Huston et al., Methods in Enzymology 203:46-88 (1991).
Hwang et al., Proc Natl Acad Sci USA 77:4030-4034 (1980).
Hwu et al., J Immunol 150:4104-4115 (1993).
International Search Report for Application No. PCT/US2011/034598, 4 pages, dated Jul. 12, 2011.
International Search Report for Application No. PCT/US2011/034672, 19 pages, dated Jul. 27, 2011.
International Search Report, PCT/US2011/0345989, dated Jul. 12, 2011.
Israel et al., Immunology 89(4):573-578 (1996).
Stijlemans et al., J Biol Chem 279:1256-1261 (2004).
Stocks et al., Drug Discov Today 9(22):960-966 (2004).
Supplementary European Search Report dated Sep. 3, 2013; Application No. EP 11 77 5670.
Suresh et al., Methods in Enzymology 121:210 (1986).
Taylor et al., International Immunology 6:579-591 (1994).
Taylor et al., Nucleic Acids Res 20:6287-6295 (1992).
Thomas et al., Mol Immunol 33(17-18):1389-1401 (1996).
Ting et al., British J Pharma 153:1043-1053 (2008).
Tofukuji et al,, J Thorac Cardiovasc Surg 116(6): 1060-1068 (1998).
Tomizuka et al., Proc Natl Acad Sci USA 97:722-727 (2000).
Toth et al., Prot Sci 3:1159-1168 (1994).
Tuaillon et al., J Immunol 154:6453-6465 (1995).
Tuaillon et al., Proc Natl Acad Sci USA 90:3720-3724 (1993).
Tuaillon et al., Eur J Immunol 10:2998-3005 (2000).
Tuaillon et al.,, J Immunol 152:2912-2920 (1994).
Tull et al., J Immunol 147:60-69 (1991).
U.S. Appl. No. 13/695,250, filed Aug. 21, 2013, R.P. Rother.
Umana et al., Nat Biotechnol 17(2):176-180 (1999).
Vallota and Muller-Eberhard, J Exp Med 137:1109 (1973).
Van Beusechem et al, Proc Natl Acad Sci USA 89:7640-7644 (1992).
Van Epps and Chenoweth, J. Immunol. 132:2862-2867 (1984).
Van Gurp et al., Am J Transplantation 8(8):1711-1718 (2008).
Van Kuik-Romeijn et al., Transgenic Res 9(2):155-159 (2000).
Vaughan et al., Nature Biotech 14:309 (1996).
Verhoeyen et al., Science 239(4847):1534-1536 (1988).
Wang et al., J Immunol 164: 4340-4347 (2000).
Ward and Zvaifler, J Clin Invest 50(3):606-616 (1971).
Ward et al., J Mol Med 87(4):375-378 (2009).
Weng et al, The Journal of Immunology, 1992, vol. 149, No. 7, 2518-2529.
Wetsel and Kolb, J Immunol 128:2209-2216 (1982).
Wetsel et al., J Biol Chem 265:2435-2440 (1990).
Wetsel et al., Biochem 26:737-743 (1987).
Wheeler et al.,Mol Ther 8(3):355-366 (2003).
Wigler et al., Cell 16:77 (1979).
Wilson et al., Proc Natl Acad Sci USA 85:3014-3018 (1988).
Wright et al., EMBO J 10(10):2717-2723 (1991).
Wright et al., J. Exp Med 180:1087-1096 (1994).
Wright et al., Tibtech 15:26-32 (1997).
Wu et al., Nat Biotechnol 25(11):1290-1297 (2007).
Wurzner et al. Complement Inflamm 8:328-340 (1991).
Xu et al., Cell Immunol 200:16-26 (2000).
Yamamoto and Gewurz, J Immunol 120:2008-2015, (1978).
Yazaki et al., Design & Selection 17(5):481-489 (2004).
Yeung et al., Biotechnol Prog 18:212-220 (2002).
Zapata et al., Protein Eng 8(10):1057-1062 (1995).
Paczkowski et al., Br J Pharmacol 128(7): 1461-1466 (1999).
Park et al., Anesth Analg 99(1): 42-48 (1999).
Pavisic et al., Int J Pharm 387(1-2):110-119 (2010).
Pereboev et al., J Virol 75:7107-7113 (2001).
Persic et al., Gene 187:9-18 (1997).
Piccolo et al., Exp. Mol. Pathol. 66:220-226 (1999).
Pickering, M.C. et al., Rheumatology 2000; 39:133-141.
Pierangeli, S. et al., Circulation.; 99:1997-2002 (1999).
Pleschberger et al., Bioconjugate Chem 14:440-448 (2003).
Poljak et al., Structure 2(12): 1121-1123 (1994).
Pollock et al., J Immunol Methods 231(1-2):147-157 (1999).
Queen et al., Proc Natl Acad Sci USA 86:10029-10033 (1989).
Raju, BioProcess International 1(4):44-53 (2003).
Banta and Urtti, Adv Drug Delivery Rev 58(11):1164-1181 (2006).

(56) References Cited

OTHER PUBLICATIONS

Rawal and Pangburn, J Immunol 166(4):2635-2642 (2001).
Rich et al., Curr Opin Biotechnol 11:54-61 (2000).
Riechmann et al., Nature 332:323-327 (1988).
Rinder et al., J Clin Invest 96: 1564-1572 (1995).
Ritis, K. et al., The Journal of Immunology, 177; 4794-4802 (2006).
Roberts et al., Advanced Drug Delivery Reviews 54:459-476 (2002).
Rogers et al., J Nucl Med 38:1221-1229 (1997).
Roguska et al., Protein Engineering 9(10):895-904 (1996).
Romay-Penabad, Z et al., Ann. N.Y. Acad. Sci. 1108: 554-566 (2007).
Rosenfeld et al., Cell 68:143-155 (1992).
Rather et al., Nature Biotechnology 25(11):1256-1264 (2007).
Rudikoff et al., Proc Natl Acad Sci USA 79: 1979-1983 (1982).
Samulski et al., J Virol 63:3822-3828 (1989).
Sarver et al., Proc Natl Acad Sci USA 79:7147 (1984).
Sawai et al., Am J Repr Immunol 34:26-34 (1995).
Schaffitzel et al., J Immunol Methods 231:119-135 (1999).
Schmid et al., Shock 8(2): 119-124 (1997).
Schoonbroodt et al., Nucleic Acids Res, vol. 33(9):e81, pp. (2005).
Schoonooghe et al., BMC Biotechnol 9:70 (2009).
Sewell et al., J Neuroimmunol 155(1-2):55-63 (2004).
Shalaby et al., J Exp Med, vol. 175:217-225 (1992).
Shi et al., JMB 397:385-396 (2010).
Shields et al., J Biol Chem 276(9):6591-6604 (2001).
Shields et al., J Biol Chem 277(30):26733-26740 (2002).
Shin et al., Science 162:361-363 (1968).
Shinkawa et ai., J Bioi Chem 278(5):3466-3473 (2003).
Shiraishi et al., Nucleic Acids Symposium Series 51(1):129-130 (2007).
Shopes et al., J. Immunol,148:2918-2922 (1992).
Shu et al., Proc Nat Acad Sci USA, vol. 90:7995-7999 (1993).
Simantov,R. et al., J. Clin. Invest., 96, 2211-2219, (1995).
Skerra et al., Science 240:1038-1040 (1988).
Socie, G. et al., Blood, 103(1), 50-57, (2004).
Southern and Berg, Mol Appl Genet 1:327 (1982).
Sprong et al., Immunobiology 102(10):3702-3710 (2003).
Staelens et al., Mol Immunol 43:1243-1257 (2006).
Stevens et al., J Clin Invest 77:1812-1816 (1986).
U.S. Appl. No. 15/040,258, filed Feb. 10, 2016, Russel P. Rother.
U.S. Appl. No. 14/933,368, filed Nov. 5, 2015, Russel P. Rother.
U.S. Appl. No. 14/657,176, filed Mar. 13, 2015, Russel P. Rother.
U.S. Appl. No. 13/695,277, filed Apr. 4, 2013, Russel P. Rother.
U.S. Appl. No. 13/695,250, filed Aug. 21, 2013, Russel P. Rother.
U.S. Appl. No. 15/040,258, Office Action dated Mar. 30, 2016.
U.S. Appl. No. 14/933,368, Office Action dated Dec. 4, 2015.
U.S. Appl. No. 14/657,176, Office Action dated Sep. 9, 2015.
U.S. Appl. No. 14/657,176, Office Action dated Jun. 11, 2015.
U.S. Appl. No. 13/695,277, Office Action dated Mar. 3, 2015.
U.S. Appl. No. 13/695,277, Office Action dated Nov. 19, 2014.
U.S. Appl. No. 13/695,250, Office Action dated Jul. 31, 2015.
U.S. Appl. No. 13/695,250, Office Action dated Mar. 3, 2016.
Jakobovits et al., Nature 362:255-258 (1993).
Jakobovits et al., Proc Natl Acad Sci USA 90:2551-2155 (1993).
Johne et al., J Immunol Methods 160:191-198 (1993).
Johnson et al., J Med Chem 42:4640-4649 (1999).
Jones et al., Nature 321:522-525 (1986).
Jonsson et al., Ann Biol Clin 51:19-26 (1993).
Jonsson et al., Biotechniques 11:620-627 (1991).
Jungi and Pepys, Immunology 43(2):271-279 (1981).
Kaneko et al., J Immunol 86(1):149-154 (1995).
Kaplan, Curr Opin Investig Drugs 3(7): 1017-1023 (2002).
Karlsson and Larsson, Methods Mol Biol 248: 389-415 (2004).
Kaszubska et al., Protein Expression and Purification 18:213-220 (2000).
Kay et al., Human Gene Therapy 3:641-647 (1992).
Kettleborough et al., Design and Selection 4:773-783 (1991).
Kettleborough et al.,Eur J Immunol 24:952-958 (1994).
Kieke et al., Protein Eng 10:1303-1310 (1997).
Kim et al., Ophthalmic Res 39:244-254 (2007).
Kinstler et al., Advanced Drug Delivery Reviews 54:477-485 (2002).
Klein et al., Proc Natl Acad Sci USA 78:524-528 (1981).
Klemm et al., Microbiology 146:3025-3032 (2000).
Kobayashi, N. et al., "Two-Step in Vitro Antibody Affinity Maturation Enables Estradiol-17beta Assays with More than 10-Fold Higher Sensitivity," Anal. Chem., vol. 82, pp. 1027-1038 (2010).
Kola, Axel et al., "Epitope mapping of a C5a neutralizing mAb using a combined approach of phage display, synthetic peptides and site-directed mutagenesis," Immunotechnology, vol. 2:115-126 (1996).
Kostelny et al., J Immunol 148(5):1547-1553 (1992).
Kussie et al., J. Immunol. 152: 146-152 (1994).
Larrick, James W. et al., "Characterization of Murine Monoclonal Antibodies That Recognize Neutralizing Epitopes on Human C5a," Infection and Immunity, vol. 55(8):1867-1872 (1987).
Lee et al., Bioconjug Chem 10(6):973-978 (1999).
Levy and Ladda,Nat New Biol 229(2):51-52 (1971).
Lodmell et al., Vaccine 18:1059-1066 (2000).
Lonberg et al., Nature 368(6474):856-859 (1994).
Lusky and Botchan, Nature 293:79 (1981).
Manderino et al., J Immunol Methods 53(1):41-50 (1982).
Marks et al., J Mol Biol 222:581-597 (1991).
McCarthy and Henson, J Immunol 123(6):2511-2517 (1979).
McLaughlin et al., J Virol 62:1963-1973 (1988).
Mendez et al., Nature Genetics 15:146-156 (1997).
Mery and Boulay, Eur J Haematol 51(5):282-287 (1993).
Merz et al., J Neurosci Methods 62(1-2):213-219 (1995).
Michael et al., Gene Ther 2:660-668 (1995).
Mihu et al., J Gastrointestin Liver Dis 16(4):419-424 (2007).
Milstein and Cuello, Nature 305:537-539 (1983).
Minta and Man, J Immunol 119:1597-1602 (1997).
Mollnes, T.E. et al., "Complement activation in septic baboons detected by neoepitope-specific assays for C3b/C3b/C3c, C5a and the terminal C5b-9 complement complex (TCC)," Clin. Exp. Immunol., vol. 91:295-300 (1993).
Montz, Hildegard et al., "Regulation of the Human Autologous T Cell Proliferation by Endogenously Generated C5a," Cellular Immunology, vol. 127:337-351 (1990).
Mueller et al., Mol Immunol 34(6):441-452 (1997).
Mullett et al., Methods 22:77-91 (2000).
Mulligan and Berg, Proc Natl Acad Sci USA 78:2072-2076 (1981).
Mullinax et al., Bio Techniques 12(6):864-869 (1992).
Nandakumar et al., PLoS One 5:E13511 (2010).
Newkirk et al., Clin Exp Immunol 106(2):259-264 (1996).
Ostberg et al., Hybridoma 2:361-367 (1983).
Ambati and Adamis, Prog Retin Eye Res 21(2):145-151 (2002).
Ames et al., J Immunol Methods 184:177-186 (1995).
Ames, Robert S. et al., "Isolation of Neutralizing Anti-C5a Monoclonal Antibodies from a Filamentous Phage Monovalent Fab Display Library," Journal of Immunology, vol. 152:4572-4581 (1994).
Amsterdam et al., Am. J. Physiol. 268:448-H457 (1995).
Appel et al., J Am Soc Nephrol 16:1392-1404 (2005).
Armentano et al., Proc Acad Sci USA 87:6141-6145 (1990).
Baldridge et al., Methods 19:103-107 (1999).
Bao, Lihua et al., "C5a promotes development of experimental lupus nephritis which can be blocked with a specific receptor antagonist," Eur. J. Immunol., vol. 35:2496-2506 (2005).
Barocas et al., Expert Opin Drug Delivery 5(1):1-10 (2008).
Baudino et al., J Immunol 181:6664-6669 (2008).
Berge et al., J Pharm Sci 66:1-19 (1977).
Bergh, Kare et al., "Production of monoclonal antibodies against the human anaphylatoxin C5a des Arg and their application in the neoepitope-specific sandwich-ELISA for the quantification of C5a des Arg in plasma," Journal of Immunological Methods, vol. 152(1):79-87 (1992).
Berkner et al., BioTechniques 6:616 (1988).
Better et al., Science 240:1041-1043 (1988).
Bieg et al., Autoimmunity 31(1):15-24 (1999).
Bless et al., Am J Physiol 276(1): L57-L63 (1999).
Boder et al., Methods Enzymology 328:430-444 (2000).

(56) References Cited

OTHER PUBLICATIONS

Brennan et al., Science 229:81 (1985).
Brinkman et al., J Immunol Methods 182:41-50 (1995).
Brodsky et al., Blood 113(26):6522-6527 (2009).
Bruggemann et al., Year in Immunol 7:33 (1993).
Burton et al., Adv Immun 51:1-18 (1992).
Burton et al., Advances in Immunology 57:191-280 (1994).
Canfield et al., J Exp Med 173:1483-1491 (1991).
Caron et al., J Exp Med 176:1191-1195 (1992).
Chakraverty, R., et al. JEM, 203(8):2021-2031 (2006).
Chasteen et al., Nucleic Acids Res 34(21):e145 (2006).
Chen et al., EMBO J., 14: 2784-2794 (1995).
Chen et al., International Immunology 5:647-656 (1993).
Chen et al., Nature 446(7132):203-207 (2007).
Choi et al., Nature Genetics 4:117-123 (1993).
Chothia et al., Nature 342:877-883 (1989).
Chowdhury et al., Science 254:1802-1805 (1991).
Co et al., Mol Immunol 30:1361 (1993).
Colman, Research in Immunology 145: 33-36 (1994).
Cook et al., Acta Cryst. Section D:190-197 (2010.
Cornelis, Curr Opin Biotechnol 11:450-454 (2000.
Crocker et al., J Clin Pathol 27(2):122-124 (1974).
Dai et al., Proc Natl Acad Sci USA 89:10892-10895 (1992).
Damerau et al., Molec Immunol 26:1133-1142 (1989).
Dande, E. Transplantation, 88, (11): 1261-1272 (2009).
Danos and Mulligan, Proc Natl Acad Sci USA 85:6460-6464 (1988).
Daugherty et al., Nucleic Acids Res 19(9):2471-2476 (1991).
Deans et al., Proc Natl Acad Sci USA 81:1292 (1984).
Di Niro et al., Biochem J 388(Pt 3)889-894 (2005).
Dong et al., Reviews in Mol Biotech 82:303-323 (2002).
Duchosal et al., Nature 355:258 (1992).
Dumoulin et al., Nature 424:783-788 (2003).
Duncan and Winter, Nature 322:738-740 (1988).
Eglitis et al., Science 230:1395-1398 (1985).
U.S. Appl. No. 15/161,893, filed May 23, 2016, Russell P. Rother.
U.S. Appl. No. 15/040,258, Office Action dated Apr. 25, 2016.
U.S. Appl. No. 15/161,893, Office Action dated Jul. 19, 2016.
U.S. Appl. No. 15/161,893, Office Action dated Jun. 16, 2016.

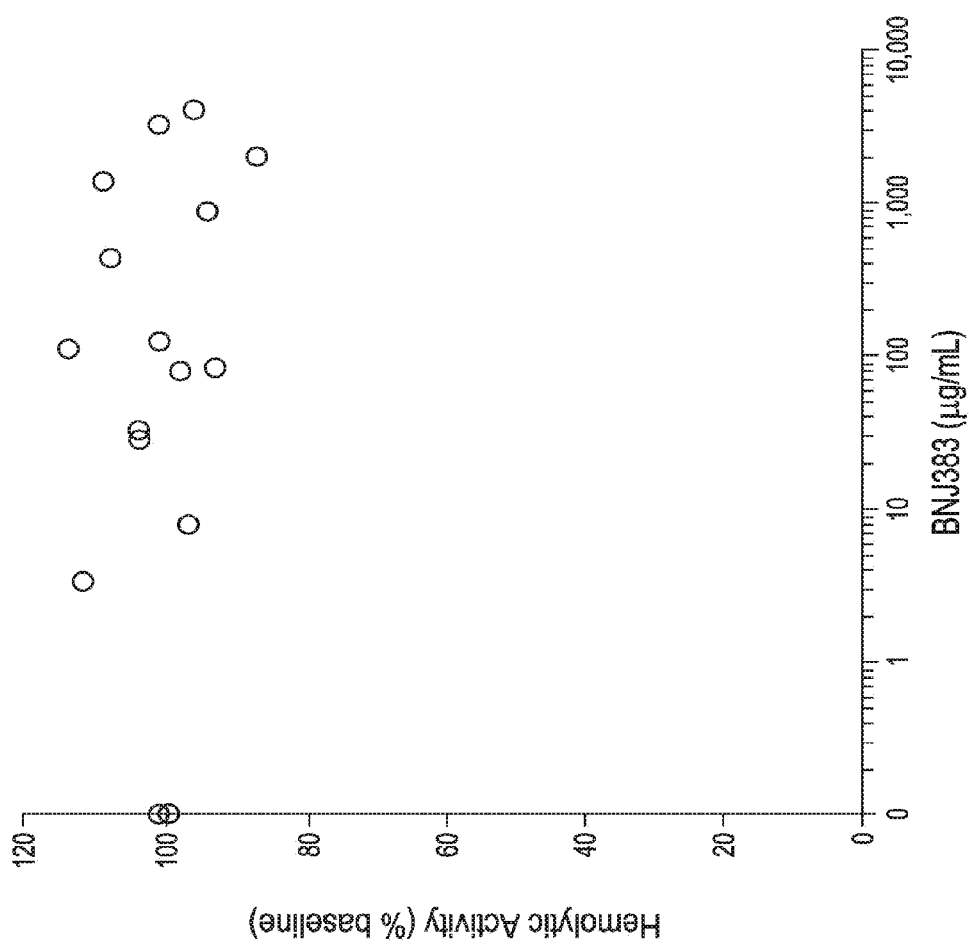

US 9,469,690 B2

METHODS OF TREATING COMPLEMENT-ASSOCIATED DISORDERS WITH ANTI-C5A ANTIBODIES

CROSS-REFERENCE TO RELATED APPLICATIONS

This application is a divisional of U.S. patent application Ser. No. 15/040,258, filed Feb. 10, 2016, which is a continuation of U.S. patent application Ser. No. 14/933,368, filed Nov. 5, 2015 (now U.S. Pat. No. 9,309,310), which is a divisional of U.S. patent application Ser. No. 14/657,176, filed Mar. 13, 2015 (now U.S. Pat. No. 9,221,901), which is a divisional of U.S. patent application Ser. No. 13/695,277, filed Apr. 4, 2013 (now U.S. Pat. No. 9,011,852), which is a national stage filing under 35 U.S.C. §371 of International Application No. PCT/US2011/034672, filed Apr. 29, 2011, which claims the benefit of the filing date under 35 U.S.C. §119(e) to U.S. Provisional Patent Application Ser. Nos. 61/330,260, filed on Apr. 30, 2010, and 61/471,465, filed on Apr. 4, 2011, the entire contents of which are hereby incorporated by reference in their entireties. International Application No. PCT/US2011/034672 was published under PCT Article 21(2) in English.

SEQUENCE LISTING

The instant application contains a Sequence Listing which has been submitted via EFS-Web and is hereby incorporated by reference in its entirety. Said ASCII copy, created on Apr. 1, 2016, is named AXJ_154USDV2CNDV_Seq_List.txt, and is 144,048 bytes in size.

TECHNICAL FIELD

The field of the invention is medicine, immunology, molecular biology, and protein chemistry.

BACKGROUND

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16th Edition.

The complement cascade progresses via the classical pathway, the alternative pathway, or the lectin pathway. These pathways share many components, and while they differ in their initial steps, they converge and share the same "terminal complement" components (C5 through C9) responsible for the activation and destruction of target cells.

The classical pathway (CP) is typically initiated by antibody recognition of, and binding to, an antigenic site on a target cell. The alternative pathway (AP) can be antibody independent, and can be initiated by certain molecules on pathogen surfaces. Additionally, the lectin pathway is typically initiated with binding of mannose-binding lectin (MBL) to high mannose substrates. These pathways converge at the point where complement component C3 is cleaved by an active protease to yield C3a and C3b. Other pathways activating complement attack can act later in the sequence of events leading to various aspects of complement function.

C3a is an anaphylatoxin. C3b binds to bacterial and other cells, as well as to certain viruses and immune complexes, and tags them for removal from the circulation. (C3b in this role is known as opsonin.) The opsonic function of C3b is generally considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways. This property of C3b is regulated by the serum protease Factor I, which acts on C3b to produce iC3b. While still functional as opsonin, iC3b cannot form an active C5 convertase.

C5 is a 190 kDa beta globulin found in normal serum at a concentration of approximately 75 μg/mL (0.4 μM). C5 is glycosylated, with about 1.5 to 3 percent of its mass attributed to carbohydrate. Mature C5 is a heterodimer of a 999 amino acid 115 kDa alpha chain that is disulfide linked to a 655 amino acid 75 kDa beta chain. C5 is synthesized as a single chain precursor protein product of a single copy gene (Haviland et al. (1991) *J Immunol* 146:362-368). The cDNA sequence of the transcript of this gene predicts a secreted pro-C5 precursor of 1658 amino acids along with an 18 amino acid leader sequence (see, e.g., U.S. Pat. No. 6,355, 245).

The pro-C5 precursor is cleaved after amino acids 655 and 659, to yield the beta chain as an amino terminal fragment (amino acid residues +1 to 655 of the above sequence) and the alpha chain as a carboxyl terminal fragment (amino acid residues 660 to 1658 of the above sequence), with four amino acids (amino acid residues 656-659 of the above sequence) deleted between the two.

C5a is cleaved from the alpha chain of C5 by either alternative or classical C5 convertase as an amino terminal fragment comprising the first 74 amino acids of the alpha chain (i.e., amino acid residues 660-733 of the above sequence). Approximately 20 percent of the 11 kDa mass of C5a is attributed to carbohydrate. The cleavage site for convertase action is at, or immediately adjacent to, amino acid residue 733 of the above sequence. A compound that would bind at, or adjacent to, this cleavage site would have the potential to block access of the C5 convertase enzymes to the cleavage site and thereby act as a complement inhibitor.

C5 can also be activated by means other than C5 convertase activity. Limited trypsin digestion (see, e.g., Minta and Man (1997) *J Immunol* 119:1597-1602 and Wetsel and Kolb (1982) *J Immunol* 128:2209-2216), thrombin, and acid treatment (Yamamoto and Gewurz (1978) *J Immunol* 120:2008 and Damerau et al. (1989) *Molec Immunol* 26:1133-1142) can also cleave C5 and produce active C5b.

Cleavage of C5 releases C5a, a potent anaphylatoxin and chemotactic factor, and C5b which through a series of protein interactions leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

C5a receptors are found on the surfaces of bronchial and alveolar epithelial cells and bronchial smooth muscle cells. C5a receptors have also been found on eosinophils, mast cells, monocytes, neutrophils, and activated lymphocytes.

SUMMARY

The present disclosure relates to, inter alia, the generation by the inventors of a series of humanized monoclonal antibodies that specifically bind to free C5a protein (that is, C5a that has been proteolytically cleaved from C5 protein), but not to paralog protein fragments free C4a or free C3a [the antibodies are, often, referred to herein as anti-C5a antibodies or anti-C5a neoepitope antibodies]. As described herein and exemplified in the working examples, the generated anti-C5a antibodies exhibit a high affinity for free C5a. For example, all of the humanized anti-C5a antibodies described herein bind to free C5a with a $K_D$ that is less than 1.25 nanomolar. Many of the antibodies bind to free C5a (e.g., free human C5a) with a $K_D$ that is less than 300 picomolar; several of the antibodies bind to free C5a with a $K_D$ that is less than 100 picomolar. In addition, the humanized anti-C5a antibodies described herein also inhibit C5a-mediated signaling. Further structural and functional properties of the antibodies described herein are elaborated on below and exemplified in the working examples.

The inventors have also demonstrated, using an animal model of rheumatoid arthritis (RA) and a surrogate anti-mouse C5a antibody with properties similar to the humanized antibody counterparts, efficacy of anti-C5a antibodies in treating RA. Also shown in the working examples are experiments demonstrating the positive therapeutic effects of a humanized anti-C5a antibody in an animal model of human C5a-induced neutropenia.

Accordingly, the inventors believe that the anti-C5a antibodies, or antigen-binding fragments thereof, described herein are useful in a host of diagnostic and therapeutic methods related to disorders in which C5a-mediated signaling contributes to pathogenesis. For example, the inventors assert that the humanized anti-C5a antibodies described herein are useful for treating or preventing RA and other complement-associated disorders including, but not limited to: atypical hemolytic uremic syndrome (aHUS), age-related macular degeneration (AMD), sepsis, burn (e.g., severe burn), antiphospholipid syndrome (APS), acute respiratory distress syndrome (ARDS), inflammation-related pain, asthma, lupus nephritis, intrauterine growth restriction (IUGR), HELLP syndrome (Hemolytic anemia, Elevated Liver enzymes and Low Platelet count), Goodpasture's syndrome, and chronic obstructive pulmonary disease (COPD). Additional disorders that are particularly amenable to treatment with a humanized anti-C5a antibody, or antigen-binding fragment thereof, are known in the art and recited herein.

The humanized anti-C5a antibodies described herein feature a number of advantages, e.g., over agents that bind to, and inhibit cleavage of, full-length or mature C5. Like such agents, the anti-C5a antibodies (and antigen-binding fragments thereof) described herein are capable of inhibiting the anaphylatoxic downstream effects of C5 activation as mediated through C5 fragment C5a. That is, the anti-C5a antibodies described herein can inhibit the C5a-mediated inflammatory response, which is known to play an integral part in the pathogenesis of complement-associated disorders such as, but not limited to, sepsis, RA, and asthma. However, as the concentration of C5 in human serum is approximately 0.37 µM (Rawal and Pangburn (2001) *J Immunol* 166(4):2635-2642), the use of high concentrations and/or frequent administration of anti-C5 antibodies is often necessary to effectively inhibit C5, and thereby inhibit the C5a-mediated inflammatory response, in a human. Unlike C5, C5a is present in blood at much lower concentrations and is often restricted to specific areas of local complement activation such as, e.g., the lungs in asthma patients, the joints of RA patients, or the drusen in the eyes of patients with AMD. Thus, the anti-C5a antibodies described herein can be administered (e.g., locally administered to sites of complement activation) to a human at a much lower dose and/or less frequently than, e.g., an anti-C5 antibody, and effectively provide the same or greater inhibition of C5a in a human. The ability to administer a lower dose of the anti-C5a antibody, as compared to the required dose of an anti-C5 antibody, also allows for additional delivery routes such as, e.g., subcutaneous administration, intramuscular administration, intrapulmonary delivery, and administration via the use of biologically degradable microspheres. A lower concentration of antigen C5a versus C5 also favors a longer half-life of the anti-C5a antibody, as compared to, e.g., the half-life of a therapeutic antibody that targets terminal complement, due to a reduced contribution of antigen-mediated antibody clearance.

In addition, the anti-C5a antibodies described herein can also be distinguished from therapeutic agents that inhibit terminal complement (such as C5 inhibitors) by their safety profile. A notable consequence of inhibiting terminal complement components such as C5, C5b, C6, C7, C8, or C9 is decreased protection by the host immune system against the encapsulated bacteria that terminal complement ordinarily lyses—for example, *Neisseria meningitides* and *Neisseria gonorrhoeae*. See, e.g., Haeney et al. (1980) *Clin Exp Immunol* 40:16-24 and Brodsky (2009) *Blood* 113(26): 6522-6527. As the anti-C5a antibodies inhibit the C5a-mediated inflammatory response, but do not prevent the formation of the terminal complement complex that lyses those encapsulated bacteria, patients receiving a therapeutic anti-C5a antibody described herein would not require a protective vaccination, e.g., a vaccination against *Neisseria meningitides* and *Neisseria gonorrhoeae*.

Accordingly, in one aspect, the disclosure features an isolated antibody, or antigen-binding fragment thereof, that binds to free C5a. In some embodiments, the antibody or antigen-binding fragment thereof binds to free human C5a (hC5a; e.g., a human C5a protein comprising, or consisting of, the amino acid sequence depicted in SEQ ID NO: 1). In some embodiments, the antibody can bind to a designated form of free C5a, e.g., the designated form of human C5a comprising, or consisting of, the amino acid sequence depicted in SEQ ID NO:2. The antibody can bind to a neoepitope of free C5a, which epitope is not present on uncleaved C5 or is present on only a minor fraction of total uncleaved C5.

While the disclosure is in no way limited to any particular theory or mechanism of action, in some embodiments, the anti-C5a antibody or antigen-binding fragment thereof binds to free C5a (e.g., free hC5a) and may also bind to a subpopulation of uncleaved, processed C5 (e.g., plasma C5) constituting less than 10 (e.g., less than 9.5, 9, 8.5, 8, 7.5, 7, 6.5, 6, 5.5, 5, 4.5, 4, 3.5, 3, 2.5, 2, 1.5, 1, 0.5, 0.4, 0.3, 0.2, or less than 0.1) % of the total population of full length C5 in a sample (e.g., a blood or plasma sample or a sample comprising recombinant full length C5), which subpopulation is, in whole or in part, denatured such that an otherwise occluded C5a neoepitope, to which the anti-C5a antibody or fragment binds, is exposed. Thus, an anti-C5a antibody or antigen-binding fragment thereof described herein can, in some embodiments, bind to free C5a, but not to the uncleaved C5 protein of the 90% or greater uncleaved, native C5 population. In some embodiments, the above-described partially or fully denatured subpopulation of C5 is inactive or has reduced activity (e.g., less than 90, 85, 80, 75, 70, 65, 60, 55, 50, 45, 40, 35, 30, 25, 20, 15, 10, 5% of the activity of fully-functional, full-length C5 protein) in any number of suitable assays useful for testing C5 activity, e.g., a hemolytic assay or a CH50eq assay (see below). Suitable methods for testing the activity of the minor subpopulation to which an anti-C5a antibody described herein may, in some embodiments, bind are known in the art and described herein.

In some embodiments, any of the anti-C5a antibodies or antigen-binding fragments thereof described herein do not inhibit C5 activity in an in vitro hemolysis assay or an in vitro CH50eq assay even in the presence of at least, equal to, or greater than a 5 (e.g., 5.6, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200)-fold excess of the anti-C5a antibody or antigen-binding fragment thereof to uncleaved C5 (e.g., uncleaved, native C5). In some embodiments, any of the anti-C5a antibodies or antigen-binding fragments thereof described herein do not inhibit C5 activity in an in vitro hemolysis assay or an in vitro CH50eq assay even in the presence of between about a 5-fold to 200-fold (e.g., between about 5-fold and 100-fold, between about 10-fold and 100-fold, between about 20-fold and 100-fold, or between about 10-fold and 150-fold) excess of the anti-C5a antibody or antigen-binding fragment thereof to uncleaved, native C5. Inhibition, e.g., as it pertains to C5 activity, includes at least a 5 (e.g., at least a 6, 7, 8, 9, 10, 15, 20, 25, 30, 35, 40, 45, 50, 55, or 60) % decrease in the activity of uncleaved, native C5 in, e.g., a hemolytic assay or CH50eq assay as compared to the effect of a control antibody (or antigen-binding fragment thereof) under similar conditions and at an equimolar concentration. Substantial inhibition, as used herein, refers to inhibition of a given activity (e.g., of C5 activity) of at least 40 (e.g., at least 45, 50, 55, 60, 65, 70, 75, 80, 85, 90, or 95 or greater) %. In some embodiments, the C5 is obtained from plasma (e.g., purified from or present in plasma, e.g., human plasma).

In some embodiments, the antibody or antigen-binding fragment thereof binds to a C5a protein (e.g., a human C5a protein) with a $K_D$ that is less than 2 nM. In some embodiments, the antibody or antigen-binding fragment thereof binds to a C5a protein with a $K_D$ that is less than 1 nM [also referred to herein as "subnanomolar affinity"].

In some embodiments, the anti-C5a antibody or antigen-binding fragment thereof binds to free C5a with a subnanomolar affinity [e.g., a $K_D$ of less than or equal to $9.9 \times 10^{-10}$ (e.g., less than or equal to $9 \times 10^{-10}$, $8 \times 10^{-10}$, $7 \times 10^{-10}$, $6 \times 10^{-10}$, $5 \times 10^{-10}$, $4 \times 10^{-10}$, $3 \times 10^{-10}$, $2.5 \times 10^{-10}$, $2 \times 10^{-10}$, $1 \times 10^{-10}$, $8.0 \times 10^{-11}$, $7.0 \times 10^{-11}$, $6.0 \times 10^{-11}$, $5.0 \times 10^{-11}$, $4.0 \times 10^{-11}$, or $3.0 \times 10^{-11}$) M] in the presence of a molar excess of uncleaved, native C5 (e.g., purified and/or recombinant C5). In some embodiments, any of the anti-C5a antibodies or antigen-binding fragments thereof described herein have at least a 100 (e.g., at least 110, 120, 130, 140, 150, 160, 170, 180, 190, 200, 225, 250, 275, 300, 400, 500, 600, 700, 800, 900, 1000, 2000, 3000, 4000, 5000, 6000, 7000, 8000, 9000, or 10000)-fold greater affinity (e.g., represented by its $K_D$) for free C5a than for uncleaved, native C5 protein.

Thus, in another aspect, the disclosure features an antibody or antigen-binding fragment thereof that (a) binds to free C5a (e.g., hC5a) with a subnanomolar affinity and (b) binds to free C5a with an affinity that is at least 100 (e.g., at least 110, 120, 130, 140, 150, 160, 170, 180, 190, 200, 225, 250, 275, 300, 400, 500, 600, 700, 800, 900, 1000, 2000, 3000, 4000, 5000, 6000, 7000, 8000, 9000, or 10000)-fold greater than its corresponding affinity for uncleaved, native C5 protein. For example, an anti-C5a antibody or antigen-binding fragment thereof described herein can, in some embodiments, bind to free hC5a with a $K_D$ of 100 nM and to at least a subpopulation of uncleaved human C5 protein with a $K_D$ that is at least 100-fold higher (e.g., at least 10 nM).

In another aspect, the disclosure features an isolated antibody or antigen-binding fragment thereof that binds to a free human C5a polypeptide having the amino acid sequence depicted in SEQ ID NO: 1, wherein the antibody or antigen-binding fragment thereof binds to the human C5a polypeptide with a $K_D$ that is less than $1.25 \times 10^{-9}$ M in the presence of a molar excess (e.g., a 2, 3, 4, 5, 6, 7, 8, 9, 10, 15, 20, 25, 30, 35, 40, 45, 50, 60, 70, 80, 90, 100, 150, 200, 300, 400, or 500-fold molar excess) of uncleaved, native human C5 over human C5a (hC5a). In some embodiments, the antibody or antigen-binding fragment thereof binds to a free hC5a polypeptide with a subnanomolar affinity (e.g., any of the subnanomolar $K_D$'s recited herein) in the presence of at least, or greater than, a 2-fold molar excess, but no greater or less than a 500 (e.g., 500, 450, 400, 350, 300, 250, 200, 150, 100, 90, 80, 70, 60, 50, 40, 30, 25, 20, or 15)-fold molar excess of uncleaved, native C5 over free hC5a. In some embodiments, the antibody or antigen-binding fragment thereof binds to a free hC5a polypeptide with a subnanomolar affinity (e.g., any of the subnanomolar $K_D$'s recited herein) in the presence of between 2-fold and 20-fold molar excess of uncleaved, native C5 over free hC5a. In some embodiments, an antibody or antigen-binding fragment thereof binds to a free hC5a polypeptide with a subnanomolar affinity (e.g., any of the subnanomolar $K_D$'s recited herein) in the presence of between 10-fold and 20-fold molar excess of uncleaved, native C5 over free hC5a. In some embodiments, an antibody or antigen-binding fragment thereof binds to a free hC5a polypeptide with a subnanomolar affinity (e.g., any of the subnanomolar $K_D$'s recited herein) in the presence of between 5-fold and 15-fold molar excess of uncleaved, native C5 over free hC5a. In some embodiments, an antibody or antigen-binding fragment thereof binds to a free hC5a polypeptide with a subnanomolar affinity (e.g., any of the subnanomolar $K_D$'s recited herein) in the presence of at least 2-fold, but no greater than a 20-fold molar excess of uncleaved, native C5 over free hC5a. Such measurements can be in vitro measurements using, e.g., standard affinity determination techniques, many of which are recited and/or described herein.

In another aspect, the disclosure features an isolated antibody or antigen-binding fragment thereof that binds to a human C5a polypeptide having the amino acid sequence depicted in SEQ ID NO: 1, wherein the antibody or antigen-binding fragment thereof binds to the human C5a polypeptide with a $K_D$ that is less than $1.25 \times 10^{-9}$ M and wherein the antibody or antigen-binding fragment thereof does not substantially inhibit, as compared to an equimolar amount of a control antibody or antigen-binding fragment thereof, C5 activity even in the presence of less than, or equal to, a 10-fold molar excess of the anti-C5a antibody or antigen-binding fragment thereof to uncleaved, native C5.

In some embodiments of any of the anti-C5a antibodies or antigen-binding fragments thereof described herein, the antibody or antigen-binding fragment thereof binds to free human C5a and is cross-reactive with free C5a from at least one non-human mammalian species. For example, in some embodiments, an anti-C5a antibody (or antigen-binding fragment thereof) binds to free C5a from human (e.g., with subnanomolar affinity) and also binds to free C5a from a non-human primate (e.g., cynomolgus macaque, rhesus macaque, ape, baboon, chimpanzee, orangutan, or gorilla), a rodent (e.g., mouse, rat, hamster, Guinea pig, or rabbit), cow, goat, donkey, pig, dog, cat, or horse. In some embodiments, an anti-C5a antibody or antigen-binding fragment thereof described herein binds to free hC5a with a $K_D$ of less than or equal to $9.9 \times 10^{-10}$ (e.g., less than or equal to $9 \times 10^{-10}$, $8 \times 10^{-10}$, $7 \times 10^{-10}$, $6 \times 10^{-10}$, $5 \times 10^{-10}$, $4 \times 10^{-10}$, $3 \times 10^{-10}$, $2.5 \times 10^{-10}$, $2 \times 10^{-10}$, $1 \times 10^{-10}$, $8.0 \times 10^{-11}$, $7.0 \times 10^{-11}$, $6.0 \times 10^{-11}$, $5.0 \times 10^{-11}$, $4.0 \times 10^{-11}$, or $3.0 \times 10^{-11}$) M and also binds to free C5a from cynomolgus macaque (or another non-human primate species), wherein the affinity (e.g., represented by its $K_D$) for human C5a is no more than 500 (e.g., no more than 5, 10, 20, 30, 40, 50, 60, 70, 80, 90, 100, 125, 150, 200, 250, 300, 350, 400, 450, or 475)-fold greater than the affinity for cynomolgus macaque (or other non-human primate species) C5a. For example, in some embodiments, the anti-C5a antibody binds to free hC5a with an affinity that is no more than 50-fold greater than the corresponding affinity of the antibody for non-human primate C5a (e.g., a $K_D$ for free hC5a of 100 nM and a $K_D$ for non-human primate C5a of no more than 5 nM). In some embodiments, an anti-C5a antibody or antigen-binding fragment thereof described herein binds to free hC5a with a $K_D$ of less than or equal to $9.9 \times 10^{-10}$ (e.g., less than or equal to $9 \times 10^{-10}$, $8 \times 10^{-10}$, $7 \times 10^{-10}$, $6 \times 10^{-10}$, $5 \times 10^{-10}$, $4 \times 10^{-10}$, $3 \times 10^{-10}$, $2.5 \times 10^{-10}$, $2 \times 10^{-10}$, $1 \times 10^{-10}$, $8.0 \times 10^{-11}$, $7.0 \times 10^{-11}$, $6.0 \times 10^{-11}$, $5.0 \times 10^{-11}$, $4.0 \times 10^{-11}$, or $3.0 \times 10^{-11}$) M and also binds to C5a from a rodent (e.g., mouse, rat, or rabbit), wherein the affinity (e.g., represented by its $K_D$) for human C5a is no more than 1000 (e.g., no more than 5, 10, 20, 30, 40, 50, 60, 70, 80, 90, 100, 125, 150, 200, 250, 300, 350, 400, 450, 475, 500, 550, 600, 650, 700, 750, 800, 850, 900, 950, or 975)-fold greater than the affinity for rodent C5a. In some embodiments, any of the anti-C5a antibodies or antigen-binding fragments thereof described herein bind with subnanomolar affinity to both human C5a and to C5a from a non-human mammal (e.g., a rodent or a non-human primate such as cynomolgus macaque). An antibody or antigen-binding fragment thereof can, in some embodiments, bind to human C5a and non-human primate C5a with equal affinity (e.g., an equivalent $K_D$).

For example, the disclosure features an antibody or antigen-binding fragment thereof that binds to free human C5a with subnanomolar affinity [e.g., a $K_D$ of less than or equal to $9.9 \times 10^{-10}$ (e.g., less than or equal to $9 \times 10^{-10}$, $8 \times 10^{-10}$, $7 \times 10^{-10}$, $6 \times 10^{-10}$, $5 \times 10^{-10}$, $4 \times 10^{-10}$, $3 \times 10^{-10}$, $2.5 \times 10^{-10}$, $2 \times 10^{-10}$, $1 \times 10^{-10}$, $8.0 \times 10^{11}$, $7.0 \times 10^{-11}$, $6.0 \times 10^{-11}$, $5.0 \times 10^{-11}$, $4.0 \times 10^{-11}$, or $3.0 \times 10^{-11}$) M] and is cross-reactive with free C5a from cynomolgus macaque (or other non-human primate), the antibody or antigen-binding fragment thereof binding to cynomolgus macaque (or other non-human primate) C5a with a $K_D$ of less than $10 \times 10^{-9}$, $9 \times 10^{-9}$, $8 \times 10^{-9}$, $7 \times 10^{-9}$, $6 \times 10^{-9}$, $5 \times 10^{-9}$, $4 \times 10^{-9}$, $3 \times 10^{-9}$, $2 \times 10^{-9}$, $1 \times 10^{-9}$, $9.9 \times 10^{-10}$ (e.g., less than $9 \times 10^{-10}$, $8 \times 10^{-10}$, $7 \times 10^{-10}$, $6 \times 10^{-10}$, $5 \times 10^{-10}$, $4 \times 10^{-10}$, $3 \times 10^{-10}$, $2.5 \times 10^{-10}$, $2 \times 10^{-10}$, $1 \times 10^{-10}$, or $8.0 \times 10^{-11}$) M], wherein the affinity for human C5a is no more than 500 (e.g., no more than 5, 10, 20, 30, 40, 50, 60, 70, 80, 90, 100, 125, 150, 200, 250, 300, 350, 400, 450, or 475)-fold greater than the affinity for cynomolgus macaque (or non-human primate) C5a (e.g., $K_D$ for human C5a of 100 nM and a $K_D$ for non-human primate C5a of no more than 50 nM). Suitable methods for determining the affinity of an antibody or antigen-binding fragment thereof for a given antigen are known in the art and described and exemplified herein.

In some embodiments, the cross-reactive anti-C5a antibody or antigen-binding fragment thereof functionally inhibits both free hC5a and the non-human mammalian C5a to which it binds. For example, an antibody inhibits by at least 70 (e.g., at least 75, 80, 85, 90, or 95 or greater) % human C5a-dependent human neutrophil activation at a molar ratio of 1:1 (antigen-binding site:C5a) and inhibits by at least 70 (e.g., at least 75, 80, 85, 90, or 95 or greater) % non-human mammalian C5a-dependent neutrophil activation (the neutrophils being from the same species as the non-human mammalian C5a to which the antibody binds) at a molar ratio of 1:1 (antigen-binding site:C5a).

In another aspect, the disclosure features an isolated antibody or antigen-binding fragment thereof that binds to a free hC5a polypeptide having the amino acid sequence depicted in SEQ ID NO: 1, wherein the antibody or antigen-binding fragment thereof binds to the human C5a polypeptide with a $K_D$ that is less than $1.25 \times 10^{-9}$ M and wherein the antibody or antigen-binding fragment thereof binds to both hC5a and to C5a from a non-human mammalian species. The non-human mammalian species can be, e.g., a non-human primate such as cynomolgus macaque, rhesus macaque, or baboon. In some embodiments, the non-human mammalian species is a rodent such as a mouse, rat, rabbit, Guinea pig, gerbil, or hamster. In some embodiments, the antibody or antigen-binding fragment thereof binds to hC5a with an affinity no greater than 100-fold higher than the corresponding affinity for C5a from the non-human mammalian species. In some embodiments, the antibody or antigen-binding fragment inhibits by at least 50% human C5a-dependent human neutrophil activation at a molar ratio of 1:1 (antigen-binding site: C5a).

In some embodiments, the antibody or antigen-binding fragment thereof binds to free C5a from a non-human primate (e.g., a cynomolgus macaque or rhesus macaque), the free C5a protein having an amino acid sequence comprising, or consisting of, the amino acid sequence depicted in SEQ ID NO: 179 or SEQ ID NO: 180.

As described in the working examples, the inventors have also discovered a bivalent anti-C5a antibody, BNJ383, that binds to free C5a (in this case human C5a) with high affinity and, with a much lower affinity, uncleaved human C5 (hC5), wherein, in a composition (e.g., an aqueous solution) under physiological conditions at equilibrium, and in the presence of a molar excess of uncleaved human C5 as compared to the molar amount of the antigen-binding sites of the antibodies, at least 95% of the plurality of antibodies each bind no more than one hC5 molecule. The second antigen-binding site of the at least 95% of the plurality of antibodies remains available (e.g., substantially available) to bind to free C5a. While the disclosure is in no way bound by any particular theory or mechanism of action, the inventors believe that the bivalent anti-C5a antibody binds to uncleaved C5 in such a way (e.g., at such an epitope) that steric hindrance precludes, or at least substantially inhibits, the binding of the second antigen-binding site of the anti-C5a antibody to a second uncleaved C5 protein, although the antibody can easily accommodate the binding to two hC5a molecules. Thus, the antibody, even in a molar excess of uncleaved C5, retains the ability to bind to free C5a with high affinity and thereby retains, even in that molar excess, the ability to inhibit the pro-inflammatory activity of C5a.

One of ordinary skill in the art would easily and readily appreciate the myriad therapeutic benefits of such an anti-C5a antibody. For example, as noted above, the concentration of circulating C5 in human serum is very high. Thus, when introduced into a mammal, an anti-C5a antibody that is capable of simultaneously binding to two uncleaved C5 molecules would be rapidly inactivated in the molar excess of C5 and would then no longer be capable of binding to free C5a in the event of complement activation. And, as with anti-C5 antibodies, use of high concentrations and/or frequent administration of this type of anti-C5a antibody would be necessary to effectively inhibit C5a, in the event that it is produced. In contrast, the anti-C5a antibody described herein that retains the ability to bind to free C5a, even in a molar excess of uncleaved C5, can thus be administered to a human at a much lower dose and/or less frequently than, e.g., an anti-C5 antibody and effectively provide the same or greater inhibition of C5a in the human.

Accordingly, in yet another aspect, the disclosure features an isolated antibody comprising two antigen-binding sites, wherein each antigen-binding site independently can bind to free human C5a (hC5a) or uncleaved human C5 (hC5), wherein, in an aqueous solution comprising: (i) a plurality of said antibodies and (ii) a molar excess of hC5 as compared to the molar amount of the antigen-binding sites, at equilibrium and under physiological conditions, at least 95 (e.g., at least 95.5, 96, 96.5, 97, 97.5, or 97.7) % of said plurality of antibodies bind no more than one hC5 molecule, i.e., no more than 5% of the antibodies are binding two molecules of hC5 at equilibrium.

In another aspect, the disclosure features an isolated antibody comprising two antigen-binding sites, wherein each antigen-binding site independently can bind to free human C5a (hC5a) or uncleaved human C5 (hC5), wherein, at equilibrium and under physiological conditions, in an aqueous solution comprising: (i) a plurality of said antibodies and (ii) a molar excess of hC5 as compared to the molar amount of the antigen-binding sites (or antibodies), at least 95% of said plurality of antibodies retain at least one antigen-binding site available to bind free hC5a.

In another aspect, the disclosure features an isolated antibody comprising two antigen-binding sites, wherein each antigen-binding site independently can bind to free human C5a (hC5a) or uncleaved human C5 (hC5), wherein, at equilibrium and under physiological conditions, in an aqueous solution comprising: (i) a plurality of said antibodies and (ii) a molar excess of hC5 as compared to the molar amount of the antigen-binding sites (or antibodies), each antigen-binding site of no more than 5% of said plurality of antibodies is bound to a hC5 molecule.

In some embodiments of any of the isolated antibodies described herein, the molar excess is at least a two-fold (e.g., at least a 2-fold, 3-fold, 4-fold, 5-fold, 6-fold, 7-fold, 8-fold, 9-fold, or even 10-fold) molar excess.

In some embodiments of any of the isolated antibodies described herein, the physiological condition is 3.9 mM $NaH_2PO_4$, 6.1 mM $Na_2HPO_4$, and 150 mM NaCl, at pH7.0.

In some embodiments of any of the isolated antibodies described herein, each antigen-binding site independently can bind to free hC5a with a $K_D$ that is less than $1.25 \times 10^{-9}$ M. In some embodiments, each antigen-binding site can independently bind to free hC5a with a subnanomolar affinity (see above).

In some embodiments of any of the isolated antibodies described herein, the isolated antibody comprises a light chain polypeptide comprising the amino acid sequence depicted in SEQ ID NO:42 and a heavy chain polypeptide comprising the amino acid sequence depicted in SEQ ID NO:45.

In some embodiments of any of the isolated antibodies described herein, the isolated antibody comprises: (i) a light chain CDR1 comprising the amino acid sequence depicted in SEQ ID NO:20; (ii) a light chain CDR2 comprising the amino acid sequence depicted in SEQ ID NO:21; (iii) a light chain CDR3 comprising the amino acid sequence depicted in SEQ ID NO:22; (iv) a heavy chain CDR1 comprising the amino acid sequence depicted in SEQ ID NO:28; (v) a heavy chain CDR2 comprising the amino acid sequence depicted in SEQ ID NO:46; and (vi) a heavy chain CDR3 comprising the amino acid sequence depicted in SEQ ID NO:47.

In some embodiments, the isolated antibody can comprise any of the light chain CDR sets described herein, any of the light chain variable regions described herein (e.g., any of the humanized light chain variable regions), any of the heavy chain CDR sets described herein, any of the heavy chain variable regions described herein (e.g., any of the humanized heavy chain variable regions), or any suitable combinations thereof. See, e.g., Tables 1 or 2.

In another aspect, the disclosure features a method for treating a human afflicted with a complement-associated disorder (e.g., a C5a-associated complement disorder), wherein the method includes administering to the human any of the isolated antibodies described herein in an amount sufficient to treat the complement-associated disorder.

In another aspect, the disclosure features a method for treating a human afflicted with a C5a-associated complement disorder, wherein the method comprises administering to the human at least 0.6 (e.g., at least 0.7, 0.8, 0.9, or 1) mg of any of the isolated antibodies described herein per kg body weight of the human to thereby partially or completely bind and sequester nanogram levels of free C5a for greater than, equal to, or at least 12 (e.g., 13, 14, 15, 16, 17, 18, 19, 20, 21, 22, 23, 24, or 25) days.

In another aspect, the disclosure features a method for treating a human afflicted with a C5a-associated complement disorder, wherein the method comprises administering to the human at least 10 mg of any of the isolated antibodies described herein per kg body weight of the human to thereby partially or completely bind and sequester nanogram levels of free C5a for at least 24 days.

In another aspect, the disclosure features a method for treating a human afflicted with a C5a-associated complement disorder, wherein the method comprises administering to the human any of the isolated antibodies described herein (or for example a pharmaceutical composition comprising any of the isolated antibodies described herein) in an amount sufficient to (a) achieve molar Cmax values equal to or less than the physiologic molar concentration of uncleaved hC5 and (b) partially or completely bind and sequester pathophysiologic levels of free C5a.

In some embodiments of any of the methods described herein, an antibody is administered to a subject (e.g., a human) in an amount sufficient to achieve a molar Cmax value that is substantially lower than the physiologic molar concentration of uncleaved C5 (e.g., hC5).

In some embodiments of any of the methods described herein, the Cmax value is, e.g., no greater than 80 nM (or approximately 0.6 mg/kg). In some embodiments, Cmax levels are no greater than 70 (e.g., 60, 50, 40, 30, or 20) nM. In some embodiments, the Cmax value is no greater than approximately 100 nM. In some embodiments, the Cmax value is no greater than 200 nM. In some embodiments of any of the methods described herein, the Cmax value is, e.g., no greater than 400 nM (or approximately 3 mg/kg). In some embodiments, the Cmax value is no greater than 400 (e.g. 350, 300, 250, 200, 150, 100, 90, 80, 70, 60, 50, 40, 30, 20 or 10) nM.

In another aspect, the disclosure features a method for treating a human afflicted with a C5a-associated complement disorder, wherein the method comprises administering to the human any of the isolated antibodies described herein (or for example a pharmaceutical composition comprising any of the isolated antibodies described herein) in an amount sufficient to (a) achieve molar Cmax values equal to, less than, or substantially lower than the molar physiologic concentration of uncleaved hC5 and (b) partially or completely bind and sequester nanogram levels of free C5a for at least 12 days (e.g., at least 24 days). Suitable Cmax values are described above.

In some embodiments of any of the methods described herein, the C5a-associated complement disorder can be, e.g., one selected from the group consisting of sepsis, acute respiratory distress syndrome (ARDS), septic shock, anti-phospholipid syndrome, catastrophic anti-phospholipid syndrome, disseminated intravascular coagulation, lupus nephritis, Goodpasture's Syndrome, burn or severe burn, asthma, HELLP syndrome (Hemolytic anemia, Elevated Liver enzymes and Low Platelet count), inflammation-induced pain, C5a-mediated neutropenia, age-related macular degeneration (AMD), chronic obstructive pulmonary disease, and rheumatoid arthritis.

In yet another aspect, the disclosure features a composition comprising a plurality of isolated antibodies, each antibody of the plurality comprising two antigen-binding sites, wherein each antigen-binding site independently can bind to free human C5a (hC5a) or uncleaved human C5 (hC5), and wherein, in the presence of human C5 (hC5) and under physiological conditions, no more than 5% of the antibodies of the plurality at equilibrium comprise two antigen-binding sites simultaneously bound to uncleaved hC5.

In some embodiments of any of the compositions described herein, the percentage of the plurality in any particular binding configuration can be evaluated using high performance liquid chromatography (HPLC). In some embodiments, the physiological conditions in which the antibodies are evaluated comprises the following conditions: incubation of hC5 (e.g., a molar excess (e.g., a 2-fold molar excess) of hC5) with the plurality of antibodies at 4° C. for 84 hours in an aqueous solution comprising 3.9 mM $NaH_2PO_4$, 6.1 mM $Na_2HPO_4$, and 150 mM NaCl, at pH7.0. For the purposes of this disclosure, the solution obtained at 84 hours at 4° C. is considered to be at equilibrium.

In some embodiments of any of the compositions described herein, no more than 5% of the antibodies of the plurality comprise two antigen-binding sites simultaneously bound to uncleaved hC5 under physiological conditions and in the presence of at least a 2-fold molar excess of hC5 to antibody.

In some embodiments of any of the compositions described herein, no more than 5% of the antibodies of the plurality comprise two antigen-binding sites simultaneously bound to uncleaved hC5 molecules as evaluated using HPLC following incubation of the plurality of antibodies with hC5 at 4° C. for 84 hours in an aqueous solution comprising 3.9 mM $NaH_2PO_4$, 6.1 mM $Na_2HPO_4$, and 150 mM NaCl, at pH7.0.

In another aspect, the disclosure features a composition comprising a plurality of isolated antibodies, each antibody of the plurality comprising two antigen-binding sites, wherein each antigen-binding site independently can bind to free human C5a (hC5a) or uncleaved human C5 (hC5), and wherein no more than 5% of the antibodies of the plurality comprise two antigen-binding sites simultaneously bound to uncleaved hC5 as evaluated (e.g., using HPLC) following incubation of the plurality of antibodies with hC5 at 4° C. for 84 hours in an aqueous solution comprising 3.9 mM $NaH_2PO_4$, 6.1 mM $Na_2HPO_4$, and 150 mM NaCl, at pH7.0.

In yet another aspect, the disclosure features a composition comprising a plurality of isolated antibodies, each antibody of the plurality comprising a first antigen-binding site and a second antigen-binding site, wherein each antigen-binding site independently can bind to free human C5a (hC5a) or uncleaved human C5 (hC5), wherein each anti-gen-binding site independently can bind to the free hC5a polypeptide with a $K_D$ that is less than $1.25 \times 10^{-9}$ M, and wherein, in the presence of human C5 (hC5) and as evaluated (e.g., using high performance liquid chromatography (HPLC)) under physiological conditions, the two antigen-binding sites of at least 95% of the plurality of antibodies are occupied by uncleaved hC5 in the following configurations: (i) the first antigen-binding site binds uncleaved hC5 and the second antigen-binding site is unbound; or (ii) the first antigen-binding site is unbound and the second antigen-binding site binds uncleaved hC5.

In yet another aspect, the disclosure features a composition comprising a plurality of isolated antibodies, each antibody of the plurality comprising two antigen-binding sites, wherein each antigen-binding site independently can bind to free human C5a (hC5a) or uncleaved human C5 (hC5), and wherein, in the presence of human C5 (hC5) and as evaluated (e.g., using high performance liquid chromatography (HPLC)) under physiological conditions, at least 95% of the antibodies of the plurality comprise at least one antigen-binding site capable of binding to free hC5a.

In some embodiments of any of the compositions described herein, the plurality of antibodies is evaluated in the presence of at least a 2-fold molar excess of hC5: antibody. In some embodiments of any of the compositions described herein, the plurality of antibodies is evaluated in the presence of at least a 2-fold molar excess of hC5:antigen-binding sites.

In yet another aspect, the disclosure features an isolated antibody comprising two antigen-binding sites, wherein the antibody binds to free C5a or uncleaved C5, and wherein one of the antigen-binding sites of the antibody remains available to bind free C5a in the presence of a molar excess (e.g., at least or greater than a 2-fold, 5-fold, 10-fold, 15-fold, or even a 20-fold molar excess) of uncleaved C5.

In some embodiments, the antigen-binding sites have the same specificity (e.g., the CDRs of each of the two antigen-binding sites share identical amino acid sequences). In some embodiments, free C5a is human C5a. In some embodiments, the antibody is cross-reactive between human C5a and C5a from a non-human mammalian species. The antibody can, in some embodiments, bind to free C5a with a subnanomolar affinity. In some embodiments, the antibody has an affinity for C5a that is at least 100-fold greater than its corresponding affinity for uncleaved C5.

In another aspect, the disclosure features an isolated antibody comprising two antigen-binding sites, wherein each antigen-binding site independently binds to free human C5a (hC5a) or uncleaved human C5 (hC5), and wherein, at any concentration of uncleaved hC5 (e.g., in a molar excess of uncleaved hC5 over hC5a), at least one of the antigen-binding sites of the antibody remains available to bind to free hC5a (e.g., under human physiological conditions, e.g., in human blood or serum).

In another aspect, the disclosure features a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), and wherein, at a molar ratio of 1:1 (antibody:hC5), no more than, or less than, 5 (e.g., no more than, or less than 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1) % of the antibodies of the plurality comprise two antigen-binding sites simultaneously bound to uncleaved hC5. In some embodiments, each antigen-binding site independently can bind to free hC5a with a $K_D$ that is less than $1.25 \times 10^{-9}$ M (or, for example, with subnanomolar affinity).

In another aspect, the disclosure features a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), and wherein, in the presence of physiologic levels of uncleaved hC5, the antibodies of the plurality partially or completely bind and sequester nanogram levels of free C5a for greater than, equal to, or at least 12 (e.g., 13, 14, 15, 16, 17, 18, 19, 20, 21, 22, 23, 24, or 25) days when administered to a human at doses of 1 mg/kg or higher.

In another aspect, the disclosure features a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), and wherein, in the presence of physiologic levels of uncleaved hC5, the antibodies of the plurality partially or completely bind and sequester nanogram levels of free C5a for greater than, equal to, or at least 12 (e.g., 13, 14, 15, 16, 17, 18, 19, 20, 21, 22, 23, 24, or 25) days when administered to a human at doses of 10 mg/kg or higher.

In another aspect, the disclosure features a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), and wherein, in the presence of physiologic levels of uncleaved hC5, the antibodies of the plurality partially or completely binds and sequesters nanogram levels of free C5a for greater than, equal to, or at least 12 (e.g., 13, 14, 15, 16, 17, 18, 19, 20, 21, 22, 23, 24, or 25) days when administered at doses achieving molar Cmax values substantially lower than the molar physiologic concentration of uncleaved hC5.

In another aspect, the disclosure features a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), and wherein, in the presence of physiologic levels of uncleaved hC5, the antibodies of the plurality partially or completely bind and sequester pathophysiologic levels of free C5a when administered at doses achieving molar Cmax values substantially lower than the molar physiologic concentration of un-cleaved hC5.

In another aspect, the disclosure features an isolated antibody comprising a first antigen-binding site and a second antigen-binding site, wherein each antigen-binding site independently can bind to free human C5a (hC5a) or uncleaved human C5 (hC5), and wherein, when both antigen-binding sites are fully-occupied (and, e.g., under human physiological conditions, e.g., in human blood or serum), the following binding configurations are possible: (i) the first antigen-binding site binds free hC5a and the second antigen-binding site binds uncleaved hC5; (ii) the first antigen-binding site binds free hC5a and the second antigen-binding site binds free hC5a; or (iii) the first antigen-binding site binds uncleaved hC5 and the second antigen-binding site binds free hC5a.

In yet another aspect, the disclosure features an isolated antibody comprising a first antigen-binding site and a second antigen-binding site, wherein each antigen-binding site independently can bind to free human C5a (hC5a) or uncleaved human C5 (hC5), wherein each antigen-binding site independently can bind to free hC5a with a $K_D$ that is less than $1.25 \times 10^{-9}$ M (or, for example, with subnanomolar affinity), and wherein, in a physiological solution containing a plurality of the antibodies, at least 95% of the antibodies are in the following configurations: (i) the first antigen-binding site binds free hC5a and the second antigen-binding site binds uncleaved hC5; (ii) the first antigen-binding site binds free hC5a and the second antigen-binding site binds free hC5a; (iii) the first antigen-binding site binds uncleaved hC5 and the second antigen-binding site binds free hC5a; (iv) the first antigen-binding site binds uncleaved hC5 and the second antigen-binding site is unbound; (v) the first antigen-binding site binds hC5a and the second antigen-binding site is unbound; (vi) the first antigen-binding site is unbound and the second antigen-binding site binds uncleaved hC5; (vii) the first antigen-binding site is unbound and the second antigen-binding site binds hC5a; and (viii) the first antigen-binding site is unbound and the second antigen-binding site is unbound.

In another aspect, the disclosure features an isolated antibody comprising two antigen-binding sites, wherein each antigen-binding site independently can bind to free human C5a (hC5a) or uncleaved human C5 (hC5), and wherein, in a molar excess of uncleaved hC5 over hC5a, the antibody inhibits by at least 50% hC5a-dependent human neutrophil activation at a molar ratio of 1:1 (antigen-binding site: hC5a).

In some embodiments of any of the antibodies described herein, the configurations are possible under human physiological conditions with fully-folded, native, human C5a and C5 proteins.

In some embodiments of any of the antibodies described herein, the antibody binds to free hC5a with a $K_D$ that is less than $1.25 \times 10^{-9}$ M (or, for example, with subnanomolar affinity).

In yet another aspect, the disclosure features an antibody that (a) binds to free C5a (e.g., hC5a) with a subnanomolar affinity and (b) binds to free C5a with an affinity that is at least 100 (e.g., at least 110, 120, 130, 140, 150, 160, 170, 180, 190, 200, 225, 250, 275, 300, 400, 500, 600, 700, 800, 900, 1000, 2000, 3000, 4000, 5000, 6000, 7000, 8000, 9000, or 10000)-fold greater than its corresponding affinity for uncleaved C5 protein. In a physiologic composition comprising a plurality of the antibodies, for at least 95% of the antibodies, only one antigen-binding site of the antibody binds to uncleaved C5 protein, whereas the second antigen-binding site remains available to bind to free C5a. (The hC5a can have the amino acid sequence depicted in SEQ ID NO:1.)

In another aspect, the disclosure features a method for treating a human afflicted with a C5a-associated complement disorder, the method comprising administering to the human a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), wherein at least 1 mg of the antibodies per kg body weight of the human is administered to the human, and wherein administration of the antibodies is effective to partially or completely bind and sequester nanogram levels of free C5a for at least 12 days.

In another aspect, the disclosure features a method for treating a human afflicted with a complement-associated disorder (e.g., a C5a-associated complement disorder), the method comprising administering to the human a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), wherein at least 10 mg of the antibodies per kg body weight of the human is administered to the human, and wherein administration of the antibodies is effective to partially or completely bind and sequester nanogram levels of free C5a for at least 24 days.

In another aspect, the disclosure features a method for treating a human afflicted with a complement-associated disorder (e.g., a C5a-associated complement disorder), the method comprising administering to the human a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), wherein the antibodies are administered at a dose sufficient to: (a) achieve molar Cmax values substantially lower than the molar physiologic concentration of uncleaved hC5 and (b) partially or completely bind and sequester nanogram levels of free C5a for at least 12 days.

In another aspect, the disclosure features a method for treating a human afflicted with a complement-associated disorder (e.g., a C5a-associated complement disorder), the method comprising administering to the human a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), wherein the antibodies are administered at a dose sufficient to: (a) achieve molar Cmax values substantially lower than the molar physiologic concentration of uncleaved hC5 and (b) partially or completely bind and sequester nanogram levels of free C5a for at least 24 days.

In another aspect, the disclosure features a method for treating a human afflicted with a complement-associated disorder (e.g., a C5a-associated complement disorder), the method comprising administering to the human a composition comprising a plurality of isolated antibodies, wherein each antibody of the plurality comprises two antigen-binding sites, wherein each of the antigen-binding sites independently can bind to free human C5a (hC5a) or uncleaved human C5 (hC5), wherein the antibodies are administered at a dose sufficient to: (a) achieve molar Cmax values substantially lower than the molar physiologic concentration of uncleaved hC5 and (b) partially or completely bind and sequester pathophysiologic levels of free C5a.

It is understood that any of the compositions (e.g., comprising a plurality of antibodies) or isolated antibodies (e.g., that retain, in the presence of C5 or molar excess of C5, a free Fab arm capable of binding to free C5a) described herein can be: (a) formulated as pharmaceutical compositions in accordance with the disclosure, (b) included in therapeutic kits (described herein), or (c) included in the pre-filled syringes described herein.

As described in the working examples provided herein, the inventors have also discovered an antibody, BNJ383 (see below), that not only binds with high affinity (subnanomolar affinity) to free hC5a, but at concentrations in excess of uncleaved C5 also inhibits terminal complement complex (TCC) formation in a dose dependent manner. Even at concentrations of the anti-C5a antibody in greater than 6.5-fold excess of C5, however, inhibition of TCC is not complete. While the disclosure is by no means limited by any particular theory or mechanism of action, the antibody may inhibit TCC formation by binding to at least a fraction of uncleaved C5 and preventing its cleavage and/or otherwise preventing the successful association of C5 with additional TCC components. The inventors appreciated that such an antibody is useful for treating complement-associated disorders, e.g., in which C5a plays a significant role and the C5b-containing TCC may play a less substantial role. Such disorders can include, e.g., sepsis, acute respiratory distress syndrome (ARDS), septic shock, anti-phospholipid syndrome, catastrophic anti-phospholipid syndrome, disseminated intravascular coagulation, lupus nephritis, Goodpasture's Syndrome, burn or severe burn, asthma, HELLP syndrome (Hemolytic anemia, Elevated Liver enzymes and Low Platelet count), inflammation-induced pain, C5a-mediated neutropenia, age-related macular degeneration (AMD), chronic obstructive pulmonary disease, and rheumatoid arthritis.

The inventors also appreciated that use of such an anti-C5a antibody to treat these conditions, among others, may provide an even more beneficial safety profile as compared to use of terminal complement inhibitory drugs. As noted above, one notable consequence of inhibiting terminal complement components such as C5, C5b, C6, C7, C8, or C9 is decreased protection by the host immune system against the encapsulated bacteria that terminal complement ordinarily lyses—for example, *Neisseria meningitides* and *Neisseria gonorrhoeae*. As the anti-C5a antibodies described in this section inhibit the C5a-mediated inflammatory response, but do not completely inhibit the formation of the terminal complement complex that lyses those encapsulated bacteria, patients receiving a therapeutic anti-C5a antibody described herein may not require a protective vaccination, e.g., a vaccination against *Neisseria meningitides* and *Neisseria gonorrhoeae*. Partial inhibition of the TCC, while not wholly abrogating terminal complement's anti-microbial response, may in fact reduce TCC-induced inflammation as tissue injury. The partial TCC inhibition, in combination with inhibition of C5a, is believed to make the anti-C5a antibody an even more potent anti-inflammatory compound.

Accordingly, in another aspect, the disclosure features an antibody or antigen-binding fragment thereof that binds to free C5a, wherein the free C5a is human C5a having the amino acid sequence depicted in SEQ ID NO: 1, wherein the antibody inhibits the binding of C5a to C5a receptor, and wherein the antibody partially inhibits formation of the terminal complement complex (TCC). Partial inhibition by an anti-C5a antibody or antigen-binding fragment thereof described herein can be, e.g., a complement activity that is, in the presence of the antibody, up to, or no greater than, 80 (e.g., 75, 70, 65, 60, 55, 50, 45, 40, 35, 30, or 25) % of the complement activity in the absence of the antibody or antigen-binding fragment thereof. In some embodiments, the antibody or antigen-binding fragment thereof binds to free C5a (e.g., free hC5a) with a subnanomolar affinity. In some embodiments, the antibody or antigen-binding fragment thereof has an affinity for free C5a that is at least 100-fold greater than the corresponding affinity of the antibody or antigen-binding fragment for uncleaved C5. In some embodiments, the antibody or antigen-binding fragment thereof inhibits by at least 50% formation of TCC at concentrations exceeding 200 (e.g., 210, 220, 230, 240, 250, 260, 270, 280, 290, 300, 320, 340, 360, 380, or 400 or more) μg/mL as measured using a CH50eq assay. In some embodiments, the antibody or antigen-binding fragment thereof inhibits by at least 50% classical complement pathway activation at concentrations exceeding 200 (e.g., 210, 220, 230, 240, 250, 260, 270, 280, 290, 300, 320, 340, 360, 380, or 400 or more) μg/mL as measured using the Wieslab® Classical Pathway Complement Kit as described in the working examples.

In another aspect, the disclosure features a method for treating a human afflicted with a complement-associated disorder (e.g., a C5a-associated complement disorder or a complement-associated inflammatory disorder). The method includes administering to the human an effective amount of an antibody or antigen-binding fragment thereof that inhibits the binding of C5a to C5a receptor, and wherein the antibody partially inhibits formation of the terminal complement complex (TCC). See above. The disorder can be any of those known in the art or described herein.

In another aspect, the disclosure features an isolated antibody or antigen-binding fragment thereof that binds to a human C5a polypeptide having the amino acid sequence depicted in SEQ ID NO: 1, but does not bind to the alpha chain of uncleaved, native C5, wherein the antibody or antigen-binding fragment thereof binds to the human C5a polypeptide with a $K_D$ that is less than $1.25 \times 10^{-9}$ M.

In another aspect, the disclosure features an isolated antibody or antigen-binding fragment thereof that binds to a human C5a polypeptide having the amino acid sequence depicted in SEQ ID NO: 1, but does not bind to the alpha chain of uncleaved, native C5, wherein the antibody inhibits by at least 50% human C5a-dependent human neutrophil activation at a molar ratio of 1:1 (antigen-binding site:C5a). In some embodiments, the antibody inhibits by at least 50% human C5a-dependent human neutrophil migration in an assay in which 0.4 nM of antibody is used to inhibit the neutrophil-activation activity of 2 nM human C5a as described in Example 5. In some embodiments, the antibody does not comprise exemplary CDR pairing 3 depicted in Table 1. In some embodiments, the antibody is not BNJ371.

In some embodiments, an isolated antibody or antigen-binding fragment thereof described herein binds to a human C5a polypeptide having the amino acid sequence depicted in SEQ ID NO:2.

In some embodiments, an isolated antibody or antigen-binding fragment thereof described herein comprises a light chain polypeptide comprising: a light chain CDR1 comprising the amino acid sequence depicted in SEQ ID NO:20; a light chain CDR2 comprising the amino acid sequence depicted in SEQ ID NO:21; and a light chain CDR3 comprising the amino acid sequence depicted in SEQ ID NO:22.

In some embodiments, an isolated antibody or antigen-binding fragment thereof described herein comprises a light chain polypeptide comprising: a light chain CDR1 comprising the amino acid sequence depicted in SEQ ID NO:20; a light chain CDR2 comprising the amino acid sequence depicted in SEQ ID NO:38; and a light chain CDR3 comprising the amino acid sequence depicted in SEQ ID NO:22.

In some embodiments, an isolated antibody or antigen-binding fragment thereof described herein comprises a heavy chain polypeptide comprising: a heavy chain CDR1 comprising the amino acid sequence depicted in SEQ ID NO:28; a heavy chain CDR2 comprising the amino acid sequence depicted in SEQ ID NO:29; and a heavy chain CDR3 comprising the amino acid sequence depicted in SEQ ID NO:30.

In some embodiments, an isolated antibody or antigen-binding fragment thereof described herein comprises a heavy chain polypeptide comprising: a heavy chain CDR1 comprising the amino acid sequence depicted in SEQ ID NO:28; a heavy chain CDR2 comprising the amino acid sequence depicted in SEQ ID NO:67; and a heavy chain CDR3 comprising the amino acid sequence depicted in SEQ ID NO:30.

In some embodiments, an isolated antibody or antigen-binding fragment thereof described herein comprises a heavy chain polypeptide comprising: a heavy chain CDR1 comprising the amino acid sequence depicted in SEQ ID NO:28; a heavy chain CDR2 comprising the amino acid sequence depicted in SEQ ID NO:46; and a heavy chain CDR3 comprising the amino acid sequence depicted in SEQ ID NO:47.

In some embodiments, an isolated antibody or antigen-binding fragment thereof described herein comprises a light chain polypeptide comprising the amino acid sequence depicted in SEQ ID NO:37 or SEQ ID NO:36.

In some embodiments, an isolated antibody or antigen-binding fragment thereof described herein comprises a heavy chain polypeptide comprising the amino acid sequence depicted in SEQ ID NO:27 or SEQ ID NO:33.

In some embodiments, an isolated antibody or antigen-binding fragment thereof described herein comprises a light chain polypeptide comprising the amino acid sequence depicted in SEQ ID NO:37 and a heavy chain polypeptide comprising the amino acid sequence depicted in SEQ ID NO:27.

In some embodiments, an isolated antibody or antigen-binding fragment thereof described herein comprises a light chain polypeptide comprising the amino acid sequence depicted in SEQ ID NO:36 and a heavy chain polypeptide comprising the amino acid sequence depicted in SEQ ID NO:33.

In some embodiments, an isolated antibody or antigen-binding fragment thereof described herein comprises a light chain polypeptide comprising the amino acid sequence depicted in SEQ ID NO:19 or SEQ ID NO:17.

In some embodiments, an isolated antibody or antigen-binding fragment thereof described herein comprises a heavy chain polypeptide comprising the amino acid sequence depicted in SEQ ID NO:27 or SEQ ID NO:25.

In some embodiments, an isolated antibody or antigen-binding fragment thereof described herein comprises a light chain polypeptide comprising the amino acid sequence depicted in SEQ ID NO: 19 and a heavy chain polypeptide comprising the amino acid sequence depicted in SEQ ID NO:27.

In some embodiments, an isolated antibody or antigen-binding fragment thereof described herein comprises a light chain polypeptide comprising the amino acid sequence depicted in SEQ ID NO: 17 and a heavy chain polypeptide comprising the amino acid sequence depicted in SEQ ID NO:25.

In some embodiments, an isolated antibody or antigen-binding fragment thereof described herein comprises a light chain polypeptide comprising the amino acid sequence depicted in SEQ ID NO:42 or SEQ ID NO:40.

In some embodiments, an isolated antibody or antigen-binding fragment thereof described herein comprises a heavy chain polypeptide comprising the amino acid sequence depicted in SEQ ID NO:27 or SEQ ID NO:33.

In some embodiments, an isolated antibody or antigen-binding fragment thereof described herein comprises a light chain polypeptide comprising the amino acid sequence depicted in SEQ ID NO:42 and a heavy chain polypeptide comprising the amino acid sequence depicted in SEQ ID NO:27.

In some embodiments, an isolated antibody or antigen-binding fragment thereof described herein comprises a light chain polypeptide comprising the amino acid sequence depicted in SEQ ID NO:40 and a heavy chain polypeptide comprising the amino acid sequence depicted in SEQ ID NO:33.

In some embodiments, an isolated antibody or antigen-binding fragment thereof described herein comprises a light chain polypeptide comprising the amino acid sequence depicted in SEQ ID NO: 17 and a heavy chain polypeptide comprising the amino acid sequence depicted in SEQ ID NO:33.

In some embodiments, an isolated antibody or antigen-binding fragment thereof described herein comprises a heavy chain polypeptide comprising the amino acid sequence depicted in any one of SEQ ID NO:45, SEQ ID NO:44, or SEQ ID NO:49.

In some embodiments, an isolated antibody or antigen-binding fragment thereof described herein comprises a light chain polypeptide comprising the amino acid sequence depicted in SEQ ID NO: 19 and a heavy chain polypeptide comprising the amino acid sequence depicted in SEQ ID NO:45.

In some embodiments, an isolated antibody or antigen-binding fragment thereof described herein comprises a light chain polypeptide comprising the amino acid sequence depicted in SEQ ID NO: 17 and a heavy chain polypeptide comprising the amino acid sequence depicted in SEQ ID NO:44.

In some embodiments, an isolated antibody or antigen-binding fragment thereof described herein comprises a light chain polypeptide comprising the amino acid sequence depicted in SEQ ID NO: 17 and a heavy chain polypeptide comprising the amino acid sequence depicted in SEQ ID NO:49.

In some embodiments, an isolated antibody or antigen-binding fragment thereof described herein comprises a light chain polypeptide comprising the amino acid sequence depicted in SEQ ID NO:37 or SEQ ID NO:36.

In some embodiments, an isolated antibody or antigen-binding fragment thereof described herein comprises a heavy chain polypeptide comprising the amino acid sequence depicted in SEQ ID NO:45 or SEQ ID NO:49.

In some embodiments, an isolated antibody or antigen-binding fragment thereof described herein comprises a light chain polypeptide comprising the amino acid sequence depicted in SEQ ID NO:37 and a heavy chain polypeptide comprising the amino acid sequence depicted in SEQ ID NO:45.

In some embodiments, an isolated antibody or antigen-binding fragment thereof described herein comprises a light chain polypeptide comprising the amino acid sequence depicted in SEQ ID NO:36 and a heavy chain polypeptide comprising the amino acid sequence depicted in SEQ ID NO:49.

In some embodiments, an isolated antibody or antigen-binding fragment thereof described herein comprises a light chain polypeptide comprising the amino acid sequence depicted in SEQ ID NO:42 or SEQ ID NO:40.

In some embodiments, an isolated antibody or antigen-binding fragment thereof described herein comprises a heavy chain polypeptide comprising the amino acid sequence depicted in SEQ ID NO:45 or SEQ ID NO:49.

In some embodiments, an isolated antibody or antigen-binding fragment thereof described herein comprises a light chain polypeptide comprising the amino acid sequence depicted in SEQ ID NO:42 and a heavy chain polypeptide comprising the amino acid sequence depicted in SEQ ID NO:45.

In some embodiments, an isolated antibody or antigen-binding fragment thereof described herein comprises a light chain polypeptide comprising the amino acid sequence depicted in SEQ ID NO:40 and a heavy chain polypeptide comprising the amino acid sequence depicted in SEQ ID NO:49.

In some embodiments, an isolated antibody or antigen-binding fragment thereof described herein binds to hC5a with a $K_D$ that is less than $7 \times 10^{-10}$ M.

In some embodiments, an isolated antibody or antigen-binding fragment thereof described herein binds to hC5a with a $K_D$ that is less than $5 \times 10^{-10}$ M.

In some embodiments, an isolated antibody or antigen-binding fragment thereof described herein binds to hC5a with a $K_D$ that is less than $3 \times 10^{-10}$ M.

In some embodiments, an isolated antibody or antigen-binding fragment thereof described herein binds to hC5a with a $K_D$ that is less than $2.5 \times 10^{-10}$ M.

In some embodiments, an isolated antibody or antigen-binding fragment thereof described herein binds to hC5a with a $K_D$ that is less than $1.5 \times 10^{-10}$ M.

In some embodiments, an isolated antibody or antigen-binding fragment thereof described herein binds to hC5a with a $K_D$ that is less than $1.0 \times 10^{-10}$ M.

In some embodiments, an isolated antibody or antigen-binding fragment thereof described herein binds to hC5a with a $K_D$ that is less than $8.0 \times 10^{-11}$ M.

In some embodiments, an antibody inhibits by at least 70 (e.g., at least 75, 80, 85, 90, or 95 or greater) % human C5a-dependent human neutrophil activation at a molar ratio of 1:1 (antigen-binding site:C5a). In some embodiments, the antibody does not comprise exemplary CDR pairing 3 depicted in Table 1. In some embodiments, the antibody is not BNJ371.

In yet another aspect, the disclosure features an isolated antibody or antigen-binding fragment thereof that comprises a light chain CDR set as set forth in Table 3 or Table 7. For example, the isolated antibody or antigen-binding fragment thereof can comprise a light chain polypeptide comprising: (i) a light chain CDR1 comprising the amino acid sequence depicted in SEQ ID NO: 140; a light chain CDR2 comprising the amino acid sequence depicted in SEQ ID NO:96; and a light chain CDR3 comprising the amino acid sequence depicted in SEQ ID NO: 142; (ii) a light chain CDR1 comprising the amino acid sequence depicted in SEQ ID NO:156; a light chain CDR2 comprising the amino acid sequence depicted in SEQ ID NO:157; and a light chain CDR3 comprising the amino acid sequence depicted in SEQ ID NO:158; (iii) a light chain CDR1 comprising the amino acid sequence depicted in SEQ ID NO: 164; a light chain CDR2 comprising the amino acid sequence depicted in SEQ ID NO: 165; and a light chain CDR3 comprising the amino acid sequence depicted in SEQ ID NO:166; (iv) a light chain CDR1 comprising the amino acid sequence depicted in SEQ ID NO: 172; a light chain CDR2 comprising the amino acid sequence depicted in SEQ ID NO: 173; and a light chain CDR3 comprising the amino acid sequence depicted in SEQ ID NO:174; (v) a light chain CDR1 comprising the amino acid sequence depicted in SEQ ID NO:84; a light chain CDR2 comprising the amino acid sequence depicted in SEQ ID NO:85; and a light chain CDR3 comprising the amino acid sequence depicted in SEQ ID NO:86; (vi) a light chain CDR1 comprising the amino acid sequence depicted in SEQ ID NO:92; a light chain CDR2 comprising the amino acid sequence depicted in SEQ ID NO:89; and a light chain CDR3 comprising the amino acid sequence depicted in SEQ ID NO:93; (vii) a light chain CDR1 comprising the amino acid sequence depicted in SEQ ID NO:88; a light chain CDR2 comprising the amino acid sequence depicted in SEQ ID NO:89; and a light chain CDR3 comprising the amino acid sequence depicted in SEQ ID NO:90; (viii) a light chain CDR1 comprising the amino acid sequence depicted in SEQ ID NO:95; a light chain CDR2 comprising the amino acid sequence depicted in SEQ ID NO:96; and a light chain CDR3 comprising the amino acid sequence depicted in SEQ ID NO:97; (ix) a light chain CDR1 comprising the amino acid sequence depicted in SEQ ID NO:99; a light chain CDR2 comprising the amino acid sequence depicted in SEQ ID NO: 100; and a light chain CDR3 comprising the amino acid sequence depicted in SEQ ID NO:101;
(x) a light chain CDR1 comprising the amino acid sequence depicted in SEQ ID NO:84; a light chain CDR2 comprising the amino acid sequence depicted in SEQ ID NO:85; and a light chain CDR3 comprising the amino acid sequence depicted in SEQ ID NO: 103; (xi) a light chain CDR1 comprising the amino acid sequence depicted in SEQ ID NO:105; a light chain CDR2 comprising the amino acid sequence depicted in SEQ ID NO: 106; and a light chain CDR3 comprising the amino acid sequence depicted in SEQ ID NO:107; (xii) a light chain CDR1 comprising the amino acid sequence depicted in SEQ ID NO:92; a light chain CDR2 comprising the amino acid sequence depicted in SEQ ID NO:89; and a light chain CDR3 comprising the amino acid sequence depicted in SEQ ID NO: 108; (xiii) a light chain CDR1 comprising the amino acid sequence depicted in SEQ ID NO:20; a light chain CDR2 comprising the amino acid sequence depicted in SEQ ID NO: 110; and a light chain CDR3 comprising the amino acid sequence depicted in SEQ ID NO:111; or (xiv) a light chain CDR1 comprising the amino acid sequence depicted in SEQ ID NO:20; a light chain CDR2 comprising the amino acid sequence depicted in SEQ ID NO:21; and a light chain CDR3 comprising the amino acid sequence depicted in SEQ ID NO: 113. In some embodiments, the antibody or antigen-binding fragment thereof comprising the light chain CDR set also comprises a heavy chain polypeptide comprising any one of the heavy chain CDR sets as set forth in Table 8.

In another aspect, the disclosure features an isolated antibody or antigen-binding fragment thereof that comprises a heavy chain CDR set as set forth in Table 3 or Table 8. For example, in some embodiments an isolated antibody or antigen-binding fragment thereof described herein comprises a heavy chain polypeptide comprising: (i) a heavy chain CDR1 comprising the amino acid sequence depicted in SEQ ID NO: 115; a heavy chain CDR2 comprising the amino acid sequence depicted in SEQ ID NO: 144; and a heavy chain CDR3 comprising the amino acid sequence depicted in SEQ ID NO:117; (ii) a heavy chain CDR1 comprising the amino acid sequence depicted in SEQ ID NO:28; a heavy chain CDR2 comprising the amino acid sequence depicted in SEQ ID NO:67; and a heavy chain CDR3 comprising the amino acid sequence depicted in SEQ ID NO:30; (iii) a heavy chain CDR1 comprising the amino acid sequence depicted in SEQ ID NO: 160; a heavy chain CDR2 comprising the amino acid sequence depicted in SEQ ID NO:161; and a heavy chain CDR3 comprising the amino acid sequence depicted in SEQ ID NO: 162; (iv) a heavy chain CDR1 comprising the amino acid sequence depicted in SEQ ID NO: 168; a heavy chain CDR2 comprising the amino acid sequence depicted in SEQ ID NO: 169; and a heavy chain CDR3 comprising the amino acid sequence depicted in SEQ ID NO: 170; (v) a heavy chain CDR1 comprising the amino acid sequence depicted in SEQ ID NO: 176; a heavy chain CDR2 comprising the amino acid sequence depicted in SEQ ID NO:177; and a heavy chain CDR3 comprising the amino acid sequence depicted in SEQ ID NO: 178; (vi) a heavy chain CDR1 comprising the amino acid sequence depicted in SEQ ID NO:115; a heavy chain CDR2 comprising the amino acid sequence depicted in SEQ ID NO: 116; and a heavy chain CDR3 comprising the amino acid sequence depicted in SEQ ID NO: 117; (vii) a heavy chain CDR1 comprising the amino acid sequence depicted in SEQ ID NO: 119; a heavy chain CDR2 comprising the amino acid sequence depicted in SEQ ID NO: 120; and a heavy chain CDR3 comprising the amino acid sequence depicted in SEQ ID NO:121; (viii) a heavy chain CDR1 comprising the amino acid sequence depicted in SEQ ID NO: 115; a heavy chain CDR2 comprising the amino acid sequence depicted in SEQ ID NO: 123; and a heavy chain CDR3 comprising the amino acid sequence depicted in SEQ ID NO: 117; (ix) a heavy chain CDR1 comprising the amino acid sequence depicted in SEQ ID NO:115; a heavy chain CDR2 comprising the amino acid sequence depicted in SEQ ID NO: 124; and a heavy chain CDR3 comprising the amino acid sequence depicted in SEQ ID NO: 117; (x) a heavy chain CDR1 comprising the amino acid sequence depicted in SEQ ID NO: 119; a heavy chain CDR2 comprising the amino acid sequence depicted in SEQ ID NO: 126; and a heavy chain CDR3 comprising the amino acid sequence depicted in SEQ ID NO: 127; (xi) a heavy chain CDR1 comprising the amino acid sequence depicted in SEQ ID NO: 115; a heavy chain CDR2 comprising the amino acid sequence depicted in SEQ ID NO: 129; and a heavy chain CDR3 comprising the amino acid sequence depicted in SEQ ID NO: 117; (xii) a heavy chain CDR1 comprising the amino acid sequence depicted in SEQ ID NO:131; a heavy chain CDR2 comprising the amino acid sequence depicted in SEQ ID NO: 132; and a heavy chain CDR3 comprising the amino acid sequence depicted in SEQ ID NO:133; (xiii) a heavy chain CDR1 comprising the amino acid sequence depicted in SEQ ID NO:28; a heavy chain CDR2 comprising the amino acid sequence depicted in SEQ ID NO:46; and a heavy chain CDR3 comprising the amino acid sequence depicted in SEQ ID NO:47; or (xiv) a heavy chain CDR1 comprising the amino acid sequence depicted in SEQ ID NO: 136; a heavy chain CDR2 comprising the amino acid sequence depicted in SEQ ID NO: 137; and a heavy chain CDR3 comprising the amino acid sequence depicted in SEQ ID NO: 138. In some embodiments, the antibody or antigen-binding fragment thereof comprising the heavy chain CDR set also comprises a light chain polypeptide comprising any one of the light chain CDR sets as set forth in Table 7.

In another aspect, the disclosure features an isolated antibody or antigen-binding fragment thereof comprising a light chain CDR set from Table 7 and its cognate heavy chain CDR set as set forth in Table 8. In another aspect, the disclosure features an isolated antibody or antigen-binding fragment thereof comprising a paired light chain and heavy chain CDR set as set forth in Table 3 or Table 9. For example, in some embodiments an isolated antibody, or antigen-binding fragment thereof, described herein comprises: (i) a light chain CDR1 comprising the amino acid sequence depicted in SEQ ID NO: 140; a light chain CDR2 comprising the amino acid sequence depicted in SEQ ID NO:96; a light chain CDR3 comprising the amino acid sequence depicted in SEQ ID NO: 142; a heavy chain CDR1 comprising the amino acid sequence depicted in SEQ ID NO: 115; a heavy chain CDR2 comprising the amino acid sequence depicted in SEQ ID NO: 144; and a heavy chain CDR3 comprising the amino acid sequence depicted in SEQ ID NO: 117; (ii) a light chain CDR1 comprising the amino acid sequence depicted in SEQ ID NO:20; a light chain CDR2 comprising the amino acid sequence depicted in SEQ ID NO:21; and a light chain CDR3 comprising the amino acid sequence depicted in SEQ ID NO:22; a heavy chain CDR1 comprising the amino acid sequence depicted in SEQ ID NO:28; a heavy chain CDR2 comprising the amino acid sequence depicted in SEQ ID NO:67; and a heavy chain CDR3 comprising the amino acid sequence depicted in SEQ ID NO:30; (iii) a light chain CDR1 comprising the amino acid sequence depicted in SEQ ID NO:156; a light chain CDR2 comprising the amino acid sequence depicted in SEQ ID NO:157; a light chain CDR3 comprising the amino acid sequence depicted in SEQ ID NO:158; a heavy chain CDR1 comprising the amino acid sequence depicted in SEQ ID NO: 160; a heavy chain CDR2 comprising the amino acid sequence depicted in SEQ ID NO: 161; and a heavy chain CDR3 comprising the amino acid sequence depicted in SEQ ID NO: 162; (iv) a light chain CDR1 comprising the amino acid sequence depicted in SEQ ID NO: 164; a light chain CDR2 comprising the amino acid sequence depicted in SEQ ID NO: 165; a light chain CDR3 comprising the amino acid sequence depicted in SEQ ID NO: 166; a heavy chain CDR1 comprising the amino acid sequence depicted in SEQ ID NO: 168; a heavy chain CDR2 comprising the amino acid sequence depicted in SEQ ID NO: 169; and a heavy chain CDR3 comprising the amino acid sequence depicted in SEQ ID NO: 170; (v) a light chain CDR1 comprising the amino acid sequence depicted in SEQ ID NO: 172; a light chain CDR2 comprising the amino acid sequence depicted in SEQ ID NO: 173; a light chain CDR3 comprising the amino acid sequence depicted in SEQ ID NO: 174; a heavy chain CDR1 comprising the amino acid sequence depicted in SEQ ID NO: 176; a heavy chain CDR2 comprising the amino acid sequence depicted in SEQ ID NO: 177; and a heavy chain CDR3 comprising the amino acid sequence depicted in SEQ ID NO: 178; (vi) a light chain CDR1 comprising the amino acid sequence depicted in SEQ ID NO:88; a light chain CDR2 comprising the amino acid sequence depicted in SEQ ID NO:89; a light chain CDR3 comprising the amino acid sequence depicted in SEQ ID NO:90; a heavy chain CDR1 comprising the amino acid sequence depicted in SEQ ID NO: 119; a heavy chain CDR2 comprising the amino acid sequence depicted in SEQ ID NO: 120; and a heavy chain CDR3 comprising the amino acid sequence depicted in SEQ ID NO:121; (vii) a light chain CDR1 comprising the amino acid sequence depicted in SEQ ID NO: 105; a light chain CDR2 comprising the amino acid sequence depicted in SEQ ID NO: 106; a light chain CDR3 comprising the amino acid sequence depicted in SEQ ID NO: 107; a heavy chain CDR1 comprising the amino acid sequence depicted in SEQ ID NO: 115; a heavy chain CDR2 comprising the amino acid sequence depicted in SEQ ID NO: 124; and a heavy chain CDR3 comprising the amino acid sequence depicted in SEQ ID NO:117; (viii) a light chain CDR1 comprising the amino acid sequence depicted in SEQ ID NO:84; a light chain CDR2 comprising the amino acid sequence depicted in SEQ ID NO:85; a light chain CDR3 comprising the amino acid sequence depicted in SEQ ID NO:86; a heavy chain CDR1 comprising the amino acid sequence depicted in SEQ ID NO: 115; a heavy chain CDR2 comprising the amino acid sequence depicted in SEQ ID NO: 116; and a heavy chain CDR3 comprising the amino acid sequence depicted in SEQ ID NO: 117; (ix) a light chain CDR1 comprising the amino acid sequence depicted in SEQ ID NO:20; a light chain CDR2 comprising the amino acid sequence depicted in SEQ ID NO: 110; a light chain CDR3 comprising the amino acid sequence depicted in SEQ ID NO: 111; a heavy chain CDR1 comprising the amino acid sequence depicted in SEQ ID NO: 136; a heavy chain CDR2 comprising the amino acid sequence depicted in SEQ ID NO: 137; and a heavy chain CDR3 comprising the amino acid sequence depicted in SEQ ID NO:138; (x) a light chain CDR1 comprising the amino acid sequence depicted in SEQ ID NO:20; a light chain CDR2 comprising the amino acid sequence depicted in SEQ ID NO:21; a light chain CDR3 comprising the amino acid sequence depicted in SEQ ID NO: 113; a heavy chain CDR1 comprising the amino acid sequence depicted in SEQ ID NO:28; a heavy chain CDR2 comprising the amino acid sequence depicted in SEQ ID NO:46; and a heavy chain CDR3 comprising the amino acid sequence depicted in SEQ ID NO:47; (xi) a light chain CDR1 comprising the amino acid sequence depicted in SEQ ID NO:99; a light chain CDR2 comprising the amino acid sequence depicted in SEQ ID NO: 100; a light chain CDR3 comprising the amino acid sequence depicted in SEQ ID NO: 101; a heavy chain CDR1 comprising the amino acid sequence depicted in SEQ ID NO: 119; a heavy chain CDR2 comprising the amino acid sequence depicted in SEQ ID NO: 126; and a heavy chain CDR3 comprising the amino acid sequence depicted in SEQ ID NO: 127; (xii) a light chain CDR1 comprising the amino acid sequence depicted in SEQ ID NO:95; a light chain CDR2 comprising the amino acid sequence depicted in SEQ ID NO:96; a light chain CDR3 comprising the amino acid sequence depicted in SEQ ID NO:97; a heavy chain CDR1 comprising the amino acid sequence depicted in SEQ ID NO: 115; a heavy chain CDR2 comprising the amino acid sequence depicted in SEQ ID NO: 144; and a heavy chain CDR3 comprising the amino acid sequence depicted in SEQ ID NO: 117;

(xiii) a light chain CDR1 comprising the amino acid sequence depicted in SEQ ID NO: 140; a light chain CDR2 comprising the amino acid sequence depicted in SEQ ID NO:96; a light chain CDR3 comprising the amino acid sequence depicted in SEQ ID NO: 142; a heavy chain CDR1 comprising the amino acid sequence depicted in SEQ ID NO: 115; a heavy chain CDR2 comprising the amino acid sequence depicted in SEQ ID NO: 123; and a heavy chain CDR3 comprising the amino acid sequence depicted in SEQ ID NO: 117; (xiv) a light chain CDR1 comprising the amino acid sequence depicted in SEQ ID NO: 105; a light chain CDR2 comprising the amino acid sequence depicted in SEQ ID NO: 106; a light chain CDR3 comprising the amino acid sequence depicted in SEQ ID NO: 107; a heavy chain CDR1 comprising the amino acid sequence depicted in SEQ ID NO: 115; a heavy chain CDR2 comprising the amino acid sequence depicted in SEQ ID NO: 123; and a heavy chain CDR3 comprising the amino acid sequence depicted in SEQ ID NO:117; (xv) a light chain CDR1 comprising the amino acid sequence depicted in SEQ ID NO:92; a light chain CDR2 comprising the amino acid sequence depicted in SEQ ID NO:89; a light chain CDR3 comprising the amino acid sequence depicted in SEQ ID NO: 108; a heavy chain CDR1 comprising the amino acid sequence depicted in SEQ ID NO: 115; a heavy chain CDR2 comprising the amino acid sequence depicted in SEQ ID NO: 144; and a heavy chain CDR3 comprising the amino acid sequence depicted in SEQ ID NO:117; (xvi) a light chain CDR1 comprising the amino acid sequence depicted in SEQ ID NO:92; a light chain CDR2 comprising the amino acid sequence depicted in SEQ ID NO:89; a light chain CDR3 comprising the amino acid sequence depicted in SEQ ID NO:93; a heavy chain CDR1 comprising the amino acid sequence depicted in SEQ ID NO: 115; a heavy chain CDR2 comprising the amino acid sequence depicted in SEQ ID NO: 123; and a heavy chain CDR3 comprising the amino acid sequence depicted in SEQ ID NO:117; (xvii) a light chain CDR1 comprising the amino acid sequence depicted in SEQ ID NO:92; a light chain CDR2 comprising the amino acid sequence depicted in SEQ ID NO:89; a light chain CDR3 comprising the amino acid sequence depicted in SEQ ID NO:93; a heavy chain CDR1 comprising the amino acid sequence depicted in SEQ ID NO: 115; a heavy chain CDR2 comprising the amino acid sequence depicted in SEQ ID NO: 144; and a heavy chain CDR3 comprising the amino acid sequence depicted in SEQ ID NO: 117; (xviii) a light chain CDR1 comprising the amino acid sequence depicted in SEQ ID NO:84; a light chain CDR2 comprising the amino acid sequence depicted in SEQ ID NO:85; a light chain CDR3 comprising the amino acid sequence depicted in SEQ ID NO: 103; a heavy chain CDR1 comprising the amino acid sequence depicted in SEQ ID NO: 115; a heavy chain CDR2 comprising the amino acid sequence depicted in SEQ ID NO: 129; and a heavy chain CDR3 comprising the amino acid sequence depicted in SEQ ID NO: 117; (xix) a light chain CDR1 comprising the amino acid sequence depicted in SEQ ID NO:95; a light chain CDR2 comprising the amino acid sequence depicted in SEQ ID NO:96; a light chain CDR3 comprising the amino acid sequence depicted in SEQ ID NO:97; a heavy chain CDR1 comprising the amino acid sequence depicted in SEQ ID NO: 115; a heavy chain CDR2 comprising the amino acid sequence depicted in SEQ ID NO: 123; and a heavy chain CDR3 comprising the amino acid sequence depicted in SEQ ID NO: 117; (xx) a light chain CDR1 comprising the amino acid sequence depicted in SEQ ID NO:84; a light chain CDR2 comprising the amino acid sequence depicted in SEQ ID NO:85; a light chain CDR3 comprising the amino acid sequence depicted in SEQ ID NO:103; a heavy chain CDR1 comprising the amino acid sequence depicted in SEQ ID NO: 115; a heavy chain CDR2 comprising the amino acid sequence depicted in SEQ ID NO: 144; and a heavy chain CDR3 comprising the amino acid sequence depicted in SEQ ID NO: 117; or (xxi) a light chain CDR1 comprising the amino acid sequence depicted in SEQ ID NO:20; a light chain CDR2 comprising the amino acid sequence depicted in SEQ ID NO:21; a light chain CDR3 comprising the amino acid sequence depicted in SEQ ID NO: 113; a heavy chain CDR1 comprising the amino acid sequence depicted in SEQ ID NO: 131; a heavy chain CDR2 comprising the amino acid sequence depicted in SEQ ID NO: 132; and a heavy chain CDR3 comprising the amino acid sequence depicted in SEQ ID NO: 133.

In some embodiments, an antibody or antigen-binding fragment thereof comprises a paired light chain CDR set and heavy chain CDR set as set forth in Table 3. In some embodiments, an antibody or antigen-binding fragment thereof comprises a paired light chain CDR set and heavy chain CDR set as set forth in Table 2. For example, the disclosure features an antibody comprising: (i) a light chain CDR1 comprising the amino acid sequence depicted in SEQ ID NO:20; (ii) a light chain CDR2 comprising the amino acid sequence depicted in SEQ ID NO:21; and (iii) a light chain CDR3 comprising the amino acid sequence depicted in SEQ ID NO:22; (iv) a heavy chain CDR1 comprising the amino acid sequence depicted in SEQ ID NO:28; (v) a heavy chain CDR2 comprising the amino acid sequence depicted in SEQ ID NO:46; and (vi) a heavy chain CDR3 comprising the amino acid sequence depicted in SEQ ID NO:47.

In some embodiments, the antibody or antigen-binding fragment thereof comprises a light chain variable region set forth in Table 2, which light chain is paired with any one of the heavy chain variable regions set forth in Table 2. For example, the disclosure features an antibody (or an antigen-binding fragment thereof) comprising: (a) a light chain variable region having an amino acid sequence comprising the amino acid sequence depicted in SEQ ID NO:42 and (b) a heavy chain variable region having an amino acid sequence comprising the amino acid sequence depicted in SEQ ID NO:45.

In some embodiments, an antibody or antigen-binding fragment thereof described herein comprises: (i) a heavy chain variable region framework region 1 comprising the amino acid sequence depicted in SEQ ID NO:68 or SEQ ID NO:69; (ii) a heavy chain variable region framework region 2 comprising the amino acid sequence depicted in SEQ ID NO:70 or SEQ ID NO:71; and a heavy chain variable region framework region 3 comprising the amino acid sequence depicted in any one of SEQ ID NOs:72 to 74. In some embodiments, the antibody or antigen-binding fragment thereof comprises a heavy chain variable region framework region 4 comprising the amino acid sequence depicted in SEQ ID NO:75. In some embodiments, the antibody or antigen-binding fragment thereof comprises a heavy chain variable region comprising the amino acid sequence depicted in any one of SEQ ID NOs:76 to 80. The antibody heavy chain can comprise any of the heavy chain CDR sets described herein. The heavy chain variable region can be, in some embodiments, paired with the variable region polypeptide comprising the amino acid sequence depicted in SEQ ID NO: 16.

In some embodiments, an antibody or antigen-binding fragment thereof binds to a non-human C5a protein. For example, the antibody or antigen-binding fragment thereof can bind to mouse C5a and/or desarginated mouse C5a protein. In some embodiments, an isolated antibody or antigen-binding fragment thereof can bind to mouse C5a (and/or desarginated mouse C5a) and comprise: (i) a light chain CDR1 comprising the amino acid sequence depicted in SEQ ID NO:54; (ii) a light chain CDR2 comprising the amino acid sequence depicted in SEQ ID NO:55; (iii) a light chain CDR3 comprising the amino acid sequence depicted in SEQ ID NO:56; (iv) a heavy chain CDR1 comprising the amino acid sequence depicted in SEQ ID NO:62; (v) a heavy chain CDR2 comprising the amino acid sequence depicted in SEQ ID NO:63; and (vi) a heavy chain CDR3 comprising the amino acid sequence depicted in SEQ ID NO:64. In some embodiments, the anti-mouse C5a antibody can comprise a light chain polypeptide comprising the amino acid sequence depicted in SEQ ID NO:59; and a heavy chain polypeptide comprising the amino acid sequence depicted in SEQ ID NO:66.

In some embodiments, an isolated antibody or antigen-binding fragment thereof described herein inhibits the interaction between C5a and a C5a receptor. The C5a receptor can be, e.g., C5aR1 or C5L2.

In some embodiments, an isolated antibody or antigen-binding fragment thereof described herein does not substantially inhibit complement-mediated hemolysis of red blood cells in vitro and/or in vivo.

In some embodiments, an isolated antibody (and accordingly any antigen-binding fragment thereof) is a monoclonal antibody, a humanized antibody, or a fully-human antibody.

In some embodiments, an isolated antibody or antigen-binding fragment thereof described herein is selected from the group consisting of a recombinant antibody, a single chain antibody, a diabody, an intrabody, a chimerized or chimeric antibody, a deimmunized human antibody, an Fv fragment, an Fd fragment, an Fab fragment, an Fab' fragment, and an F(ab')$_2$ fragment.

In some embodiments, an isolated antibody or antigen-binding fragment thereof described herein is multispecific (e.g., bispecific) in that the antibody or fragment binds to at least two different epitopes. The two different epitopes can be, e.g., two different epitopes from the same protein (e.g., C5a) or the antibody can bind to a first epitope from a first protein (e.g., C5a) and a second epitope from a second protein.

In some embodiments, an isolated antibody or antigen-binding fragment thereof described herein comprises a heterologous moiety. The heterologous moiety can be, e.g., a sugar. For example, the antibody or antigen-binding fragment thereof can be glycosylated. The heterologous moiety can be, e.g., a detectable label such as, but not limited to, a fluorescent label, a luminescent label, a heavy metal label, a radioactive label, or an enzymatic label.

In some embodiments, an isolated anti-C5a antibody or antigen-binding fragment thereof described herein is modified with a moiety that improves the stabilization and/or retention of the antibody in circulation. For example, the modification can be PEGylation or hesylation. In another embodiment, the anti-C5a antibody can contain an altered constant region that has reduced (or no) effector function, as compared to the effector function of its corresponding unaltered constant region. In some embodiments, the anti-C5a antibody contains an altered constant region that has between about 0 to about 20% of the effector function of the unaltered constant region. Exemplary embodiments of such decreased-effector function antibodies are described herein.

In another aspect, the disclosure features an isolated antibody or antigen-binding fragment thereof that cross-blocks the binding of any one of the foregoing antibodies.

In yet another aspect, the disclosure features a pharmaceutical composition comprising one or more of any of the isolated antibodies or antigen-binding fragments thereof described herein and a pharmaceutically-acceptable carrier, diluent, and/or excipient.

In another aspect, the disclosure features: (i) a nucleic acid encoding one or more of any of the antibodies or antigen-binding fragments thereof described herein; (ii) a vector comprising the nucleic acid; (iii) an expression vector comprising the nucleic acid; and/or (iv) a cell comprising the vector or the expression vector. In another aspect, the disclosure features a method for producing a polypeptide (such as any of the antibodies or antigen-binding fragments thereof described herein). The method comprises culturing the aforementioned cell (comprising the expression vector) under conditions and for a time sufficient to allow expression by the cell of the antibody or antigen-binding fragment encoded by the nucleic acid in the vector. The method can also include isolated the antibody or antigen-binding fragment from the cell or from the medium in which the cell is cultured.

In another aspect, the disclosure features an isolated nucleic acid encoding any of the amino acid sequences described herein or a polypeptide having an amino acid sequence comprising, or consisting of, any of the amino acid sequences set forth herein. The nucleic acid can be included in a vector, e.g., an expression vector, and/or can be present in a cell.

In yet another aspect, the disclosure features a therapeutic kit comprising: (i) one or more of the isolated antibodies or antigen-binding fragments described herein (e.g., one or more of any of the humanized antibodies or antigen-binding fragments thereof described herein); and (ii) means for delivery of the antibody or antigen-binding fragment to a subject. The means can be suitable for, e.g., subcutaneous delivery, intraocular delivery, or intraarticular delivery of the antibody or antigen-binding fragment thereof to the subject. The means can be, e.g., a syringe, a double-barreled syringe, or two separate syringes incorporated for use in administering a therapeutic antibody or antigen-binding fragment thereof, while drawing off knee fluid (e.g., for analysis) in a push-pull fashion. In some embodiments, the means is for ocular delivery and comprises a trans-scleral patch or a contact lens, each of which comprises the antibody or antigen-binding fragment thereof. In some embodiments, the means is suitable for intrapulmonary delivery. For example, the means can be an inhaler or a nebulizer. In some embodiments, the means is a pre-filled syringe such as a pen device. The pre-filled syringe can contain, e.g., at least one pharmaceutical unit dosage form of one or more of the antibodies or antigen-binding fragments thereof provided herein.

In some embodiments, the therapeutic kits described herein can contain at least one additional active agent for use in treating a complement-associated disorder in a subject. The additional active agent can be, e.g., any of the additional agents described herein.

In yet another aspect, the disclosure features a method for treating or preventing a complement-associated disorder. The method includes administering to a human in need thereof a therapeutic antibody or antigen-binding fragment thereof described herein in an amount sufficient to treat a complement-associated disorder afflicting the human. The method can also include identifying the subject as having a complement-associated disorder. The complement-associated disorder can be, e.g., a complement-associated inflammatory disorder, atypical hemolytic uremic syndrome, age-related macular degeneration, rheumatoid arthritis, sepsis, or antiphospholipid syndrome. In some embodiments, the complement-associated disorder is a complement-associated pulmonary disorder. For example, the complement-associated pulmonary disorder can be, e.g., asthma or chronic obstructive pulmonary disease. Other complement-associated disorders amenable to treatment or prevention as set forth in the method are described herein. The mode of administration, which can vary depending on the type of complement-associated disorder to be treated, can be, e.g., intravenous administration, intrapulmonary administration, intraocular administration, subcutaneous administration, or intraarticular administration.

In some embodiments, the antibody or antigen-binding fragment thereof is administered to the human in an amount and with a frequency sufficient to maintain a reduced level of systemic C5a activity for the duration of the treatment. In some embodiments, the methods can include after the administering, monitoring the human for an improvement in one or more symptoms of the complement-associated disorder.

In some embodiments, the methods can include administering to the human one or more additional therapeutic agents.

In yet another aspect, the disclosure features an article of manufacture, which comprises: (i) a container with a label and (ii) a composition comprising an antibody or antigen-binding fragment thereof described herein. The label can indicate that the composition is to be administered to a human having, suspected of having, or at risk for developing, a complement-associated disorder. The article of manufacture can also include one or more additional active agents.

As used throughout the present disclosure, the term "antibody" refers to a whole or intact antibody (e.g., IgM, IgG, IgA, IgD, or IgE) molecule that is generated by any one of a variety of methods that are known in the art and described herein. The term "antibody" includes a polyclonal antibody, a monoclonal antibody, a chimerized or chimeric antibody, a humanized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to an antigen (e.g., an epitope present in C5a, but not in the alpha chain of uncleaved, native C5 protein), e.g., a single chain antibody (scFv), an Fd fragment, an Fab fragment, an Fab' fragment, or an F(ab')$_2$ fragment. An scFv is a single polypeptide chain that includes both the heavy and light chain variable regions of the antibody from which the scFv is derived. In addition, diabodies (Poljak (1994) *Structure* 2(12): 1121-1123; Hudson et al. (1999) *J Immunol Methods* 23(1-2):177-189, the disclosures of both of which are incorporated herein by reference in their entirety), minibodies, triabodies (Schoonooghe et al. (2009) *BMC Biotechnol* 9:70), domain antibodies (also known as "heavy chain immunoglobulins" or camelids; Holt et al. (2003) *Trends Biotechnol* 21(11):484-490); and intrabodies (Huston et al. (2001) *Hum Antibodies* 10(3-4): 127-142; Wheeler et al. (2003) *Mol Ther* 8(3):355-366; Stocks (2004) *Drug Discov Today* 9(22): 960-966, the disclosures of each of which are incorporated herein by reference in their entirety) are included in the definition of antibody fragments and can be incorporated into the compositions, and used in the methods, described herein.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating complement-associated disorders in a subject, will be apparent from the following description, the examples, and from the claims.

Figure 6:
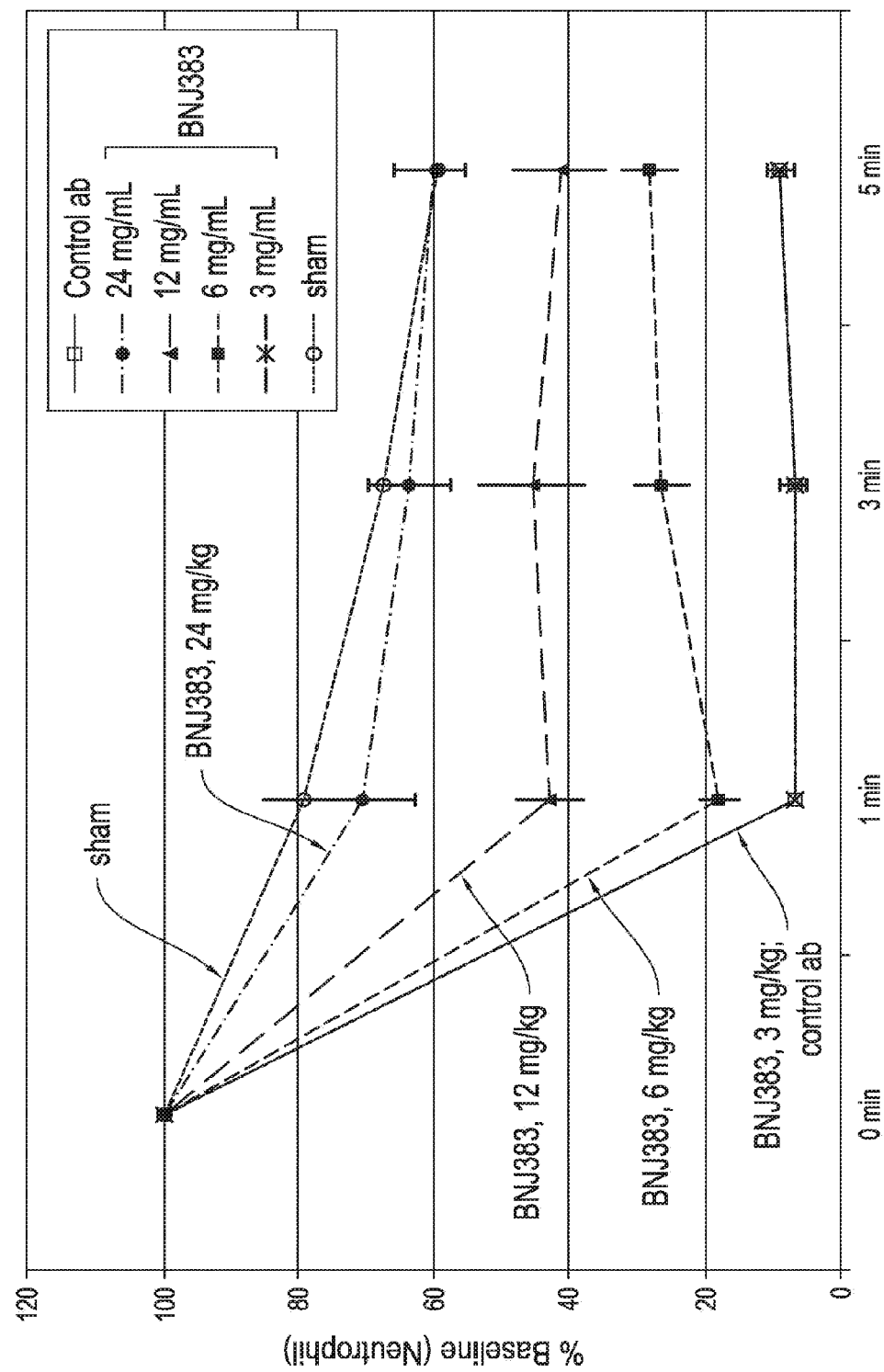

FIG. 6 is a line graph depicting the percentage of circulating neutrophils in the blood of mice following administration of hC5a to the mice. On the Y-axis, neutrophil counts are expressed as a percentage of "baseline," which is the neutrophil count at time 0 (or 100% neutrophils). The X-axis represents time in minutes. Mouse cohorts were intravenously administered a control antibody [anti-anthrax protective antigen 63, IgG2/G4 isotype]("control"; five mice) or the anti-human C5a antibody BNJ383 at one of the following doses: 24 mg/kg (five mice); 12 mg/kg (five mice); 6 mg/kg (five mice); and 3 mg/kg (five mice) and then later were administrated hC5a. See Example 13. Six mice, "sham," were not administered human C5a.

Figure 7:
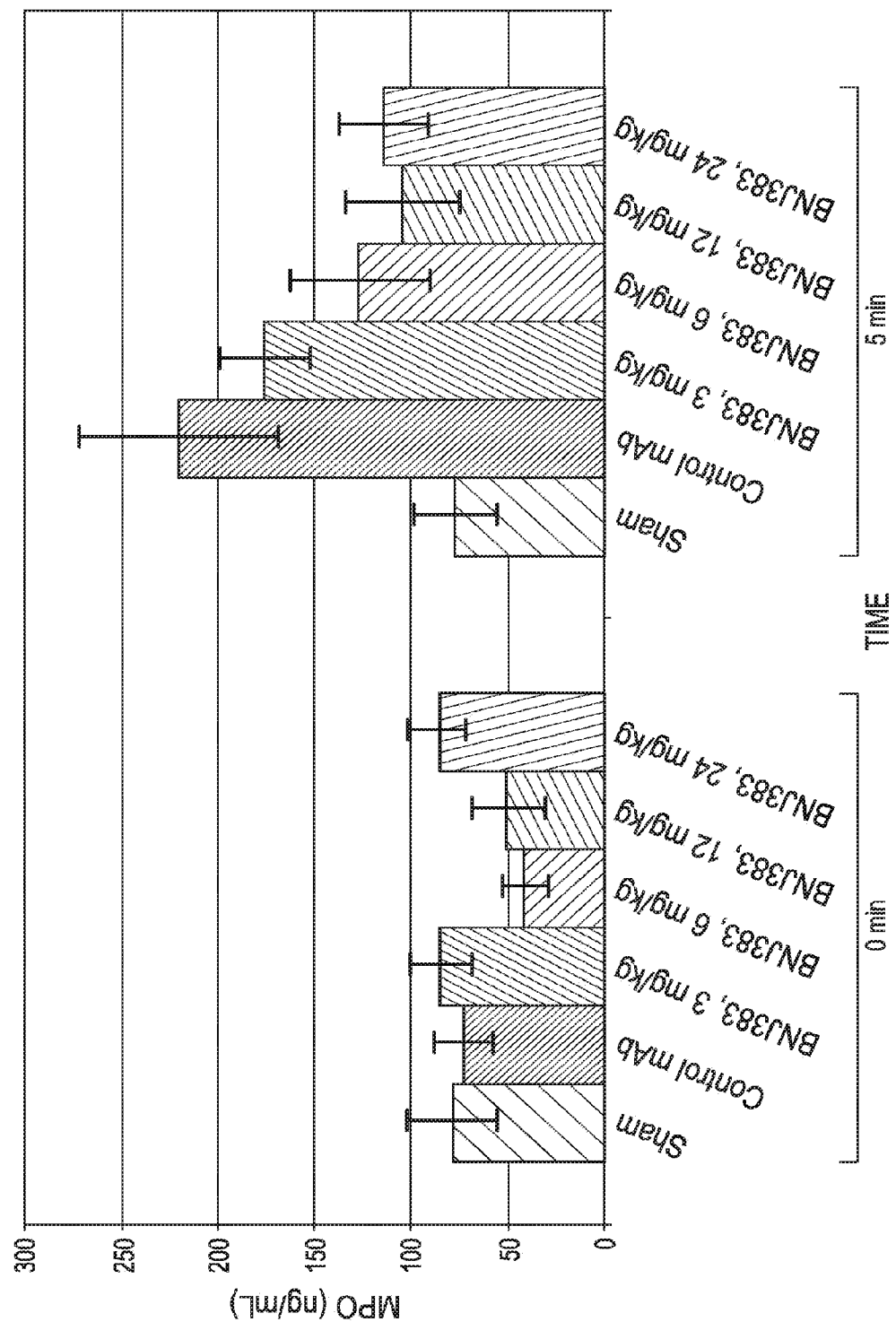

FIG. 7 is a bar graph depicting the myeloperoxidase (MPO) level in the plasma of mice before and following administration of human C5a to the mice. The Y-axis represents the concentration (ng/mL) of MPO in mouse plasma. The X-axis represents time in minutes. Mouse cohorts were intravenously administered a control antibody [anti-anthrax protective antigen 63, IgG2/G4 isotype]("control"; eight mice) or the anti-human C5a antibody BNJ383 at one of the following doses: 24 mg/kg (five mice); 12 mg/kg (five mice); 6 mg/kg (five mice); and 3 mg/kg (five mice) and then later were administrated hC5a. Four mice, "sham," were not administered human C5a.

Figure 8:
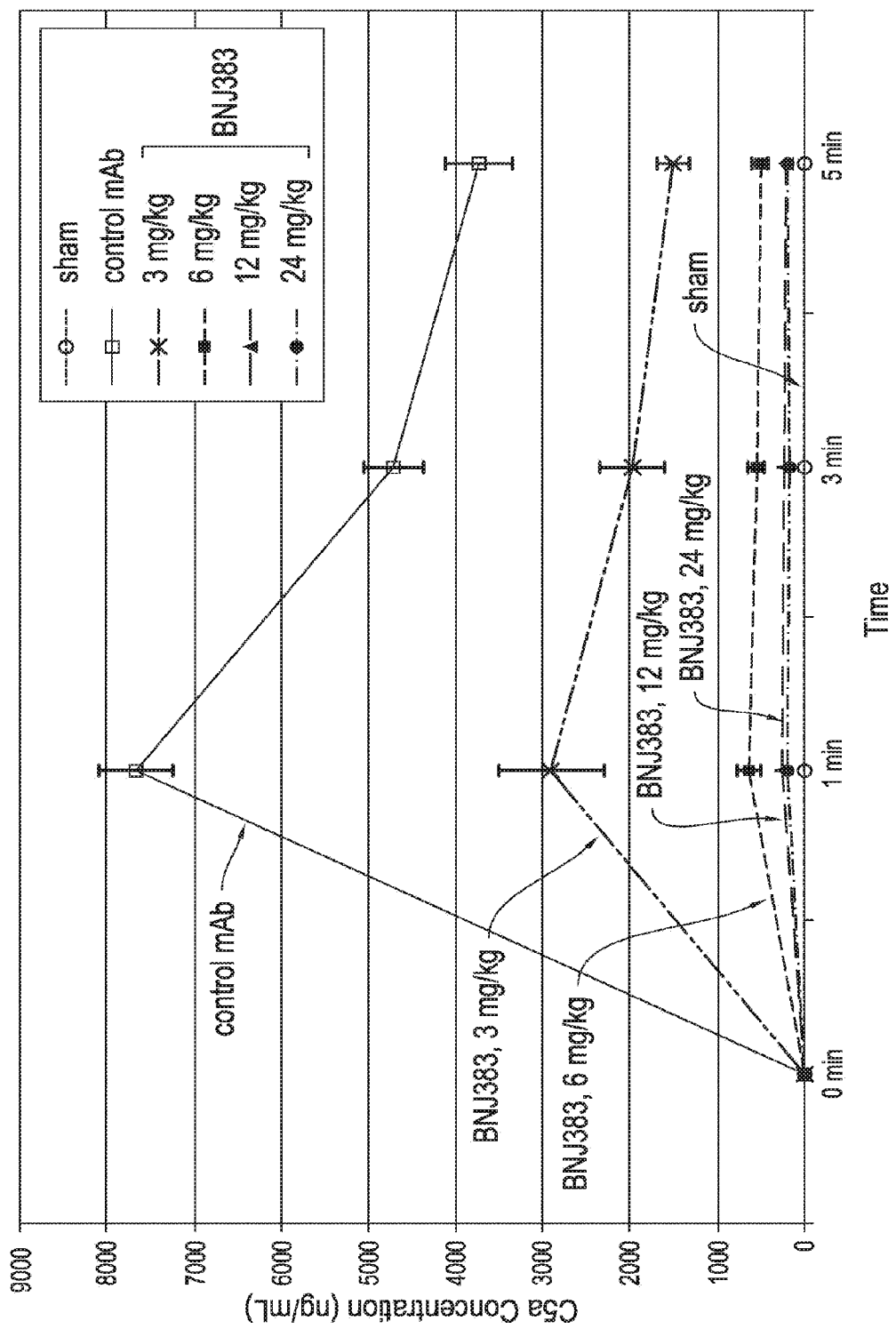

FIG. 8 is a line graph depicting the change in human C5a level in plasma of mice (administered human C5a) in the presence or absence of different concentrations of an anti-hC5a antibody (BNJ383). The Y-axis represents the concentration (ng/mL) of hC5a in mouse plasma. The X-axis represents time in minutes. Mouse cohorts were intravenously administered a control antibody [anti-anthrax protective antigen 63, IgG2/G4 isotype]("control"; six mice) or the anti-human C5a antibody BNJ383 at one of the following doses: 24 mg/kg (three mice); 12 mg/kg (three mice); 6 mg/kg (three mice); and 3 mg/kg (three mice) and then later were administrated hC5a. Four mice, "sham," were not administered human C5a.

Figure 9:
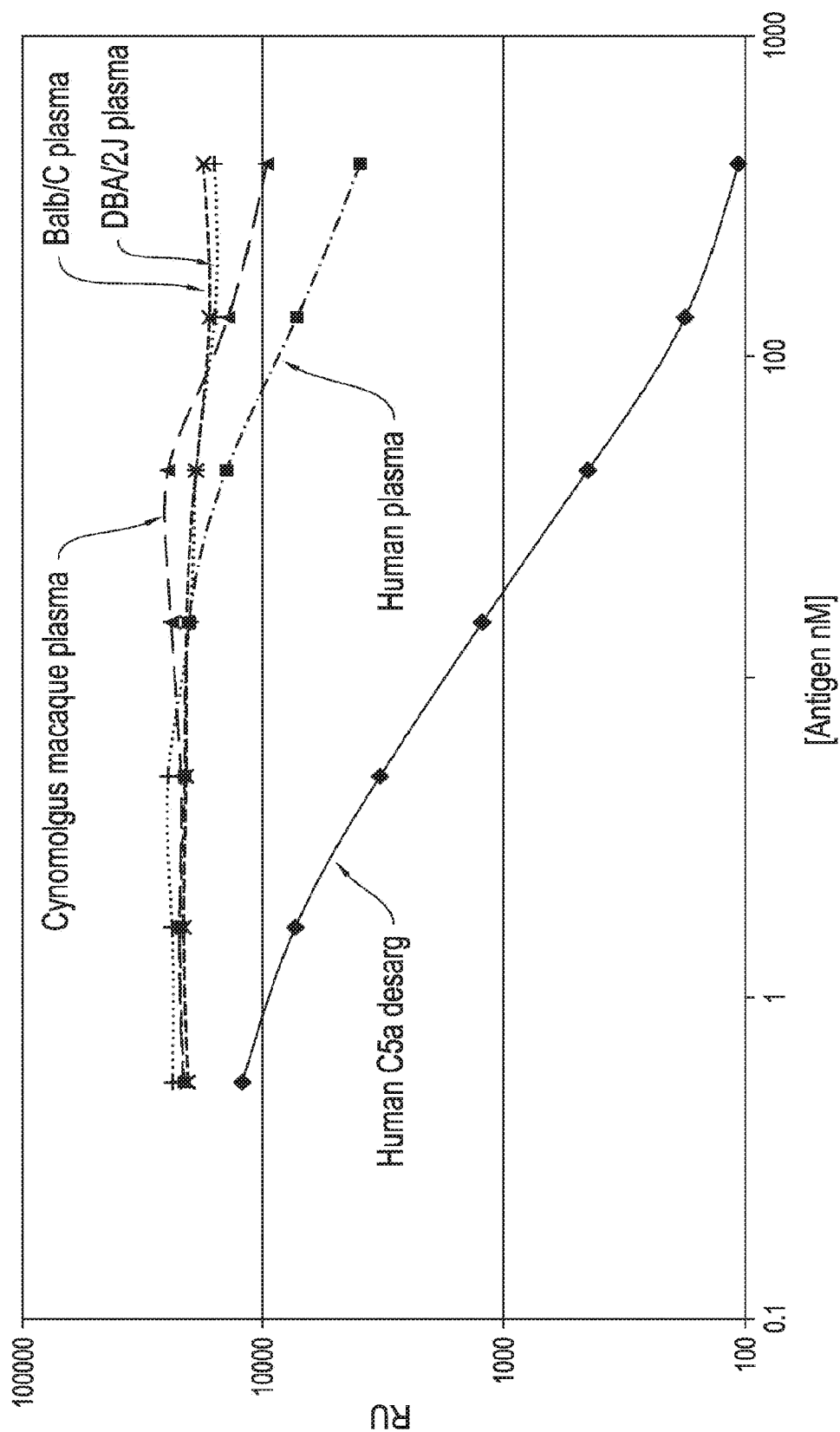

FIG. 9 is a line graph depicting the competition for binding to human C5a in vitro. 250 pM of ruthenium-labeled anti-C5a antibody (BNJ383) was incubated with 1 nM biotinylated hC5a, along with various concentrations (e.g., 400, 133, 44.4, 14.8, 4.9, 1.6, and 0.5 nM) of one of the following: (a) human C5a desarg protein in phosphate-buffered saline, (b) human plasma, (c) cynomolgus macaque plasma, (d) Balb/C (mouse) plasma, or (e) DBA/2J (mouse) plasma. With respect to the plasma components (b), (c), (d), and (e), the concentration refers to the approximate final concentration of C5 antigen in the incubation mixture. The Y-axis represents arbitrary fluorescence units as a function of the amount of ruthenium-labeled anti-C5a antibody detected. The X-axis represents concentration (nM) of the antigen competitor.

Figure 10:
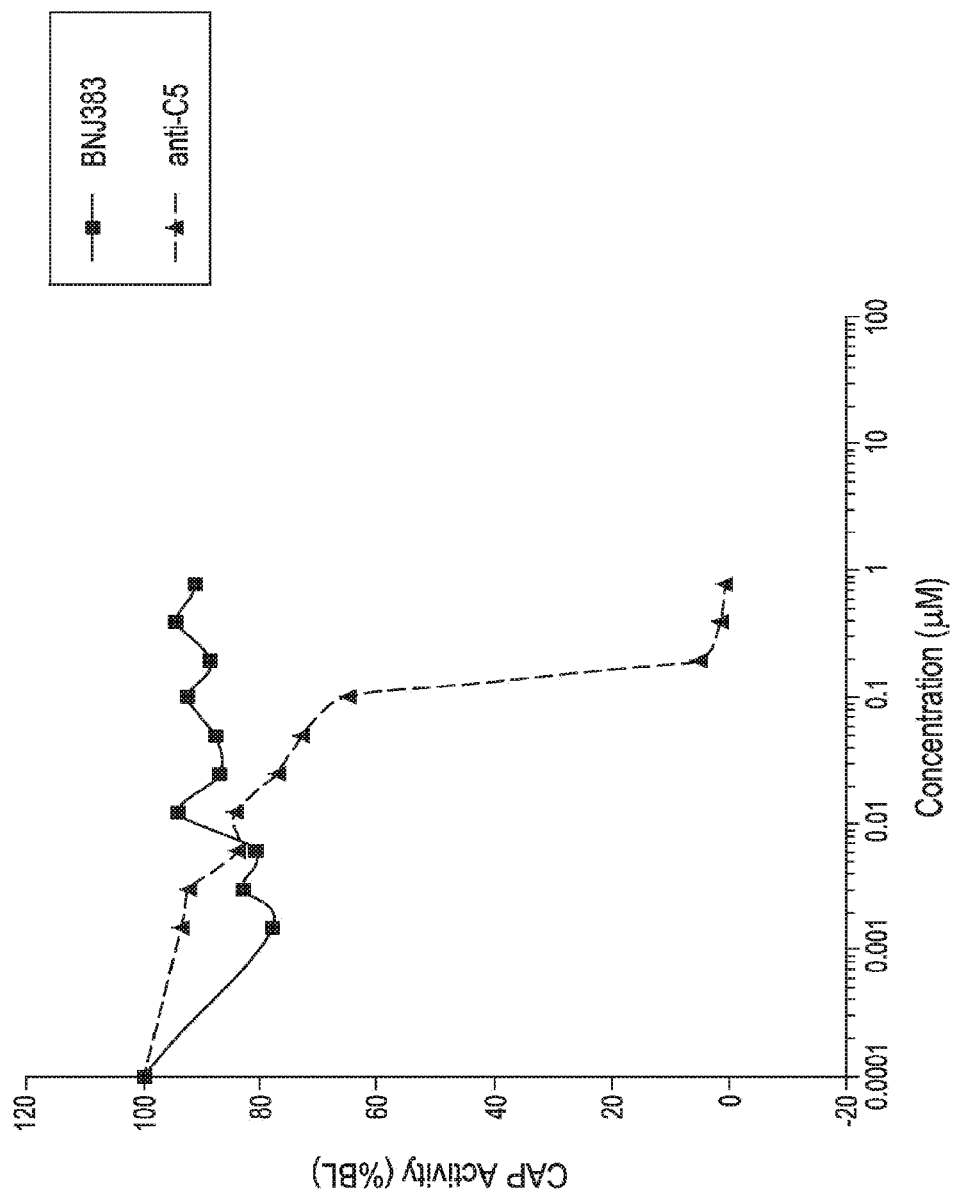

FIG. 10 is a line graph depicting the effect of several complement inhibitory proteins on the alternative pathway (AP) of complement. The Y-axis represents the percentage of AP complement activity as compared to baseline (BL; the level of activity in the absence of a complement inhibitor). The X-axis represents the concentration of a given complement inhibitor (µM). The effects of the anti-hC5a antibody, BNJ383, along with an anti-C5 antibody on AP activity were each evaluated.

Figure 11:
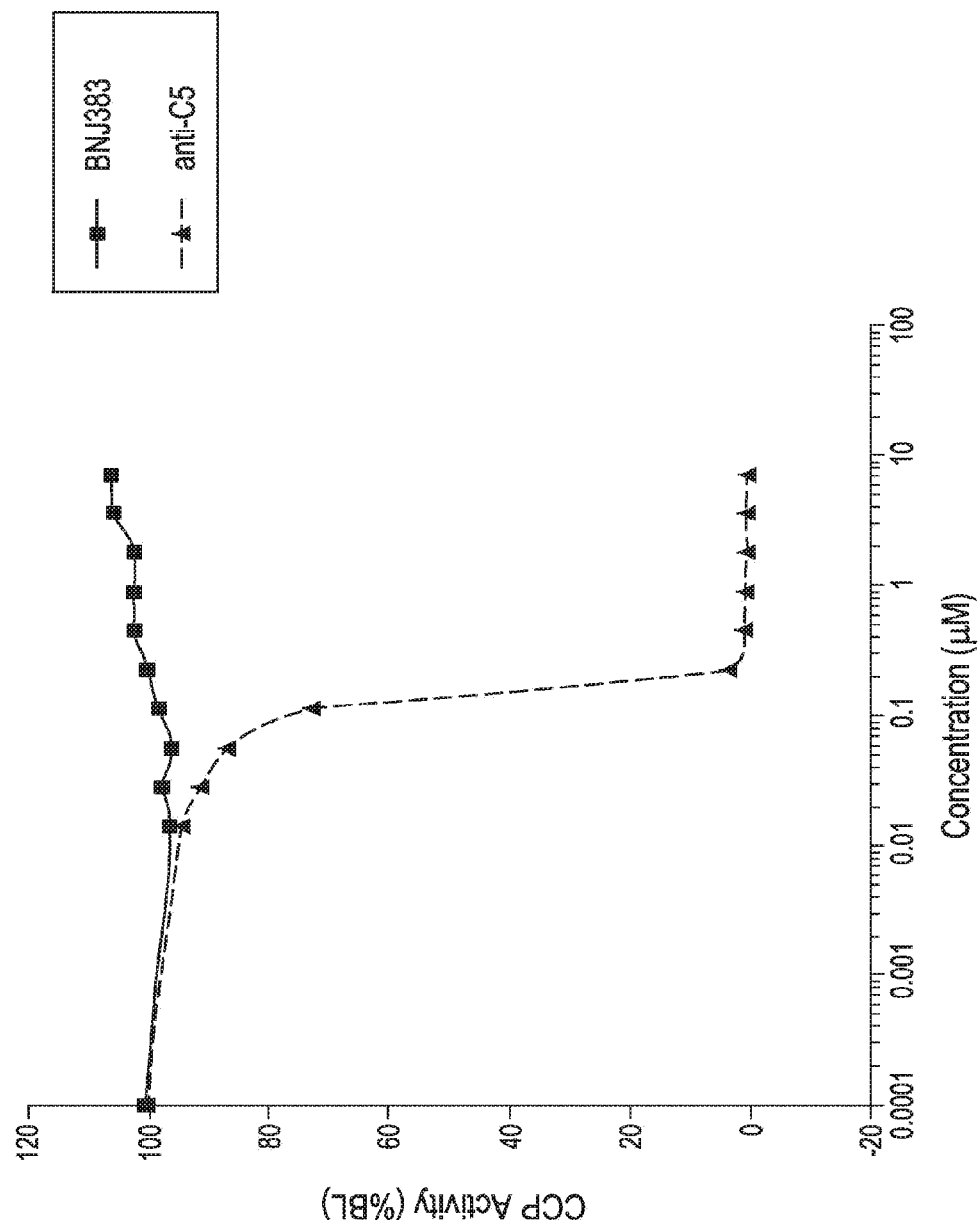

FIG. 11 is a line graph depicting the effect of several complement inhibitory proteins on the classical pathway (CP) of complement. The Y-axis represents the percentage of CP complement activity as compared to baseline (BL; the level of activity in the absence of a complement inhibitor). The X-axis represents the concentration of a given complement inhibitor (µM). The effects of the anti-hC5a antibody, BNJ383, along with an anti-C5 antibody on CP activity were each evaluated.

FIGS. 12A, 12B, 12C, and 12D are a series of chromatographs depicting the retention times of the anti-C5a antibody (BNJ383) and an anti-hC5 antibody in the presence or absence of hC5 protein. For all of the panels, the X-axis represents retention time in minutes and the Y-axis represents the absorbance units at 214 nm wavelength. In each panel, the inlayed subpanel depicts an enhanced view of the featured peaks.

Figure 12A:
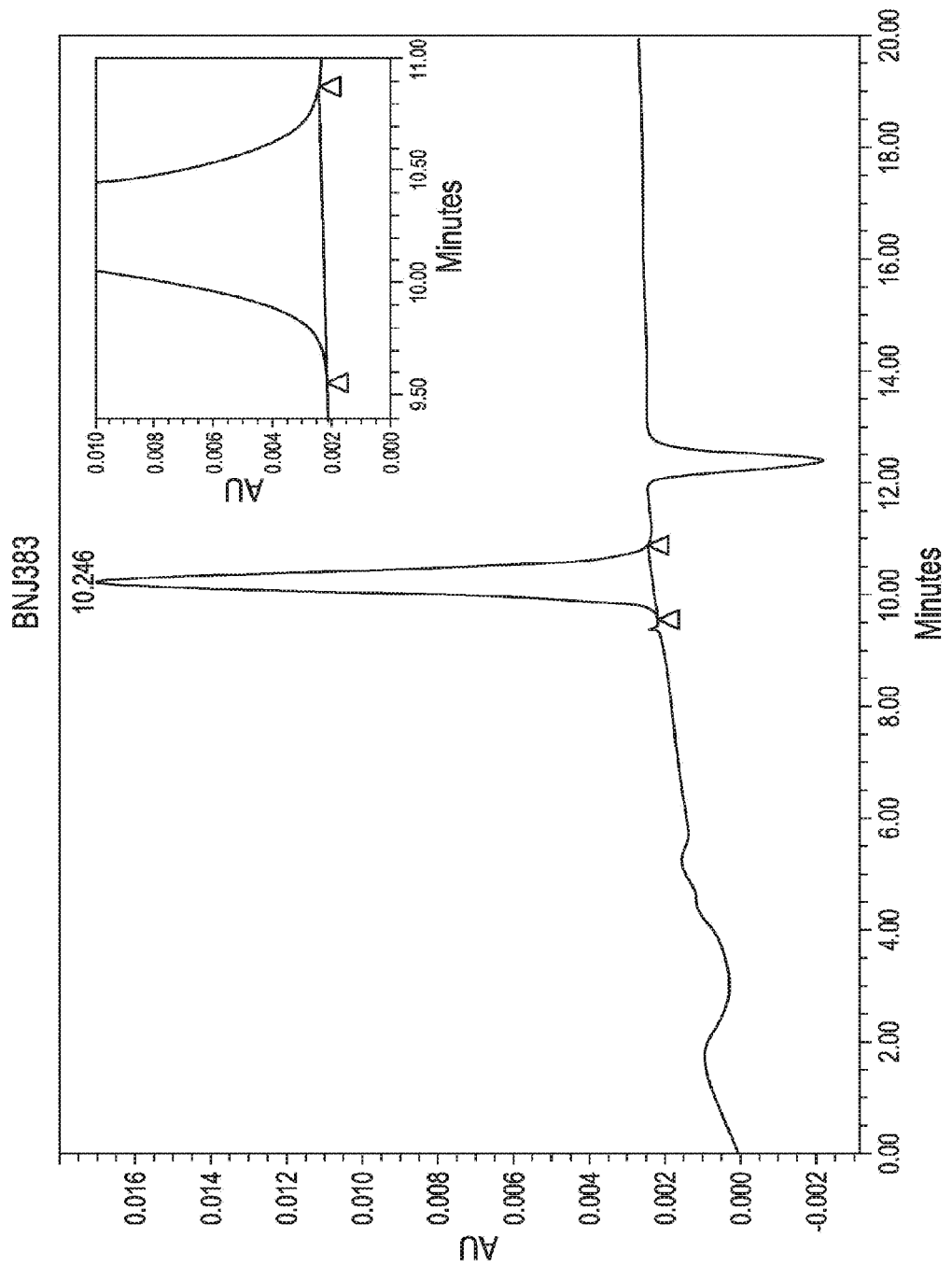

FIG. 12A depicts the retention time for BNJ383 in the absence of hC5 protein.

Figure 12B:
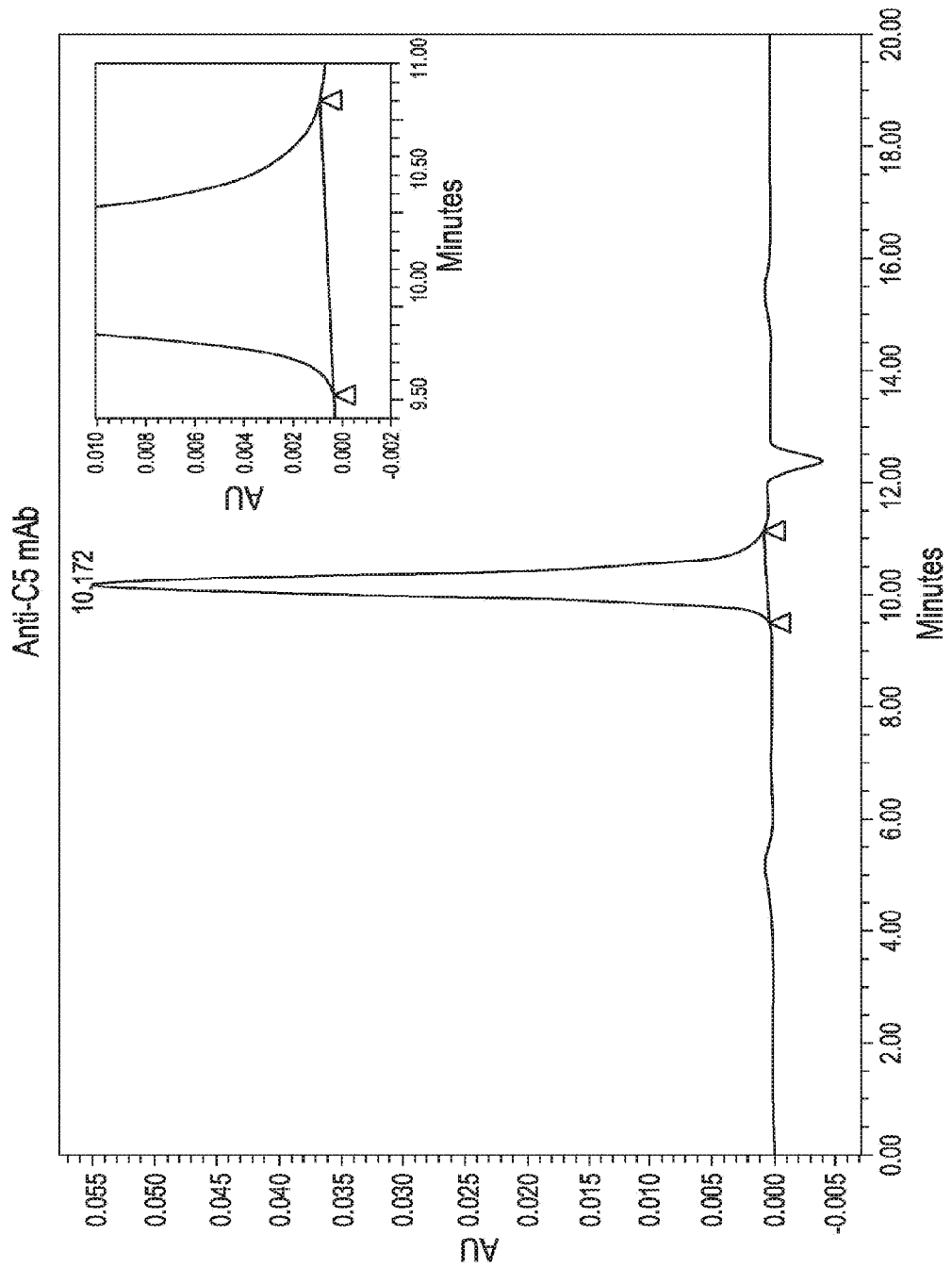

FIG. 12B depicts the retention time for the anti-C5 antibody in the absence of hC5 protein.

Figure 12C:
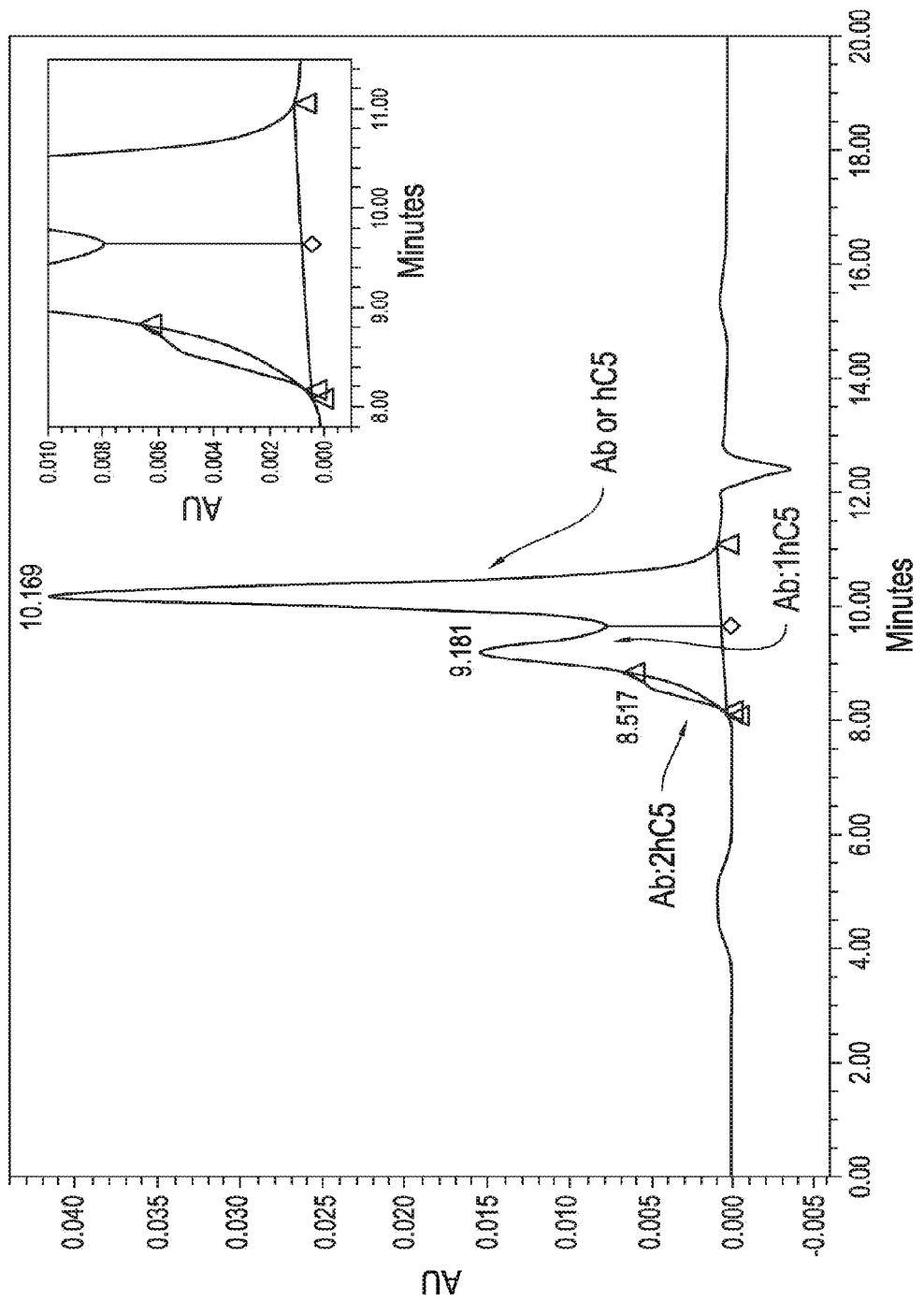

FIG. 12C depicts the retention time for BNJ383 in the presence of hC5 (2.1-fold molar excess of hC5 over BNJ383). From right to left, the enumerated peaks represent: (a) uncomplexed BNJ383 or hC5; (b) BNJ383 with one antigen-binding site bound to uncleaved hC5; and (c) a minor fraction consistent with dual occupancy of BNJ383 with uncleaved hC5.

Figure 12D:
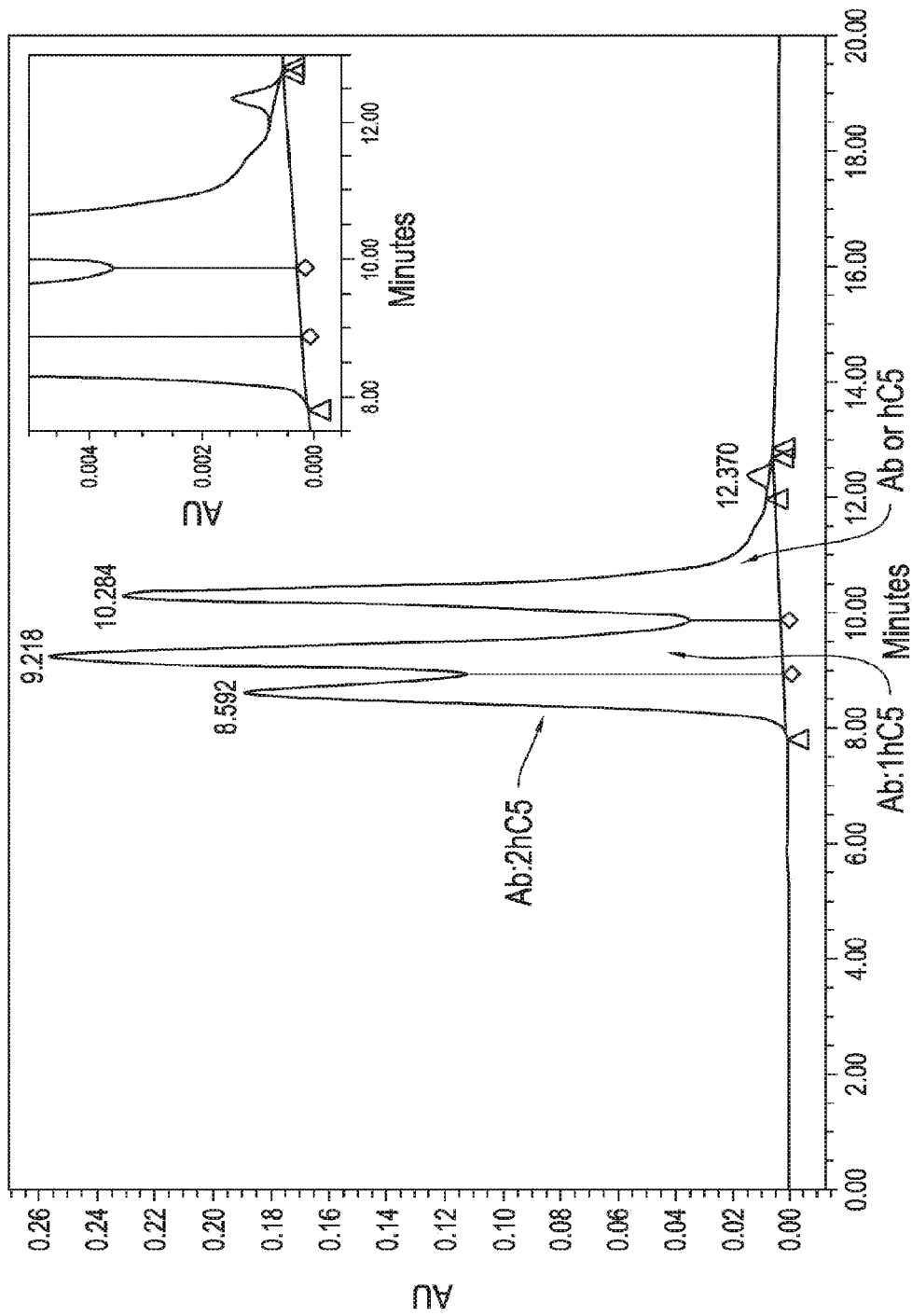

FIG. 12D depicts the retention time for the anti-C5 antibody in the presence of an equimolar amount of hC5. From right to left, the enumerated peaks represent: (a) uncomplexed anti-C5 antibody or hC5; (b) the anti-C5 antibody with one antigen-binding site bound to uncleaved hC5; and (c) the anti-C5 antibody bound to two uncleaved C5 molecules.

Figure 13:
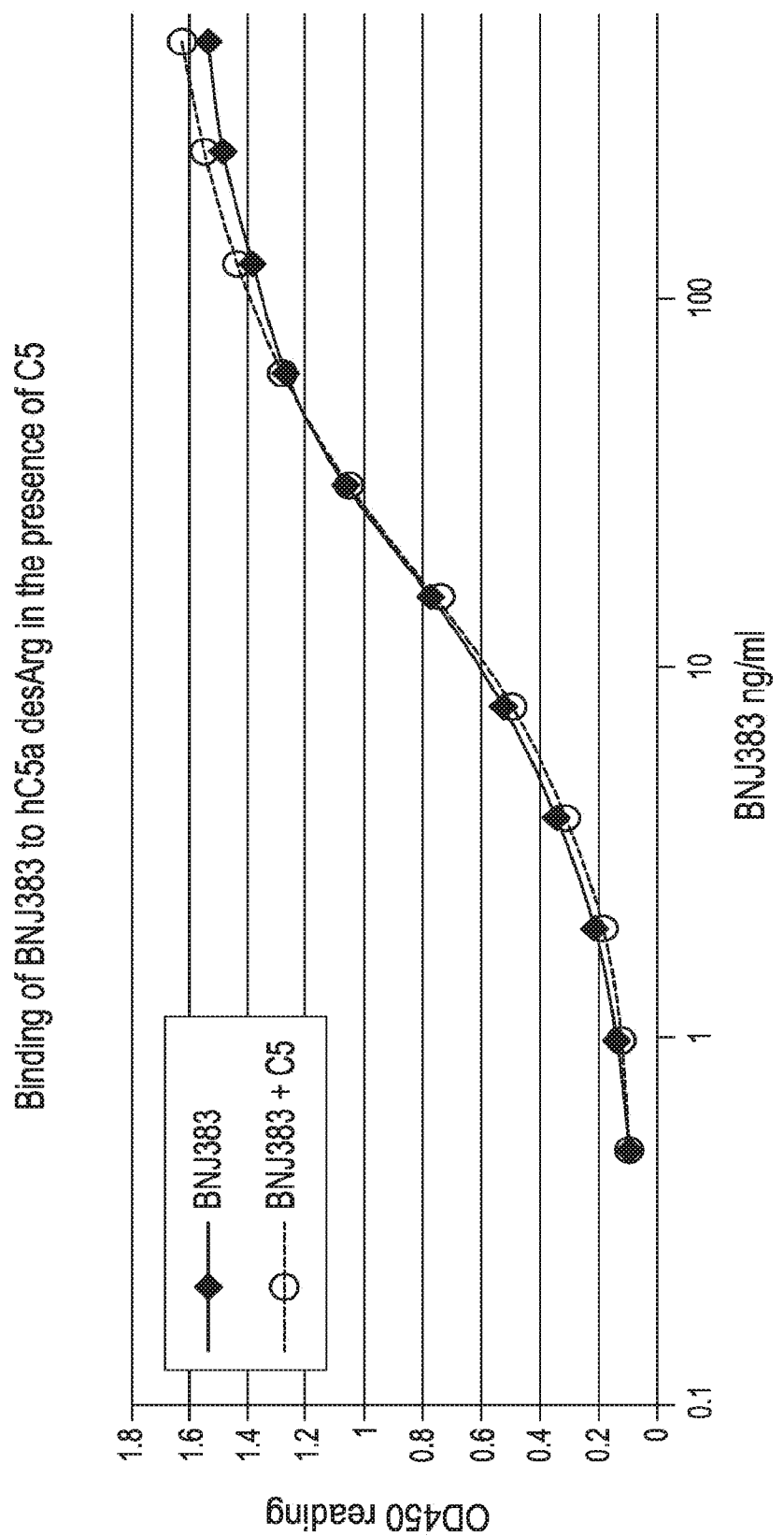

FIG. 13 is a line graph depicting the binding of the anti-C5a antibody BNJ383 to hC5a desarg in the presence of hC5 using an ELISA. The X-axis represents the concentration (ng/mL) of the antibody. The Y-axis represents the optical density at 450 nm wavelength.

Figure 14:
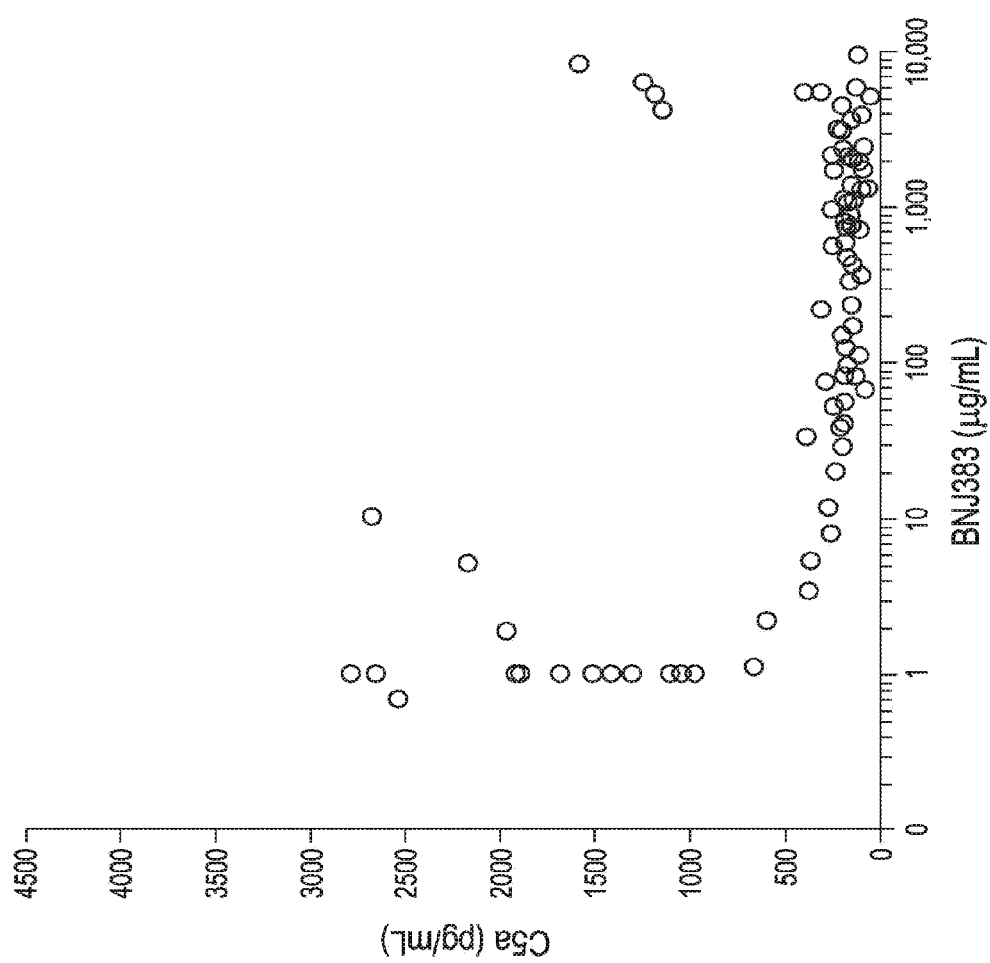

FIG. 14 is a scatter plot depicting the concentration of free C5a/C5a desarg present in the plasma of cynomolgus macaques as a function of the plasma concentration of anti-C5a antibody (BNJ383). The Y-axis depicts the concentration (pg/mL) of C5a/C5a desarg detected in plasma samples from cynomolgus macaques at time points ranging from 1 day to 30 days following a single dose intravenous administration of BNJ383 at 1 mg/kg, 10 mg/kg, 100 mg/kg, 250 mg/kg, or 400 mg/kg body weight of the animals. The X-axis represents the concentration of the BNJ383 (µg/mL) in each of the samples.

FIG. 15A is a scatter plot depicting the percentage of hemolytic activity in serum samples relative to baseline values (Y-axis) initiated via the classical pathway as a function of the concentration of anti-C5a antibody (BNJ383) in circulation (X-axis).

Figure 15B:
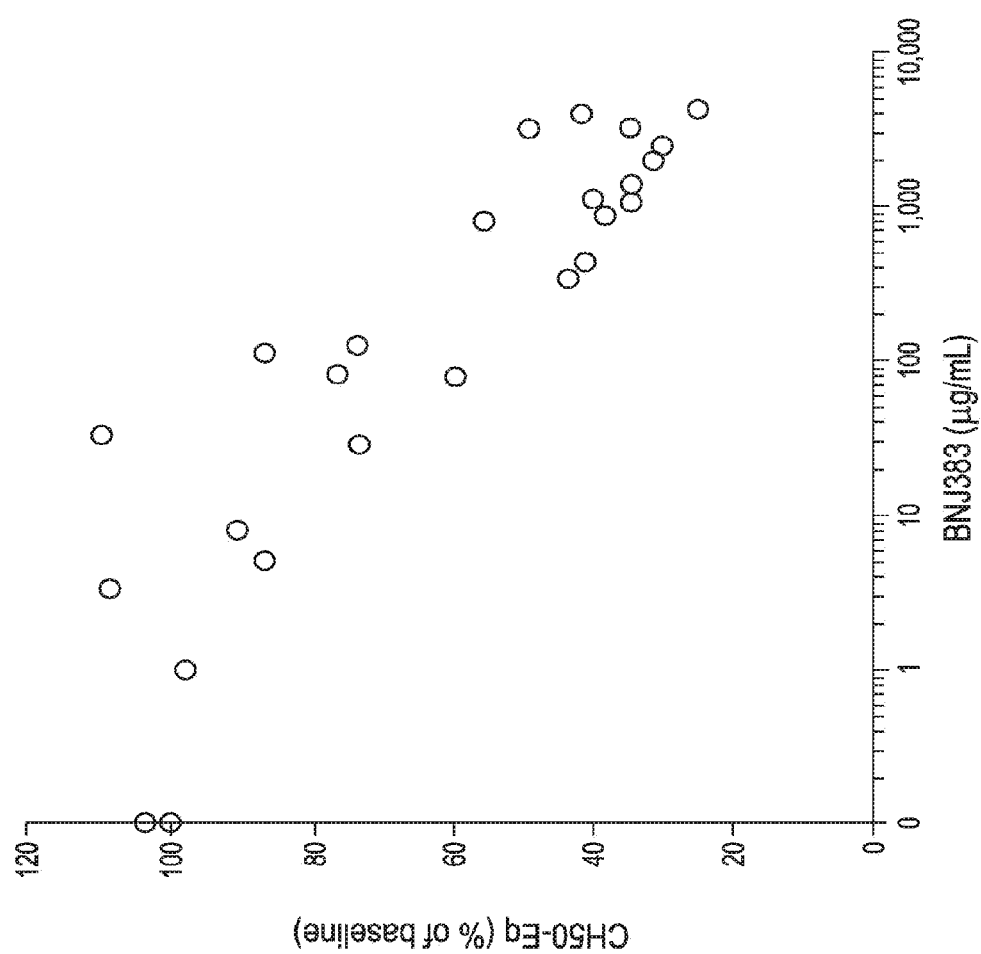

FIG. 15B is a scatter plot depicting the percentage of terminal complement complex formation initiated via the classical pathway in serum samples measured by a CH50eq assay relative to baseline values (Y-axis) as a function of the concentration of anti-C5a antibody (BNJ383) in circulation (X-axis).

Figure 15C:
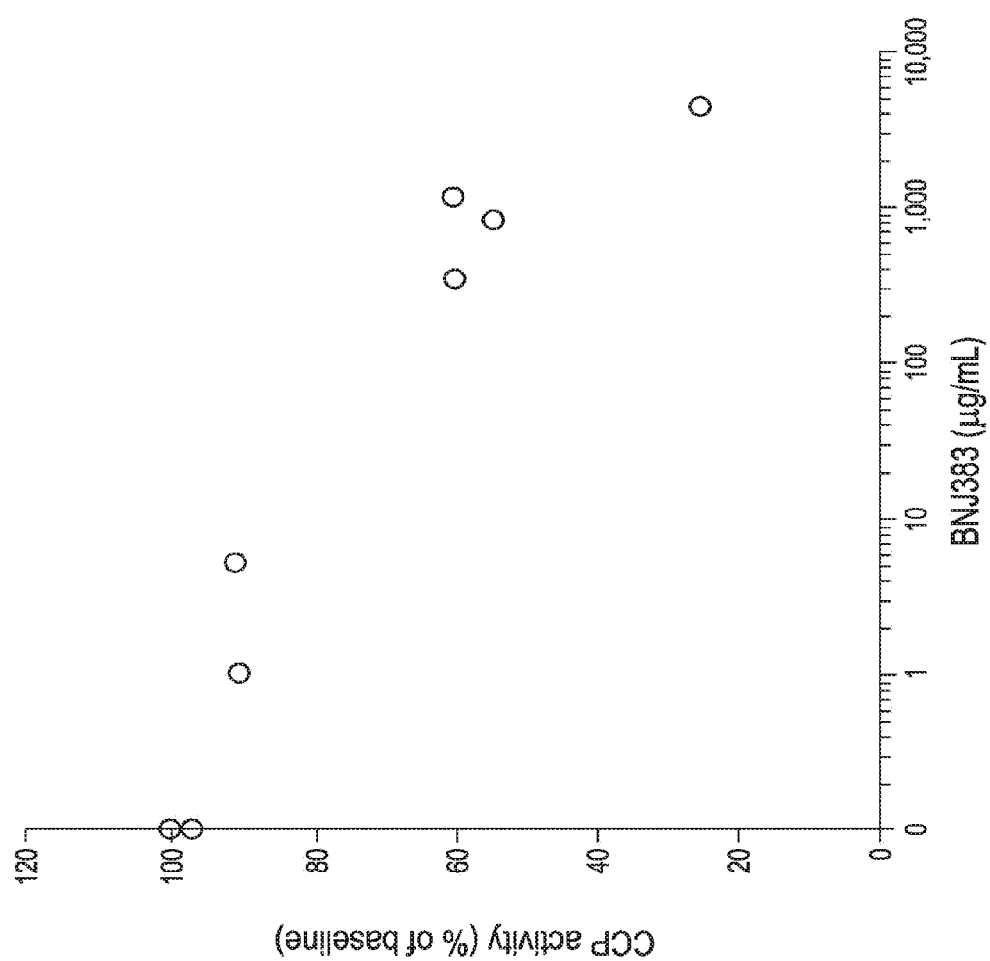

FIG. 15C is a scatter plot depicting the percentage of terminal complement complex formation initiated via the classical pathway in serum samples measured by a CCP assay relative to baseline values (Y-axis) as a function of the concentration of anti-C5a antibody (BNJ383) in circulation (X-axis).

DETAILED DESCRIPTION

The present disclosure provides antibodies and antigen-binding fragments thereof that bind to free C5a (e.g., free human C5a), compositions containing the antibodies or their fragments, and methods for using any of the foregoing to treat or prevent complement-associated disorders such as, but not limited to, aHUS, macular degeneration (e.g., AMD), RA, sepsis, antiphospholipid syndrome, burn (e.g., severe burn), Goodpasture's syndrome, lupus nephritis, or a complement-associated pulmonary disorder such as asthma or chronic obstructive pulmonary disease (COPD). The disclosure also provides anti-C5a antibodies (and fragments thereof) that are cross-reactive between free C5a from human and free C5a from a non-human mammalian species such as a non-human primate (e.g., cynomolgus macaque or rhesus macaque). While in no way intended to be limiting, exemplary antibodies (and antigen-binding fragments), compositions (e.g., pharmaceutical compositions and formulations), and methods for using the compositions are elaborated on below and exemplified in the working Examples.

Anti-C5a Antibodies and Antigen-Binding Fragments Thereof

The disclosure provides antibodies that bind to complement component C5a. As discussed above, the proform of C5, a 1676 amino acid residue precursor protein, is processed by a series of proteolytic cleavage events. The first 18 peptides (numbered −18 to −1) constitute a signal peptide that is cleaved from the precursor protein. The remaining 1658 amino acid protein is cleaved in two places to form the alpha and beta chains. The first cleavage event occurs between amino acid residues 655 and 656. The second cleavage occurs between amino acid residues 659 and 660. The two cleavage events result in the formation of three distinct polypeptide fragments: (i) a fragment comprising amino acids 1 to 655, which is referred to as the beta chain; (ii) a fragment comprising amino acids 660 to 1658, which is referred to as the alpha chain; and (iii) a tetrapeptide fragment consisting of amino acids 656 to 659. The alpha chain and the beta chain polypeptide fragments are connected to each other via disulfide bond and constitute the mature C5 protein. The CP or AP C5 convertase activates mature C5 by cleaving the alpha chain between residues 733 and 734, which results in the liberation of C5a fragment (amino acids 660 to 733). The remaining portion of mature C5 is fragment C5b, which contains the residues 734 to 1658 of the alpha chain disulfide bonded to the beta chain.

In vivo, C5a is rapidly metabolized by a serum enzyme, carboxypeptidase B, to a 73 amino acid form termed "C5a desarg," which has lost the carboxyterminal arginine residue. Accordingly, in some embodiments, an antibody that binds to free C5a also binds to desarginated C5a. In some embodiments, an antibody that binds to C5a does not bind to desarginated C5a.

In some embodiments, the anti-C5a antibody binds to a neoepitope present in C5a, i.e., an epitope that becomes exposed upon the liberation of C5a from the alpha chain fragment of mature C5. That is, in some embodiments, an anti-C5a antibody described herein binds to C5a and/or C5a desarg, but not to uncleaved, native (fully-folded) C5.

As described above, in some embodiments, the anti-C5a antibody or antigen-binding fragment thereof can bind to a subpopulation of uncleaved, processed C5 (e.g., plasma C5) constituting less than 10 (e.g., less than 9.5, 9, 8.5, 8, 7.5, 7, 6.5, 6, 5.5, 5, 4.5, 4, 3.5, 3, 2.5, 2, 1.5, 1, 0.5, 0.4, 0.3, 0.2, or less than 0.1) % of the total population of full length C5 in a sample (e.g., a blood or plasma sample or a sample comprising recombinant full length C5), which subpopulation is in whole, or in part, denatured such that an otherwise occluded C5a neoepitope is exposed. Thus, an anti-C5a antibody or antigen-binding fragment thereof described herein can, in some embodiments, bind to free C5a, but not to C5 of the 90% or greater uncleaved, native C5 population. In some embodiments, the partially or fully denatured subpopulation is inactive or has reduced activity (e.g., less than 90, 85, 80, 75, 70, 65, 60, 55, 50, 45, 40, 35, 30, 25, 20, 15, 10, 5% of the activity of fully-functional, full-length C5 protein) in any number of suitable assays useful for testing C5 activity, e.g., a hemolytic assay or a CH50eq assay. Suitable methods for testing the activity of the minor subpopulation to which an anti-C5a antibody described herein may, in some embodiments, bind are known in the art and described herein.

In some embodiments, the anti-C5a antibody binds to a mammalian (e.g., human) C5a protein. For example, the anti-C5a antibody can bind to a human C5a protein having the following amino acid sequence: TLQKKIEE-IAAKYKHSVVKKCCYDGACVNNDETCEQRAARIS-LGPRCIKAFTE CCVVASQLRANISHKDMQLGR (SEQ ID NO:1). In some embodiments, an anti-C5a antibody can bind to a desarginated human C5a protein having the following amino acid sequence: TLQKKIEEIAAKYKHSV-VKKCCYDGACVNNDETCEQRAARISLGPRCIKAFTE CCVVASQLRANISHKDMQLG (SEQ ID NO:2). An anti-C5a antibody described herein can bind to both full-length human C5a and desarginated human C5a.

In some embodiments, the antibody can bind to human C5a at an epitope within or overlapping with a structural fragment of the protein having the amino acid sequence: TLQKKIEEIAAKYK (SEQ ID NO:3); HSVVKKCCYD-GAC (SEQ ID NO:4); VNNDE (SEQ ID NO:5); TCEQRAAR (SEQ ID NO:6); ISLG (SEQ ID NO:7); PRCIKAFTECCVVASQLRANIS (SEQ ID NO:8); HKD-MQLG (SEQ ID NO:9); or HKDMQLGR (SEQ ID NO: 10). See, e.g., Cook et al. (2010) *Acta Cryst* D66:190-197. In some embodiments, the antibody can bind to C5a at an epitope within or overlapping with the amino acid sequence of a peptide fragment of C5a comprising at least two of the paired cysteine residues. For example, an anti-C5a antibody can bind to fragment comprising, or consisting of, the amino acid sequence: CCYDGACVNNDETC (SEQ ID NO: 11); CYDGACVNNDETCEQRAARISLGPRCIKAFTEC (SEQ ID NO: 12; and CEQRAARISLGPRCIKAFTECC (SEQ ID NO: 13), wherein, in each of the peptide fragments, the first and final cysteine residues are paired by disulfide bonds. In some embodiments, an anti-C5a antibody described herein can bind to a human C5a protein at an epitope within, or overlapping with, the amino acid sequence: YDGACVNNDETCEQRAAR (SEQ ID NO:14) or CYDGACVNNDETCEQRAA (SEQ ID NO:15). In some embodiments, an antibody can bind to a human C5a protein or fragment thereof containing an amino acid sequence that contains, or consists of, at least four (e.g., at least four, five, six, seven, eight, nine, 10, 11, 12, 13, 14, 15, 16, or 17 or more) consecutive amino acids depicted in any one of SEQ ID NOs:1 to 15. In some embodiments, an anti-C5a antibody described herein binds to a ternary epitope comprising two or more (e.g., at least two, three, or four) discontinuous peptide regions of C5a protein, e.g., two or more discontinuous C5a peptide regions joined together by way of a disulfide linkage.

Methods for identifying the epitope to which a particular antibody (e.g., an anti-C5a antibody) binds are also known in the art. For example, the binding epitope within C5a (or desarginated C5a) to which an anti-C5a antibody binds can be identified by measuring the binding of the antibody to several (e.g., three, four, five, six, seven, eight, nine, 10, 15, 20, or 30 or more) overlapping peptide fragments of a complement component C5a protein (e.g., several overlapping fragments of a human C5a protein having the amino acid sequence depicted in SEQ ID NO: 1 or SEQ ID NO:2). Each of the different overlapping peptides is then bound to a unique address on a solid support, e.g., separate wells of a multi-well assay plate. Next, the anti-C5a antibody is interrogated by contacting it to each of the peptides in the assay plate for an amount of time and under conditions that allow for the antibody to bind to its epitope. Unbound anti-C5a antibody is removed by washing each of the wells. Next, a detectably-labeled secondary antibody that binds to the anti-C5a antibody, if present in a well of the plate, is contacted to each of the wells, and unbound secondary antibody is removed by washing steps. The presence or amount of the detectable signal produced by the detectably-labeled secondary antibody in a well is an indication that the anti-C5a antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2 (May 1994); and Johne et al. (1993) *J Immunol Methods* 160:20191-8).

In some embodiments, an anti-C5a antibody described herein contains a specific set of light chain complementarity determining regions (CDRs) and/or a specific set of heavy chain CDRs. For example, in some embodiments an anti-C5a antibody or antigen-binding fragment thereof described herein can comprise a light chain CDR set obtained from a light chain polypeptide comprising the amino acid sequence depicted in any one of SEQ ID NOs: 19, 37, or 42. In some embodiments, an anti-C5a antibody or antigen-binding fragment thereof described herein can comprise a heavy chain CDR set obtained from a heavy chain polypeptide comprising the amino acid sequence depicted in SEQ ID NO:27 or 45. Exemplary light chain and heavy chain CDR sets obtained from the aforementioned light chain variable regions and heavy chain variable regions are described below in more detail (see Table 1).

The exact boundaries of CDRs, and framework regions, have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (1989) *Nature* 342:877-883. Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs." In some embodiments, the positions of the CDRs and/or framework regions within a light or heavy chain variable domain can be as defined by Honnegger and Plückthun (2001) *J Mol Biol* 309: 657-670. Identification of the CDRs within a light chain or heavy chain variable region using the aforementioned definitions is well known in the art of antibody engineering. For example, Thomas et al. [(1996) *Mol Immunol* 33(17/18):1389-1401] exemplifies the identification of light chain and heavy chain CDR boundaries according to Kabat and Chothia definitions.

Accordingly, in some embodiments an anti-C5a antibody or antigen-binding fragment thereof described herein can comprise a Kabat-defined, a Chothia-defined, or a combined Kabat-Chothia-defined light chain CDR set obtained from a light chain polypeptide comprising the amino acid sequence depicted in any one of SEQ ID NOs: 19, 37, or 42. In some embodiments, an anti-C5a antibody or antigen-binding fragment thereof described herein can comprise a Kabat-defined, a Chothia-defined, or a combined Kabat-Chothia-defined heavy chain CDR set obtained from a heavy chain polypeptide comprising the amino acid sequence depicted in SEQ ID NO:27 or 45.

In some embodiments, an anti-C5a antibody described herein comprises a light chain variable region containing one or more of: a light chain CDR1 comprising or consisting of the following amino acid sequence: RASESVDSYGNSFMH (SEQ ID NO:20); a light chain CDR2 comprising or consisting of the following amino acid sequence: RASNLES (SEQ ID NO:21); and a light chain CDR3 comprising or consisting of the following amino acid sequence: QQSNEDPYT (SEQ ID NO:22). In some embodiments, an anti-C5a antibody described herein comprises a light chain variable region containing each of a light chain CDR1 comprising or consisting of the following amino acid sequence: RASESVDSYGNSFMH (SEQ ID NO:20); a light chain CDR2 comprising or consisting of the following amino acid sequence: RASNLES (SEQ ID NO:21); and a light chain CDR3 comprising or consisting of the following amino acid sequence: QQSNEDPYT (SEQ ID NO:22). Exemplary anti-C5a antibodies comprising such a light chain variable domain include, e.g., the BNJ364, BNJ367, BNJ378, BNJ366, BNJ369, and BNJ383 anti-C5a antibodies described herein (vide infra; Table 2).

In some embodiments, an anti-C5a antibody described herein comprises a light chain variable region containing one or more of: a light chain CDR1 comprising or consisting of the following amino acid sequence: RASESVDSYGNSFMH (SEQ ID NO:20); a light chain CDR2 comprising or consisting of the following amino acid sequence: WAST- RES (SEQ ID NO:38); and a light chain CDR3 comprising or consisting of the following amino acid sequence: QQSNEDPYT (SEQ ID NO:22). In some embodiments, an anti-C5a antibody described herein comprises a light chain variable region containing each of a light chain CDR1 comprising or consisting of the following amino acid sequence: RASESVDSYGNSFMH (SEQ ID NO:20); a light chain CDR2 comprising or consisting of the following amino acid sequence: WASTRES (SEQ ID NO:38); and a light chain CDR3 comprising or consisting of the following amino acid sequence: QQSNEDPYT (SEQ ID NO:22). Exemplary anti-C5a antibodies comprising such a light chain variable domain include, e.g., the BNJ371 and BNJ381 anti-C5a antibodies described herein (vide infra; Table 2).

In some embodiments, an anti-C5a antibody described herein comprises a heavy chain variable region containing one or more of: a heavy chain CDR1 comprising or consisting of the following amino acid sequence: DYSMD (SEQ ID NO:28); a heavy chain CDR2 comprising or consisting of the following amino acid sequence: AINPNSGGTNYNQKFKD (SEQ ID NO:29); and a heavy chain CDR3 comprising or consisting of the following amino acid sequence: SGSYDGYYAMDY (SEQ ID NO:30). In some embodiments, an anti-C5a antibody described herein comprises a heavy chain variable region containing each of a heavy chain CDR1 comprising or consisting of the following amino acid sequence: DYSMD (SEQ ID NO:28); a heavy chain CDR2 comprising or consisting of the following amino acid sequence: AINPNSGGTNYNQKFKD (SEQ ID NO:29); and a heavy chain CDR3 comprising or consisting of the following amino acid sequence: SGSYDGYYAMDY (SEQ ID NO:30). Exemplary anti-C5a antibodies comprising such a heavy chain variable domain include, e.g., the BNJ364, BNJ367, BNJ371, and BNJ378 anti-C5a antibodies described herein (vide infra; Table 2).

In some embodiments, an anti-C5a antibody described herein comprises a heavy chain variable region containing one or more of: a heavy chain CDR1 comprising or consisting of the following amino acid sequence: DYSMD (SEQ ID NO:28); a heavy chain CDR2 comprising or consisting of the following amino acid sequence: AIHLNTGYTNYNQKFKG (SEQ ID NO:46); and a heavy chain CDR3 comprising or consisting of the following amino acid sequence: GFYDGYSPMDY (SEQ ID NO:47). In some embodiments, an anti-C5a antibody described herein comprises a heavy chain variable region containing each of a heavy chain CDR1 comprising or consisting of the following amino acid sequence: DYSMD (SEQ ID NO:28); a heavy chain CDR2 comprising or consisting of the following amino acid sequence: AIHLNTGYTNYNQKFKG (SEQ ID NO:46); and a heavy chain CDR3 comprising or consisting of the following amino acid sequence: GFYDGYSPMDY (SEQ ID NO:47). Exemplary anti-C5a antibodies comprising such a heavy chain variable domain include, e.g., the BNJ366, BNJ369, BNJ381, and BNJ383 anti-C5a antibodies described herein (vide infra; Table 2).

In some embodiments, an anti-C5a antibody or antigen-binding fragment thereof described herein can contain a heavy chain CDR2 region comprising the amino acid sequence: AINPNSGGTNYSQKFKD (SEQ ID NO:67). For example, an anti-C5a antibody described herein can comprise a heavy chain variable region containing one or more of: a heavy chain CDR1 comprising or consisting of the following amino acid sequence: DYSMD (SEQ ID NO:28); a heavy chain CDR2 comprising or consisting of the following amino acid sequence: AINPNSGGTNYSQKFKD (SEQ ID NO:67); and a heavy chain CDR3 comprising or consisting of the following amino acid sequence: SGSYDGYYAMDY (SEQ ID NO:30). In some embodiments, an anti-C5a antibody described herein comprises a heavy chain variable region containing each of a heavy chain CDR1 comprising or consisting of the following amino acid sequence: DYSMD (SEQ ID NO:28); a heavy chain CDR2 comprising or consisting of the following amino acid sequence: AINPNSGGTNYSQKFKD (SEQ ID NO:67); and a heavy chain CDR3 comprising or consisting of the following amino acid sequence: SGSYDGYYAMDY (SEQ ID NO:30). An example of an anti-C5a antibody described herein, which contains such a heavy chain polypeptide and binds to human C5a with a $K_D$ that is less than 1 nM is the 5an101ME antibody described below.

In some embodiments, an anti-C5a antibody or antigen-binding fragment thereof described herein contains one of the exemplary light chain CDR set and heavy chain CDR set pairings 1 to 4 depicted in Table 1.

TABLE 1

Exemplary Heavy and Light Chain CDR Pairings

| Exemplary CDR Pairings | Light Chain | | | Heavy Chain | | | Exemplary Antibodies with such Pairings |
|---|---|---|---|---|---|---|---|
| | CDR1 | CDR2 | CDR3 | CDR1 | CDR2 | CDR3 | |
| 1 | SIN: 20 | SIN: 21 | SIN: 22 | SIN: 28 | SIN: 29 | SIN: 30 | BNJ364, BNJ367, BNJ378 |
| 2 | SIN: 20 | SIN: 21 | SIN: 22 | SIN: 28 | SIN: 46 | SIN: 47 | BNJ366, BNJ369, BNJ383 |
| 3 | SIN: 20 | SIN: 38 | SIN: 22 | SIN: 28 | SIN: 29 | SIN: 30 | BNJ371 |
| 4 | SIN: 20 | SIN: 38 | SIN: 22 | SIN: 28 | SIN: 46 | SIN: 47 | BNJ381 |

"SIN" refers to "SEQ ID NO."

The amino acid sequences represented by the SEQ ID NOs in Table 1 are set forth in Table 2.

In some embodiments, the anti-C5a antibody does not comprise exemplary CDR pairing 3. In some embodiments, the anti-C5a antibody is not BNJ371.

In some embodiments, the light chain polypeptide of an anti-C5a antibody described herein can be a λ light chain polypeptide (e.g., a fully human or humanized λ light chain polypeptide). In some embodiments, the light chain polypeptide of an anti-C5a antibody described herein is a κ light chain polypeptide (e.g., a fully human or humanized κ light chain polypeptide). The amino acid sequences of numerous light chain polypeptides (e.g., numerous human light chain polypeptides) are well-known in the art and set forth in, e.g., Kabat et al. (1991), supra. Exemplary κ light chain polypeptide amino acid sequences are set forth in Table 2.

In some embodiments, an anti-C5a antibody described herein can comprise a light chain constant region. For example, the light chain constant region can be a λ light chain polypeptide constant region or a κ light chain constant region. The amino acid sequence for a number of human λ and κ light chain constant regions are known in the art and described in, e.g., Kabat et al. (1991), supra. Exemplary κ light chain polypeptide amino acid sequences are set forth in Table 2.

The heavy chain polypeptide can comprise a constant region (e.g., a heavy chain constant region 1 (CH1), heavy chain constant region 2 (CH2), heavy chain constant region 3 (CH3), a heavy chain constant region 4 (CH4), or a combination of any of the foregoing). The heavy chain polypeptide can comprise an Fc portion of an immunoglobulin molecule. The Fc region can be, e.g., an Fc region from an IgG1, IgG2, IgG3, IgG4, IgA, IgM, IgE, or IgD immunoglobulin molecule or a combination of portions of each of these. To be clear, the anti-C5a antibodies described herein can be, e.g., of IgG1, IgG2, IgG3, IgG4, IgA, IgM, IgE, or IgD isotype. The amino acid sequences for a number of human heavy chain constant regions are known in the art and described in, e.g., Kabat et al. (1991), supra.

In some embodiments, the heavy chain polypeptide can comprise a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). For example (and in accordance with Kabat numbering), the IgG1 and IgG4 constant regions comprise $G_{249}G_{250}$ residues whereas the IgG2 constant region does not comprise residue 249, but does comprise $G_{250}$. In a G2/G4 hybrid constant region, where the 249-250 region comes from the G2 sequence, the constant region can be further modified to introduce a glycine residue at position 249 to produce a G2/G4 fusion having $G_{249}/G_{250}$. Other constant domain hybrids that comprise $G_{249}/G_{250}$ can also be part of engineered antibodies in accordance with the disclosure. Exemplary heavy chain polypeptide amino acid sequences are set forth in Table 2.

The anti-C5a antibody can be, e.g., one of the specific antibodies exemplified in the working examples: BNJ364, BNJ367, BNJ378, BNJ366, BNJ369, BNJ383, BNJ371, or BNJ381. The amino acid sequences for these exemplified anti-C5a antibodies, which can be used in conjunction with any of the methods described herein, are set forth in Table 2.

TABLE 2

Amino Acid Sequences for Select Humanized Anti-C5a Antibodies

| SIN | Ab | Description | Amino Acid Sequence |
|---|---|---|---|
| 16 | BNJ364 | Full light chain sequence with signal peptide | MVLQTQVFISLLLWISGAYGDIVMTQSPDSLAVSLGERATINCRASESVDSYGNSFMHWYQQKPGQPP KLLIYRASNLESGVPDRFSGSGSGTDFTLTISSLQAEDVAVYYCQQSNEDPYTFGGGTKVEIKRTVAAP SVFIFPPSDEQLKSGTASVVCLLNNFYPREAKVQWKVDNALQSGNSQESVTEQDSKDSTYSLSSTLTLS KADYEKHKVYACEVTHQGLSSPVTKSFNRGEC |
| 17 | BNJ364 | Full light chain sequence without signal peptide | DIVMTQSPDSLAVSLGERATINCRASESVDSYGNSFMHWYQQKPGQPPKWYRASNLESGVPDRFSGS GSGTDFTLTISSLQAEDVAVYYCQQSNEDPYTFGGGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLS SPVTKSFNRGEC |
| 18 | BNJ364 | Light chain variable region sequence signal peptide | MVLQTQVFISLLLWISGAYG |
| 19 | BNJ364 | Light chain variable region sequence | DIVMTQSPDSLAVSLGERATINCRASESVDSYGNSFMHWYQQKPGQPPKWYRASNLESGVPDRFSGS GSGTDFTLTISSLQAEDVAVYYCQQSNEDPYTFGGGTKVEIKR |
| 20 | BNJ364 | Light chain variable region sequence Kabat LCDR1 | RASESVDSYGNSFMH |
| 21 | BNJ364 | Light chain variable region sequence Kabat LCDR2 | RASNLES |
| 22 | BNJ364 | Light chain variable region sequence Kabat LCDR3 | QQSNEDPYT |
| 23 | BNJ364 | Light chain constant region sequence | TVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |

TABLE 2-continued

Amino Acid Sequences for Select Humanized Anti-C5a Antibodies

| SIN: | Ab | Description | Amino Acid Sequence |
|---|---|---|---|
| 24 | BNJ364 | Full heavy chain sequence with signal peptide | MDWTWRVFCLLAVAPGAHSQVQLVQSGAEVKKPGASVKVSCKASGYTFTDYSMDWVRQAPGQGLE WMGAINPNSGGTNYNQKFKDRVTMTRDTSTSTVYMELSSLRSEDTAVYYCARSGSYDGYYAMDYW GQGTTVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKD TLMISRTPEVTCVVVDVSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLVKGFYPSDISVEWESN GQPENNYKTTPPMLDSDGSFFLYSKLTVDKSRWQQGNVFSC SVMHEALHNHYTQKSLSLSPGK |
| 25 | BNJ364 | Full heavy chain sequence without signal peptide | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSSASTKGPSVFPL APCSRSTSESTAALGCLVKDYFPEPVTVSWNSGALTSGVHTFPAVLQSSGLYSLSSVVTVPSSNFGTQT YTCNVDHKPSNTKVDKTVERKCCVECPPCPAPPVAGPSVFLFPPKPKDTLMISRTPEVTCVVVDVSHE DPEVQFNWYVDGVEVHNAKTKPREEQFNSTFRVVSVLTVVHQDWLNGKEYKCKVSNKGLPAPIEKTI SKTKGQPREPQVYTLPPSREEMTKNQVSLTCLVKGFYPSDISVEWESNGQPENNYKTTPPMLDSDGSFF LYSKLTVDKSRWQQGNVFSCSVMHEALHNHYTQKSLSLSPGK |
| 26 | BNJ364 | Heavy chain variable region sequence signal peptide | MDWTWRVFCLLAVAPGAHS |
| 27 | BNJ364 | Heavy chain variable region sequence | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSS |
| 28 | BNJ364 | Heavy chain variable region sequence Kabat HCDR1 | DYSMD |
| 29 | BNJ364 | Heavy chain variable region sequence Kabat HCDR2 | AINPNSGGTNYNQKFKD |
| 30 | BNJ364 | Heavy chain variable region sequence Kabat HCDR3 | SGSYDGYYAMDY |
| 31 | BNJ364 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSHEDPEVQFNWYVDGVEVHNAKTKPREEQFNSTFRVVSVLTVVHQDWLNGKEYKCKVS NKGLPAPIEKTISKTKGQPREPQVYTLPPSREEMTKNQVSLTCLVKGFYPSDISVEWESNGQPENNYKT TPPMLDSDGSFFLYSKLTVDKSRWQQGNVFSCSVMHEALHNHYTQKSLSLSPGK |
| 16 | BNJ367 | Full light chain sequence with signal peptide | MVLQTQVFISLLLWISGAYGDIVMTQSPDSLAVSLGERATINCRASESVDSYGNSFMHWYQQKPGQPP KLLIYRASNLESGVPDRFSGSGSGTDFTLTISSLQAEDVAVYYCQQSNEDPYTFGGGTKVEIKRTVAAP SVFIFPPSDEQLKSGTASVVCLLNNFYPREAKVQWKVDNALQSGNSQESVTEQDSKDSTYSLSSTLTLS KADYEKHKVYACEVTHQGLSSPVTKSFNRGEC |
| 17 | BNJ367 | Full light chain sequence without signal peptide | DIVMTQSPDSLAVSLGERATINCRASESVDSYGNSFMHWYQQKPGQPPKWYRASNLESGVPDRFSGS GSGTDFTLTISSLQAEDVAVYYCQQSNEDPYTFGGGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLS SPVTKSFNRGEC |
| 18 | BNJ367 | Light chain variable region sequence signal peptide | MVLQTQVFISLLLWISGAYG |

TABLE 2-continued

Amino Acid Sequences for Select Humanized Anti-C5a Antibodies

| SIN: | Ab | Description | Amino Acid Sequence |
|---|---|---|---|
| 19 | BNJ367 | Light chain variable region sequence | DIVMTQSPDSLAVSLGERATINCRASESVDSYGNSFMHWYQQKPGQPPKWYRASNLESGVPDRFSGS GSGTDFTLTISSLQAEDVAVYYCQQSNEDPYTFGGGTKVEIKR |
| 20 | BNJ367 | Light chain variable region sequence Kabat LCDR1 | RASESVDSYGNSFMH |
| 21 | BNJ367 | Light chain variable region sequence Kabat LCDR2 | RASNLES |
| 22 | BNJ367 | Light chain variable region sequence Kabat LCDR3 | QQSNEDPYT |
| 23 | BNJ367 | Light chain constant region sequence | TVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 32 | BNJ367 | Full heavy chain sequence with signal peptide | MDWTWRVFCLLAVAPGAHSQVQLVQSGAEVKKPGASVKVSCKASGYTFTDYSMDWVRQAPGQGLE WMGAINPNSGGTNYNQKFKDRVTMTRDTSTSTVYMELSSLRSEDTAVYYCARSGSYDGYYAMDYW GQGTTVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKD TLMISRTPEVTCVVVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQKSLSLSLGK |
| 33 | BNJ367 | Full heavy chain sequence without signal peptide | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSSASTKGPSVFPL APCSRSTSESTAALGCLVKDYFPEPVTVSWNSGALTSGVHTFPAVLQSSGLYSLSSVVTVPSSNFGTQT YTCNVDHKPSNTKVDKTVERKCCVECPPCPAPPVAGPSVFLFPPKPKDTLMISRTPEVTCVVVDVSQE DPEVQFNWYVDGVEVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPENNYKTTPPVLDSDGSF FLYSRLTVDKSRWQEGNVFSCSVMHEALHNHYTQKSLSLSLGK |
| 26 | BNJ367 | Heavy chain variable region sequence signal peptide | MDWTWRVFCLLAVAPGAHS |
| 27 | BNJ367 | Heavy chain variable region sequence | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSS |
| 28 | BNJ367 | Heavy chain variable region sequence Kabat HCDR1 | DYSMD |
| 29 | BNJ367 | Heavy chain variable region sequence Kabat HCDR2 | AINPNSGGTNYNQKFKD |
| 30 | BNJ367 | Heavy chain variable region sequence Kabat HCDR3 | SGSYDGYYAMDY |

TABLE 2-continued

Amino Acid Sequences for Select Humanized Anti-C5a Antibodies

| SIN: | Ab | Description | Amino Acid Sequence |
|---|---|---|---|
| 34 | BNJ367 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSQEDPEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK |
| 35 | BNJ371 | Full light chain sequence with signal peptide | MVLQTQVFISLLLWISGAYGDIVMTQSPDSLAVSLGERATINCRASESVDSYGNSFMHWYQQKPGQPP KLLIYWASTRESGVPDRFSGSGSGTDFTLTISSLQAEDVAVYYCQQSNEDPYTFGGGTKVEIKRTVAAP SVFIFPPSDEQLKSGTASVVCLLNNFYPREAKVQWKVDNALQSGNSQESVTEQDSKDSTYSLSSTLTLS KADYEKHKVYACEVTHQGLSSPVTKSFNRGEC |
| 36 | BNJ371 | Full light chain sequence without signal peptide | DIVMTQSPDSLAVSLGERATINCRASESVDSYGNSFMHWYQQKPGQPPKLLIYWASTRESGVPDRFSG SGSGTDFTLTISSLQAEDVAVYYCQQSNEDPYTFGGGTKVEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |
| 18 | BNJ371 | Light chain variable region sequence signal peptide | MVLQTQVFISLLLWISGAYG |
| 37 | BNJ371 | Light chain variable region sequence | DIVMTQSPDSLAVSLGERATINCRASESVDSYGNSFMHWYQQKPGQPPKLLIYWASTRESGVPDRFSG SGSGTDFTLTISSLQAEDVAVYYCQQSNEDPYTFGGGTKVEIKR |
| 20 | BNJ371 | Light chain variable region sequence Kabat LCDR1 | RASESVDSYGNSFMH |
| 38 | BNJ371 | Light chain variable region sequence Kabat LCDR2 | WASTRES |
| 22 | BNJ371 | Light chain variable region sequence Kabat LCDR3 | QQSNEDPYT |
| 23 | BNJ371 | Light chain constant region sequence | TVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 32 | BNJ371 | Full heavy chain sequence with signal peptide | MDWTWRVFCLLAVAPGAHSQVQLVQSGAEVKKPGASVKVSCKASGYTFTDYSMDWVRQAPGQGLE WMGAINPNSGGTNYNQKFKDRVTMTRDTSTSTVYMELSSLRSEDTAVYYCARSGSYDGYYAMDYW GQGTTVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKD TLMISRTPEVTCVVVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQKSLSLSLGK |
| 33 | BNJ371 | Full heavy chain sequence without signal peptide | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSSASTKGPSVFPL APCSRSTSESTAALGCLVKDYFPEPVTVSWNSGALTSGVHTFPAVLQSSGLYSLSSVVTVPSSNFGTQT YTCNVDHKPSNTKVDKTVERKCCVECPPCPAPPVAGPSVFLFPPKPKDTLMISRTPEVTCVVVDVSQE DPEVQFNWYVDGVEVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPENNYKTTPPVLDSDGSF FLYSRLTVDKSRWQEGNVFSCSVMHEALHNHYTQKSLSLSLGK |
| 26 | BNJ371 | Heavy chain variable region sequence signal peptide | MDWTWRVFCLLAVAPGAHS |

TABLE 2-continued

Amino Acid Sequences for Select Humanized Anti-C5a Antibodies

| SIN: | Ab | Description | Amino Acid Sequence |
|---|---|---|---|
| 27 | BNJ371 | Heavy chain variable region sequence | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSS |
| 28 | BNJ371 | Heavy chain variable region sequence Kabat HCDR1 | DYSMD |
| 29 | BNJ371 | Heavy chain variable region sequence Kabat HCDR2 | AINPNSGGTNYNQKFKD |
| 30 | BNJ371 | Heavy chain variable region sequence Kabat HCDR3 | SGSYDGYYAMDY |
| 34 | BNJ371 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSQEDPEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK |
| 39 | BNJ378 | Full light chain sequence with signal peptide | MDMRVPAQLLGLLLLWLRGARCDIQMTQSPSSLSASVGDRVTITCRASESVDSYGNSFMHWYQQKPG KAPKLLIYRASNLESGVPSRFSGSGSGTDFTLTISSLQPEDFATYYCQQSNEDPYTFGGGTKVEIKRTVA APSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 40 | BNJ378 | Full light chain sequence without signal peptide | DIQMTQSPSSLSASVGDRVTITCRASESVDSYGNSFMHWYQQKPGKAPKWYRASNLESGVPSRFSGS GSGTDFTLTISSLQPEDFATYYCQQSNEDPYTFGGGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLS SPVTKSFNRGEC |
| 41 | BNJ378 | Light chain variable region sequence signal peptide | MDMRVPAQLLGLLLLWLRGARC |
| 42 | BNJ378 | Light chain variable region sequence | DIQMTQSPSSLSASVGDRVTITCRASESVDSYGNSFMHWYQQKPGKAPKLLIYRASNLESGVPSRFSGS GSGTDFTLTISSLQPEDFATYYCQQSNEDPYTFGGGTKVEIKR |
| 20 | BNJ378 | Light chain variable region sequence Kabat LCDR1 | RASESVDSYGNSFMH |
| 21 | BNJ378 | Light chain variable region sequence Kabat LCDR2 | RASNLES |
| 22 | BNJ378 | Light chain variable region sequence Kabat LCDR3 | QQSNEDPYT |

TABLE 2-continued

Amino Acid Sequences for Select Humanized Anti-C5a Antibodies

| SIN: | Ab | Description | Amino Acid Sequence |
|---|---|---|---|
| 23 | BNJ378 | Light chain constant region sequence | TVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 32 | BNJ378 | Full heavy chain sequence with signal peptide | MDWTWRVFCLLAVAPGAHSQVQLVQSGAEVKKPGASVKVSCKASGYTFTDYSMDWVRQAPGQGLE WMGAINPNSGGTNYNQKFKDRVTMTRDTSTSTVYMELSSLRSEDTAVYYCARSGSYDGYYAMDYW GQGTTVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKD TLMISRTPEVTCVVVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQKSLSLSLGK |
| 33 | BNJ378 | Full heavy chain sequence without signal peptide | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSSASTKGPSVFPL APCSRSTSESTAALGCLVKDYFPEPVTVSWNSGALTSGVHTFPAVLQSSGLYSLSSVVTVPSSNFGTQT YTCNVDHKPSNTKVDKTVERKCCVECPPCPAPPVAGPSVFLFPPKPKDTLMISRTPEVTCVVVDVSQE DPEVQFNWYVDGVEVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPENNYKTTPPVLDSDGSF FLYSRLTVDKSRWQEGNVFSCSVMHEALHNHYTQKSLSLSLGK |
| 26 | BNJ378 | Heavy chain variable region sequence signal peptide | MDWTWRVFCLLAVAPGAHS |
| 27 | BNJ378 | Heavy chain variable region sequence | QVQLVQSGAEVKKPGASVKVSCKASGYTFTDYSMDWVRQAPGQGLEWMGAINPNSGGTNYNQKFK DRVTMTRDTSTSTVYMELSSLRSEDTAVYYCARSGSYDGYYAMDYWGQGTTVTVSS |
| 28 | BNJ378 | Heavy chain variable region sequence Kabat HCDR1 | DYSMD |
| 29 | BNJ378 | Heavy chain variable region sequence Kabat HCDR2 | AINPNSGGTNYNQKFKD |
| 30 | BNJ378 | Heavy chain variable region sequence Kabat HCDR3 | SGSYDGYYAMDY |
| 34 | BNJ378 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSQEDPEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK |
| 16 | BNJ366 | Full light chain sequence with signal peptide | MVLQTQVFISLLLWISGAYGDIVMTQSPDSLAVSLGERATINCRASESVDSYGNSFMHWYQQKPGQPP KLLIYRASNLESGVPDRFSGSGSGTDFTLTISSLQAEDVAVYYCQQSNEDPYTFGGGTKVEIKRTVAAP SVFIFPPSDEQLKSGTASVVCLLNNFYPREAKVQWKVDNALQSGNSQESVTEQDSKDSTYSLSSTLTLS KADYEKHKVYACEVTHQGLSSPVTKSFNRGEC |
| 17 | BNJ366 | Full light chain sequence without signal peptide | DIVMTQSPDSLAVSLGERATINCRASESVDSYGNSFMHWYQQKPGQPPKWYRASNLESGVPDRFSGS GSGTDFTLTISSLQAEDVAVYYCQQSNEDPYTFGGGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLS SPVTKSFNRGEC |
| 18 | BNJ366 | Light chain variable region sequence signal peptide | MVLQTQVFISLLLWISGAYG |

TABLE 2-continued

Amino Acid Sequences for Select Humanized Anti-C5a Antibodies

| SIN: | Ab | Description | Amino Acid Sequence |
|---|---|---|---|
| 19 | BNJ366 | Light chain variable region sequence | DIVMTQSPDSLAVSLGERATINCRASESVDSYGNSFMHWYQQKPGQPPKWYRASNLESGVPDRFSGSGSGTDFTLTISSLQAEDVAVYYCQQSNEDPYTFGGGTKVEIKR |
| 20 | BNJ366 | Light chain variable region sequence Kabat LCDR1 | RASESVDSYGNSFMH |
| 21 | BNJ366 | Light chain variable region sequence Kabat LCDR2 | RASNLES |
| 22 | BNJ366 | Light chain variable region sequence Kabat LCDR3 | QQSNEDPYT |
| 23 | BNJ366 | Light chain constant region sequence | TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 43 | BNJ366 | Full heavy chain sequence with signal peptide | MDWTWRVFCLLAVAPGAHSQVQLVQSGAEVKKPGASVKVSCKASGYTFTDYSMDWVRQAPGQGLEWMGAIHLNTGYTNYNQKFKGRVTMTRDTSTSTVYMELSSLRSEDTAVYYCARGFYDGYSPMDYWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPGK |
| 44 | BNJ366 | Full heavy chain sequence without signal peptide | QVQLVQSGAEVKKPGASVKVSCKASGYTFTDYSMDWVRQAPGQGLEWMGAIHLNTGYTNYNQKFKGRVTMTRDTSTSTVYMELSSLRSEDTAVYYCARGFYDGYSPMDYWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPGK |
| 26 | BNJ366 | Heavy chain variable region sequence signal peptide | MDWTWRVFCLLAVAPGAHS |
| 45 | BNJ366 | Heavy chain variable region sequence | QVQLVQSGAEVKKPGASVKVSCKASGYTFTDYSMDWVRQAPGQGLEWMGAIHLNTGYTNYNQKFKGRVTMTRDTSTSTVYMELSSLRSEDTAVYYCARGFYDGYSPMDYWGQGTTVTVSS |
| 28 | BNJ366 | Heavy chain variable region sequence Kabat HCDR1 | DYSMD |
| 46 | BNJ366 | Heavy chain variable region sequence Kabat HCDR2 | AIHLNTGYTNYNQKFKG |
| 47 | BNJ366 | Heavy chain variable region sequence Kabat HCDR3 | GFYDGYSPMDY |

TABLE 2-continued

Amino Acid Sequences for Select Humanized Anti-C5a Antibodies

| SIN: | Ab | Description | Amino Acid Sequence |
|---|---|---|---|
| 31 | BNJ366 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSHEDPEVQFNWYVDGVEVHNAKTKPREEQFNSTFRVVSVLTVVHQDWLNGKEYKCKVS NKGLPAPIEKTISKTKGQPREPQVYTLPPSREEMTKNQVSLTCLVKGFYPSDISVEWESNGQPENNYKT TPPMLDSDGSFFLYSKLTVDKSRWQQGNVFSCSVMHEALHNHYTQKSLSLSPGK |
| 16 | BNJ369 | Full light chain sequence with signal peptide | MVLQTQVFISLLLWISGAYGDIVMTQSPDSLAVSLGERATINCRASESVDSYGNSFMHWYQQKPGQPP KLLIYRASNLESGVPDRFSGSGSGTDFTLTISSLQAEDVAVYYCQQSNEDPYTFGGGTKVEIKRTVAAP SVFIFPPSDEQLKSGTASVVCLLNNFYPREAKVQWKVDNALQSGNSQESVTEQDSKDSTYSLSSTLTLS KADYEKHKVYACEVTHQGLSSPVTKSFNRGEC |
| 17 | BNJ369 | Full light chain sequence without signal peptide | DIVMTQSPDSLAVSLGERATINCRASESVDSYGNSFMHWYQQKPGQPPKWYRASNLESGVPDRFSGS GSGTDFTLTISSLQAEDVAVYYCQQSNEDPYTFGGGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLS SPVTKSFNRGEC |
| 18 | BNJ369 | Light chain variable region sequence signal peptide | MVLQTQVFISLLLWISGAYG |
| 19 | BNJ369 | Light chain variable region sequence | DIVMTQSPDSLAVSLGERATINCRASESVDSYGNSFMHWYQQKPGQPPKWYRASNLESGVPDRFSGS GSGTDFTLTISSLQAEDVAVYYCQQSNEDPYTFGGGTKVEIKR |
| 20 | BNJ369 | Light chain variable region sequence Kabat LCDR1 | RASESVDSYGNSFMH |
| 21 | BNJ369 | Light chain variable region sequence Kabat LCDR2 | RASNLES |
| 22 | BNJ369 | Light chain variable region sequence Kabat LCDR3 | QQSNEDPYT |
| 23 | BNJ369 | Light chain constant region sequence | TVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 48 | BNJ369 | Full heavy chain sequence with signal peptide | MDWTWRVFCLLAVAPGAHSQVQLVQSGAEVKKPGASVKVSCKASGYTFTDYSMDWVRQAPGQGLE WMGAIHLNTGYTNYNQKFKGRVTMTRDTSTSTVYMELSSLRSEDTAVYYCARGFYDGYSPMDYWG QGTTVTVSSASTKGPSVFPLAPCSRSTSESTAALGCLVKDYFPEPVTVSWNSGALTSGVHTFPAVLQSS GLYSLSSVVTVPSSNFGTQTYTCNVDHKPSNTKVDKTVERKCCVECPPCPAPPVAGPSVFLFPPKPKDT LMISRTPEVTCVVVDVSQEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQKSLSLSLGK |
| 49 | BNJ369 | Full heavy chain sequence without signal peptide | QVQLVQSGAEVKKPGASVKVSCKASGYTFTDYSMDWVRQAPGQGLEWMGAIHLNTGYTNYNQKFK GRVTMTRDTSTSTVYMELSSLRSEDTAVYYCARGFYDGYSPMDYWGQGTTVTVSSASTKGPSVFPLA PCSRSTSESTAALGCLVKDYFPEPVTVSWNSGALTSGVHTFPAVLQSSGLYSLSSVVTVPSSNFGTQTY TCNVDHKPSNTKVDKTVERKCCVECPPCPAPPVAGPSVFLFPPKPKDTLMISRTPEVTCVVVDVSQEDP EVQFNWYVDGVEVHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYKTTPPVLDSDGSFFL YSRLTVDKSRWQEGNVFSCSVMHEALHNHYTQKSLSLSLGK |
| 26 | BNJ369 | Heavy chain variable region sequence signal peptide | MDWTWRVFCLLAVAPGAHS |

TABLE 2-continued

Amino Acid Sequences for Select Humanized Anti-C5a Antibodies

| SIN | Ab | Description | Amino Acid Sequence |
|---|---|---|---|
| 45 | BNJ369 | Heavy chain variable region sequence | QVQLVQSGAEVKKPGASVKVSCKASGYTFTDYSMDWVRQAPGQGLEWMGAIHLNTGYTNYNQKFK GRVTMTRDTSTSTVYMELSSLRSEDTAVYYCARGFYDGYSPMDYWGQGTTVTVSS |
| 28 | BNJ369 | Heavy chain variable region sequence Kabat HCDR1 | DYSMD |
| 46 | BNJ369 | Heavy chain variable region sequence Kabat HCDR2 | AIHLNTGYTNYNQKFKG |
| 47 | BNJ369 | Heavy chain variable region sequence Kabat HCDR3 | GFYDGYSPMDY |
| 34 | BNJ369 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSQEDPEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK |
| 35 | BNJ381 | Full light chain sequence with signal peptide | MVLQTQVFISLLLWISGAYGDIVMTQSPDSLAVSLGERATINCRASESVDSYGNSFMHWYQQKPGQPP KLLIYWASTRESGVPDRFSGSGSGTDFTLTISSLQAEDVAVYYCQQSNEDPYTFGGGTKVEIKRTVAAP SVFIFPPSDEQLKSGTASVVCLLNNFYPREAKVQWKVDNALQSGNSQESVTEQDSKDSTYSLSSTLTLS KADYEKHKVYACEVTHQGLSSPVTKSFNRGEC |
| 36 | BNJ381 | Full light chain sequence without signal peptide | DIVMTQSPDSLAVSLGERATINCRASESVDSYGNSFMHWYQQKPGQPPKWYWASTRESGVPDRFSG SGSGTDFTLTISSLQAEDVAVYYCQQSNEDPYTFGGGTKVEIKRTVAAPSVFIFPPSDEQLKSGTASVVC LLNNFYPREAKVQWKVDNALQSGNSQESVTEQDSKDSTYSLSSTLTLSKADYEKHKVYACEVTHQGL SSPVTKSFNRGEC |
| 18 | BNJ381 | Light chain variable region sequence signal peptide | MVLQTQVFISLLLWISGAYG |
| 37 | BNJ381 | Light chain variable region sequence | DIVMTQSPDSLAVSLGERATINCRASESVDSYGNSFMHWYQQKPGQPPKLLIYWASTRESGVPDRFSG SGSGTDFTLTISSLQAEDVAVYYCQQSNEDPYTFGGGTKVEIKR |
| 20 | BNJ381 | Light chain variable region sequence Kabat LCDR1 | RASESVDSYGNSFMH |
| 38 | BNJ381 | Light chain variable region sequence Kabat LCDR2 | WASTRES |
| 22 | BNJ381 | Light chain variable region sequence Kabat LCDR3 | QQSNEDPYT |

TABLE 2-continued

Amino Acid Sequences for Select Humanized Anti-C5a Antibodies

| SIN: | Ab | Description | Amino Acid Sequence |
|---|---|---|---|
| 23 | BNJ381 | Light chain constant region sequence | TVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 48 | BNJ381 | Full heavy chain sequence with signal peptide | MDWTWRVFCLLAVAPGAHSQVQLVQSGAEVKKPGASVKVSCKASGYTFTDYSMDWVRQAPGQGLE WMGAIHLNTGYTNYNQKFKGRVTMTRDTSTSTVYMELSSLRSEDTAVYYCARGFYDGYSPMDYWG QGTTVTVSSASTKGPSVFPLAPCSRSTSESTAALGCLVKDYFPEPVTVSWNSGALTSGVHTFPAVLQSS GLYSLSSVVTVPSSNFGTQTYTCNVDHKPSNTKVDKTVERKCCVECPPCPAPPVAGPSVFLFPPKPKDT LMISRTPEVTCVVVDVSQEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQKSLSLSLGK |
| 49 | BNJ381 | Full heavy chain sequence without signal peptide | QVQLVQSGAEVKKPGASVKVSCKASGYTFTDYSMDWVRQAPGQGLEWMGAIHLNTGYTNYNQKFK GRVTMTRDTSTSTVYMELSSLRSEDTAVYYCARGFYDGYSPMDYWGQGTTVTVSSASTKGPSVFPLA PCSRSTSESTAALGCLVKDYFPEPVTVSWNSGALTSGVHTFPAVLQSSGLYSLSSVVTVPSSNFGTQTY TCNVDHKPSNTKVDKTVERKCCVECPPCPAPPVAGPSVFLFPPKPKDTLMISRTPEVTCVVVDVSQEDP EVQFNWYVDGVEVHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYKTTPPVLDSDGSFFL YSRLTVDKSRWQEGNVFSCSVMHEALHNHYTQKSLSLSLGK |
| 26 | BNJ381 | Heavy chain variable region sequence signal peptide | MDWTWRVFCLLAVAPGAHS |
| 45 | BNJ381 | Heavy chain variable region sequence | QVQLVQSGAEVKKPGASVKVSCKASGYTFTDYSMDWVRQAPGQGLEWMGAIHLNTGYTNYNQKFK GRVTMTRDTSTSTVYMELSSLRSEDTAVYYCARGFYDGYSPMDYWGQGTTVTVSS |
| 28 | BNJ381 | Heavy chain variable region sequence Kabat HCDR1 | DYSMD |
| 46 | BNJ381 | Heavy chain variable region sequence Kabat HCDR2 | AIHLNTGYTNYNQKFKG |
| 47 | BNJ381 | Heavy chain variable region sequence Kabat HCDR3 | GFYDGYSPMDY |
| 34 | BNJ381 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSQEDPEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK |
| 39 | BNJ383 | Full light chain sequence with signal peptide | MDMRVPAQLLGLLLLWLRGARCDIQMTQSPSSLSASVGDRVTITCRASESVDSYGNSFMHWYQQKPG KAPKWYRASNLESGVPSRFSGSGSGTDFTLTISSLQPEDFATYYCQQSNEDPYTFGGGTKVEIKRTVA APSVFIFPPSDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 40 | BNJ383 | Full light chain sequence without signal peptide | DIQMTQSPSSLSASVGDRVTITCRASESVDSYGNSFMHWYQQKPGKAPKWYRASNLESGVPSRFSGS GSGTDFTLTISSLQPEDFATYYCQQSNEDPYTFGGGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLS SPVTKSFNRGEC |
| 41 | BNJ383 | Light chain variable region sequence signal peptide | MDMRVPAQLLGLLLLWLRGARC |

TABLE 2-continued

Amino Acid Sequences for Select Humanized Anti-C5a Antibodies

| SIN: | Ab | Description | Amino Acid Sequence |
|---|---|---|---|
| 42 | BNJ383 | Light chain variable region sequence | DIQMTQSPSSLSASVGDRVTITCRASESVDSYGNSFMHWYQQKPGKAPKLLIYRASNLESGVPSRFSGS GSGTDFTLTISSLQPEDFATYYCQQSNEDPYTFGGGTKVEIKR |
| 20 | BNJ383 | Light chain variable region sequence Kabat LCDR1 | RASESVDSYGNSFMH |
| 21 | BNJ383 | Light chain variable region sequence Kabat LCDR2 | RASNLES |
| 22 | BNJ383 | Light chain variable region sequence Kabat LCDR3 | QQSNEDPYT |
| 23 | BNJ383 | Light chain constant region sequence | TVAAPSVFIFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 48 | BNJ383 | Full heavy chain sequence with signal peptide | MDWTWRVFCLLAVAPGAHSQVQLVQSGAEVKKPGASVKVSCKASGYTFTDYSMDWVRQAPGQGLE WMGAIHLNTGYTNYNQKFKGRVTMTRDTSTSTVYMELSSLRSEDTAVYYCARGFYDGYSPMDYWG QGTTVTVSSASTKGPSVFPLAPCSRSTSESTAALGCLVKDYFPEPVTVSWNSGALTSGVHTFPAVLQSS GLYSLSSVVTVPSSNFGTQTYTCNVDHKPSNTKVDKTVERKCCVECPPCPAPPVAGPSVFLFPPKPKDT LMISRTPEVTCVVVDVSQEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQKSLSLSLGK |
| 49 | BNJ383 | Full heavy chain sequence without signal peptide | QVQLVQSGAEVKKPGASVKVSCKASGYTFTDYSMDWVRQAPGQGLEWMGAIHLNTGYTNYNQKFK GRVTMTRDTSTSTVYMELSSLRSEDTAVYYCARGFYDGYSPMDYWGQGTTVTVSSASTKGPSVFPLA PCSRSTSESTAALGCLVKDYFPEPVTVSWNSGALTSGVHTFPAVLQSSGLYSLSSVVTVPSSNFGTQTY TCNVDHKPSNTKVDKTVERKCCVECPPCPAPPVAGPSVFLFPPKPKDTLMISRTPEVTCVVVDVSQEDP EVQFNWYVDGVEVHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYKTTPPVLDSDGSFFL YSRLTVDKSRWQEGNVFSCSVMHEALHNHYTQKSLSLSLGK |
| 26 | BNJ383 | Heavy chain variable region sequence signal peptide | MDWTWRVFCLLAVAPGAHS |
| 45 | BNJ383 | Heavy chain variable region sequence | QVQLVQSGAEVKKPGASVKVSCKASGYTFTDYSMDWVRQAPGQGLEWMGAIHLNTGYTNYNQKFK GRVTMTRDTSTSTVYMELSSLRSEDTAVYYCARGFYDGYSPMDYWGQGTTVTVSS |
| 28 | BNJ383 | Heavy chain variable region sequence Kabat HCDR1 | DYSMD |
| 46 | BNJ383 | Heavy chain variable region sequence Kabat HCDR2 | AIHLNTGYTNYNQKFKG |
| 47 | BNJ383 | Heavy chain variable region sequence Kabat HCDR3 | GFYDGYSPMDY |

TABLE 2-continued

Amino Acid Sequences for Select Humanized Anti-C5a Antibodies

| SIN: | Ab | Description | Amino Acid Sequence |
|---|---|---|---|
| 34 | BNJ383 | Heavy chain constant region sequence | ASTKGPSVFPLAPCSRSTSESTAALGCLVKDYFPEPVTVSWNSGALTSGVHTFPAVLQSSGLYSLSSVV TVPSSNFGTQTYTCNVDHKPSNTKVDKTVERKCCVECPPCPAPPVAGPSVFLFPPKPKDTLMISRTPEV TCVVVDVSQEDPEVQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK |

"SIN" refers to SEQ ID NO.
"Ab" in Table 2 refers to the alphanumeric designation assigned to a given antibody. Each of the antibodies is exemplified in the working examples.

In some embodiments, an anti-C5a antibody described herein comprises a Chothia-defined light chain CDR set or a combined Kabat-Chothia-defined light chain CDR set obtained from any of the light chain variable regions described in Tables 2 or 3. In some embodiment, an anti-C5a antibody, or antigen-binding fragment thereof, described herein comprises a Chothia-defined heavy chain CDR set or a combined Kabat-Chothia-defined heavy chain CDR set obtained from any of the heavy chain variable regions described in Tables 2 or 3.

In preferred embodiments, an anti-C5a antibody described herein binds to C5a, but not to native, full-length C5. In some embodiments, an anti-C5a antibody binds to C5a, but does not bind to the alpha chain of uncleaved, native C5. As used herein, "uncleaved C5" refers to a C5 protein that has not been cleaved into fragments C5a and C5b by an AP or CP C5 convertase. An exemplary amino acid sequence for a human C5 alpha chain is set forth in Haviland et al. (1991), supra, the sequence of which is incorporated herein by reference in its entirety.

In some embodiments, an anti-C5a antibody described herein does not bind to paralogs of human C5 such as human C3a or human C4a.

The disclosure also features antibodies that crossblock binding of an anti-C5a antibody described herein (e.g., crossblocks any one of BNJ364, BNJ367, BNJ378, BNJ366, BNJ369, BNJ371, BNJ381, or BNJ383). As used herein, the term "crossblocking antibody" refers to an antibody that lowers the amount of binding (or prevents binding) of an anti-C5a antibody to an epitope on a complement component C5a protein relative to the amount of binding of the anti-C5a antibody to the epitope in the absence of the crossblocking antibody. Suitable methods for determining whether a first antibody crossblocks binding of a second antibody to an epitope are known in the art. For example, crossblocking antibodies can be identified by comparing the binding of the BNJ364 monoclonal anti-C5a antibody in the presence and absence of a test antibody. Decreased binding of the BNJ364 antibody in the presence of the test antibody as compared to binding of the BNJ364 antibody in the absence of the test antibody indicates the test antibody is a crossblocking antibody.

In some embodiments, the binding of an antibody to C5a can inhibit the biological activity of C5a. Methods for measuring C5a activity include, e.g., chemotaxis assays, radioimmunoassays (RIAs), or enzyme-linked immunospecific assays (ELISA) (see, e.g., Ward and Zvaifler (1971) *J Clin Invest* 50(3):606-16 and Wurzner et al. (1991) *Complement Inflamm* 8:328-340). In some embodiments, the binding of an antibody or antigen-binding fragment thereof to C5a can inhibit C5a-mediated neutrophil activation in vitro. Suitable methods for determining whether an anti-C5a antibody inhibits C5a-mediated neutrophil activation in vitro, or the extent to which the antibody inhibits activation, are known in the art and exemplified in the working examples below. For example, human neutrophils obtained from healthy donors can be isolated and contacted with isolated human C5a in the presence or absence of a test anti-C5a antibody. C5a-dependent activation of human neutrophils can be measured as a function of myeloperoxidase (MPO) release from the cells in the presence of C5a. An inhibition of the amount of MPO released from the cells in the presence of C5a and the test antibody, as compared to the amount of MPO released from cells in the presence of C5a and a control antibody, indicates that the test antibody inhibits C5a-mediated neutrophil activation.

In some embodiments, an anti-C5a antibody or antigen-binding fragment thereof does not inhibit (or does not substantially inhibit) the activity of complement component C5, as compared to the level of inhibition (if any) observed by a corresponding control antibody or antigen-binding fragment thereof (i.e., an antibody that does not bind to free C5a or C5). C5 activity can be measured as a function of its cell-lysing ability in a subject's body fluids. The cell-lysing ability, or a reduction thereof, of C5 can be measured by methods well known in the art such as, for example, by a conventional hemolytic assay such as the hemolysis assay described by Kabat and Mayer (eds), "Experimental Immunochemistry, 2$^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552.

In some embodiments, C5 activity, or inhibition thereof, is quantified using a CH50eq assay. The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured.

The assay is well known and commonly practiced by those of skill in the art. Briefly, to activate the classical complement pathway, undiluted serum samples (e.g., human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and, to each well, is added a detection reagent that is detectably labeled and recognizes the bound TCC. The detectable label can be, e.g., a fluorescent label or an enzymatic label. The assay results are expressed in CH50 unit equivalents per milliliter (CH50 U Eq/mL).

Additional methods for detecting and/or measuring C5 activity in vitro are set forth and exemplified in the working examples.

In some embodiments, the binding of an antibody to C5a can inhibit the interaction between C5a and C5aR1. Suitable methods for detecting and/or measuring the interaction between C5a and C5aR1 (in the presence and absence of an antibody) are known in the art and described in, e.g., Mary and Boulay (1993) *Eur J Haematol* 51(5):282-287; Kaneko et al. (1995) *Immunology* 86(1):149-154; Giannini et al. (1995) *J Biol Chem* 270(32):19166-19172; and U.S. Patent Application Publication No. 20060160726. For example, the binding of detectably labeled (e.g., radioactively labeled) C5a to C5aR1-expressing peripheral blood mononuclear cells can be evaluated in the presence and absence of an antibody. A decrease in the amount of detectably-labeled C5a that binds to C5aR1 in the presence of the antibody, as compared to the amount of binding in the absence of the antibody, is an indication that the antibody inhibits the interaction between C5a and C5aR1.

In some embodiments, the binding of an antibody to C5a can inhibit the interaction between C5a and C5L2. Methods for detecting and/or measuring the interaction between C5a and C5L2 are known in the art and described in, e.g., Ward (2009) *J Mol Med* 87(4):375-378 and Chen et al. (2007) *Nature* 446(7132):203-207. Additional methods for evaluating the biological effect of an anti-C5a antibody described herein are exemplified in the working examples below.

In some embodiments, the anti-C5a antibody specifically binds to a human complement component C5a protein (e.g., the human C5a protein having the amino acid sequence depicted in SEQ ID NO: 1 or SEQ ID NO:2). The terms "specific binding," "specifically binds," and like grammatical terms, as used herein, refer to two molecules forming a complex (e.g., a complex between an antibody and a complement component C5a protein) that is relatively stable under physiologic conditions. Typically, binding is considered specific when the association constant ($k_a$) is higher than $10^6$ M$^{-1}$s$^{-1}$. Thus, an antibody can specifically bind to a C5a protein with a $k_a$ of at least (or greater than) $10^6$ (e.g., at least or greater than $10^7$, $10^8$, $10^9$, $10^{10}$, $10^{11}$, $10^{12}$, $10^{13}$, $10^{14}$, or $10^{15}$ or higher) M$^{-1}$s$^{-1}$. In some embodiments, an anti-C5a antibody described herein has a dissociation constant ($k_d$) of less than or equal to $10^{-3}$ (e.g., $8\times10^{-4}$, $5\times10^{-4}$, $2\times10^{-4}$, $10^{-4}$, or $10^{-5}$) s$^{-1}$.

In some embodiments, an anti-C5a antibody described herein has a $K_D$ of less than $10^{-8}$, $10^{-9}$, $10^{-10}$, $10^{-11}$, or $10^{-12}$ M. The equilibrium constant $K_D$ is the ratio of the kinetic rate constants—$k_d/k_a$. In some embodiments, an anti-C5a antibody described herein has a $K_D$ of less than $1.25\times10^{-9}$ M. Examples of anti-C5a antibodies that bind to C5a with a $K_D$ that is less than $1.25\times10^{-9}$ M include, e.g., the BNJ364, BNJ367, BNJ371, BNJ378, BNJ366, BNJ369, BNJ381, and BNJ383 anti-C5a antibodies.

In some embodiments, an anti-C5a antibody described herein has a $K_D$ of less than $1\times10^{-9}$ M. Examples of anti-C5a antibodies that bind to C5a with a $K_D$ that is less than $10^{-9}$ M include, e.g., the BNJ364, BNJ367, BNJ378, BNJ366, BNJ369, BNJ381, and BNJ383 anti-C5a antibodies.

In some embodiments, an anti-C5a antibody described herein has a $K_D$ of less than $5\times10^{-10}$ M. Examples of anti-C5a antibodies that bind to C5a with a $K_D$ that is less than $5\times10^{-10}$ M include, e.g., the BNJ367, BNJ378, BNJ366, BNJ369, BNJ381, and BNJ383 anti-C5a antibodies.

In some embodiments, an anti-C5a antibody described herein has a $K_D$ of less than $2\times10^{-10}$ M. Examples of anti-C5a antibodies that bind to C5a with a $K_D$ that is less than $2\times10^{-10}$ M include, e.g., the BNJ367, BNJ366, BNJ369, BNJ381, and BNJ383 anti-C5a antibodies.

In some embodiments, an anti-C5a antibody described herein has a $K_D$ of less than $1\times10^{-10}$ M. Examples of anti-C5a antibodies that bind to C5a with a $K_D$ that is less than $1\times10^{-10}$ M include, e.g., the BNJ369, BNJ381, and BNJ383 anti-C5a antibodies.

In some embodiments, an anti-C5a antibody described herein has a $K_D$ of less than $7.5\times10^{-11}$ M. Examples of anti-C5a antibodies that bind to C5a with a $K_D$ that is less than $7.5\times10^{-11}$ M include, e.g., the BNJ369 and BNJ383 anti-C5a antibodies.

Methods for determining the affinity of an antibody for a protein antigen are known in the art. For example, the affinity of an antibody for a protein antigen can be quantified using a variety of techniques such as, but not limited to, Western blot, dot blot, Biolayer Interferometry, Surface Plasmon Resonance (SPR) method (e.g., BIAcore system; Pharmacia Biosensor AB, Uppsala, Sweden and Piscataway, N.J.), or enzyme-linked immunospecific assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2$^{nd}$ Edition, Oxford University Press, NY, Oxford; Johne et al. (1993) *J Immunol Meth* 160:191-198; Jonsson et al. (1993) *Ann Biol Clin* 51:19-26; and Jonsson et al. (1991) *Biotechniques* 11:620-627.

Any of the light chain CDR sets or light chain variable regions described herein can be paired with any of the heavy chain CDR sets or heavy chain variable regions described herein. It is well within the purview of the ordinarily skilled artisan to, e.g., confirm (test) that an anti-C5a antibody generated by such a pairing possesses the desired affinity or activity. Suitable methods for confirming the activity and/or affinity of an anti-C5a antibody are described herein.

In some embodiments, the anti-C5a antibodies described herein bind to both human C5a (hC5a) and C5a from a non-human mammal such as a non-human primate (e.g., cynomolgus macaque). In some embodiments, an anti-C5a antibody or antigen-binding fragment thereof described herein does not bind to paralogs of human C5a such as C3a or C4a from the same non-human mammalian species.

In some embodiments, an anti-C5a antibody or antigen-binding fragment thereof described herein binds to free hC5a and a cynomolgus macaque C5a protein comprising, or consisting of, the following amino acid sequence: MLQEKIEEIAAKYKHLVVKK CCYDGVRINH DETCEQRAAR ISVGPRCVKA FTECCVVASQLRANNSHKDLQLGR (SEQ ID NO: 179). In some embodiments, an anti-C5a antibody or antigen-binding fragment thereof described herein binds to free hC5a and a rhesus macaque C5a protein comprising, or consisting of, the amino acid sequence depicted in SEQ ID NO: 179.

In some embodiments, an antibody, or an antigen-binding fragment thereof, can bind to a desarginated form of C5a protein from a non-human mammalian species (e.g., a non-human primate species). For example, the antibody or antigen-binding fragment thereof can bind to a free C5a-desarg protein from cynomolgus macaque or rhesus macaque, the protein comprising, or consisting of, the following amino acid sequence: MLQEKIEEIAAKYKHLV-VKK CCYDGVRINH DETCEQRAAR ISVGPRCVKA FTECCVVASQLRANNSHKDLQLG (SEQ ID NO:180).

In some embodiments, the anti-C5a antibodies described herein bind to mouse C5a (i.e., the free C5a from mouse). In some embodiments, the anti-C5a antibodies described herein bind to mouse C5a, but not to human C5a. In some embodiments, an anti-C5a antibody described herein does not bind to uncleaved, native (fully-folded) mouse C5. In some embodiments, an anti-C5a antibody described herein does not bind to paralogs of mouse C5a such as mouse C3a or mouse C4a.

An anti-mouse C5a antibody, or an antigen-binding fragment thereof, can bind to a mouse C5a protein comprising, or consisting of, the following amino acid sequence: LRQKIEEQAAKYKHSVPKKCCYDGARVNFYET-CEERVARVTIGPLCIRAFNECCT IANKIRKESPHK-PVQLGR (SEQ ID NO:51). See also, e.g., Wetsel et al. (1987) *Biochem* 26:737-743. In some embodiments, an anti-mouse C5a antibody, or an antigen-binding fragment thereof, can bind to a desarginated form of mouse C5a protein comprising, or consisting of, the following amino acid sequence: LRQKIEEQAAKYKHSVPKKCCYD-GARVNFYETCEERVARVTIGPLCIRAFNECCT IANKIRKESPHKPVQLG (SEQ ID NO:52). In some embodiments, the anti-mouse C5a antibody binds to both the full-length mouse C5a protein and the desarginated form of the mouse C5a protein.

An anti-mouse C5a antibody described herein can, e.g., contain a light chain CDR set obtained from a light chain variable region polypeptide comprising the following amino acid sequence: EIVLTQSPAIMSASLGEKVTMSCRASSS-VNYIYWYQQKSDASPKLWIYYTSNLAP GVPARF-SGSGSGNSYSLTISSMEGEDAATYYCQQFTSSPLTF-GVGTKLELKR (SEQ ID NO:53). For example, an anti-mouse C5a antibody can contain: (i) a Kabat-defined light chain CDR1 comprising, or consisting of, the following amino acid sequence: RASSSVNYIY (SEQ ID NO:54); (ii) a Kabat-defined light chain CDR2 comprising, or consisting of, the following amino acid sequence: YTSNLAP (SEQ ID NO:55); and/or (iii) a Kabat-defined light chain CDR3 comprising, or consisting of, the following amino acid sequence: QQFTSSPLT (SEQ ID NO:56).

The anti-mouse C5a antibody can contain a light chain constant region, e.g., the mouse kappa light chain constant region comprising, or consisting of, the following amino acid sequence: ADAAPTVSIFPPSSEQLTSGGASVVC-FLNNFYPKDINVKWKIDGSERQNGVLNSW TDQD-SKDSTYSMSSTLTLTKDEYERHNSYTCEATHKTST-SPIVKSFNRNEC (SEQ ID NO:57).

In some embodiments, an anti-mouse C5a antibody described herein can contain an amino-terminal signal peptide, e.g., a signal peptide comprising, or consisting of, the following amino acid sequence: MGWSCIILFLVATAT-GVHS (SEQ ID NO:58).

In some embodiments, an anti-mouse C5a antibody described herein can contain a light chain polypeptide comprising, or consisting of, the following amino acid sequence: REIVLTQSPAIMSASLGEKVTMSCRASSS-VNYIYWYQQKSDASPKLWIYYTSNLA PGVPARF-SGSGSGNSYSLTISSMEGEDAATYYCQQFTSSPLTF-GVGTKLELKRAD AAPTVSIFPPSSEQLTSGGASVVCFLNNFYPKDINVK-WKIDGSERQNGVLNSWTD QDSKDSTYSMSSTLTLT-KDEYERHNSYTCEATHKTSTSPIVKSFNRNEC (SEQ ID NO:59) or MGWSCIILFLVATATGVHSREIVLTQS-PAIMSASLGEKVTMSCRASSSVNYIYWY QQKS-DASPKLWIYYTSNLAPGVPARFSGSGSGNSYSLTISS-MEGEDAATYYCQQF TSSPLTFGVGTKLELKRADAAPTVSIFPPSSE-QLTSGGASVVCFLNNFYPKDINVK WKIDGSER-QNGVLNSWTDQDSKDSTYSMSSTLTLTKDEYERHN-SYTCEATHKTS TSPIVKSFNRNEC (SEQ ID NO:60). In some embodiments, an anti-mouse C5a antibody described herein contains a light chain polypeptide comprising amino acids 2 to 214 of SEQ ID NO:59. In some embodiments, an anti-mouse C5a antibody described herein contains a light chain polypeptide comprising amino acids 1 to 19 and 21 to 233 of SEQ ID NO:60.

An anti-mouse C5a antibody described herein can, e.g., contain a heavy chain CDR set obtained from a heavy chain variable region polypeptide comprising the following amino acid sequence: LEVQLQQSGPELVKPGASVKISCKAS-GYTFTDYYYINWVKQSHGKSLEWIGYIYP NDGDT-NYNQKFKGKATLTVDKSSSTAYMELRSLTSED-SAVYYCARPYYSDYGM DYWGQGTSVTVSS (SEQ ID NO:61). For example, an anti-mouse C5a antibody can contain: (i) a Kabat-defined heavy chain CDR1 comprising, or consisting of, the following amino acid sequence: DYYYIN (SEQ ID NO:62); (ii) a Kabat-defined heavy chain CDR2 comprising, or consisting of, the following amino acid sequence: YIYPNDGDTNYNQKFKG (SEQ ID NO:63); and/or (iii) a Kabat-defined heavy chain CDR3 comprising, or consisting of, the following amino acid sequence: PYYSDYGMDY (SEQ ID NO:64).

The anti-mouse C5a antibody can contain a heavy chain constant region. In some embodiments, an anti-mouse C5a antibody described herein can contain an amino-terminal signal peptide, e.g., a signal peptide comprising, or consisting of, the following amino acid sequence: MGWSCIILFL-VATATGVHS (SEQ ID NO:65).

In some embodiments, an anti-mouse C5a antibody described herein can contain a heavy chain polypeptide comprising, or consisting of, the following amino acid sequence: LEVQLQQSGPELVKPGASVKISCKASGYT-FTDYYYINWVKQSHGKSLEWIGYIYP NDGDTNYN-QKFKGKATLTVDKSSSTAYMELRSLTSEDSAVYY-CARPYYSDYGM DYWGQGTSVTVSS (SEQ ID NO:66) or MGWSCIILFLVATATGVHSLEVQLQQSGPELVKP-GASVKISCKASGYTFTDYYYI NWVKQSHGKSLEWI-GYIYPNDGDTNYNQKFKGKATLTVDKSSSTAYMEL-RSLT SEDSAVYYCARPYYSDYGMDYWGQGTSVTVSS (SEQ ID NO:67). In some embodiments, an anti-mouse C5a antibody described herein contains a heavy chain polypeptide comprising amino acids 2 to 121 of SEQ ID NO:66. In some embodiments, an anti-mouse C5a antibody described herein contains a heavy chain polypeptide comprising amino acids 1 to 19 and 21 to 140 of SEQ ID NO:67. In some embodiments, an anti-mouse C5a antibody described herein contains a heavy chain constant region polypeptide comprising one or more amino acid substitutions from the above described sequence.

In some embodiments, an anti-mouse C5a antibody described herein contains a light chain polypeptide comprising: (i) a light chain CDR1 comprising, or consisting of, the amino acid sequence depicted in SEQ ID NO:54; (ii) a light chain CDR2 comprising, or consisting of, the amino acid sequence depicted in SEQ ID NO:55; and (iii) a light chain CDR3 comprising, or consisting of, the amino acid sequence depicted in SEQ ID NO:56; (iv) a heavy chain CDR1 comprising, or consisting of, the amino acid sequence depicted in SEQ ID NO:62; (v) a heavy chain CDR2 comprising, or consisting of, the amino acid sequence depicted in SEQ ID NO:63; and/or (vi) a heavy chain CDR3 comprising, or consisting of, the amino acid sequence depicted in SEQ ID NO:64.

In some embodiments, an anti-mouse C5a antibody described herein contains a light chain polypeptide comprising, or consisting of, the amino acid sequence depicted in SEQ ID NO:59 and a heavy chain polypeptide comprising, or consisting of, the amino acid sequence depicted in SEQ ID NO:66.

In some embodiments, an anti-C5a antibody described herein can bind to human C5a and to mouse C5a.

Methods for Producing the Anti-C5a Antibodies and Antigen-Binding Fragments Thereof The disclosure also features methods for producing any of the anti-C5a antibodies or antigen-binding fragments thereof described herein. In some embodiments, methods for preparing an antibody described herein can include immunizing a subject (e.g., a non-human mammal) with an appropriate immunogen. Suitable immunogens for generating any of the antibodies described herein are set forth herein. For example, to generate an antibody that binds to C5a, a skilled artisan can immunize a suitable subject (e.g., a non-human mammal such as a rat, a mouse, a gerbil, a hamster, a dog, a cat, a pig, a goat, a horse, or a non-human primate) with a full-length C5a polypeptide such as a full-length C5a polypeptide comprising the amino acid sequence depicted in SEQ ID NO: 1 or the desarginated form of C5a (e.g., the human C5a desarg comprising the amino acid sequence depicted in SEQ ID NO:2). In some embodiments, the non-human mammal is C5 deficient, e.g., a C5-deficient mouse described in, e.g., Levy and Ladda (1971) *Nat New Biol* 229(2):51-52; Crocker et al. (1974) *J Clin Pathol* 27(2):122-124; Wetsel et al. (1990) *J Biol Chem* 265:2435-2440; and Jungi and Pepys (1981) *Immunology* 43(2):271-279. Human C5a can be purified from human serum as described in, e.g., McCarthy and Henson (1979) *J Immunol* 123(6):2511-2517 and Manderino et al. (1982) *J Immunol Methods* 53(1):41-50. See also the working examples. Human C5a can also be generated in vitro as described in, e.g., Vallota and Müller-Eberhard (1973) *J Exp Med* 137: 1109. Purified human C5a is also commercially available from, e.g., Complement Technology, Inc. (catalog number A144; Tyler, Tex.). Recombinant C5a can also be generated by one of ordinary skill in the art as described in, e.g., Tothe et al. (1994) *Prot Sci* 3:1159-1168.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) *Autoimmunity* 31(1):15-24. See also, e.g., Lodmell et al. (2000) *Vaccine* 18:1059-1066; Johnson et al. (1999) *J Med Chem* 42:4640-4649; Baldridge et al. (1999) *Methods* 19:103-107; and Gupta et al. (1995) *Vaccine* 13(14): 1263-1276.

In some embodiments, the methods include preparing a hybridoma cell line that secretes a monoclonal antibody that binds to the immunogen. For example, a suitable mammal such as a laboratory mouse is immunized with a C5a polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies, e.g., an antibody that binds to C5a and inhibits the interaction between C5a and a C5a receptor (e.g., C5aR1).

In some embodiments, a skilled artisan can identify an anti-C5a antibody from a non-immune biased library as described in, e.g., U.S. Pat. No. 6,300,064 (to Knappik et al.; Morphosys AG) and Schoonbroodt et al. (2005) *Nucleic Acids Res* 33(9):e81.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) *JMB* 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with C5a polypeptide as described above. mRNA can be isolated from the cells and converted to cDNA using standard molecular biology techniques. See, e.g., Sambrook et al. (1989) "Molecular Cloning: A Laboratory Manual, $2^{nd}$ Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some embodiments, require use of a helper phage. In some embodiments, no helper phage is required (see, e.g., Chasteen et al. (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

In some embodiments, the immobilized phage are the phage of interest. Accordingly, the unbound phage are removed by washing the support. Following the wash step, bound phage are then eluted from the solid support, e.g., using a low pH buffer or a free target antigen competitor, and recovered by infecting bacteria. In some embodiments, the phage that are not immobilized are the phage of interest. In such embodiments, the population of phage can be contacted to the antigen two or more times to deplete from the population any of the phage that bind to the support. Unbound phage are then collected and used for subsequent screening steps.

To enrich the phage population for phage particles that contain antibodies having a higher affinity for the target antigen (while reducing the proportion of phage that may bind to the antigen non-specifically), the eluted phage (described above) can be used to re-infect a population of bacterial host cells. The expressed phage are then isolated from the bacteria and again contacted to a target antigen. The concentration of antigen, pH, temperature and inclusion of detergents and adjuvants during contact can be modulated to enrich for higher affinity antibody fragments. The unbound phage are removed by washing the solid support. The number or cycles, duration, pH, temperature and inclusion of detergents and adjuvants during washing can also be modulated to enrich for higher affinity antibody fragments. Following the wash step, bound phage are then eluted from the solid support. Anywhere from one to six iterative cycles of panning may be used to enrich for phage containing antibodies having higher affinity for the target antigen. In some embodiments, a deselection step can also be performed in conjunction with any of the panning approaches described herein.

Individual phage of the population can be isolated by infecting bacteria and then plating at a density to allow formation of monoclonal antibodies.

For example, to identify using phage display techniques an antibody that binds to C5a, but not to C5, the following panning approach can be employed. The population can first be contacted to a surface containing bound native, full-length human C5. The process can be repeated two or more times, each time collecting the unbound phage. The population can also be contacted to a solid support containing surface-bound C4 and/or C3 proteins. Unbound phage from the foregoing steps are then contacted to a surface containing bound C5a or desarginated C5a. Phage that bind to C5a are eluted from the surface and recovered by infecting bacteria. Iterative rounds of phage selection may be performed. After one to six rounds of selection, individual recovered phagemid can be screened for expression of antibody fragments with the desired specificity and affinity.

A subpopulation of antibodies screened using the above methods can be characterized for their specificity and binding affinity for a particular immunogen (e.g., C5a) using any immunological or biochemical based method known in the art. For example, specific binding of an antibody to C5a, as compared to native, full-length C5, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbant assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

Antibodies can also be assayed using any SPR-based assays known in the art for characterizing the kinetic parameters of the interaction of the antibody with C5a. Any SPR instrument commercially available including, but not limited to, BIAcore Instruments (Biacore AB; Uppsala, Sweden); 1Asys instruments (Affinity Sensors; Franklin, Mass.); IBIS system (Windsor Scientific Limited; Berks, UK), SPR-CELLIA systems (Nippon Laser and Electronics Lab; Hokkaido, Japan), and SPR Detector Spreeta (Texas Instruments; Dallas, Tex.) can be used in the methods described herein. See, e.g., Mullett et al. (2000) *Methods* 22: 77-91; Dong et al. (2002) *Reviews in Mol Biotech* 82: 303-323;

Fivash et al. (1998) *Curr Opin Biotechnol* 9: 97-101; and Rich et al (2000) *Curr Opin Biotechnol* 11: 54-61.

It is understood that the above methods can also be used to determine if, e.g., an anti-C5a antibody does not bind to full-length, native C5, C3, and/or C4 proteins. The above methods can also be used to determine if an antibody that binds to C5a also inhibits the interaction between C5a and a C5a receptor. The above methods can also be used to determine if an antibody that binds to C5a also inhibits the activity of C5a.

As described in the above references, after phage selection, the antibody coding regions from the phage can be isolated and used to generate whole antibodies, including human antibodies, or any desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication no. WO 92/22324; Mullinax et al. (1992) *BioTechniques* 12(6):864-869; and Sawai et al. (1995) *Am J Repr Immunol* 34:26-34; and Better et al. (1988) *Science* 240:1041-1043. Examples of techniques which can be used to produce single-chain Fvs and antibodies include those described in U.S. Pat. Nos. 4,946,778 and 5,258,498; Huston et al. (1991) *Methods in Enzymology* 203:46-88; Shu et al. (1993) *Proc Nat Acad Sci USA* 90:7995-7999; and Skerra et al. (1988) *Science* 240:1038-1040.

Phage display technology can also be used to, e.g., increase the affinity of an antibody for its cognate antigen. The technology, referred to as affinity maturation, can employ mutagenesis or CDR walking and re-selection to identify antibodies that bind with higher affinity to an antigen as compared to the initial or parental antibody. See, e.g., Glaser et al. (1992) *J Immunol* 149:3903-3913. Libraries can be constructed consisting of a pool of variant clones, each differing by one or more amino acid substitutions. Mutants with increased binding affinity for the antigen can be selected for by contacting the immobilized mutants with labeled antigen or any combination of methods described above. Any screening method known in the art can be used to identify mutant antibodies with increased affinity to the antigen (e.g., SPR or ELISA techniques).

In some embodiments, epitope mapping can be used to identify, e.g., the region of C5a that interacts with an antibody, e.g., a region of C5a that binds to C5aR1. Methods for identifying the epitope to which a particular antibody binds are also known in the art and are described above.

The antibodies and fragments thereof identified herein can be or can be made "chimeric." Chimeric antibodies and antigen-binding fragments thereof comprise portions from two or more different species (e.g., mouse and human). Chimeric antibodies can be produced with mouse variable regions of desired specificity fused to human constant domains (for example, U.S. Pat. No. 4,816,567). In this manner, non-human antibodies can be modified to make them more suitable for human clinical application (e.g., methods for treating or preventing a complement-mediated disorder in a subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent frameworks or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which the CDR region amino acid residues of the non-human antibody (e.g., mouse, rat, rabbit, or non-human primate antibody) having the desired specificity, affinity, and binding capacity are grafted onto the framework scaffold of a human antibody. Additional humanization methods are described below in the working examples.

Methods for grafting CDR sequences from a donor antibody (e.g., a non-human antibody) to the framework regions of an acceptor antibody (e.g., a human antibody) are well known in the art and are described in, e.g., Jones et al. (1986) *Nature* 321:522-525; Verhoeyen et al. (1988) *Science* 239 (4847):1534-1536; Riechmann et al. (1988) *Nature* 332: 323-327; Queen et al. (1989) *Proc Natl Acad Sci USA* 86:10029-10033; PCT publication no. WO 93/011237; Kettleborough et al. (1991) *Protein Engineering, Design and Selection* 4:773-783; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; and Borrebaek (1995) "Antibody Engineering," $2^{nd}$ Edition, Oxford University Press, NY, Oxford. For example, CDRs from a donor antibody can be grafted onto framework regions of an acceptor antibody using overlap extension polymerase chain reaction (PCR) techniques as described in, e.g., Daugherty et al. (1991) *Nucleic Acids Res* 19(9):2471-2476; Roguska et al. (1996) *Protein Engineering* 9(10):895-904; and Yazaki et al. (2004) *Protein Engineering, Design & Selection* 17(5):481-489.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

In some instances, one or more framework region amino acid residues of the human immunoglobulin are also replaced by corresponding amino acid residues of the non-human antibody (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human immunoglobulin sequences, preferably human germline sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. See, e.g., Jakobovits et al. (1993) *Proc Natl Acad Sci USA* 90:2551; Jakobovits et al. (1993) *Nature* 362:255-258; Bruggemann et al. (1993) *Year in Immunol.* 7:33; and Duchosal et al. (1992) *Nature* 355: 258. Transgenic mouse strains can be engineered to contain gene sequences from unrearranged human immunoglobulin genes. One example of such a mouse is the HuMAb Mouse® (Medarex, Inc.), which contains human immunoglobulin transgene miniloci that encode unrearranged human µ heavy and κ light chain immunoglobulin sequences, together with targeted mutations that inactivate the endogenous µ and κ chain loci. See, e.g., Lonberg, et al. (1994) *Nature* 368 (6474):856-859. The preparation and use of HuMab mice, and the genomic modifications carried by such mice, are further described in Taylor et al. (1992) *Nucleic Acids Res* 20:6287-6295; Chen, J. et al. (1993) *International Immunology* 5: 647-656; Tuaillon et al. (1993) *Proc Natl Acad Sci USA* 90:3720-3724; Choi et al. (1993) *Nature Genetics* 4:1 17-123; Tuaillon et al. (1994) *J Immunol* 152:2912-2920; Taylor et al. (1994) *International Immunology* 6:579-591; and Fishwild et al. (1996) *Nature Biotechnol* 14:845-851. An alternative transgenic mouse system for expressing human immunoglobulin genes is referred to as the Xenomouse (Abgenix, Inc.) and is described in, e.g., U.S. Pat. Nos. 6,075,181; 6,114,598; 6,150,584; and 6,162,963. Like the HuMAb Mouse® system, the Xenomouse system involves disruption of the endogenous mouse heavy and light chain genes and insertion into the genome of the mouse transgenes carrying unrearranged human heavy and light chain immunoglobulin loci that contain human variable and constant region sequences. Other systems known in the art for expressing human immunoglobulin genes include the KM Mouse® system, described in detail in PCT Publication WO 02/43478 and the TC mouse system described in Tomizuka et al. (2000) *Proc Natl Acad Sci USA* 97:722-727.

The human sequences may code for both the heavy and light chains of human antibodies and would function correctly in the mice, undergoing rearrangement to provide a wide antibody repertoire similar to that in humans. The transgenic mice can be immunized with the target protein immunogen to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be selected and screened for display of antibodies binding to a target.

In addition, the phage-display libraries screened above can include human antibodies (Hoogenboom et al. (1992) *J Mol Biol* 227:381; Marks et al. (1991) *J Mol Biol* 222:581-597; and Vaughan et al. (1996) *Nature Biotech* 14:309). Synthetic phage libraries can be created which use randomized combinations of synthetic human antibody V-regions. By selection on antigen, fully human antibodies can be made in which the V-regions are very human-like in nature. See, e.g., U.S. Pat. Nos. 6,794,132; 6,680,209; 4,634,666; and Ostberg et al. (1983) *Hybridoma* 2:361-367, the contents of each of which are incorporated herein by reference in their entirety.

For the generation of human antibodies, also see Mendez et al. (1998) *Nature Genetics* 15:146-156 and Green and Jakobovits (1998) *J Exp Med* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Publication Nos. 20030229905 A1, 20040010810 A1, 20040093622 A1, 20060040363 A1, 20050054055 A1, 20050076395 A1, and 20050287630 A1. See also International Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; and 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference in their entirety. See also European Patent No. 0 546 073 B1, International Patent Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res* 20: 6287; Chen et al. (1993) *Int Immunol* 5: 647; Tuaillon et al. (1993) *Proc Natl Acad Sci USA* 90: 3720-4; Choi et al. (1993) *Nature Genetics* 4: 117; Lonberg et al. (1994) *Nature* 368: 856-859; Taylor et al. (1994) *International Immunology* 6: 579-591; Tuaillon et al. (1995) *J. Immunol* 154: 6453-65; Fishwild et al. (1996) *Nature Biotechnology* 14: 845; and Tuaillon et al. (2000) *Eur J Immunol.* 10: 2998-3005, the disclosures of each of which are hereby incorporated by reference in their entirety.

In certain embodiments, de-immunized forms of the antibodies, or antigen-binding fragments described herein are provided. De-immunized antibodies or antigen-binding fragments thereof are antibodies that have been modified so as to render the antibody or antigen-binding fragment thereof non-immunogenic, or less immunogenic, to a given species. De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized antibodies described herein include de-immunized antigen-binding fragments, Fab, Fv, scFv, Fab' and F(ab')$_2$, monoclonal antibodies, murine antibodies, fully human antibodies, engineered antibodies (such as, for example, chimeric, single chain, CDR-grafted, humanized, and artificially selected antibodies), synthetic antibodies and semi-synthetic antibodies.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for C5a, the other one is for any other antigen.

Methods for making bispecific antibodies are within the purview of those skilled in the art. Traditionally, the recombinant production of bispecific antibodies is based on the co-expression of two immunoglobulin heavy-chain/light-chain pairs, where the two heavy chain/light-chain pairs have different specificities (Milstein and Cuello (1983) *Nature* 305:537-539). Antibody variable domains with the desired binding specificities (antibody-antigen combining sites) can be fused to immunoglobulin constant domain sequences. The fusion of the heavy chain variable region is preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; PCT Publication No. WO 96/27011; Brennan et al. (1985) *Science* 229:81; Shalaby et al., *J Exp Med* (1992) 175:217-225; Kostelny et al. (1992) *J Immunol* 148(5):1547-1553; Hollinger et al. (1993) *Proc Natl Acad Sci USA* 90:6444-6448; Gruber et al. (1994) *J Immunol* 152:5368; and Tutt et al. (1991) *J Immunol* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng.* 8(10):1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific.

Antibodies with more than two valencies (e.g., trispecific antibodies) are contemplated and described in, e.g., Tutt et al. (1991) *J Immunol* 147:60.

The disclosure also embraces variant forms of multispecific antibodies such as the dual variable domain immunoglobulin (DVD-Ig) molecules described in Wu et al. (2007) *Nat Biotechnol* 25(11): 1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain $C_H1$ and Fc region. Methods for making DVD-Ig molecules from two parent antibodies are further described in, e.g., PCT Publication Nos. WO 08/024188 and WO 07/024715.

The disclosure also provides camelid or dromedary antibodies (e.g., antibodies derived from *Camelus bactrianus, Camelus dromedarius,* or *lama pacos*). Such antibodies, unlike the typical two-chain (fragment) or four-chain (whole antibody) antibodies from most mammals, generally lack light chains. See U.S. Pat. No. 5,759,808; Stijlemans et al.

(2004) *J Biol Chem* 279:1256-1261; Dumoulin et al. (2003) *Nature* 424:783-788; and Pleschberger et al. (2003) *Bioconjugate Chem* 14:440-448. Engineered libraries of camelid antibodies and antibody fragments are commercially available, for example, from Ablynx (Ghent, Belgium). As with other antibodies of non-human origin, an amino acid sequence of a camelid antibody can be altered recombinantly to obtain a sequence that more closely resembles a human sequence, i.e., the nanobody can be "humanized" to thereby further reduce the potential immunogenicity of the antibody.

In some embodiments, the anti-C5a antibodies described herein comprise an altered heavy chain constant region that has reduced (or no) effector function relative to its corresponding unaltered constant region. Effector functions involving the constant region of the anti-C5a antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-C5a antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-C5a antibody described herein comprising an altered constant region displaying reduced ADCC and/or CDC may exhibit reduced or no ADCC and/or CDC activity as exemplified herein.

In certain embodiments, the altered constant region has at least one amino acid substitution, insertion, and/or deletion, compared to a native sequence constant region or to the unaltered constant region, e.g. from about one to about one hundred amino acid substitutions, insertions, and/or deletions in a native sequence constant region or in the constant region of the parent polypeptide. In some embodiments, the altered constant region herein will possess at least about 70% homology (similarity) or identity with the unaltered constant region and in some instances at least about 75% and in other instances at least about 80% homology or identity therewith, and in other embodiments at least about 85%, 90% or 95% homology or identity therewith. The altered constant region may also contain one or more amino acid deletions or insertions. Additionally, the altered constant region may contain one or more amino acid substitutions, deletions, or insertions that results in altered post-translational modifications, including, for example, an altered glycosylation pattern (e.g., the addition of one or more sugar components, the loss of one or more sugar components, or a change in composition of one or more sugar components relative to the unaltered constant region).

Antibodies with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, $2^{nd}$ Edition," Cold Spring Harbor Laboratory Press, Cold Spring Harbor, N.Y.; Harlow and Lane (1988), supra; Borrebaek (1992), supra; Johne et al. (1993), supra; PCT publication no. WO 06/53301; and U.S. Pat. No. 7,704,497.

In some embodiments, an anti-C5a antibody described herein exhibits reduced or no effector function. In some embodiments, an anti-C5a antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In addition to using a G2/G4 construct as described above, an anti-C5a antibody described herein having reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. Thus, in some embodiments, an anti-C5a antibody with one or more mutations within the constant region including the Ala-Ala mutation has reduced or no effector function. According to these embodiments, the constant region of the antibody can comprise a substitution to an alanine at position 234 or a mutation to an alanine at position 235. Additionally, the altered constant region may contain a double mutation: a mutation to an alanine at position 234 and a second mutation to an alanine at position 235. In one embodiment, an anti-C5a antibody comprises an IgG4 framework, wherein the Ala-Ala mutation would describe a mutation(s) from phenylalanine to alanine at position 234 and/or a mutation from leucine to alanine at position 235. In another embodiment, the anti-C5a antibody comprises an IgG1 framework, wherein the Ala-Ala mutation would describe a mutation(s) from leucine to alanine at position 234 and/or a mutation from leucine to alanine at position 235. An anti-C5a antibody may alternatively or additionally carry other mutations, including the point mutation K322A in the CH2 domain (Hezareh et al. (2001) *J Virol* 75:12161-12168). An antibody with said mutation(s) in the constant region may furthermore be a blocking or non-blocking antibody.

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, an anti-C5a antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) *TIBTECH* 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) *Immunology* 89(4):573-578; Newkirk et al. (1996) *Clin Exp Immunol* 106(2):259-264. Differences in effector function may be related to the IgG's ability to bind to the Fcγ receptors (FcγRs) on the effector cells. Shields et al. have shown that IgG, with alterations in amino acid sequence that have improved binding to FcγR, can exhibit up to 100% enhanced ADCC using human effector cells. (2001) *J Biol Chem* 276(9):6591-6604. While these alterations include changes in amino acids not found at the binding interface, both the nature of the sugar component as well as its structural pattern may also contribute to the differences observed. In addition, the presence or absence of fucose in the oligosaccharide component of an IgG can improve binding and ADCC. See, e.g., Shields et al. (2002) *J Biol Chem* 277(30):26733-26740. An IgG that lacked a fucosylated carbohydrate linked to Asn$^{297}$ exhibited normal receptor binding to the FcγRI receptor. In contrast, binding to the FcγRIIIA receptor was improved 50-fold and accompanied by enhanced ADCC, especially at lower antibody concentrations.

Shinkawa et al. demonstrated that an antibody to the human IL-5 receptor produced in a rat hybridoma showed more than 50% higher ADCC when compared to the antibody produced in Chinese hamster ovary cells (CHO) (Shinkawa et al. (2003) *J Biol Chem* 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

A different approach was taken by Umana et al. who changed the glycosylation pattern of chCE7, a chimeric IgG1 anti-neuroblastoma antibody. (1999) *Nat Biotechnol* 17(2):176-180). Using tetracycline, they regulated the activity of a glycosyltransferase enzyme (GnTIII) which bisects oligosaccharides that have been implicated in ADCC activity. The ADCC activity of the parent antibody was barely above background level. Measurement of ADCC activity of the chCE7 produced at different tetracycline levels showed an optimal range of GnTIII expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation and showed that antibodies produced in this cell line were incapable of complement-mediated cytolysis. (1994) *J Exp Med* 180:1087-1096. Thus, as known alterations that affect effector function include modifications in the glycosylation pattern or a change in the number of glycosylated residues, the present disclosure relates to an anti-C5a antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for altering the effector function of antibodies. For example, antibody-producing cells can be hypermutagenic, thereby generating antibodies with randomly altered polypeptide residues throughout an entire antibody molecule. See, e.g., PCT publication no. WO 05/011735. Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s). Additional details of molecular biology techniques useful for preparing an antibody or antigen-binding fragment thereof described herein are set forth below.

Recombinant Antibody Expression and Purification

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the antibodies and fragments thereof can be isolated. The term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, $3^{rd}$ edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, endotoxin can be removed from the antibodies or fragments. Methods for removing endotoxin from a protein sample are known in the art and exemplified in the working examples. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Mirus), or Acrodisc™-Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000 Chromogenic kit (BioWhittaker), the limulus amebocyte lysate (LAL)-based kits such as the Pyrotell®, Pyrotell®-T, Pyrochrome®, Chromo-LAL, and CSE kits available from the Associates of Cape Cod Incorporated.

While in no way intended to be limiting, exemplary methods for generating the antibodies described herein are set forth in the working Examples.

Modification of the Antibodies or Antigen-Binding Fragments Thereof

The antibodies or antigen-binding fragments thereof can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO:50)), polyhistidine (6-His; HHHHHH (SEQ ID NO:81), hemagglutinin (HA; YPYDVPDYA (SEQ ID NO:82)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2): 110-119). The stabilization moiety can improve the stability, or retention of, the antibody (or fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(1:2717-2723; and Co et al. (1993) *Mol Immunol* 30:1361.

Pharmaceutical Compositions

Compositions containing an antibody or an antigen-binding fragment thereof described herein can be formulated as a pharmaceutical composition, e.g., for administration to a subject for the treatment or prevention of a complement-associated disorder. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66: 1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing an antibody or fragment intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The compositions can be formulated as a solution, microemulsion, dispersion, liposome, or other ordered structure suitable for stable storage at high concentration. Sterile injectable solutions can be prepared by incorporating an antibody (or a fragment of the antibody) described herein in the required amount in an appropriate solvent with one or a combination of ingredients enumerated above, as required, followed by filtered sterilization. Generally, dispersions are prepared by incorporating an antibody or fragment described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of an antibody, or an antigen-binding fragment thereof, described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The anti-C5a antibodies, or antigen-binding fragments thereof, described herein can also be formulated in immunoliposome compositions. Liposomes containing the antibody can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, an antibody or an antigen-binding fragment thereof can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, an antibody or antigen-binding fragment described herein can be formulated in a composition suitable for intrapulmonary administration (e.g., for administration via nebulizer; see below) to a mammal such as a human. Methods for preparing such compositions are well known in the art and described in, e.g., U.S. patent application publication no. 20080202513; U.S. Pat. Nos. 7,112,341 and 6,019,968; and PCT application publication nos. WO 00/061178 and WO 06/122257, the disclosures of each of which are incorporated herein by reference in their entirety. Dry powder inhaler formulations and suitable systems for administration of the formulations are described in, e.g., U.S. patent application publication no. 20070235029, PCT Publication No. WO 00/69887; and U.S. Pat. No. 5,997,848.

In some embodiments, an anti-C5a antibody or antigen-binding fragment thereof described herein can be formulated in a composition suitable for delivery to the eye. In some embodiments, one or more of the anti-C5a antibodies (or antigen-binding fragments thereof) described herein can be administered locally, for example, by way of topical application or intravitreal injection. For example, in some embodiments, the anti-C5a antibodies can be formulated for administration by way of an eye drop.

The therapeutic preparation for treating the eye can contain one or more of the anti-C5a antibodies in a concentration from about 0.01 to about 1% by weight, preferably from about 0.05 to about 0.5% in a pharmaceutically acceptable solution, suspension or ointment. The preparation will preferably be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents.

Suitable preservatives for use in such a solution include benzalkonium chloride, benzethonium chloride, chlorobutanol, thimerosal and the like. Suitable buffers include, e.g., boric acid, sodium and potassium bicarbonate, sodium and potassium borates, sodium and potassium carbonate, sodium acetate, and sodium biphosphate, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, and sodium chloride.

Suitable antioxidants and stabilizers include sodium bisulfite, sodium metabisulfite, sodium thiosulfite, and thiourea. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The preparation can be administered topically to the eye of the subject in need of treatment (e.g., a subject afflicted with AMD) by conventional methods, e.g., in the form of drops, or by bathing the eye in a therapeutic solution, containing one or more anti-C5a antibodies.

In addition, a variety of devices have been developed for introducing drugs into the vitreal cavity of the eye. For example, U.S. patent application publication no. 20020026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. The device comprises an inner core containing an effective amount of a low solubility agent covered by a non-bioerodible polymer that is permeable to the low solubility agent. During operation, the low solubility agent permeates the bioerodible polymer cover for sustained release out of the device. Additional methods and devices (e.g., a transscleral patch and delivery via contact lenses) for delivery of a therapeutic agent to the eye are described in, e.g., Ambati and Adamis (2002) *Prog Retin Eye Res* 21(2): 145-151; Ranta and Urtti (2006) *Adv Drug Delivery Rev* 58(11):1164-1181; Barocas and Balachandran (2008) *Expert Opin Drug Delivery* 5(1):1-10(10); Gulsen and Chauhan (2004) *Invest Ophthalmol Vis Sci* 45:2342-2347; Kim et al. (2007) *Ophthalmic Res* 39:244-254; and PCT publication no. WO 04/073551, the disclosures of which are incorporated herein by reference in their entirety.

Nucleic acids encoding an antibody (or an antigen-binding fragment thereof) can be incorporated into a gene construct to be used as a part of a gene therapy protocol to deliver nucleic acids that can be used to express and produce agents within cells (see below). Expression constructs of such components may be administered in any therapeutically effective carrier, e.g., any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized (e.g., antibody conjugated), polylysine conjugates, gramicidin S, artificial viral envelopes or other such intracellular carriers, as well as direct injection of the gene construct or $CaPO_4$ precipitation (see, e.g., WO04/060407) carried out in vivo. (See also, "Ex vivo Approaches," below.) Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc. Natl. Acad. Sci. USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol.* 150:4104-4115; U.S. Pat. Nos. 4,868,116 and 4,980,286; PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989)*J Virol* 62:1963-1973.

In some embodiments, an antibody, or antigen-binding fragment thereof, described herein can be formulated with one or more additional active agents useful for treating or preventing a complement-associated disorder in a subject. Additional agents for treating a complement-associated disorder in a subject will vary depending on the particular disorder being treated, but can include, without limitation, an antihypertensive (e.g., an angiotensin-converting enzyme inhibitor), an anticoagulant, a corticosteroid (e.g., prednisone), or an immunosuppressive agent (e.g., vincristine or cyclosporine A). Examples of anticoagulants include, e.g., warfarin (Coumadin), heparin, phenindione, fondaparinux, idraparinux, and thrombin inhibitors (e.g., argatroban, lepirudin, bivalirudin, or dabigatran). An antibody or fragment thereof described herein can also be formulated with a fibrinolytic agent (e.g., ancrod, ϵ-aminocaproic acid, antiplasmin-$a_1$, prostacyclin, and defibrotide) for the treatment of a complement-mediated disorder. In some embodiments, an antibody can be formulated with a lipid-lowering agent such as an inhibitor of hydroxymethylglutaryl CoA reductase. In some embodiments, an antibody can be formulated with, or for use with, an anti-CD20 agent such as rituximab (Rituxan™; Biogen Idec, Cambridge, Mass.). In some embodiments, e.g., for the treatment of RA, the antibody or antigen-binding fragment thereof can be formulated with one or both of infliximab (Remicade®; Centocor, Inc.) and methotrexate (Rheumatrex®, Trexall®). In some embodiments, an antibody or an antigen-binding fragment thereof described herein can be formulated with a non-steroidal anti-inflammatory drug (NSAID). Many different NSAIDS are available, some over the counter including ibuprofen (Advil®, Motrin®, Nuprin®) and naproxen (Aleve®) and many others are available by prescription including meloxicam (Mobic®), etodolac (Lodine®), nabumetone (Relafen®), sulindac (Clinoril®), tolementin (Tolectin®), choline magnesium salicylate (Trilisate®), diclofenac (Cataflam®, Voltaren®, Arthrotec®), Diflunisal (Dolobid®), indomethacin (Indocin®), Ketoprofen (Orudis®, Oruvail®), oxaprozin (Daypro®), and piroxicam (Feldene®). In some embodiments an antibody or a fragment thereof can be formulated for use with an anti-hypertensive, an anti-seizure agent (e.g., magnesium sulfate), or an anti-thrombotic agent. Anti-hypertensives include, e.g., labetalol, hydralazine, nifedipine, calcium channel antagonists, nitroglycerin, or sodium nitroprussiate. See, e.g., Mihu et al. (2007) *J Gasrointestin Liver Dis* 16(4):419-424. Anti-thrombotic agents include, e.g., heparin, antithrombin, prostacyclin, or low dose aspirin.

In some embodiments, an antibody or antigen-binding fragment thereof can be formulated for administration to a subject along with intravenous gamma globulin therapy (IVIG), plasmapheresis, or plasma exchange. In some embodiments, an anti-C5a antibody or antigen-binding fragment thereof can be formulated for use before, during, or after, a kidney transplant.

When an antibody or antigen-binding fragment thereof is to be used in combination with a second active agent, the agents can be formulated separately or together. For example, the respective pharmaceutical compositions can be mixed, e.g., just prior to administration, and administered together or can be administered separately, e.g., at the same or different times (see below).

As described above, a composition can be formulated such that it includes a therapeutically effective amount of an anti-C5a antibody or antigen-binding fragment thereof described herein. In some embodiments, a composition can be formulated to include a sub-therapeutic amount of the antibody (or fragment) and a sub-therapeutic amount of one or more additional active agents such that the components in total are therapeutically effective for treating or preventing a complement-associated disorder. Methods for determining a therapeutically effective dose of an agent such as a therapeutic antibody are known in the art and described herein.

Applications

The antibodies, antigen-binding fragments thereof, conjugates, and compositions of any of the foregoing can be used in a number of diagnostic and therapeutic applications. For example, detectably-labeled anti-C5a antibodies (e.g., anti-human C5a antibodies or anti-mouse C5a antibodies) can be used in assays to detect the presence or amount of C5a present in a biological sample. Determining the amount of C5a in a sample, e.g., a patient blood sample, can be useful to evaluate the level of complement activation in the sample. Suitable methods for using the antibodies in diagnostic assays are known in the art and include, without limitation, ELISA, fluorescence resonance energy transfer applications, Western blot, and dot blot techniques. See, e.g., Sambrook et al., supra and Ausubel et al., supra.

In some embodiments, the antibodies and antigen-binding fragments described herein can be used as positive controls in assays designed to identify additional novel compounds for treating complement-mediated disorders. For example, an anti-C5a antibody that inhibits C5a activity can be used as a positive control in an assay to identify additional compounds (e.g., small molecules, aptamers, or antibodies) that inhibit C5a or C5a-dependent C5a receptor signaling.

In some embodiments, the cross-reactive anti-C5a antibodies or antigen-binding fragments thereof (e.g., cross-reactive with human C5a and, e.g., cynomolgus macaque C5a) described herein can be used for pre-clinical testing in non-human mammals, e.g., pharmacokinetic or pharmacodynamic studies in non-human primates. Accordingly, a researcher wishing to evaluate the efficacy of an anti-C5a antibody in treating a complement-associate disorder of interest (e.g., RA or sepsis) can use a cross-reactive anti-C5a antibody described herein in an appropriate non-human primate model of the disease. If the researcher, for example, establishes efficacy of the antibody in the non-human primate model, these results may provide sufficient proof-of-concept support for regulatory approval for use of the antibody in treating humans. Alternatively, or in addition, a researcher may administer the cross-reactive antibody to a non-human primate to study, e.g., antibody clearance and/or pharmacodynamics properties. Based on such studies using the cross-reactive antibody, the researcher can better approximate the dose required to treat human disease.

In some embodiments, the anti-mouse C5a antibodies or antigen-binding fragments thereof described herein, as well as antibodies that crossreact with human and mouse C5a, can be used as a surrogate antibody in mouse models of human disease. This can be especially useful where a humanized anti-human C5a antibody does not crossreact with mouse C5a and/or is likely to cause an anti-human antibody response in a mouse to which the humanized antibody is administered. Accordingly, a researcher wishing to study the effect of an anti-C5a antibody in treating a disease (e.g., ischemia-reperfusion injury) can use an anti-mouse C5a antibody described herein in an appropriate mouse model of the disease. If the researcher can establish efficacy in the mouse model of disease using the anti-mouse C5a antibody, the results may establish proof-of-concept for use of an anti-human C5a antibody in treating the disease in humans. The working examples disclose an exemplary study using an anti-mouse C5a antibody surrogate in a mouse model of RA establishing proof-of-concept for the use of an anti-human C5a antibody to treat RA in man.

The anti-C5a antibodies described herein can also be used in methods for purifying C5a from a sample (e.g., a biological sample). In some embodiments, an anti-C5a antibody can be immobilized on a solid phase support using methods well known in the art. A sample containing the antigen to be purified, in this case C5a, is contacted to the antibody on the solid support under conditions and for a time sufficient to allow the antigen to bind to the antibody. The solid support is then washed one or more times with a suitable buffer to remove unbound material. The solid support can be then contacted with a second buffer that results in the release of the antigen from the antibody. The released antigen is then collected and characterized (e.g., for purity and activity) using well known methods in the art.

The anti-C5a antibodies and antigen-binding fragments thereof described herein can also be used in therapeutic methods as elaborated on below.

Methods for Treatment

The above-described compositions are useful in, inter alia, methods for treating or preventing a variety of complement-associated disorders in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as silastic membranes, or fibers. The implant can be configured for sustained or periodic release of the composition to the subject. See, e.g., U.S. Patent Application Publication No. 20080241223; U.S. Pat. Nos.

5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, an anti-C5a antibody or antigen-binding fragment thereof is therapeutically delivered to a subject by way of local administration. As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

In some embodiments, an anti-C5a antibody or antigen-binding fragment thereof can be locally administered to a joint (e.g., an articulated joint). For example, in embodiments where the complement-associated disorder is arthritis, the complement inhibitor can be administered directly to a joint (e.g., into a joint space) or in the vicinity of a joint. Examples of intraarticular joints to which an anti-C5a antibody or antigen-binding fragment thereof can be locally administered include, e.g., the hip, knee, elbow, wrist, sternoclavicular, temporomandibular, carpal, tarsal, ankle, and any other joint subject to arthritic conditions. An anti-C5a antibody or antigen-binding fragment thereof can also be administered to bursa such as, e.g., acromial, bicipitoradial, cubitoradial, deltoid, infrapatellar, ischial, and any other bursa known in the art of medicine.

In some embodiments, an anti-C5a antibody or antigen-binding fragment thereof can be locally administered to the eye. As used herein, the term "eye" refers to any and all anatomical tissues and structures associated with an eye. The eye has a wall composed of three distinct layers: the outer sclera, the middle choroid layer, and the inner retina. The chamber behind the lens is filled with a gelatinous fluid referred to as the vitreous humor. At the back of the eye is the retina, which detects light. The cornea is an optically transparent tissue, which conveys images to the back of the eye. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

In some embodiments, an anti-C5a antibody or antigen-binding fragment thereof is administered to the posterior chamber of the eye. In some embodiments, an anti-C5a antibody or antigen-binding fragment thereof is administered intravitreally. In some embodiments, an anti-C5a antibody or antigen-binding fragment thereof is administered trans-sclerally.

In some embodiments, e.g., in embodiments for treatment or prevention of a complement-associated pulmonary disorder such as COPD or asthma, an anti-C5a antibody or antigen-binding fragment thereof described herein can also be administered to a subject by way of the lung. Pulmonary drug delivery may be achieved by inhalation, and administration by inhalation herein may be oral and/or nasal. Examples of pharmaceutical devices for pulmonary delivery include metered dose inhalers, dry powder inhalers (DPIs), and nebulizers. For example, an anti-C5a antibody or an antigen-binding fragment thereof can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TurboHaler® (AstraZeneca; London, England) the AIR® inhaler (Alkermes®; Cambridge, Mass.); Rotahaler® (GlaxoSmithKline; London, England); and Eclipse™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, an anti-C5a antibody or an antigen-binding fragment thereof can be intrapulmonarily administered by way of a metered dose inhaler. These inhalers rely on a propellant to deliver a discrete dose of a compound to the lungs. Examples of compounds administered by metered dose inhalers include, e.g., Atrovent® (Boehringer-Ingelheim; Ridgefield, Conn.) and Flovent® (GlaxoSmithKline). See also, e.g., U.S. Pat. Nos. 6,170,717; 5,447,150; and 6,095,141.

In some embodiments, an anti-C5a antibody or antigen-binding fragment thereof can be administered to the lungs of a subject by way of a nebulizer. Nebulizers use compressed air to deliver a compound as a liquefied aerosol or mist. A nebulizer can be, e.g., a jet nebulizer (e.g., air or liquid-jet nebulizers) or an ultrasonic nebulizer. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, the antibodies or antigen-binding fragments thereof provided herein are present in unit dosage form, which can be particularly suitable for self-administration. A formulated product of the present disclosure can be included within a container, typically, for example, a vial, cartridge, prefilled syringe or disposable pen. A doser such as the doser device described in U.S. Pat. No. 6,302,855 may also be used, for example, with an injection system of the present disclosure.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering the solution to a subject with as little pain as possible.

One medication delivery pen includes a vial holder into which a vial of insulin or other medication may be received. The vial holder is an elongate generally tubular structure with proximal and distal ends. The distal end of the vial holder includes mounting means for engaging a double-ended needle cannula. The proximal end also includes mounting means for engaging a pen body which includes a driver and dose setting apparatus. A disposable medication (e.g., a high concentration solution of an anti-C5a antibody or antigen-binding fragment thereof) containing vial for use with the prior art vial holder includes a distal end having a pierceable elastomeric septum that can be pierced by one end of a double-ended needle cannula. The proximal end of this vial includes a stopper slidably disposed in fluid tight engagement with the cylindrical wall of the vial. This medication delivery pen is used by inserting the vial of medication into the vial holder. A pen body then is connected to the proximal end of the vial holder. The pen body includes a dose setting apparatus for designating a dose of medication to be delivered by the pen and a driving apparatus for urging the stopper of the vial distally for a distance corresponding to the selected dose. The user of the pen mounts a double-ended needle cannula to the distal end of the vial holder such that the proximal point of the needle cannula pierces the septum on the vial. The patient then selects a dose and operates the pen to urge the stopper distally to deliver the selected dose. The dose selecting apparatus returns to zero upon injection of the selected dose. The patient then removes and discards the needle cannula, and keeps the medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above. Accordingly, a medication delivery pen generally has a drive mechanism for accurate dosing and ease of use.

A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user. See U.S. Pat. No. 6,192,891.

In some embodiments, the needle of the pen device is disposable and the kits include one or more disposable replacement needles. Pen devices suitable for delivery of the any one of the presently featured antibodies or antigen-binding fragments thereof are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, Molly™, manufactured by Scandinavian Health Ltd.

The present disclosure also presents controlled-release or extended-release formulations suitable for chronic and/or self-administration of a medication such as an anti-C5a antibody or an antigen-binding fragment thereof described herein. The various formulations can be administered to a patient in need of treatment with the medication as a bolus or by continuous infusion over a period of time.

In some embodiments, a high concentration anti-C5a antibody (or antigen-binding fragment thereof) described herein is formulated for sustained-release, extended-release, timed-release, controlled-release, or continuous-release administration. In some embodiments, depot formulations are used to administer the antibody to the subject in need thereof. In this method, the antibody is formulated with one or more carriers providing a gradual release of active agent over a period of a number of hours or days. Such formulations are often based upon a degrading matrix which gradually disperses in the body to release the active agent.

In some embodiments, a C5a-binding fragment (e.g., a single chain antibody, a diabody, or a Fab' fragment) of an anti-C5a antibody described herein is administered by way of intrapulmonary administration to a subject in need thereof. For example, a single chain antibody form of any of the anti-C5a antibodies described herein can be delivered by way of a nebulizer or an inhaler to a subject (e.g., a human) afflicted with a complement-associated pulmonary disorder such as asthma or COPD.

A suitable dose of an antibody or fragment thereof described herein, which dose is capable of treating or preventing a complement-associated disorder in a subject, can depend on a variety of factors including, e.g., the age, sex, and weight of a subject to be treated and the particular inhibitor compound used. For example, a different dose of a whole anti-C5a antibody may be required to treat a subject with RA as compared to the dose of a C5a-binding Fab' antibody fragment required to treat the same subject. Other factors affecting the dose administered to the subject include, e.g., the type or severity of the complement-mediated disorder. For example, a subject having RA may require administration of a different dosage of an anti-C5a antibody than a subject with AMD. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse).

An antibody described herein can be administered as a fixed dose, or in a milligram per kilogram (mg/kg) dose. In some embodiments, the dose can also be chosen to reduce or avoid production of antibodies or other host immune responses against one or more of the active antibodies in the composition. While in no way intended to be limiting, exemplary dosages of an antibody, such as an anti-C5a antibody include, e.g., 1-1000 µg/kg, 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, 0.100 mg/kg to 1 mg/kg, and 1-10 mg/kg. Exemplary dosages of an antibody or antigen-binding fragment thereof described herein include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, 8 mg/kg, and 20 mg/kg.

A pharmaceutical composition can include a therapeutically effective amount of an anti-C5a antibody or antigen-binding fragment thereof described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody or fragment thereof described herein can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of the complement-mediated disorder. For example, a therapeutically effective amount of an anti-C5a antibody can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the antibodies or fragments thereof described herein can further be evaluated in, e.g., Phase I dose escalation studies. See, e.g., van Gurp et al. (2008) *Am J Transplantation* 8(8): 1711-1718; Hanouska et al. (2007) *Clin Cancer Res* 13(2, part 1):523-531; and Hetherington et al. (2006) *Antimicrobial Agents and Chemotherapy* 50(10): 3499-3500.

The terms "therapeutically effective amount" or "therapeutically effective dose," or similar terms used herein are intended to mean an amount of an agent (e.g., an anti-C5a antibody or an antigen-binding fragment thereof) that will elicit the desired biological or medical response (e.g., an improvement in one or more symptoms of a complement-associated disorder). In some embodiments, a composition described herein contains a therapeutically effective amount of an antibody, or antigen-binding fragment thereof, which specifically binds to a neo-epitope present in C5a. In some embodiments, the composition contains any of the antibodies or antigen-binding fragments thereof described herein and one or more (e.g., two, three, four, five, six, seven, eight, nine, 10, or 11 or more) additional therapeutic agents such that the composition as a whole is therapeutically effective. For example, a composition can contain an anti-C5a antibody described herein and an immunosuppressive agent, wherein the antibody and agent are each at a concentration that when combined are therapeutically effective for treating or preventing a complement-associated disorder (e.g., a complement-associated inflammatory disorder such as COPD, asthma, sepsis, or RA) in a subject.

Toxicity and therapeutic efficacy of such compositions can be determined by known pharmaceutical procedures in cell cultures or experimental animals (e.g., animal models of any of the complement-mediated disorders described herein). Use of an anti-C5a antibody in an animal model of RA is exemplified in the working examples. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An antibody or antigen-binding fragment thereof that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. For an anti-C5a antibody described herein, the therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for complement-associated disorders. For example, the composition can be administered to a subject at the same time, prior to, or after, plasmapheresis, IVIG therapy, or plasma exchange. See, e.g., Appel et al. (2005) *J Am Soc Nephrol* 16:1392-1404. In some embodiments, the composition can be administered to a subject at the same time, prior to, or after, a kidney transplant.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-C5a antibody).

The term "preventing" is art-recognized, and when used in relation to a condition, is well understood in the art, and includes administration of a composition which reduces the frequency of, or delays the onset of, symptoms of a medical condition in a subject relative to a subject which does not receive the composition. Thus, prevention of a complement-associated disorder such as asthma includes, for example, reducing the extent or frequency of coughing, wheezing, or chest pain in a population of patients receiving a prophylactic treatment relative to an untreated control population, and/or delaying the occurrence of coughing or wheezing in a treated population versus an untreated control population, e.g., by a statistically and/or clinically significant amount.

As described above, the antibodies and biologically-active fragments described herein can be used to treat a variety of complement-associated disorders such as, but not limited to: rheumatoid arthritis (RA); lupus nephritis; ischemia-reperfusion injury; atypical hemolytic uremic syndrome (aHUS); typical or infectious hemolytic uremic syndrome (tHUS); dense deposit disease (DDD); paroxysmal nocturnal hemoglobinuria (PNH); multiple sclerosis (MS); macular degeneration (e.g., age-related macular degeneration (AMD)); hemolysis, elevated liver enzymes, and low platelets (HELLP) syndrome; sepsis; dermatomyositis; diabetic retinopathy; thrombotic thrombocytopenic purpura (TTP); spontaneous fetal loss; Pauci-immune vasculitis; epidermolysis bullosa; recurrent fetal loss; multiple sclerosis (MS); and traumatic brain injury. See, e.g., Holers (2008) *Immunological Reviews* 223:300-316 and Holers and Thurman (2004) *Molecular Immunology* 41:147-152. In some embodiments, the complement-mediated disorder is a complement-mediated vascular disorder such as, but not limited to, a cardiovascular disorder, myocarditis, a cerebrovascular disorder, a peripheral (e.g., musculoskeletal) vascular disorder, a renovascular disorder, a mesenteric/enteric vascular disorder, revascularization to transplants and/or replants, vasculitis, Henoch-Schönlein purpura nephritis, systemic lupus erythematosus-associated vasculitis, vasculitis associated with rheumatoid arthritis, immune complex vasculitis, Takayasu's disease, capillary leak syndrome, dilated cardiomyopathy, diabetic angiopathy, thoracic-abdominal aortic aneurysm, Kawasaki's disease (arteritis), venous gas embolus (VGE), and restenosis following stent placement, rotational atherectomy, and percutaneous transluminal coronary angioplasty (PTCA). (See, e.g., U.S. patent application publication no. 20070172483.) In some embodiments, the complement-associated disorder is myasthenia gravis, cold-agglutinin disease (CAD), paroxysmal cold hemoglobinuria (PCH), dermatomyositis, scleroderma, warm autoimmune hemolytic anemia, Graves' disease, Hashimoto's thyroiditis, type I diabetes, psoriasis, pemphigus, autoimmune hemolytic anemia (AIHA), idiopathic thrombocytopenic purpura (ITP), Goodpasture syndrome, antiphospholipid syndrome (APS), Degos disease, and catastrophic APS (CAPS).

In some embodiments, an anti-C5a antibody or antigen-binding fragment thereof described herein, alone or in combination with a second anti-inflammatory agent, can be used to treat an inflammatory disorder such as, but not limited to, RA (above), inflammatory bowel disease, sepsis (above), septic shock, acute lung injury, disseminated intravascular coagulation (DIC), or Crohn's disease. In some embodiments, the second anti-inflammatory agent can be one selected from the group consisting of NSAIDs, corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept.

In some embodiments, the complement-associated disorder is a complement-associated neurological disorder such as, but not limited to, amyotrophic lateral sclerosis (ALS), brain injury, Alzheimer's disease, and chronic inflammatory demyelinating neuropathy.

Complement-associated disorders also include complement-associated pulmonary disorders such as, but not limited to, asthma, bronchitis, a chronic obstructive pulmonary disease (COPD), an interstitial lung disease, α-1 anti-trypsin deficiency, emphysema, bronchiectasis, bronchiolitis obliterans, alveolitis, sarcoidosis, pulmonary fibrosis, and collagen vascular disorders.

In the case of complement-associated hemolytic disorders such as PNH, CAD, and PCH, a medical practitioner will appreciate that C5 fragment C5b (by way of the terminal complement complex) contributes significantly to the pathogenesis of these disorders. See, e.g., Kaplan (2002) *Curr Opin Investig Drugs* 3(7):1017-23; Hill (2005) *Clin Adv Hematol Oncol* 3:(1:849-50; and Rother et al. (2007) *Nature Biotechnology* 25(11):1256-1488. Accordingly, a medical practitioner may elect to administer one or more of the anti-C5a antibodies described herein in conjunction with one or more additional therapies for the hemolytic disorder such as a complement inhibitor that prevents formation of the C5b-9 terminal complement complex. In some embodiments of the methods described herein, the complement-associated disorder is not a complement-associated hemolytic disorder. In some embodiments, an anti-C5a antibody or an antigen-binding fragment thereof is administered to a subject to treat, prevent, or ameliorate at least one symptom of a complement-associated inflammatory response (e.g., the complement-associated inflammatory response aspect of a complement-associated disorder) in a subject. For example, an anti-C5a antibody described herein can be used to treat, prevent, and/or ameliorate one or more symptoms associated with a complement-associated inflammatory response such as graft rejection/graft-versus-host disease (GVHD), reperfusion injuries (e.g., following cardiopulmonary bypass or a tissue transplant), and tissue damage following other forms of traumatic injury such as a burn (e.g., a severe burn), blunt trauma, spinal injury, or frostbite. See, e.g., Park et al. (1999) *Anesth Analg* 99(1):42-48; Tofukuji et al. (1998) *J Thorac Cardiovasc Surg* 116(6): 1060-1068; Schmid et al. (1997) *Shock* 8(2):119-124; and Bless et al. (1999) *Am J Physiol* 276(1):L57-L63.

In some embodiments, an anti-C5a antibody or an antigen-binding fragment thereof described herein can be administered to a subject as a monotherapy. Alternatively, as described above, the antibody or fragment thereof can be administered to a subject as a combination therapy with another treatment, e.g., another treatment for a complement-associated disorder or a complement-associated inflammatory response. For example, the combination therapy can include administering to the subject (e.g., a human patient) one or more additional agents (e.g., anti-coagulants, anti-hypertensives, or anti-inflammatory drugs (e.g., steroids)) that provide a therapeutic benefit to a subject who has, or is at risk of developing, sepsis. In another example, the combination therapy can include administering to the subject one or more additional agents (e.g., an anti-IgE antibody, an anti-IL-4 antibody, an anti-IL-5 antibody, or an anti-histamine) that provide therapeutic benefit to a subject who has, is at risk of developing, or is suspected of having a complement-associated pulmonary disorder such as COPD or asthma. In some embodiments, an anti-C5a antibody and the one or more additional active agents are administered at the same time. In other embodiments, the anti-C5a antibody is administered first in time and the one or more additional active agents are administered second in time. In some embodiments, the one or more additional active agents are administered first in time and the anti-C5a antibody is administered second in time.

An anti-C5a antibody or an antigen-binding fragment thereof described herein can replace or augment a previously or currently administered therapy. For example, upon treating with an anti-C5a antibody or antigen-binding fragment thereof, administration of the one or more additional active agents can cease or diminish, e.g., be administered at lower levels. In some embodiments, administration of the previous therapy can be maintained. In some embodiments, a previous therapy will be maintained until the level of the anti-C5a antibody reaches a level sufficient to provide a therapeutic effect. The two therapies can be administered in combination.

Monitoring a subject (e.g., a human patient) for an improvement in a complement-associated disorder (e.g., sepsis, severe burn, RA, lupus nephritis, Goodpasture syndrome, or asthma), as defined herein, means evaluating the subject for a change in a disease parameter, e.g., an improvement in one or more symptoms of a given disorder. The symptoms of complement-associated disorders are well known in the art of medicine. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a complement-associated disorder described herein.

Therapeutic and Diagnostic Kits

The disclosure also features therapeutic and diagnostic kits containing, among other things, one or more of the anti-C5a antibodies, and/or antigen-binding fragments thereof, described herein. The therapeutic kits can contain, e.g., a suitable means for delivery of the antibody or antigen-binding fragment to a subject. In some embodiments, the means is suitable for subcutaneous delivery of the antibody or antigen-binding fragment thereof to the subject. The means can be, e.g., a syringe or an osmotic pump. That is, a therapeutic kit described herein can contain a syringe pre-filled with an anti-C5a antibody or antigen-binding fragment thereof (e.g., a pen device containing the antibody or fragment) described herein or the kit can contain a pump (e.g., an osmotic pump) and one or more disposable cassettes configured for use with the pump, the cassettes pre-filled with an anti-C5a antibody or antigen-binding fragment thereof described herein (e.g., prefilled with an aqueous solution containing the anti-C5a antibody or antigen-binding fragment thereof). In another example, the kit can contain a transscleral or implantable delivery device (e.g., a plug) that is pre-filled with (or otherwise contains) a solution containing an anti-C5a antibody or antigen-binding fragment thereof described herein.

In some embodiments, the means for delivering an anti-C5a antibody or antigen-binding fragment thereof is a pen device for drug delivery.

In some embodiments, the means is suitable for intrapulmonary delivery of the antibody or antigen-binding fragment thereof to a subject, e.g., for use in treatment or prevention of a complement-associated pulmonary disorder such as, but not limited to, COPD or asthma. Accordingly, the means can be, e.g., an oral or nasal inhaler (see above). The inhaler can be, e.g., a metered dose inhaler (MDI), dry powder inhaler (DPI), or a nebulizer. Such a kit can also, optionally, include instructions for administering (e.g., self-administration of) the anti-C5a antibody or antigen-binding fragment thereof to a subject.

The therapeutic kits can include, e.g., one or more additional active agents for treating or preventing a complement-associated disorder and/or ameliorating a symptom thereof. For example, therapeutic kits designed for use in treating or preventing a complement-associated pulmonary disorder can include one or more additional active agents including, but not limited to, another antibody therapeutic (e.g., an anti-IgE antibody, an anti-IL-4 antibody, or an anti-IL-5 antibody), a small molecule anti-IgE inhibitor (e.g., montelukast sodium), a sympathomimetic (e.g., albuterol), an antibiotic (e.g., tobramycin), a deoxyribonuclease (e.g., pulmozyme), an anticholinergic drug (e.g., ipratropium bromide), a corticosteroid (e.g., dexamethasone), a β-adrenoreceptor agonist, a leukotriene inhibitor (e.g., zileuton), a 5-lipoxygenase inhibitor, a phosphodiesterase (PDE) inhibitor, a CD23 antagonist, an IL-13 antagonist, a cytokine release inhibitor, a histamine H1 receptor antagonist, an anti-histamine, an anti-inflammatory agent (e.g., cromolyn sodium or any other anti-inflammatory agent known in the art or described herein), or a histamine release inhibitor.

In some embodiments, the means can be suitable for intraocular administration of an anti-C5a antibody, or an antigen-binding fragment thereof, described herein to a subject in need thereof, e.g., a subject afflicted with AMD or any other complement-associated ocular disorder. The means can be, e.g., a syringe, a trans-scleral patch, or even a contact lens containing the antibody or fragment. The means can, in some embodiments, be an eye dropper, wherein the anti-C5a antibody or antigen-binding fragment thereof is formulated for such administration. Such therapeutic kits can also include, e.g., one or more additional therapeutic agents for use in treating complement-associated disorder of the eye. The therapeutic agents can be, e.g., bevacizumab or the Fab fragment of bevacizumab, ranibizumab, both sold by Roche Pharmaceuticals, Inc., or pegaptanib sodium (Mucogen®; Pfizer, Inc.). Such a kit can also, optionally, include instructions for administering the anti-C5a antibody or antigen-binding fragment thereof to a subject.

In some embodiments, the means can be suitable for intraarticular administration of an anti-C5a antibody, or antigen-binding fragment thereof, described herein to a subject in need thereof, e.g., a subject afflicted with RA. The means can be, e.g., a syringe or a double-barreled syringe. See, e.g., U.S. Pat. Nos. 6,065,645 and 6,698,622. A double-barreled syringe is useful for administering to a joint two different compositions with only one injection. Two separate syringes may be incorporated for use in administering the therapeutic while drawing off knee fluid for analysis (tapping) in a push-pull fashion. Additional therapeutic agents that can be administered with the anti-C5a antibodies or fragments in conjunction with the double-barreled syringe, or which can otherwise be generally included in the therapeutic kits described herein, include, e.g., NSAIDs, corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept. Such a kit can also, optionally, include instructions for administering the anti-C5a antibody or antigen-binding fragment thereof to a subject. It will be appreciated that the disclosure embraces kits comprising one or more of the anti-C5a antibodies described herein and one or more anti-inflammatory agents selected from the group consisting of NSAIDs, corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept. The antibodies and agents can be, e.g., formulated separately or together. The kits can be used to treat an inflammatory condition such as RA, Crohn's disease, inflammatory bowel disease, or any other inflammatory disorder known in the art or recited herein.

Also featured are diagnostic kits containing the anti-C5a antibodies or antigen-binding fragments thereof described herein. For example, the kits can contain a detectably-labeled form of an anti-C5a antibody (e.g., an anti-C5a antibody or an anti-mouse C5a antibody) described herein for use in detecting or quantitating the amount of C5a in a biological sample. In some embodiments, the kits can contain isolated C5a protein (e.g., one or both of human and mouse C5a protein) and/or a control sample comprising one or both of human and mouse C5a protein. In some embodiments, the kit contains a multi-well plate coated with a first anti-C5a antibody having a first specificity. The kit also contains a second anti-C5a antibody (e.g., a detectably-labeled second anti-C5a antibody) having a second specificity. Such a kit is designed for use in capturing, with the first antibody bound to the plate, C5a protein (e.g., human C5a protein) in a sample (e.g., a biological sample) contacted to the plate and then detecting the captured C5a protein using the second antibody. In some embodiments, diagnostic kits include both an anti-mouse C5a antibody and an anti-human C5a antibody described herein. In some embodiments, the diagnostic kits include an anti-C5a antibody that binds to both mouse C5a and human C5a.

The following examples are intended to illustrate, not limit, the invention.

EXAMPLES

Example 1

Immunization Methods

The presently described anti-C5a antibodies are humanized forms of murine antibodies generated under the following immunization protocol. Immunizations to raise antibodies against human desarginated C5a were performed on four mice including two mice of the strain DBA/2J and two mice of the strain A/J. These strains were selected because they carry the allele Hc⁰, which makes them deficient in endogenous C5. All immunizations were repeated at 14 day intervals for a total of three immunizations. All animals received a subcutaneous booster immunization of approximately 50 µg of purified C5a in 200 µL of adjuvant emulsion approximately 14 days after the last immunization and 5 to 7 days before harvesting. Titering of serum from immunized mice, using an ELISA assay, showed that the mice exhibited a strong antibody response against the human desarginated C5a immunogen.

Example 2

Determining the Specificity of the Mouse Antibodies for Human C5a

A subset of five mouse anti-human C5a Fabs that were representative of neoepitope selective Fabs were converted to full length mouse IgG2a antibodies designated as—5an048ME, 5an101ME, 5an178ME, 5an179ME, and 5an180ME. These antibodies were evaluated for specificity using Biolayer Interferometry on an Octet (ForteBio Inc.). (The amino acid sequences of the light chain and heavy chain CDR sets of each antibody, as defined by Kabat, are set forth in Table 3.) Briefly, human C5a, human C5a des Arg, human full-length C5, or C5a paralogs human C3a and human C4a were conjugated to biotin at a stoichiometry of <1(biotin):1 (antibody) through amine groups and immobilized on a streptavidin tip. Loaded tips were then exposed to a solution containing 20 nM of anti-C5a IgG antibody. Each of the antibodies bound to C5a and desarginated C5a. None of the anti-C5a IgG antibodies bound to C3a or to C4a. However, 5an178ME and 5an179ME each bound to full-length human C5. A small amount of binding was observed between 5an048ME and full-length human C5. However, the binding of 5an048ME to C5 was much less than the binding observed to C5a.

These results confirmed that mouse anti-human C5a antibodies—5an048ME, 5an101ME, and 5an180ME—bound to a neoepitope on C5a that was occluded in native, full-length C5 or generated after the cleavage of C5 into fragments C5a and C5b. The results also indicated that the three antibodies were selective for human C5a as compared to paralogs C3a or C4a.

TABLE 3

Amino Acid Sequences for Five Murine Anti-Human C5a Antibodies

| Ab | SIN | Description | Amino Acid Sequence |
|---|---|---|---|
| 5an048 ME | 151 | V_L Amino Acid Sequence | EIVLTQSPAIMSASPGEKVTMTCRASSSVSSS YLHWYQQKSGASPKLWIYSTSNLASGVPAR FSGSGSGTSYSLTISSVEAEDAATYYCQQYS GYPLTFGGGTKLEIKR |
|  | 140 | Light Chain CDR1 | RASSSVSSSYLH |
|  | 96 | Light Chain CDR2 | STSNLAS |
|  | 142 | Light Chain CDR3 | QQYSGYPLT |
|  | 152 | V_H Amino Acid Sequence | EVRLQQSGPELVKPGASVRISCKASGYTFN DYYYMNWVKQSHGKSLEWIGYIFPKTGGT HYNQRFKGKATLTVDKSSSTAYMELRSLTS EDSAVYYCASGPFAYWGQGTLVTVSA |
|  | 115 | Heavy Chain CDR1 | DYYYMN |
|  | 144 | Heavy Chain CDR2 | YIFPKTGGTHYNQRFKG |
|  | 117 | Heavy Chain CDR3 | GPFAY |
| 5an101 ME | 153 | V_L Amino Acid Sequence | DIVMTQSPASLAVSLGQRATISCRASESVDS YGNSFMHWYQQKPGQPPKLLIYRASNLESG IPARFSGSGSRTDFTLTINPVEADDVATYYC QQSNEDPYTFGGGTKLEIKR |
|  | 20 | Light Chain CDR1 | RASESVDSYGNSFMH |
|  | 21 | Light Chain CDR2 | RASNLES |
|  | 22 | Light Chain CDR3 | QQSNEDPYT |
|  | 154 | V_H Amino Acid Sequence | EVQLQQSGPELVKPGSSVKISCKASGYTFTD YSMDWVKQSHGKSLEWIGAINPNSGGTNY SQKFKDKATLTVDKSSSTAYMELRSLTSED SAVYYCASSGSYDGYYAMDYWGQGTSVT VSS |
|  | 28 | Heavy Chain CDR1 | DYSMD |
|  | 67 | Heavy Chain CDR2 | AINPNSGGTNYSQKFKD |
|  | 30 | Heavy Chain CDR3 | SGSYDGYYAMDY |
| 5an180 ME | 155 | V_L Amino Acid Sequence | DIQMTQSPASLSASVGETVTITCRASENIYSY LAWYQQKQGKSPQLLVYNAKTLAEGVPSR FSGSGSGTQFSLKINSLQPEDFGSYYCQHHY GTPYTFGGGTKLEIKR |

TABLE 3-continued

Amino Acid Sequences for Five Murine Anti-Human C5a Antibodies

| Ab | SIN: | Description | Amino Acid Sequence |
|---|---|---|---|
| | 156 | Light Chain CDR1 | RASENIYSYLA |
| | 157 | Light Chain CDR2 | NAKTLAE |
| | 158 | Light Chain CDR3 | QHHYGTPYT |
| | 159 | $V_H$ Amino Acid Sequence | EVQLQQPGAEIVRPGASVKLSCRASGYTFT DYWMNWVKQRPGQGLEWIGTIDPSDSYTI YNQKFKGKATLTVDTSSTTAYIQLSSLTSED SAVYFCARGEDYDVSSYTMDYWGQGTSVT VSS |
| | 160 | Heavy Chain CDR1 | DYWMN |
| | 161 | Heavy Chain CDR2 | TIDPSDSYTIYNQKFKG |
| | 162 | Heavy Chain CDR3 | GEDYDVSSYTMDY |
| 5an178 ME | 163 | $V_L$ Amino Acid Sequence | EIVLTQSPASLAVSLGQRATISCSASESVEYF GTSLMQWYQQKPGQPPKLLIYAASNVESG VPARFSGSGSGTDFSLNIHPVEEDDIAMYFC QQSRKVPWTFGGGTKLEIKR |
| | 164 | Light Chain CDR1 | SASESVEYFGTSLMQ |
| | 165 | Light Chain CDR2 | AASNVES |
| | 166 | Light Chain CDR3 | QQSRKVPWT |
| | 167 | $V_H$ Amino Acid Sequence | EVKLVESGGGLVQPGGSRKLSCAASGFTFS DYGMVWVRQAPGKGLEWVAFISSGSSNIY YADTVKGRFTISRDNPKNTLFLQMNSLRSE DTAIYYCGRAFSFYYGYDYWGQGTTLTVSS |
| | 168 | Heavy Chain CDR1 | DYGMV |
| | 169 | Heavy Chain CDR2 | FISSGSSNIYYADTVKG |
| | 170 | Heavy Chain CDR3 | AFSFYYGYDY |
| 5an179 ME | 171 | $V_L$ Amino Acid Sequence | DVVMTQTPLSLPVSLGDQASISCRSSQSLVH SNGNTYLHWYLQKPGQSPKLLIYKVSNRFS GVPDRFSGSGSGTDFTLKISRVEAEDLGVYF CSQSTHVPLTFGAGTKLELKR |
| | 172 | Light Chain CDR1 | RSSQSLVHSNGNTYLH |
| | 173 | Light Chain CDR2 | KVSNRFS |
| | 174 | Light Chain CDR3 | SQSTHVPLT |
| | 175 | $V_H$ Amino Acid Sequence | EVQLQQSGPELVKPGASVRMSCKASGYTFT SYLIHWVKQKPGQGLEWIGYIYPFNDGTKN NENFKGKATLTSDKSSSTVYMEVSSLTSEDS AVYYCARSHGPHYYGGSYGYHFDYWGQG TTLTVSS |
| | 176 | Heavy Chain CDR1 | SYLIH |
| | 177 | Heavy Chain CDR2 | YIYPFNDGTKNNENFKG |
| | 178 | Heavy Chain CDR3 | SHGPHYYGGSYGYHFDY |

"SIN" in the Table refers to "SEQ ID NO."
*CDR amino acid sequence defined according to Kabat et al. (supra).

Figure 1:
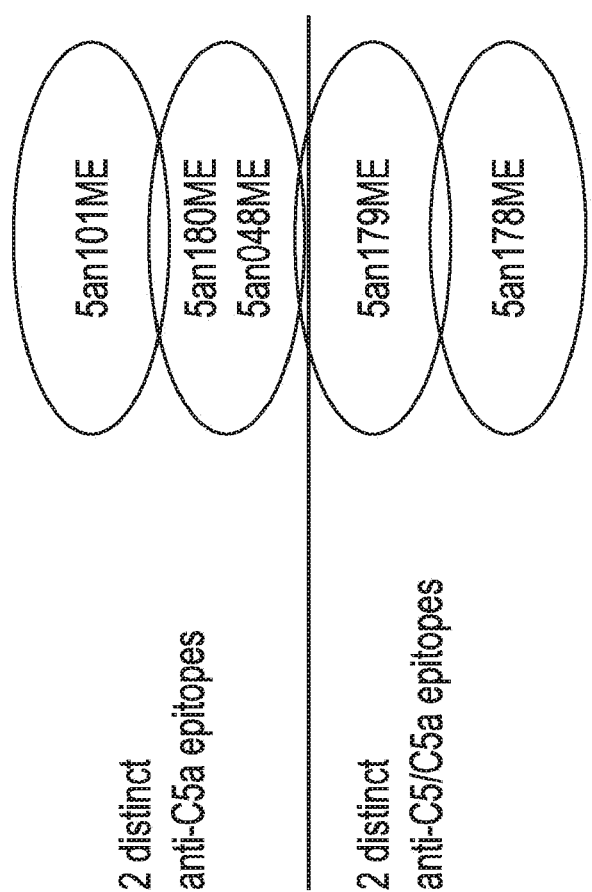
FIG. 1 is a Venn diagram depicting the degree of overlap of the epitopes in human C5a bound by a select set of murine anti-human C5a antibodies: 5an101ME, 5an180ME, 5an048ME, 5an179ME, and 5an178ME.

A series of sandwich assays were performed by Octet on the selected subset of mouse anti-human C5a IgG2a antibodies to determine the degree of overlap of the C5a epitopes for each of the five representative IgG2a antibodies. Briefly, a first antibody was biotinylated and immobilized on a streptavidin coated tip on the Octet platform. Next, human C5a was captured from a 20 nM solution on the immobilized antibody. The tip carrying the antibody-C5a complex was then exposed to a solution containing 20 nM of an unlabeled second anti-C5a IgG antibody. The elicitation of an additional association profile in the sensogram would indicate that the two antibodies bound C5a simultaneously in a ternary complex and that the binding epitopes for the two antibodies were non-overlapping. A failure to obtain a second association profile upon addition of the second antibody would indicate that the two antibodies bound C5a in a competitive manner, i.e., the epitope on C5a to which the second antibody bound was occluded after binding by the first antibody. In contrast to non-competitive binding, competitive binding does not necessarily indicate that the first and second antibodies recognized the same, or even overlapping, epitopes on human C5a. Using this approach the binding sites of the five representative anti-C5a antibodies were assigned to 4 distinct epitopes on human C5a (FIG. 1). Antibodies 5an048ME, 5an180ME, and 5an101ME competed with each other. While 5an048 and 5an180 also competed with the non-neoepitope selective 5an179ME, 5an101ME did not, which indicated that 5an048ME and 5an180ME recognize a neoepitope that is different than the epitope recognized by 5an101ME. In addition, while the non-neoepitope selective antibody 5an178ME competed with non-neoepitope selective 5an179ME, only the latter competed with 5an180ME and 5an048ME, showing that 5an179ME and 5an178ME bind different epitopes that are accessible both in C5 and C5a. The results also indicate that some combinations of the antibodies could be used in sandwich-based assays to detect and/or quantify the amount of C5a in a sample.

Example 3

Humanization of Select Mouse Anti-Human C5a Antibodies

The variable regions of two related mouse anti-human C5a antibodies—5an101ME and 5an185ME—were selected for humanization as full length IgG antibodies. Humanization of light and heavy chain variable regions was based on identifying individual framework regions from human antibodies (with a preference given to germline v-genes) with a high degree of sequence identity to the original murine parent antibody. Methods for identifying suitable candidate framework regions are described in U.S. Pat. No. 7,393,648 to Rother and Wu. Definitions of framework (FW) and complementarity determining regions (CDRs) were performed according to methods described by Kabat, Chothia and IMGT® (International ImmunoGenetics Information System; France). Briefly, database queries were performed independently for both the light and heavy chain variable regions with a variety of antibody fragments including: intact murine variable region from FW1 through FW4, intact murine variable regions excluding CDRs and all possible fragments of murine variable regions including one, two or three frameworks with or without their flanking CDRs. Human frameworks were selected from this candidate pool based on their overall sequence identity to the original murine antibodies and fragments thereof. Routine molecular biological methods were employed to assemble small combinatorial libraries, of less than $10^3$ members, in which each set of murine CDRs were flanked by all possible combinations of selected human frameworks. These humanized antibodies were expressed as soluble Fabs and evaluated for binding to desarginated C5a using ELISA. Fabs that bound to C5a were then subjected to DNA sequence analysis.

From these binders a subset of six humanized Fabs were reformatted as full length IgGs (human IgG2 or human IgG2/G4). Additional humanization was performed in two antibodies (BNJ371 and BNJ381) by replacing murine residues in CDR2 of the light chain with their corresponding human germline amino acids. The amino acid sequences of the humanized anti-C5a antibodies—BNJ364, BNJ367, BNJ371, BNJ378, BNJ366, BNJ369, BNJ381, and BNJ383—are set forth in Table 2 above.

Example 4

Determining the Affinity of the Humanized Anti-Human C5a Antibodies for C5a

The humanized antibodies were subjected to BIAcore analysis to quantify their respective affinities for human C5a. See, e.g., Karlsson and Larsson (2004)*Methods Mol Biol* 248:389-415. Briefly, each of the humanized antibodies were screened with 3-4 concentrations of human C5a (antigen) using a capture technique. The antibodies were captured by an Anti-Fc (human) directly immobilized on a CM5 sensor chip with various concentrations in the range from 0.6 nM to 5.9 nM of human C5a passed over the sensor chip surface. The surface was regenerated with 20 mM HCl, 0.02% P20 after each cycle to remove bound antibody and antigen. The data was evaluated using Biacore BIAevaluation software using a 1:1 Langmuir Model Fit (Rmax:Global Fit; RI:Local Fit). Kinetics information such as ($k_a$: Association Rate constant), ($k_d$:Dissociation Rate constant) and $K_D$ (Equilibrium Dissociation constant) was obtained from the fit. The results of the analyses are set forth in Table 4. These experiments were for screening purposes with a minimal number of analyte concentrations (3 to 4) with 1 duplicate. Therefore, the approximate kinetics values are reported in Table 4.

TABLE 4

Affinity Measurements for Select Humanized Anti-C5a Antibodies

| Antibody Designation | $k_a$ (1/Ms) ($\times 10^6$) | $k_d$ (1/s) ($\times 10^{-4}$) | $K_D$ (M) ($\times 10^{-12}$) | $\chi^2$ |
|---|---|---|---|---|
| BNJ364 | 0.991 | 6.38 | 644 | 0.819 |
| BNJ367 | 3.94 | 7.78 | 198 | 0.848 |
| BNJ371 | 2.38 | 28.2 | 1180 | 9.52 |
| BNJ378 | 1.93 | 5.76 | 298 | 3.63 |
| BNJ366 | 1.05 | 1.58 | 150 | 1.23 |
| BNJ369 | 4.19 | 2.23 | 53.1 | 0.642 |
| BNJ381 | 2.57 | 2.09 | 81.5 | 1.93 |
| BNJ383 | 2.12 | 1.5 | 70.4 | 2.52 |

All of the humanized antibodies specifically bound to human C5a with a $K_D$ less than 1.20 nanomolar. All of the antibodies with the exception of BNJ371 bound to human C5a with a $K_D$ less than 1 nanomolar. Three of the antibodies, BNJ369, BNJ381, and BNJ383 bound to human C5a with a $K_D$ less than 100 picomolar.

Example 5

Anti-C5a Antibodies Inhibit C5a-Mediated Signaling In Vitro

An in vitro neutrophil activation assay was used to evaluate the activity of the humanized antibodies. The assay is generally described in, e.g., Paczkowski et al. (1999) *Br J Pharmacol* 128(7):1461-1466, and serves to quantitate the amount of myeloperoxidase (MPO) produced by neutrophils as a measure of neutrophil activation. Briefly, polymorphonuclear cells, the majority of which being neutrophils, were isolated using density centrifugation (mono-poly resolving medium catalogue number: 91698049; MP Biochemicals; Solon, Ohio) from whole blood from a healthy donor. The cells were washed once with phosphate-buffered saline (PBS) and the red blood cells (RBC) removed from the cell population by lysis in a hypotonic solution (ACK lysis buffer catalogue number 10-548E; Lonza). After two more washes with PBS, the RBC-free cells were resuspended at a concentration of $4 \times 10^6$ cells/mL in Hank's Balanced Salt Solution (HBSS; Mediatech, catalogue number: 21-023-CV), which was supplemented with calcium and magnesium and further supplemented with 0.1% gelatin (Sigma Aldrich; St. Louis, Mo.) [hereinafter the assay buffer].

Cytochalasin B (Sigma Aldrich) was added to the cell suspension in an amount sufficient to reach a concentration of 10 μg/mL. The suspension was then incubated for 10 minutes at 37° C. 100 μL of cells was added to wells of U-bottomed 96-well plates. The wells of the plate were grouped into several different sets. Each of several of the different sets of wells contained an anti-C5a antibody: each well of set 1 contained a humanized antibody that binds to uncleaved, native C5, but not to free C5a; each well of set 2 contained the BNJ367 humanized anti-C5a antibody; each well of set 3 contained the BNJ369 humanized anti-C5a antibody; each well of set 4 contained the BNJ371 humanized anti-C5a antibody; each well of set 5 contained the BNJ378 humanized anti-C5a antibody; each well of set 6 contained the BNJ381 humanized anti-C5a antibody; and each well of set 7 contained the BNJ383 humanized anti-C5a antibody. Each well of an eighth set of wells contained no antibody. A range of antibody concentrations was evaluated in each set of wells, the range including 0.08 nM, 0.4 nM, 2 nM, and 10 nM antibody.

C5a (obtained from Complement Technologies, Inc.) was evaluated at a concentration of 2 nM. A 10× working concentration of 20 nM was prepared in the aforementioned assay buffer and 20 μL was added to each well. After addition of C5a to the wells, the plate was incubated for 10 minutes at 37° C. Following the incubation, 60 μL of PBS was added to each well of the plate. The plates were subjected to centrifugation at 1200 rpm (approximately 335×g) for 10 minutes at room temperature. 100 μL of the supernatant from each well was transferred to the corresponding well of a second plate. 25 μL of substrate (Sigma Aldrich catalogue number T0440) was added to each well of the second plate and the peroxidase reaction was allowed to develop for approximately two to five minutes. The reaction was terminated by the addition of 25 μL of 1N HCl. The OD at 450 nM was recorded.

Figure 2:
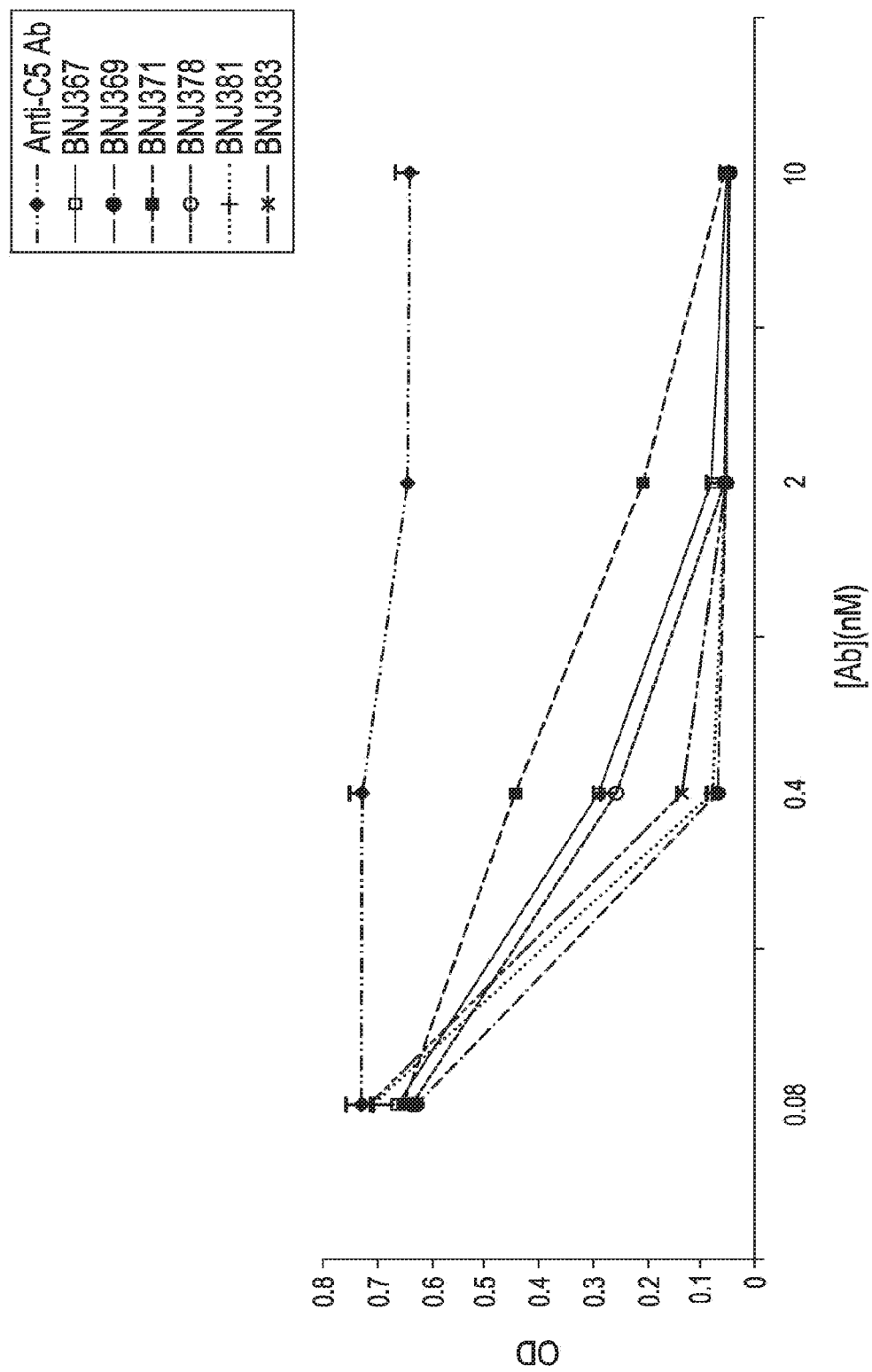
FIG. 2 is a line graph depicting the antagonism of C5a-mediating signaling in vitro using a neutrophil activation assay. The Y-axis represents the optical density (OD) measurement of a chromogenic substrate as a function of myeloperoxidase release by freshly isolated human neutrophils. The X-axis represents the concentration of antibody incubated with the cells. The humanized antibodies tested—BNJ367, BNJ369, BNJ371, BNJ378, BNJ381, BNJ383, and a humanized anti-C5 antibody—are identified in the inset legend.

As shown in FIG. 2, all of the humanized anti-C5a antibodies inhibited neutrophil activation in vitro. These results indicate that the humanized anti-C5a antibodies described herein are potent inhibitors of C5a-mediated signaling in vitro and support the conclusion by the inventors that the antibodies are useful for treating a variety of complement-associated disorders (e.g., complement-associated inflammatory disorders) in humans.

Example 6

Characterization of a Surrogate Mouse Anti-Mouse C5a Antibody

A series of sandwich assays were performed on a selected mouse anti-mouse C5a IgG antibody—5an195ME—to determine the specificity of the antibody for C5a. Briefly, the wells of an assay plate were coated with the 5an195ME antibody. The plate was washed thoroughly to remove unbound antibody. Next, wells containing 5an195ME were contacted with mouse C5a for a time and under conditions sufficient to allow the antigen to bind to the antibody. Unbound protein was removed with washing. Following the wash step, the wells were further contacted with a solution containing a second, biotinylated anti-C5a antibody. The wells were again washed to remove any unbound second antibody. The amount of binding of the second antibody to the well was quantified using streptavidin-conjugated horseradish peroxidase (HRP). The amount of binding of the second antibody was a function of the binding of C5a to 5an195ME.

In a parallel experiment, a set of 5an195ME-coated wells were incubated with full-length mouse C5 protein, rather than C5a. Following a wash step, the wells were contacted with a solution containing a second antibody: a biotinylated anti-mouse C5 antibody. The amount of binding of the second antibody, as a function of the amount of C5 bound by 5an195ME, was quantified using the streptavidin-conjugated HRP construct. A lack of binding of the second antibody indicates that 5an195ME does not bind to full-length mouse C5.

While 5an195ME bound to C5a in a dose-dependent manner, no binding between the antibody and full-length mouse C5 was detected using this assay. These results indicate that 5an195ME binds to a neo-epitope present in C5a.

The relative binding affinity of 5an195ME for mouse C5a was further quantified using BIAcore. The kinetics of 5an195ME were measured using a capture technique. The antibody was captured by an Anti-Fc (mouse) directly immobilized on a CM5 sensor chip with various concentrations between and inclusive of 0.4 nM and 25 nM of mouse C5a passed over the sensor chip surface. Duplicates of each concentration were also run. The surface of the chip was regenerated with 10 mM glycine HCl pH 1.7 after each cycle to remove bound antibody and antigen. The data were evaluated using Biacore BIAevaluation software using a 1:1 Langmuir Model Fit (Rmax:Global Fit; RI:Local Fit). Kinetics information such as $k_a$ (Association Rate constant), $k_d$ (Dissociation Rate constant) and $K_D$ (Equilibrium Dissociation constant) was obtained from the fit. The results of the kinetics analyses are shown in Table 5.

TABLE 5

Measured Kinetics of 5an195ME for Mouse C5a

| Parameter: | $k_a$ (1/Ms) | $k_d$ (1/s) | $K_D$ (M) | $\chi^2$ |
|---|---|---|---|---|
| 5an195ME | $8.47 \times 10^5$ | $1.27 \times 10^{-3}$ | $1.5 \times 10^{-9}$ | 1.17 |

These results indicate that the mouse anti-mouse C5a antibody is not only specific for C5a, as compared to full-length mouse C5, but also that the antibody binds with high affinity to mouse C5a.

Example 7

Use of the Surrogate Anti-Mouse C5a Antibody 5an195ME in an RA Animal Model

The 5an195ME anti-mouse C5a antibody was evaluated in a mouse model of collagen-induced arthritis. Male DBA/1LacJ mice (9 to 12 weeks old) were immunized by intradermal injection at the base of the tail with 300 μg of bovine type II collagen emulsified with equal volumes of Freund's complete adjuvant. The procedure was repeated two weeks after the first immunization. Mice were inspected daily to identify inflammation at an initial knee joint. Once the initial inflammation was identified, mice were intraperitoneally administered three times/week the 5an195ME anti-mouse C5a antibody (40 mg/kg) or a control antibody (40 mg/kg). The thickness of the initially inflamed joint (in mm) was measured daily to day 12.

Figure 3:
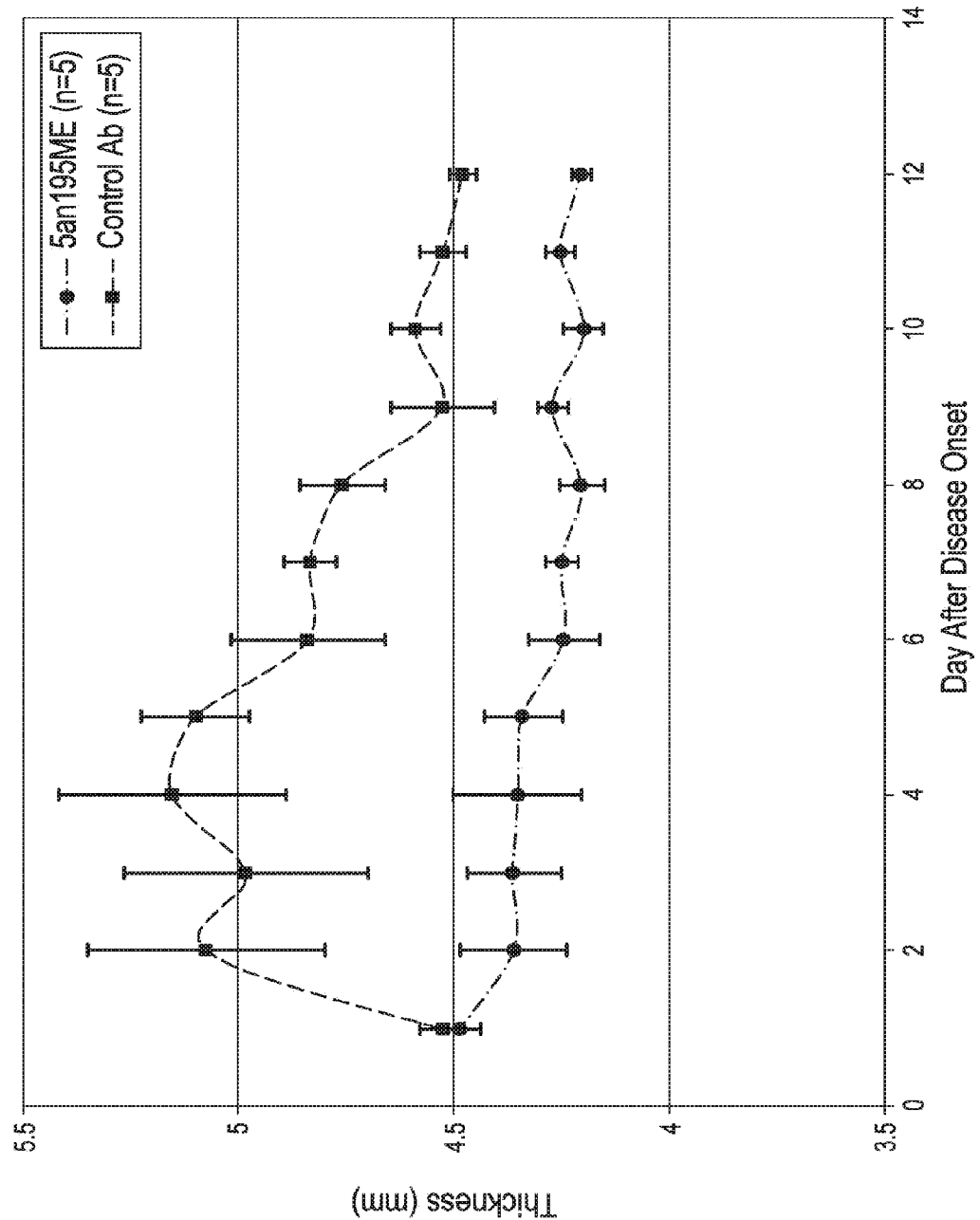
FIG. 3 is a line graph depicting the effect of several therapeutic antibodies on joint inflammation in a mouse model of rheumatoid arthritis. The Y-axis represents the thickness of the initially inflamed knee joint in millimeters. The X-axis represents the days after disease onset. The therapeutic antibodies tested—5an195ME (a mouse anti-mouse C5a antibody) and a control antibody with the same Fc region as the anti-C5a antibody—are identified in the inset legend.

As shown in FIG. 3, 5an195ME reduced knee joint thickness as compared to the control antibody. 5an195ME appeared to provide the benefit of maintaining a knee joint thickness below 4.5 mm.

In addition to evaluating the ability of the 5an195ME antibody to reduce swelling of the initially inflamed knee joint, the ability of the 5an195ME anti-C5a antibody to prevent migration of inflammation to new joints was also evaluated. The number of newly recruited joints was measured daily from day 1 to day 12. The results of the experiment are set forth in Table 6.

TABLE 6

Efficacy of 5an195ME in RA Model

| Treatment | Number of Mice | Number of joints inflamed on day 1 | Number of newly inflamed joints on day 12 | Average number of newly inflamed joints per mouse |
|---|---|---|---|---|
| Control Ab | 6 | 7 | 12 | 2 |
| 5an195ME | 6 | 7 | 2 | 0.3 |

As shown in Table 6, mice treated with 5an195ME had markedly fewer newly inflamed joints as compared with control Ab treated animals by day 12. 5an195ME-treated mice also had on average markedly fewer newly inflamed joints.

Figure 4:
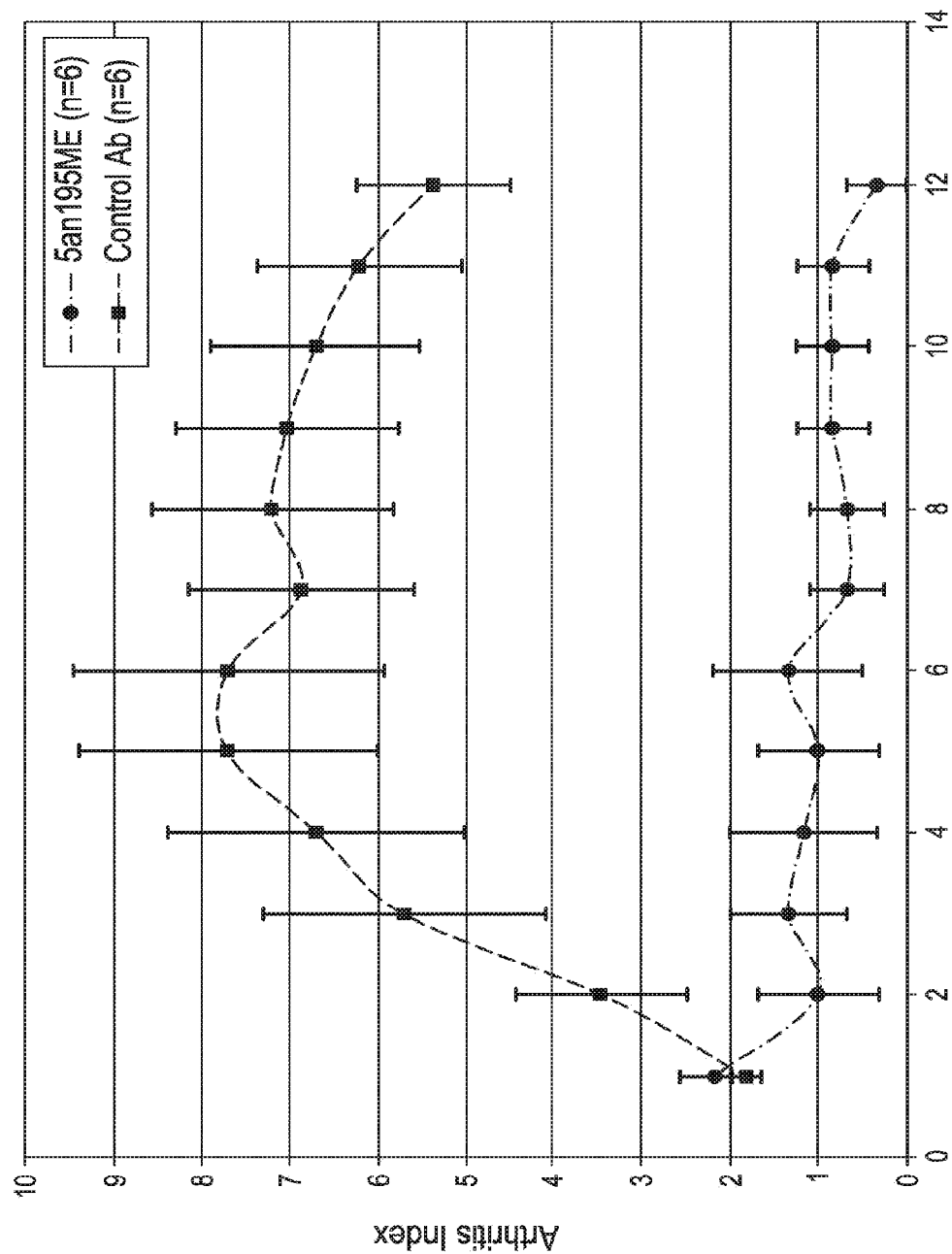
FIG. 4 is a line graph depicting the effect of several therapeutic antibodies on overall disease severity in a mouse model of rheumatoid arthritis. The Y-axis represents the arthritis index. The X-axis represents the days after disease onset. The therapeutic antibodies tested—5an195ME (a mouse anti-mouse C5a antibody) and a control antibody with the same Fc region as the anti-C5a antibody—are identified in the inset legend.

The arthritis in the mice was also monitored and defined using a clinical score/arthritis index. Each limb was graded daily according to an established scoring system (0, normal joint; 1, mild/moderate visible erythema and swelling; 2, severe erythema and swelling affecting an entire paw or joint; 3, deformed paw or joint with ankylosis.), with a maximum score of twenty-four per animal. See, e.g., Wang et al. (2000) *J Immunol* 164:4340-4347. As shown in FIG. 4, mice treated with the anti-mouse C5a antibody 5an195ME exhibited a marked reduction in clinical score (average score of less than 1), as compared to mice treated with the control antibody (average score above 6), over the course of the study.

In summary, these results indicate that the surrogate anti-mouse C5a is effective in treating RA—both at an initial joint and the migration of inflammation to secondary joints—in the mouse model of disease. The results also strongly suggest that a therapeutic anti-human C5a antibody, such as any of the humanized anti-C5a antibodies described herein, is useful for treating humans with RA.

Example 8

Use of an Anti-C5a Antibody to Treat Rheumatoid Arthritis

A human patient is identified by a medical practitioner as having rheumatoid arthritis in a single articulated joint. The patient is shortly thereafter administered intraarticularly or intraperitoneally a composition containing a humanized anti-C5a antibody described herein in an amount sufficient to reduce C5a-mediated C5aR1 signaling locally within the joint space. The patient and medical practitioner observe a substantial improvement in at least two known symptoms of rheumatoid arthritis following the treatment. The patient receives intravenously administered "maintenance doses" of the antibody every month to prevent reoccurrence of the symptoms, to prevent the progression of RA at the single joint, or to prevent the migration of RA symptoms to a second joint.

Example 9

Use of an Anti-C5a Antibody to Treat Sepsis

A human patient is identified by a medical practitioner as having sepsis. The patient is shortly thereafter administered a composition containing a humanized anti-C5a antibody described herein at a dose of approximately 600 to 900 mg by way of intravenous infusion. The patient and medical practitioner observe a substantial improvement in at least two known symptoms of sepsis during the treatment. The patient receives intravenously administered "maintenance doses" of the antibody every two weeks until the patient leaves the hospital.

Example 10

Use of an Anti-C5a Antibody to Treat Complement-Associated Pulmonary Inflammatory Disorders A human patient is identified by a medical practitioner as having a severe form of COPD. Once every two weeks for four weeks the patient is administered a composition containing a humanized anti-C5a antibody at a dose of approximately 600 mg to 900 mg by intravenous infusion. The patient and medical practitioner observe a substantial improvement in at least two known symptoms of COPD during the initial treatment. For example, the patient receiving the anti-C5a antibody has a reduced frequency and/or severity of COPD-related exacerbations. The patient continues to receive intravenously administered "maintenance doses" of the antibody every two weeks to maintain the reduced frequency and/or severity of COPD-related exacerbations.

A human patient is identified by a medical practitioner as having a severe form of asthma. The patient is prescribed a therapeutic, humanized anti-C5a antibody to be administered by way of an inhaler. During the next attack of bronchospasms, the patient self-administers the anti-C5a antibody in an amount sufficient to reduce the C5a-mediated inflammatory response in the lungs of the patient. The patient continues to use the inhaler as needed to prevent or lessen the severity of asthma attacks.

Example 11

Additional Anti-C5a Antibodies Identified from the Immunized Mice

Several additional antibodies were obtained from the immunized mice (see Example 1) and further identified by ELISA as capable of binding to human C5a. The additional antibodies include 15 unique light chain CDR sets (set forth in Table 7) and 14 unique heavy chain CDR sets (as set forth in Table 8).

TABLE 7

Amino Acid Sequences of Several Unique $V_L$ and Kabat-defined Light Chain CDR sequences from Additional Murine Anti-human C5a Antibodies

| Ab | SIN: | Description | Amino Acid Sequence* |
|---|---|---|---|
| 5an110 | 83 | $V_L$ Amino Acid Sequence | DIVMTQSQKFMSTSVGDRVSVTCKASQNVGT NVAWYQQKPGQSPKALIYSASYRYSGVPDRF TGSGSGTDFTLTISNVQSEDLAEYFCQQYNSYP FTFGSGTKLEIKR |
| | 84 | Light Chain CDR1 | KASQNVGTNVA |
| | 85 | Light Chain CDR2 | SASYRYS |
| | 86 | Light Chain CDR3 | QQYNSYPFT |

TABLE 7-continued

Amino Acid Sequences of Several Unique V<sub>L</sub> and Kabat-
defined Light Chain CDR sequences from Additional Murine
Anti-human C5a Antibodies

| Ab | SIN: | Description | Amino Acid Sequence* |
|---|---|---|---|
| 5an177 | 87 | V<sub>L</sub> Amino Acid Sequence | EIVLTQSPAIMSASPGEKVTMTCSASSSVSYMH WYQQKSGTSPKRWIYDTSKLASGVPARFSGS GSGTSYSLTISSMEAEDAATYYCQQWSSNPLT FGAGTKLELKR |
| | 88 | Light Chain CDR1 | SASSSVSYMH |
| | 89 | Light Chain CDR2 | DTSKLAS |
| | 90 | Light Chain CDR3 | QQWSSNPLT |
| 5anG12 | 91 | V<sub>L</sub> Amino Acid Sequence | QIVLTQSPAIMSASPGEKVTMTCSASSSISYMH WYQQKPGTSPKRWIYDTSKLASGVPARFSGS GSGTSYSLTISSMEAEDAATYYCHQRSSYPWT FGGGTKLEIKR |
| | 92 | Light Chain CDR1 | SASSSISYMH |
| | 89 | Light Chain CDR2 | DTSKLAS |
| | 93 | Light Chain CDR3 | HQRSSYPWT |
| 5an052 | 94 | V<sub>L</sub> Amino Acid Sequence | QIVLTQSPAIMSASPGEKVTLTCSASSSVSSSYL YWYQQKPGSSPKLWIYSTSNLASGVPARFSGS GSGTSYSLTISTVEAEDAASYFCHQWSSYPPTF GGGTKLEIKR |
| | 95 | Light Chain CDR1 | SASSSVSSSYLY |
| | 96 | Light Chain CDR2 | STSNLAS |
| | 97 | Light Chain CDR3 | HQWSSYPPT |
| 5an107 | 98 | V<sub>L</sub> Amino Acid Sequence | DIQMTQSPAPMLVSVGETVTITCRGSENIYSNL AWYQQKQGKSPQLLVYAATNLADGVPSRFSG SGSGTQYSLKINSLQSEDFGSYYCQHFWGTPR TFGGGTKLEIKR |
| | 99 | Light Chain CDR1 | RGSENIYSNLA |
| | 100 | Light Chain CDR2 | AATNLAD |
| | 101 | Light Chain CDR3 | QHFWGTPRT |
| 5anE11 | 102 | V<sub>L</sub> Amino Acid Sequence | DIVMTQSQKFMSTSVGDRVSVTCKASQNVGT NVAWYQQKPGQSPKALIYSASYRYSGVPDRF TGSGSGTDFTLTISNVQSEDLAEYFCQQYNSYP WTFGGGTKLEIKR |
| | 84 | Light Chain CDR1 | KASQNVGTNVA |
| | 85 | Light Chain CDR2 | SASYRYS |
| | 103 | Light Chain CDR3 | QQYNSYPWT |
| 5an054 | 104 | V<sub>L</sub> Amino Acid Sequence | QIVLTQSPVIMSASPGEKVTMTCSASSSVSYM YWYQQKPGSSPRLLIYDTSNLASGVPVRFSGS GSGTSYSLTISRMEAEDAATYYCQQWSSYPPT FGAGTKLELKR |
| | 105 | Light Chain CDR1 | SASSSVSYMY |
| | 106 | Light Chain CDR2 | DTSNLAS |
| | 107 | Light Chain CDR3 | QQWSSYPPT |
| 5anG10 | 141 | V<sub>L</sub> Amino Acid Sequence | QIVLTQSPAIMSASPGEKVTMTCSASSSISYMH WYQQKPGTSPKRWIYDTSKLASGVPARFSGS GSGTSYSLTISSMEAEDAATYYCHQRRSYPWT FGGGTKLEIKR |
| | 92 | Light Chain CDR1 | SASSSISYMH |
| | 89 | Light Chain CDR2 | DTSKLAS |
| | 108 | Light Chain CDR3 | HQRRSYPWT |
| 5an188 | 109 | V<sub>L</sub> Amino Acid Sequence | DIVLTQSPASLAVSLGQRATISCRASESVDSYG NSFMHWYQQKPGQPPKLLIYLASNLESGVPAR FSGSGSRTDFTLTIDPVEADDAATYYCQQNNE DPLTFGAGTKLELKR |
| | 20 | Light Chain CDR1 | RASESVDSYGNSFMH |
| | 110 | Light Chain CDR2 | LASNLES |
| | 111 | Light Chain CDR3 | QQNNEDPLT |

TABLE 7-continued

Amino Acid Sequences of Several Unique $V_L$ and Kabat-defined Light Chain CDR sequences from Additional Murine Anti-human C5a Antibodies

| Ab | SIN: | Description | Amino Acid Sequence* |
|---|---|---|---|
| 5an185 | 112 | $V_L$ Amino Acid Sequence | DIVLTQSPASLAVSLGQRATISCRASESVDSYG NSFMHWYQQKPGQPPKLLIYRASNLESGIPAR FSGSGSRTDFTLTINPVEADDVATYYCQQSNE DPLTFGAGTKLELKR |
|  | 20 | Light Chain CDR1 | RASESVDSYGNSFMH |
|  | 21 | Light Chain CDR2 | RASNLES |
|  | 113 | Light Chain CDR3 | QQSNEDPLT |

"SIN" in the Table refers to "SEQ ID NO."
*CDR amino acid sequences are defined according to Kabat et al. (supra).

TABLE 8

Amino Acid Sequences of Several Unique $V_H$ and Kabat-defined Heavy Chain CDR sequences from Additional Murine Anti-human C5a Antibodies

| Ab | SIN: | Description | Amino Acid Sequence* |
|---|---|---|---|
| 5an110 | 114 | $V_H$ Amino Acid Sequence | EVQLQQSGPELVKPGASVKISCKASGYTFSDY YYMNWVKKSHGKSLEWIGYIFPKTGGTNYS QRFKGKATLTVDKSSSTAYMELRSLTSEDSA VYYCASGPFAYWGQGTLVTVSA |
|  | 115 | Heavy Chain CDR1 | DYYYMN |
|  | 116 | Heavy Chain CDR2 | YIFPKTGGTNYSQRFKG |
|  | 117 | Heavy Chain CDR3 | GPFAY |
| 5an177 | 118 | $V_H$ Amino Acid Sequence | EVKLVESGGGLVKPGGSLKLSCAASGITFSSY YMAWVRQTPDKRLEWVATISSGGSYTYYPD NVKGRFTISRDNAKNTLYLQMSSLKSEDTAM YYCTRYYEDDAMDYWGQGTSVTVSS |
|  | 119 | Heavy Chain CDR1 | SYYMA |
|  | 120 | Heavy Chain CDR2 | TISSGGSYTYYPDNVKG |
|  | 121 | Heavy Chain CDR3 | YYEDDAMDY |
| 5an055 | 122 | $V_H$ Amino Acid Sequence | EVQLQQSGPELVKPGASVKISCKASGYTFSDY YYMNWVKKSHGKSLEWIGYIFPKTGGTNYN QRFKGKATLTVDKSSSTAYMELRSLTSEDSA VYYCASGPFAYWGQGTLVTVSA |
|  | 115 | Heavy Chain CDR1 | DYYYMN |
|  | 123 | Heavy Chain CDR2 | YIFPKTGGTNYNQRFKG |
|  | 117 | Heavy Chain CDR3 | GPFAY |
| 5an054 | 145 | $V_H$ Amino Acid Sequence | EVQLQQSGPELVKPGASVKISCKASGYTFTDY YYMNWVKQSHGKSLEWIGYIFPNTGGTTYN QRFKGKATLTVDKSSSTAYMELRSLTSEDSA VYYCASGPFAYWGQGTLVTVSA |
|  | 115 | Heavy Chain CDR1 | DYYYMN |
|  | 124 | Heavy Chain CDR2 | YIFPNTGGTTYNQRFKG |
|  | 117 | Heavy Chain CDR3 | GPFAY |
| 5an107 | 125 | $V_H$ Amino Acid Sequence | EVKLVESGGGLVKPGGSLKLSCAASGYTFSS YYMAWVRQTPDKRLEWVATIS SGGSYTYYR DNVKGRFTISRDNAKNTLYLQMSSLKSEDTA MYYCTRYFEDYPMDYWGQGTSVTVSS |
|  | 119 | Heavy Chain CDR1 | SYYMA |
|  | 126 | Heavy Chain CDR2 | TISSGGSYTYYRDNVKG |
|  | 127 | Heavy Chain CDR3 | YFEDYPMDY |
| 5an111 | 128 | $V_H$ Amino Acid Sequence | EVQLQQSGPELGKPGASGKISCKASGYTFTDY YYMNWVKQSHGKSLEWIGYIFPNTGGTSYN QRFKDKATLTVDKSSSTAYMELRSLTSEDSA VYYCASGPFAYWGQGTLVTVSA |
|  | 115 | Heavy Chain CDR1 | DYYYMN |
|  | 129 | Heavy Chain CDR2 | YIFPNTGGTSYNQRFKD |
|  | 117 | Heavy Chain CDR3 | GPFAY |
| 5an183 | 130 | $V_H$ Amino Acid Sequence | EVQLQQPGSVLVRPGATVKLSCKASGFTFTSS WMHWAKQRPGQGLEWIGEIHTSGHTNYNEK FKGKATLTLDTSSSTAYVDISSLTSEDSAVYY CARGGLRRGYAMDYWGQGTSVTVSS |

… continued

TABLE 8-continued

Amino Acid Sequences of Several Unique V_H and Kabat-defined Heavy Chain CDR sequences from Additional Murine Anti-human C5a Antibodies

| Ab | SIN: Description | Amino Acid Sequence* |
|---|---|---|
|  | 131 Heavy Chain CDR1 | SSWMH |
|  | 132 Heavy Chain CDR2 | EIHTSGHTNYNEKFKG |
|  | 133 Heavy Chain CDR3 | GGLRRGYAMDY |
| 5an185 | 134 V_H Amino Acid Sequence | EVQPQQSGPELVKPGSSVKISCKASGYTFTDY SMDWVKQSHGKSLEWIGAIHLNTGYTNYNQ KFKGKATLTVDKSSSTAYMELRSLTSEDSAV YYCARGFYDGYSPMDYWGQGTSVTVSS |
|  | 28 Heavy Chain CDR1 | DYSMD |
|  | 46 Heavy Chain CDR2 | AIHLNTGYTNYNQKFKG |
|  | 47 Heavy Chain CDR3 | GFYDGYSPMDY |
| 5an188 | 135 V_H Amino Acid Sequence | EVQLQQSGAELVKPGTSVKLSCKASGYTFTS YWMHWVKQRPGQGLEYIGEIHPSSGHTNYH EKFKSKATLTVDKSSSTAYMQLSSLTSEDSAV YYCARASLLRAYAMDYWGQGTSVTVSS |
|  | 136 Heavy Chain CDR1 | SYWMH |
|  | 137 Heavy Chain CDR2 | EIHPSSGHTNYHEKFKS |
|  | 138 Heavy Chain CDR3 | ASLLRAYAMDY |

"SIN" in the Table refers to "SEQ ID NO."
*CDR amino acid sequences are defined according to Kabat et al. (supra).

V_L and V_H pairings giving rise to the 5an177ME, 5an054ME, 5an110ME, 5an188ME, 5an185ME, and 5an107ME antibodies are evident from Tables 7 and 8.

Additional exemplary pairings of the heavy chain and light chain variable regions and/or CDR sets are set forth in Table 9 below.

TABLE 9

Amino Acid Sequences for Additional Mouse Anti-Human C5a Antibodies CDR Sets

| Ab | SIN: Description | Amino Acid Sequence* |
|---|---|---|
| 5an047 | 139 V_L Amino Acid Sequence | EIVLTQSPAIMSASPGEKVTMTCRASSSVSSSY LHWYQQKSGASPKLWIYSTSNLASGVPARFS GSGSGTSYSLTISSVEAEDAATYYCQQYSGYP LTFGAGTKLELKR |
|  | 140 Light Chain CDR1 | RASSSVSSSYLH |
|  | 96 Light Chain CDR2 | STSNLAS |
|  | 142 Light Chain CDR3 | QQYSGYPLT |
|  | 143 V_H Amino Acid Sequence | EVQLQQSGPELVKPGASVRISCKASGYTFSDY YYMNWVKKSHGKSLEWIGYIFPKTGGTHYN QRFKGKATLTVDKSSSTAYMELRSLTSEDSA VYYCASGPFAYWGQGTLVTVSA |
|  | 115 Heavy Chain CDR1 | DYYYMN |
|  | 144 Heavy Chain CDR2 | YIFPKTGGTHYNQRFKG |
|  | 117 Heavy Chain CDR3 | GPFAY |
| 5an181 | 139 V_L Amino Acid Sequence | EIVLTQSPAIMSASPGEKVTMTCRASSSVSSSY LHWYQQKSGASPKLWIYSTSNLASGVPARFS GSGSGTSYSLTISSVEAEDAATYYCQQYSGYP LTFGAGTKLELKR |
|  | 140 Light Chain CDR1 | RASSSVSSSYLH |
|  | 96 Light Chain CDR2 | STSNLAS |
|  | 142 Light Chain CDR3 | QQYSGYPLT |
|  | 122 V_H Amino Acid Sequence | EVQLQQSGPELVKPGASVKISCKASGYTFSDY YYMNWVKKSHGKSLEWIGYIFPKTGGTNYN QRFKGKATLTVDKSSSTAYMELRSLTSEDSA VYYCASGPFAYWGQGTLVTVSA |
|  | 115 Heavy Chain CDR1 | DYYYMN |
|  | 123 Heavy Chain CDR2 | YIFPKTGGTNYNQRFKG |
|  | 117 Heavy Chain CDR3 | GPFAY |
| 5an109 | 146 V_L Amino Acid Sequence | EIVLTQSPAIMSASPGEKVTMTCSASSSVSYM YWYQQKPGSSPRLLIYDTSNLASGVPVRFSGS GSGTSYSLTISRMEAEDAATYYCQQWSSYPP TFGGGTKLEIKR |

TABLE 9-continued

Amino Acid Sequences for Additional Mouse Anti-Human C5a
Antibodies CDR Sets

| Ab | SIN: | Description | Amino Acid Sequence* |
|---|---|---|---|
| | 105 | Light Chain CDR1 | SASSSVSYMY |
| | 106 | Light Chain CDR2 | DTSNLAS |
| | 107 | Light Chain CDR3 | QQWSSYPPT |
| | 122 | $V_H$ Amino Acid Sequence | EVQLQQSGPELVKPGASVKISCKASGYTFSDY YYMNWVKKSHGKSLEWIGYIFPKTGGTNYN QRFKGKATLTVDKSSTAYMELRSLTSEDSA VYYCASGPFAYWGQGTLVTVSA |
| | 115 | Heavy Chain CDR1 | DYYYMN |
| | 123 | Heavy Chain CDR2 | YIFPKTGGTNYNQRFKG |
| | 117 | Heavy Chain CDR3 | GPFAY |
| 5anG10 | 141 | $V_L$ Amino Acid Sequence | QIVLTQSPAIMSASPGEKVTMTCSASSSISYM HWYQQKPGTSPKRWIYDTSKLASGVPARFSG SGSGTSYSLTISSMEAEDAATYYCHQRRSYP WTFGGGTKLEIKR |
| | 92 | Light Chain CDR1 | SASSSISYMH |
| | 89 | Light Chain CDR2 | DTSKLAS |
| | 108 | Light Chain CDR3 | HQRRSYPWT |
| | 147 | $V_H$ Amino Acid Sequence | EVQLQQSGPELVKPGASVRISCKASGYTFND YYYMNWVKQSHGKSLEWIGYIFPKTGGTHY NQRFKGKATLTVDKSSTAYMELRSLTSEDS AVYYCASGPFAYWGQGTLVTVSA |
| | 115 | Heavy Chain CDR1 | DYYYMN |
| | 144 | Heavy Chain CDR2 | YIFPKTGGTHYNQRFKG |
| | 117 | Heavy Chain CDR3 | GPFAY |
| 5anO53 | 148 | $V_L$ Amino Acid Sequence | EIVLTQSPVIMSASPGEKVTMICSASSSISYMH WYQQKPGTSPKRWIYDTSKLASGVPARFSGS GSGTSYSLTISIMEAEDAATYYCHQRSSYPWT FGGGTKLEIKR |
| | 92 | Light Chain CDR1 | SASSSISYMEI |
| | 89 | Light Chain CDR2 | DTSKLAS |
| | 93 | Light Chain CDR3 | HQRSSYPWT |
| | 149 | $V_H$ Amino Acid Sequence | EVQMQQSGPELVKPGASVKISCKASGYTFSD YYYMNWVKKSHGKSLEWIGYIFPKTGGTNY NQRFKGKATLTVDKSSTAYMELRSLTSEDS AVYYCASGPFAYWGQGTLVTVSA |
| | 115 | Heavy Chain CDR1 | DYYYMN |
| | 123 | Heavy Chain CDR2 | YIFPKTGGTNYNQRFKG |
| | 117 | Heavy Chain CDR3 | GPFAY |
| 5anG12 | 91 | $V_L$ Amino Acid Sequence | QIVLTQSPAIMSASPGEKVTMTCSASSSISYM HWYQQKPGTSPKRWIYDTSKLASGVPARFSG SGSGTSYSLTISSMEAEDAATYYCHQRSSYPW TFGGGTKLEIKR |
| | 92 | Light Chain CDR1 | SASSSISYMH |
| | 89 | Light Chain CDR2 | DTSKLAS |
| | 93 | Light Chain CDR3 | HQRSSYPWT |
| | 147 | $V_H$ Amino Acid Sequence | EVQLQQSGPELVKPGASVRISCKASGYTFND YYYMNWVKQSHGKSLEWIGYIFPKTGGTHY NQRFKGKATLTVDKSSTAYMELRSLTSEDS AVYYCASGPFAYWGQGTLVTVSA |
| | 115 | Heavy Chain CDR1 | DYYYMN |
| | 144 | Heavy Chain CDR2 | YIFPKTGGTHYNQRFKG |
| | 117 | Heavy Chain CDR3 | GPFAY |
| 5anO52 | 94 | $V_L$ Amino Acid Sequence | QIVLTQSPAIMSASPGEKVTLTCSASSSVSSSY LYWYQQKPGSSPKLWIYSTSNLASGVPARFS GSGSGTSYSLTISTVEAEDAASYFCHQWSSYP PTFGGGTKLEIKR |
| | 95 | Light Chain CDR1 | SASSSVSSSYLY |
| | 96 | Light Chain CDR2 | STSNLAS |
| | 97 | Light Chain CDR3 | HQWSSYPPT |
| | 147 | $V_H$ Amino Acid Sequence | EVQLQQSGPELVKPGASVRISCKASGYTFND YYYMNWVKQSHGKSLEWIGYIFPKTGGTHY NQRFKGKATLTVDKSSTAYMELRSLTSEDS AVYYCASGPFAYWGQGTLVTVSA |
| | 115 | Heavy Chain CDR1 | DYYYMN |
| | 144 | Heavy Chain CDR2 | YIFPKTGGTHYNQRFKG |
| | 117 | Heavy Chain CDR3 | GPFAY |

TABLE 9-continued

Amino Acid Sequences for Additional Mouse Anti-Human C5a Antibodies CDR Sets

| Ab | SIN: | Description | Amino Acid Sequence* |
|---|---|---|---|
| 5an111 | 102 | V_L Amino Acid Sequence | DIVMTQSQKFMSTSVGDRVSVTCKASQNVGT NVAWYQQKPGQSPKALIYSASYRYSGVPDRF TGSGSGTDFTLTISNVQSEDLAEYFCQQYNSY PWTFGGGTKLEIKR |
| | 84 | Light Chain CDR1 | KASQNVGTNVA |
| | 85 | Light Chain CDR2 | SASYRYS |
| | 103 | Light Chain CDR3 | QQYNSYPWT |
| | 128 | V_H Amino Acid Sequence | EVQLQQSGPELGKPGASGKISCKASGYTFTDY YYMNWVKQSHGKSLEWIGYIFPNTGGTSYN QRFKDKATLTVDKSSSTAYMELRSLTSEDSA VYYCASGPFAYWGQGTLVTVSA |
| | 115 | Heavy Chain CDR1 | DYYYMN |
| | 129 | Heavy Chain CDR2 | YIFPNTGGTSYNQRFKD |
| | 117 | Heavy Chain CDR3 | GPFAY |
| 5an055 | 150 | V_L Amino Acid Sequence | EIVLTQSPAIMSASPGEKVTLTCSASSSVSSSY LYWYQQKPGSSPKLWIYSTSNLASGVPARFS GSGSGTSYSLTISSMEAEDAASYFCHQWSSYP PTFGGGTKLEIKR |
| | 95 | Light Chain CDR1 | SASSSVSSSYLY |
| | 96 | Light Chain CDR2 | STSNLAS |
| | 97 | Light Chain CDR3 | HQWSSYPPT |
| | 122 | V_H Amino Acid Sequence | EVQLQQSGPELVKPGASVKISCKASGYTFSDY YYMNWVKKSHGKSLEWIGYIFPKTGGTNYN QRFKGKATLTVDKSSSTAYMELRSLTSEDSA VYYCASGPFAYWGQGTLVTVSA |
| | 115 | Heavy Chain CDR1 | DYYYMN |
| | 123 | Heavy Chain CDR2 | YIFPKTGGTNYNQRFKG |
| | 117 | Heavy Chain CDR3 | GPFAY |
| 5anE11 | 102 | V_L Amino Acid Sequence | DIVMTQSQKFMSTSVGDRVSVTCKASQNVGT NVAWYQQKPGQSPKALIYSASYRYSGVPDRF TGSGSGTDFTLTISNVQSEDLAEYFCQQYNSY PWTFGGGTKLEIKR |
| | 84 | Light Chain CDR1 | KASQNVGTNVA |
| | 85 | Light Chain CDR2 | SASYRYS |
| | 103 | Light Chain CDR3 | QQYNSYPWT |
| | 143 | V_H Amino Acid Sequence | EVQLQQSGPELVKPGASVRISCKASGYTFSDY YYMNWVKKSHGKSLEWIGYIFPKTGGTHYN QRFKGKATLTVDKSSSTAYMELRSLTSEDSA VYYCASGPFAYWGQGTLVTVSA |
| | 115 | Heavy Chain CDR1 | DYYYMN |
| | 144 | Heavy Chain CDR2 | YIFPKTGGTHYNQRFKG |
| | 117 | Heavy Chain CDR3 | GPFAY |
| 5an183 | 112 | V_L Amino Acid Sequence | DIVLTQSPASLAVSLGQRATISCRASESVDSY GNSFMHWYQQKPGQPPKLLIYRASNLESGIP ARFSGSGSRTDFTLTINPVEADDVATYYCQQS NEDPLTFGAGTKLELKR |
| | 20 | Light Chain CDR1 | RASESVDSYGNSFMH |
| | 21 | Light Chain CDR2 | RASNLES |
| | 113 | Light Chain CDR3 | QQSNEDPLT |
| | 130 | V_H Amino Acid Sequence | EVQLQQPGSVLVRPGATVKLSCKASGFTFTSS WMHWAKQRPGQGLEWIGEIHTSGHTNYNEK FKGKATLTLDTSSSTAYVDISSLTSEDSAVYY CARGGLRRGYAMDYWGQGTSVTVSS |
| | 131 | Heavy Chain CDR1 | SSWMH |
| | 132 | Heavy Chain CDR2 | EIHTSGHTNYNEKFKG |
| | 133 | Heavy Chain CDR3 | GGLRRGYAMDY |

"SIN" in the Table refers to "SEQ ID NO."
*CDR amino acid sequences are defined according to Kabat et al. (supra).

Example 12

Additional Humanized Anti-Human C5a Antibodies

Figure 5:
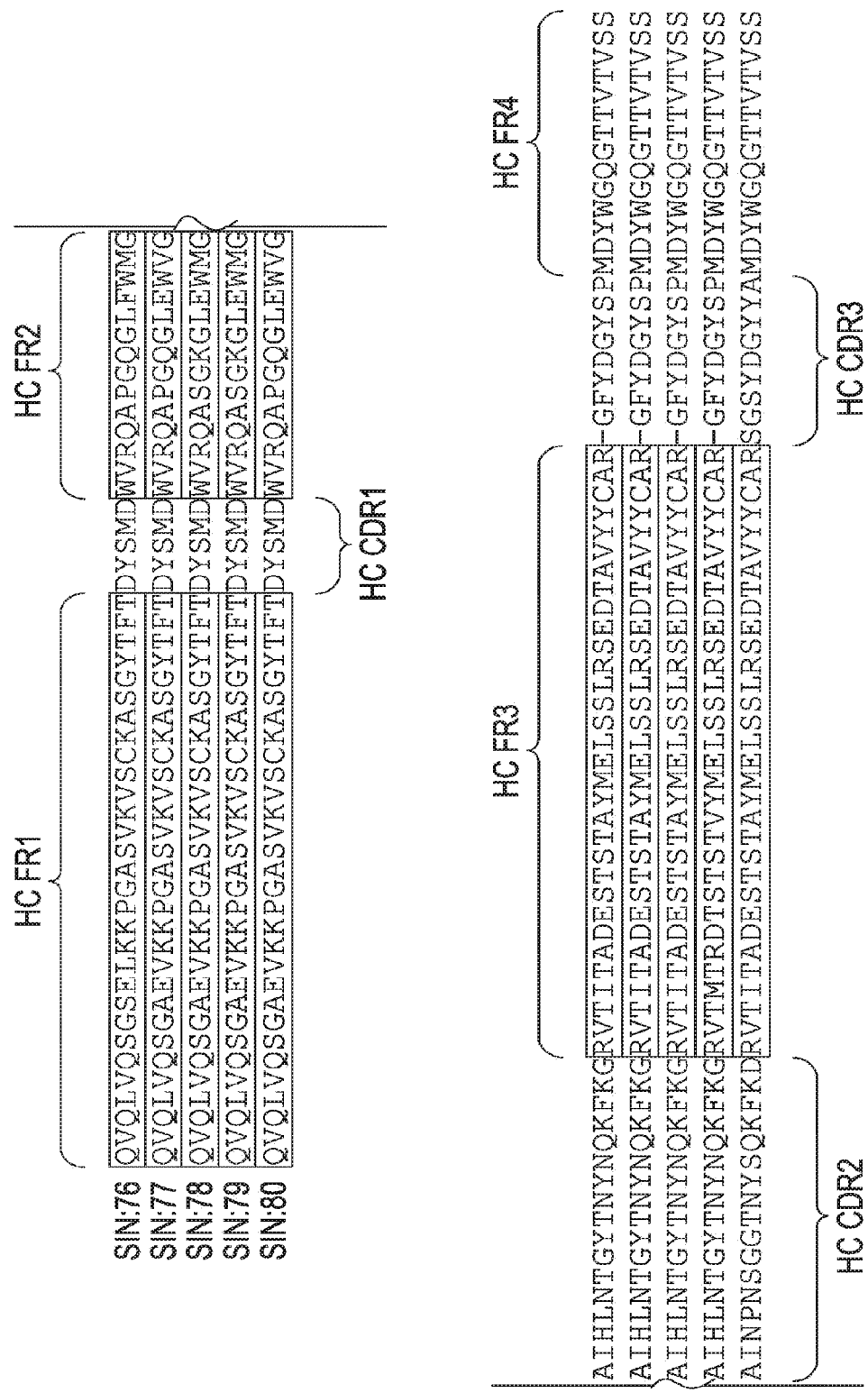
FIG. 5 sets forth a series of humanized heavy chain variable region sequences. In order from uppermost to lowermost: the heavy chain variable region of the BNJ345 humanized anti-C5a antibody (SEQ ID NO:76); the heavy chain variable region of the BNJ346 humanized anti-C5a antibody (SEQ ID NO:77); the heavy chain variable region of the BNJ347 humanized anti-C5a antibody (SEQ ID NO:78); the heavy chain variable region of the BNJ354 humanized anti-C5a antibody (SEQ ID NO:79); and the heavy chain variable region of the BNJ350 humanized anti-C5a antibody (SEQ ID NO:80). The skilled artisan will appreciate the delineation between heavy chain framework regions 1, 2, 3, and 4 and the heavy chain CDRs 1, 2, and 3. Such delineations as defined by Kabat et al. (infra) are shown in the figure. "HC FR1" refers to heavy chain variable region framework region 1, "HC FR2" refers to heavy chain variable region framework region 2, "HC FR3" refers to heavy chain variable region framework region 3, and "HC FR4" refers to heavy chain variable region framework region 4. "HC CDR1" refers to heavy chain variable region complementarity determining region (CDR) 1, "HC CDR2" refers to heavy chain variable region CDR2, and "HC CDR3" refers to heavy chain variable region CDR3.

Several additional humanized anti-C5a antibody heavy chain variable regions were generated, all of which when paired with a common light chain variable region (the light chain having the amino acid sequence depicted in SEQ ID NO: 16) bound to human C5a with a $K_D$ of less than 1 nM as determined by Biacore analysis (see above for methodology). All of these additional humanized antibodies bound specifically to human C5a, but did not bind to native, fully-folded human C5, C4a, or C3a as determined by Octet analysis (see above for methodology). The additional humanized antibodies contained: (i) a heavy chain variable region framework region 1 containing one of the following amino acid sequences: QVQLVQSGAEVKKPGASVK-VSCKASGYTFT (SEQ ID NO:68) or QVQLVQSGSELK- KPGASVKVSCKASGYTFT (SEQ ID NO:69); (ii) a heavy chain variable region framework region 2 containing one of the following amino acid sequences: WVRQAPGQ-GLEWMG (SEQ ID NO:70) or WVRQASGKGLEWVG (SEQ ID NO:71); (iii) a heavy chain variable region framework region 3 containing one of the following amino acid sequences: RVTITRDTSASTAYMELSSLRSEDTAVYY-CAR (SEQ ID NO:72); RVTITADESTSTAYMELSSL-RSEDTAVYYCAR (SEQ ID NO:73); or RVTITRDRSM-STAYMELSSLRSEDTAMYYCAR (SEQ ID NO:74); and a heavy chain variable region framework region 4 containing the following amino acid sequence: WGQGTTVTVSS (SEQ ID NO:75). Exemplary additional humanized heavy chain variable regions comprising one or more of the additional humanized framework sets described in this section are set forth in FIG. 5.

Example 13

Use of an Anti-Human C5a Antibody in a Mouse Neutropenia Model

A murine model of C5a-neutropenia was utilized to evaluate the efficacy of an anti-human free C5a antibody in vivo. To induce neutropenia, purified, native human C5a (hC5a) was administered by way of intravenous tail vein injection to Balb/c mice. The number of circulating neutrophils was evaluated up to five minutes after administration of hC5a.

Administration of 300 µg/kg of hC5a was consistently found to induce neutrophil activation as measured by the myeloperoxidase (MPO) release assay (see Example 5 for use with serum as compared to cell culture supernatant, supra) and neutropenia (a reduction in the number of circulating neutrophils). In addition, plasma levels of hC5a and the human anti-C5a antibody BNJ383 (when administered to the mice, infra) were also measured to establish the pharmacodynamic response (see below).

Peripheral blood neutrophil counts were examined before challenge with hC5a or vehicle control. Compared to sham-treated control mice ($1.37\pm0.09\times10^6$/mL), neutrophil counts in mice treated with anti-human free C5a antibody ($1.32\pm0.13\times10^6$ per mL at 24 mg/kg; P>0.05) or isotype control mAb ($1.31\pm0.10\times10^6$ per mL at 24 mg/kg; P>0.05) remained the same. These results indicated that antibody alone did not induce changes in circulating neutrophil counts.

To evaluate the efficacy of an anti-C5a antibody to inhibit hC5a-induced neutropenia in mice, different dosages (24 mg/kg, 12 mg/kg, 6 mg/kg, and 3 mg/kg) of the anti-human C5a antibody BNJ383 were administered to Balb/c mice 24 hours prior to hC5a injection. Administration of the anti-C5a antibody 24 hours ahead of hC5a allowed for the pharmacodynamics properties of the antibody to be studied during the β-phase of antibody elimination from the mice.

As shown in FIG. 6, neutrophil counts after treatment are expressed as a percentage of "baseline" (where the count at time 0 equals 100%). In sham-treated control mice, the neutrophil counts were 79.02±5.71%, 67.42±3.23%, and 59.54±2.11% of baseline at 1, 3 and 5 minutes post hC5a administration, respectively. The isotype control antibody-treated mice demonstrated a significant reduction (P<0.01) in the neutrophil count to 6.76±0.81% at 1 minute, 6.68±0.81% at 3 minutes, and 8.29±0.79% at 5 minutes after intravenous injection of hC5a. The anti-C5a antibody exhibited a dose-dependent effect on hC5a-induced neutropenia. At the highest dose, 24 mg/kg, the anti-C5a antibody completely blocked the neutropenia. Neutrophil counts were 70.35±8.64% at 1 minute, 63.35±6.08% at 3 minutes, and 59.65±6.51% at 5 minutes, which was comparable to the neutrophil levels in sham-treated control animals at the same time points. The lower doses of 12 mg/kg or 6 mg/kg of the anti-C5a antibody also significantly inhibited neutrophil depletion (12 mg/kg: 42.61±5.12% at 1 minute, 45.33±8.29% at 3 minutes, and 41.02±7.08% at 5 minutes, P<0.01; 6 mg/kg: 18.00±3.8 at 1 minute, 26.20±4.44% at 3 minutes, and 28.03±4.51% at 5 minutes, P<0.05) following administration of hC5a, as compared to the isotype control antibody group (6.76±0.81% at 1 minute, 6.68±0.81% at 3 minutes, and 8.29±0.79% at 5 minutes). The isotype control antibody is an antibody that binds anthrax protective antigen 63 and contains a human IgG2/4 isotype Fc region. Administration of the lowest dose of the anti-C5a antibody (3 mg/kg) did not significantly reduce neutropenia (6.28±0.88% at 1 minute, 6.71±2.14% at 3 minutes, and 8.75±2.98% at 5 minutes, P>0.05). See FIG. 6.

Anti-Human C5a Antibody Inhibits hC5a-Induced MPO Release In Vivo

As discussed above, human C5a activates neutrophils through cross-reactive binding of the mouse C5a receptor. Myeloperoxidase (MPO) release is a consequence of neutrophil activation through C5a binding to C5aR. See Darren et al. (2004) *Mol Pharm* 65(4):868-879. Intravenous injection of recombinant human C5a into the mouse can induce neutropenia and activate neutrophils in circulation. The ability of an anti-human free C5a antibody to inhibit MPO release due to neutrophil activation in vivo was evaluated using the anti-C5a antibody to bind free hC5a and prevent binding to the murine C5aR.

An in vivo experiment (in which human C5a was administered to mice) was performed as described above. The level of plasma MPO at time 0 was 79.25±22.88 ng/mL in the sham-treated control group. Five minutes after intravenous injection of vehicle buffer, MPO levels were not significantly changed (77.46±21.21 ng/mL, P>0.05). Prior to intravenous injection of hC5a, MPO levels in isotype control antibody-treated (75.17±14.66 ng/mL) or anti-C5a antibody-treated animals (87.57±14.86 ng/mL) were comparable with the levels observed in the sham-treated control animals. After intravenous injection of hC5a, MPO levels at all doses of C5a were raised and remained at significantly higher levels at 5 minutes (FIG. 7).

When compared to isotype control antibody-treated animals (221.00±51.02 ng/mL), the anti-hC5a antibody-treated animals showed dose-dependent reduction of MPO levels (114.83±23.26 ng/mL, P<0.05, in 24 mg/kg cohort; 104.80±29.83 ng/mL, P<0.05, in 12 mg/kg cohort; and 126.90±36.40 ng/mL, P=0.08, in 6 mg/kg cohort). The MPO levels of low dose (3 mg/kg) anti-C5a antibody-treated animals (176.55±23.05 ng/mL) were not significantly different from isotype control antibody-treated animals (P>0.05).

An Anti-C5a Antibody Reduces Circulating hC5a Levels in Mice

As noted above, C5a is a potent inflammatory peptide with several biological functions. These above studies demonstrated that human C5a cross-reacts with murine C5aR on neutrophils since intravenous injection of recombinant human C5a can induce neutropenia. While this disclosure is in no way limited by any particular theory or mechanism of action, the anti-C5a antibody may be inhibiting human C5a-induced neutropenia by forming complexes with hC5a and preventing hC5a from binding to the murine C5aR expressed on the cell surface. hC5a levels were measured in the plasma of mice before and 1, 3, and 5 minutes after intravenous administration of hC5a to confirm that the effects of the anti-hC5a antibody in vivo were due to its binding-dependent inhibition of hC5a.

An experiment was performed as described above using the mouse-hC5a-induced neutropenia model. hC5a was not detected in plasma in any group of mice prior to administration of hC5a at time 0, using an enzyme-linked immunosorbent assay (ELISA). The level of hC5a in plasma, however, increased to a peak at 1 minute (7783.50±327.73 ng/mL), then reduced to 4788.38±260.51 ng/mL at 3 minutes, and then to 3855.75±298.99 ng/mL at 5 minutes following intravenous injection of hC5a (in isotype control mAb-treated mouse). Compared to control antibody-treated mice, the level of hC5a in mice treated with 24 mg/kg of the anti-C5a antibody exhibited a 43, 30, and 23-fold decline at 1 minute (178.4±14.14 ng/mL), 3 minutes (158.4±10.43 ng/mL), and 5 minutes (167.2±15.61 ng/mL), respectively. The level of hC5a in plasma from the 12 mg/kg and 6 mg/kg cohorts were 235.00±22.33 and 609.20±78.75 ng/mL at 1 minute, 210.80±19.59 and 527.60±52.25 ng/mL at 3 minutes, 192.20±7.40 and 505.00±45.96 ng/mL at 5 minutes, respectively. The anti-C5a-treated mice exhibited significantly reduced hC5a levels in a dose-dependent manner during neutropenia following intravenous injection of hC5a ($P<0.001$). Although the mice receiving the lowest dose of anti-C5a antibody (3 mg/kg) were not spared from hC5a-induced neutropenia, the mice nonetheless had a significant reduction in plasma hC5a (3130.40±433.58 ng/mL at 1 minute; 1932.00±268.92 ng/mL at 3 minutes; 1593.00±169.68 ng/mL at 5 minutes) as compared to plasma hC5a levels found in isotype control antibody-treated mice ($P<0.05$). See FIG. 8. These data indicated that administration of anti-C5a antibody to mice significantly decreased the concentration of free hC5a in plasma, resulting in greatly ameliorated hC5a-induced neutropenia.

Taken together, these results presented in this section indicated that an anti-human C5a antibody described herein can inhibit the biological effect of human C5a in an in vivo disease setting and provide strong evidence that the antibodies (and antigen-binding fragments thereof) are useful in, among other things, treating or preventing complement-associated disorders such as any of those recited herein.

Example 14

Anti-Human C5a Antibody Crossreacts with C5a from Non-Human Primates

Several humanized anti-hC5a antibodies were tested for their ability to crossreact with C5a from one or more non-human mammalian species. As noted above, the benefits of such an anti-C5a antibody are numerous, e.g., the ability of a research or medical practitioner to model the efficacy of a therapeutic anti-C5a antibody in a non-human disease model prior to administering the antibody to humans. Testing in non-human mammals can also allow for determination or approximation of the appropriate dosage of an anti-C5a antibody required for efficacy in humans.

Briefly, BNJ369, BNJ366, BNJ364, and BNJ383 (described above) were evaluated to determine whether they could co-immunoprecipitate C5a protein in the activated serum from several non-human primates including baboon, rhesus macaque, and cynomolgus macaque. The serum was activated by addition of zymosan. Following an overnight incubation of each antibody with activated serum, the antibodies were separated from the solution phase using protein A-conjugated agarose beads. The beads were washed thoroughly and then boiled in sodium dodecyl sulfate-polyacrylamide gel electrophoresis (SDS-PAGE) sample buffer containing β-mercaptoethanol. The boiled samples were then subjected to SDS-PAGE. Non-human primate C5a was detected by western blot using the commercially-available anti-C5a neoepitope antibody #2942 (Abcam, Cambridge, Mass.). Each of the antibodies tested was capable of immunoprecipitating C5a (or C5a desarg) from baboon, rhesus macaque, and cynomolgus macaque indicating that the antibody is crossreactive with C5a from these species as well as with human C5a.

The determination of binding affinity parameters to cynomolgus macaque C5a was determined as described above. Briefly, the BNJ383 antibody was screened against 3-4 concentrations of recombinant cynomolgus macaque C5a (antigen) using a capture technique as described above. The antibody was captured by an Anti-Fc (human) directly immobilized on a CM5 sensor chip with various concentrations in the range from 0.6 nM to 5.9 nM of cynomolgus C5a passed over the sensor chip surface. The surface was regenerated with 20 mM HCl, 0.02% surfactant P20 (Biacore) after each cycle to remove bound antibody and antigen. The data was evaluated using Biacore BIAevaluation software using a 1:1 Langmuir Model Fit (Rmax:Global Fit; RI:Local Fit). These experiments were for screening purposes with a minimal number of analyte concentrations (3 to 4) with 1 duplicate. The approximate $K_D$ of the antibody for cynomolgus macaque C5a is 3.3 nM. See Table 10.

TABLE 10

Affinity Determination for non-Human C5a Proteins

| Species | $k_a$ (1/Ms) ($\times 10^6$) | $k_d$ (1/s) ($\times 10^{-4}$) | $K_D$(M) ($\times 10^{-12}$) | $\chi^2$ |
|---|---|---|---|---|
| Human | 0.77 | 8.32 | 108 | 1.23 |
| Cynomolgus macaque | 1.28 | 42.3 | 3300 | 1.45 |
| Mouse | 2.8 | 10.6 | 379* | 2.38 |

*This is only an approximation of the $K_D$ based on the quality of the curve fit.

The BNJ383 antibody was also screened against 3-4 concentrations of recombinant mouse C5a (antigen) using a capture technique as described above to determine its affinity for mouse protein. The antibody was captured, as described above, by an anti-Fc (human) directly immobilized on a CM5 sensor chip with various concentrations in the range from 0.6 nM to 5.9 nM of mouse C5a passed over the sensor chip surface. The surface was regenerated with 20 mM HCl, 0.02% P20 after each cycle to remove bound antibody and antigen. The data were evaluated using Biacore BIAevaluation software using a 1:1 Langmuir Model Fit (Rmax:Global Fit; RI:Local Fit).

The above results indicated that several of the humanized anti-hC5a antibodies described herein are crossreactive with C5a from several non-human primate species including cynomolgus macaque, rhesus macaque, and baboon. The BNJ383 antibody, e.g., also crossreacts with mouse C5a. Furthermore, the results described in this section indicate that an anti-human C5a antibody, such as BNJ383, is useful not only in clinical applications for treating complement-associated disorders, but also in a variety of pre-clinical applications in non-human mammals, which are necessary for, or supportive of, approval of clinical use in humans.

Example 15

Competition for Binding to C5a

An experiment was performed to evaluate the binding of an anti-C5a antibody described herein, BNJ383, in the presence of potentially competitive antigens. Briefly, ruthenium-labeled BNJ383 (250 pM) was incubated for two hours at room temperature with 1 nM biotinylated C5a, along with various concentrations (e.g., 400, 133, 44.4, 14.8, 4.9, 1.6, and 0.5 nM) of one of the following: (a) human C5a desarg protein in phosphate-buffered saline, (b) human plasma, (c) cynomolgus macaque plasma, (d) Balb/C (mouse) plasma, or (e) DBA/2J (mouse) plasma. With respect to the plasma components (b), (c), (d), and (e), the concentration refers to the approximate final concentration of C5 antigen in the incubation mixture.

Following the incubation period, the samples were contacted to respective individual wells of a streptavidin-coated assay plate under conditions that allowed for the binding of biotinylated C5a to the streptavidin in the wells of the plate. The wells were washed thoroughly to remove unbound material. The amount of binding of BNJ383 to C5a in the presence of competitor was determined by detecting the amount of signal produced from the detectable ruthenium label. The results are shown in FIG. 9.

Whereas human C5a desarg was an effective competitor, there was virtually no competition observed in the presence of mouse serum (17% reduction in detectable signal observed at approximately a 400:1 ratio of Balb/C mouse plasma-derived C5 to biotinylated human C5a and 25% reduction in detectable signal observed at approximately a 400:1 ratio of DBA2/J plasma-derived C5 to biotinylated human C5a). No change in the level of binding of BNJ383 to biotinylated human C5a was observed at up to approximately a 15:1 ratio of human or cynomolgus macaque plasma-derived C5 to biotinylated human C5a.

As noted above, while the disclosure is in no way limited to any particular theory or mechanism of action, the inventors hypothesize that the anti-C5a antibody may bind to a subpopulation of uncleaved, processed C5 (e.g., plasma C5) constituting less than 10% of the total population of full length C5 in a sample (e.g., a plasma sample), which subpopulation is in whole or in part denatured such that an otherwise occluded C5a neoepitope, to which the anti-C5a antibody or fragment binds, is exposed. Thus, it is believed that the antibody does not bind to a fully functional and/or fully functional species of C5 and thus does not truly bind to uncleaved, native C5. Human plasma is at least an approximately 30 to 100-fold weaker competitor for binding to biotinylated C5a than human C5a desarg.

Notwithstanding these considerations, these results further indicate that anti-human C5a antibodies described herein, such as BNJ383, preferentially bind to free human C5a even in the presence of up to approximately 20-fold excess of uncleaved, but not necessarily entirely native, plasma-derived human C5 protein.

Example 16

Effect of Anti-C5a Antibody on AP and CP Activity In Vitro

An experiment was performed to evaluate the effect of an anti-C5a antibody described herein (BNJ383) on alternative pathway (AP) complement activity in vitro using pooled normal human serum (PNHS). The experiment utilized the Wieslab® Alternative Pathway Complement Kit (Wieslab® COMPL AP330, Euro-Diagnostica, Sweden) and the associated protocol was followed with only routine optimization well within the purview of one of ordinary skill in the art. Briefly aliquots of the PNHS were incubated in wells of a lipopolysaccharide-coated plate for one hour (at 37° C.) along with various concentrations (0.778, 0.389, 0.194, 0.097, 0.049, 0.024, 0.012, 0.006, 0.003, and 0.002 µM) of an anti-hC5 antibody or an anti-hC5a antibody (BNJ383). The anti-C5 antibody inhibits the cleavage of human C5 into fragments C5a and C5b. As a negative control, several wells were incubated with PNHS under the same conditions, but in the absence of anti-hC5 antibody or anti-hC5a antibody.

Following the incubation, the wells were washed thoroughly with kit-supplied 1× wash buffer. The level of alternative pathway complement activation was measured by absorbance at 405 nm, following contact of each well with a kit-supplied enzyme conjugate (an anti-C5b-9 antibody conjugated to alkaline phosphatase) and fluorogenic substrate (which is operated upon by the enzyme) and incubation for 30 minutes at room temperature. The results are shown in FIG. 10.

While the anti-C5 antibody inhibited alternative pathway complement activity completely at concentrations greater than 0.1 µM, the anti-hC5a antibody did not significantly inhibit complement activity even at the highest concentration tested.

An experiment was performed to evaluate the effect of an anti-C5a antibody described herein (BNJ383) on classical pathway (CP) complement activity in vitro using PNHS. The experiment utilized the Wieslab® Classical Pathway Complement Kit (Wieslab® COMPL CP310, Euro-Diagnostica, Sweden) and the associated protocol was followed with only routine optimization well within the purview of the ordinarily-skilled artisan. Briefly aliquots of the PNHS were incubated in wells of a human IgM antibody-coated plate for one hour (at 37° C.) along with various concentrations (7.2, 3.6, 1.8, 0.9, 0.45, 0.2, 0.1, 0.05, 0.02, or 0.01 µM) of an anti-hC5 antibody or an anti-hC5a antibody (BNJ383). The anti-C5 antibody inhibits the cleavage of human C5 into fragments C5a and C5b. As a control, several wells were incubated with PNHS under the same conditions, but in the absence of anti-hC5 antibody or anti-hC5a antibody.

Following the incubation, the wells were washed thoroughly with kit-supplied 1× wash buffer. The level of alternative pathway complement activation was measured by absorbance at 405 nm, following contact of each well with a kit-supplied enzyme conjugate (an anti-C5b-9 antibody conjugated to alkaline phosphatase) and fluorogenic substrate (which is operated upon by the enzyme) and incubation for 30 minutes at room temperature. The results are shown in FIG. 11.

While the anti-C5 antibody inhibited classical pathway complement activity completely at concentrations greater than 0.1 µM, the anti-hC5a antibody did not significantly inhibit complement activity even at the highest concentration tested.

Taken together, these results indicate that, in vitro, the anti-hC5a antibody, BNJ383, did not significantly affect C5b-9 generation (terminal complement activation) driven by either the classical or alternative pathway of complement, thus giving further evidence that the anti-hC5a antibodies described herein specifically target the free C5a anaphylatoxin arm of complement activation.

Example 17

Anti-C5a Antibody Retains an Unoccupied Antigen-Binding Site Available to Bind to C5a Even in the Presence of a Molar Excess of hC5

The anti-C5a antibody BNJ383 (set forth above) was incubated at 4° C. for 84 hours in the presence of a 2.1-fold molar excess of human C5 (hC5) to allow for complete antibody:C5 complex formation. A parallel experiment was performed using an antibody that binds to human C5 at a 2:1 stoichiometry (hereinafter the anti-C5 antibody). Antibody: C5 complexes were resolved on a TSK™ G4000 SW size exclusion column (Tosoh, Tokyo) using a Waters™ 2690/5 HPLC system with a Waters™ W2487 dual wavelength detector to determine the occupancy of binding sites. Peaks were monitored at a wavelength of 214 nm. The mobile phase for the HPLC analysis contained the following buffer composition: 3.9 mM $NaH_2PO_4$, 6.1 mM $Na_2HPO_4$, and 150 mM NaCl, at pH7.0. The flow rate was 1.0 ml per minute and the run time was 20 minutes. Data were acquired and analyzed with Waters Empower™ 2 chromatography software.

As depicted in FIG. 12, BNJ383 alone (FIG. 12A) and hC5 alone (FIG. 12B) each resolve as a single peak centered around 10.2 minutes and >95% of the anti-C5a antibody: hC5 complexes resolve as a single peak centered around 9.2 minutes (FIG. 12C). In contrast, complexes of hC5 and the anti-C5 antibody resolve in two peaks centered at 8.6 min (39%) and 9.2 min (61%) (FIG. 12D). Thus, even in a molar excess of hC5, 95.2% of the BNJ383 has a free Fab arm that may be capable of binding to human C5a.

These samples were further examined to determine if the BNJ383 antibody retained the ability to bind C5a in the presence of saturating concentrations of C5. Free antibody or antibody:C5 complexes were titrated from 500 to 0.5 ng/mL on a streptavidin coated plate to which biotin conjugated hC5a was immobilized. Captured antibody was detected with an anti-human Fc antibody conjugated to horse radish peroxidase. The results depicted in FIG. 13 demonstrate that even BNJ383 complexed with hC5 is capable of binding C5a and that the concentration of antibody available to bind C5a is not detectably diminished in the presence of saturating C5. Thus, the results described herein indicate that the antibody, even in the presence of a molar excess of uncleaved C5, retains the ability to bind to free C5a with high affinity and thereby retains, even in that molar excess, the ability to inhibit the pro-inflammatory activity of C5a.

Example 18

BNJ383 is a Potent Antagonist of C5a but is an Incomplete/Partial Antagonist of Terminal Complement Complex Formation In Vivo

Cynomolgus macaques were administered intravenously a single dose of the BNJ383 anti-C5a antibody at 1 mg/kg, 10 mg/kg, 100 mg/kg 250 mg/kg or 400 mg/kg. Plasma samples were collected from the macaques at time points ranging from 1 day to 30 days following the administration of the antibody. Levels of C5a/C5a desarg in plasma were determined by an electrochemiluminescent (ECL) assay in which a free C5a/C5a desarg was captured on a microtiter plate coated with an antibody specific for a neoepitope on C5a/C5a desarg and detected with a non-competitive C5a antibody conjugated to a ruthenate containing ECL moiety and read on a SECTOR 2400™ plate reader (MesoScale Discovery). Circulating antibody concentrations were determined by and enzyme linked immunosorbent assay (ELISA) in which free antibody (BNJ383) was captured on a microtiter plate coated with human C5a desarg and detected with a mouse anti-human antibody conjugated to horseradish peroxidase (HRP).

As shown in FIG. 14, like the results described in Example 13, circulating concentrations of BNJ383 as low as 10 µg/mL deplete plasma C5a/C5a desarg levels to below detectable limits in cynomolgus monkeys. These results also underscore that the antibody, even in the presence of a molar excess of uncleaved C5, retains the ability to bind to free C5a with high affinity and thereby retains, even in that molar excess, the ability to inhibit the pro-inflammatory activity of C5a.

To determine whether BNJ383 had an effect on hemolytic activity of macaque serum, the antibody was evaluated in an in vitro red blood cell hemolysis assay.

The red blood cell hemolysis assay is generally described in detail in, e.g., Rinder et al. (1995) *J Clin Invest* 96:1564-1572. Briefly, serum samples obtained from macaques administered BNJ383 (as described above) were added to multiple wells of a 96 well assay plate such that the concentration of the serum in each well was approximately 10%. The serum samples, by virtue of the time points in which they were obtained, contained various concentrations of the BNJ383 antibody. The hemolytic activity of serum from macaques not receiving BNJ383 served as a negative control and as the baseline hemolytic activity level.

Chicken erythrocytes (Lampire Biological Laboratories, Piperville, Pa.) were washed and resuspended in buffer at a final concentration of $5 \times 10^7$ cells/mL. The erythrocytes were sensitized to lysis by incubating the cells with an anti-chicken red blood cell polyclonal antibody composition. The sensitized erythrocytes were added to the wells of the 96 well plate and the plate was incubated at 37° C. for 30 minutes. Hemoglobin release was measured by apparent absorbance at 415 nm using a microplate reader.

As shown in FIG. 15A, even high concentrations of BNJ383 did not substantially inhibit erythrocyte hemolysis under these ex vivo hemolytic assay experimental conditions.

The BNJ383 antibody was also evaluated to determine if it had an effect on complement activation of macaque serum using an ex vivo CH50eq assay. The CH50eq assay is a method for measuring the total classical complement activity in serum. This test is an enzyme linked immunosorbent assay, which uses human gammaglobulins and mouse monoclonal antibodies as the activator of the classical complement pathway and captures the terminal complement complex (TCC) generated on a microtiter well coated with a TCC neoepitope specific antibody. Captured TCC is detected with a goat anti-TCC antibody conjugated to horse radish peroxidase. The CH50eq assay provides a direct measure of terminal complement complex (TCC) formation.

As shown in FIG. 15B, high concentrations of BNJ383 present in the macaque serum were capable of substantially inhibiting TCC formation under these ex vivo conditions. These results indicate that the BNJ383 antibody is not only capable of binding to and sequestering free C5a but is also capable of, as a function of concentration, partially or substantially inhibiting TCC formation.

An ex vivo experiment was also performed to evaluate the effect of BNJ383 on classical pathway (CP) complement activity using the macaque serum samples described above. The experiment utilized the Wieslab® Classical Pathway Complement Kit (Wieslab® COMPL CP310, Euro-Diagnostica, Sweden) and the associated protocol was followed with only routine optimization well within the purview of the ordinarily-skilled artisan. Briefly aliquots of the macaque serum samples were incubated in wells of a human IgM antibody-coated plate for one hour. As a control, several wells were incubated under the same conditions with serum from macaques not administered the BNJ383 antibody.

Following the incubation, the wells were washed thoroughly with kit-supplied 1× wash buffer. The level of alternative pathway complement activation was measured by absorbance at 405 nm, following contact of each well with a kit-supplied enzyme conjugate (an anti-C5b-9 antibody conjugated to alkaline phosphatase) and fluorogenic substrate (which is operated upon by the enzyme) and incubation for 30 minutes at room temperature. The results are shown in FIG. 15C.

The anti-hC5a antibody did significantly, though not completely, inhibit complement activity in a dose-dependent manner. Taken together, the results described herein indicate that BNJ383 is not only a potent antagonist of C5a, but is also an incomplete/partial antagonist of terminal complement complex formation in vivo. Thus, the antibody and antibodies sharing its properties are useful for treating a variety of complement-associated disorders in which C5a-mediated inflammation is the primary contributor to deleterious pathological effects and TCC may play a less significant or even beneficial role in the pathology.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating a complement-associated disorder, the method comprising administering to a human in need thereof, an isolated antibody, or antigen-binding fragment thereof, that binds C5a, wherein the antibody, or antigen-binding fragment thereof, comprises complementarity determining regions (CDRs) of a heavy chain variable region comprising the amino acid sequence depicted in SEQ ID NO: 45 and CDRs of a light chain variable region comprising the amino acid sequence depicted in SEQ ID NO: 42.

2. A method for treating a complement-associated disorder, the method comprising administering to a human in need thereof, an isolated antibody, or antigen-binding fragment thereof, that binds human C5a, wherein the antibody, or antigen-binding fragment thereof, comprises a light chain CDR1 comprising the amino acid sequence depicted in SEQ ID NO:20; a light chain CDR2 comprising the amino acid sequence depicted in SEQ ID NO:21; a light chain CDR3 comprising the amino acid sequence depicted in SEQ ID NO:22; a heavy chain CDR1 comprising the amino acid sequence depicted in SEQ ID NO:28; a heavy chain CDR2 comprising the amino acid sequence depicted in SEQ ID NO:46; and a heavy chain CDR3 comprising the amino acid sequence depicted in SEQ ID NO:47.

3. A method for treating a complement-associated disorder, the method comprising administering to a human in need thereof, an isolated antibody, or antigen-binding fragment thereof, that binds human C5a, wherein the antibody, or antigen-binding fragment thereof, comprises heavy and light chain variable regions, wherein the heavy chain variable region comprises the amino acid sequence depicted in SEQ ID NO: 45 and the light chain variable region comprises the amino acid sequence depicted in SEQ ID NO: 42.

4. A method for treating a complement-associated disorder, the method comprising administering to a human in need thereof, an isolated antibody, or antigen-binding fragment thereof, that binds human C5a, wherein the isolated antibody, or antigen-binding fragment thereof, that binds human C5a, comprises heavy and light chains, wherein the heavy chain comprises the amino acid sequence depicted in SEQ ID NO: 49 and the light chain comprises the amino acid sequence depicted in SEQ ID NO: 40.

5. A method for treating graft-versus-host disease (GVHD), the method comprising administering to a human in need thereof, an isolated antibody, or antigen-binding fragment thereof, that binds C5a, wherein the antibody, or antigen-binding fragment thereof, comprises complementarity determining regions (CDRs) of a heavy chain variable region comprising the amino acid sequence depicted in SEQ ID NO: 45 and CDRs of a light chain variable region comprising the amino acid sequence depicted in SEQ ID NO: 42.

6. A method for treating graft-versus-host disease (GVHD), the method comprising administering to a human in need thereof, an isolated antibody, or antigen-binding fragment thereof, that binds human C5a, wherein the antibody, or antigen-binding fragment thereof, comprises a light chain CDR1 comprising the amino acid sequence depicted in SEQ ID NO:20; a light chain CDR2 comprising the amino acid sequence depicted in SEQ ID NO:21; a light chain CDR3 comprising the amino acid sequence depicted in SEQ ID NO:22; a heavy chain CDR1 comprising the amino acid sequence depicted in SEQ ID NO:28; a heavy chain CDR2 comprising the amino acid sequence depicted in SEQ ID NO:46; and a heavy chain CDR3 comprising the amino acid sequence depicted in SEQ ID NO:47.

7. A method for treating graft-versus-host disease (GVHD), the method comprising administering to a human in need thereof, an isolated antibody, or antigen-binding fragment thereof, that binds human C5a, wherein the antibody, or antigen-binding fragment thereof, comprises heavy and light chain variable regions, wherein the heavy chain variable region comprises the amino acid sequence depicted in SEQ ID NO: 45 and the light chain variable region comprises the amino acid sequence depicted in SEQ ID NO: 42.

8. A method for treating graft-versus-host disease (GVHD), the method comprising administering to a human in need thereof, an isolated antibody, or antigen-binding fragment thereof, that binds human C5a, wherein the isolated antibody, or antigen-binding fragment thereof, that binds human C5a, comprises heavy and light chains, wherein the heavy chain comprises the amino acid sequence depicted in SEQ ID NO: 49 and the light chain comprises the amino acid sequence depicted in SEQ ID NO: 40.

9. The method of any one of claims 1-8, wherein the isolated antibody, or antigen-binding fragment thereof, binds to human C5a with a $K_D$ that is less than $8.0 \times 10^{-11}$ M.

10. The method of any one of claims 1-8, wherein the isolated antibody, or antigen-binding fragment thereof, inhibits by at least 90% human C5a-dependent human neutrophil activation at a molar ratio of 1:1 (antigen-binding site: C5a).

11. The method of any one of claims 1-8, wherein the isolated antibody, or antigen-binding fragment thereof, inhibits the interaction between C5a and a C5a receptor.

12. The method of any one of claims 1-8, wherein the isolated antibody, or antigen-binding fragment thereof, binds to a free C5a polypeptide, wherein the free C5a is a human polypeptide (hC5a) having the amino acid sequence depicted in SEQ ID NO: 1, and wherein the antibody, or antigen-binding fragment thereof, binds to the free hC5a polypeptide in vitro with a $K_D$ that is less than $1.25 \times 10^{-9}$ M in the presence of a molar excess of uncleaved, native human C5.

13. The method of any one of claims 1-8, wherein the isolated antibody, or antigen-binding fragment thereof, is a humanized antibody.

14. The method of any one of claims 1-4, wherein the complement-associated disorder is graft-versus-host disease (GVHD).

* * * * *

SEQUENCE LISTING

```
<160> NUMBER OF SEQ ID NOS: 181

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 2
<211> LENGTH: 73
<212> TYPE: PRT
<213> ORGANISM: Homo sapiens

<400> SEQUENCE: 2

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly
65                  70

<210> SEQ ID NO 3
<211> LENGTH: 14
<212> TYPE: PRT
<213> ORGANISM: Homo sapiens
```

```
<400> SEQUENCE: 3

Thr Leu Gln Lys Lys Ile Glu Glu Ile Ala Ala Lys Tyr Lys
1               5                   10

<210> SEQ ID NO 4
<211> LENGTH: 13
<212> TYPE: PRT
<213> ORGANISM: Homo sapiens

<400> SEQUENCE: 4

His Ser Val Val Lys Lys Cys Cys Tyr Asp Gly Ala Cys
1               5                   10

<210> SEQ ID NO 5
<211> LENGTH: 5
<212> TYPE: PRT
<213> ORGANISM: Homo sapiens

<400> SEQUENCE: 5

Val Asn Asn Asp Glu
1               5

<210> SEQ ID NO 6
<211> LENGTH: 8
<212> TYPE: PRT
<213> ORGANISM: Homo sapiens

<400> SEQUENCE: 6

Thr Cys Glu Gln Arg Ala Ala Arg
1               5

<210> SEQ ID NO 7
<211> LENGTH: 4
<212> TYPE: PRT
<213> ORGANISM: Homo sapiens

<400> SEQUENCE: 7

Ile Ser Leu Gly
1

<210> SEQ ID NO 8
<211> LENGTH: 22
<212> TYPE: PRT
<213> ORGANISM: Homo sapiens

<400> SEQUENCE: 8

Pro Arg Cys Ile Lys Ala Phe Thr Glu Cys Cys Val Val Ala Ser Gln
1               5                   10                  15

Leu Arg Ala Asn Ile Ser
            20

<210> SEQ ID NO 9
<211> LENGTH: 7
<212> TYPE: PRT
<213> ORGANISM: Homo sapiens

<400> SEQUENCE: 9

His Lys Asp Met Gln Leu Gly
1               5

<210> SEQ ID NO 10
<211> LENGTH: 8
<212> TYPE: PRT
<213> ORGANISM: Homo sapiens
```

<400> SEQUENCE: 10

His Lys Asp Met Gln Leu Gly Arg
1               5

<210> SEQ ID NO 11
<211> LENGTH: 14
<212> TYPE: PRT
<213> ORGANISM: Homo sapiens

<400> SEQUENCE: 11

Cys Cys Tyr Asp Gly Ala Cys Val Asn Asn Asp Glu Thr Cys
1               5                   10

<210> SEQ ID NO 12
<211> LENGTH: 33
<212> TYPE: PRT
<213> ORGANISM: Homo sapiens

<400> SEQUENCE: 12

Cys Tyr Asp Gly Ala Cys Val Asn Asn Asp Glu Thr Cys Glu Gln Arg
1               5                   10                  15

Ala Ala Arg Ile Ser Leu Gly Pro Arg Cys Ile Lys Ala Phe Thr Glu
            20                  25                  30

Cys

<210> SEQ ID NO 13
<211> LENGTH: 22
<212> TYPE: PRT
<213> ORGANISM: Homo sapiens

<400> SEQUENCE: 13

Cys Glu Gln Arg Ala Ala Arg Ile Ser Leu Gly Pro Arg Cys Ile Lys
1               5                   10                  15

Ala Phe Thr Glu Cys Cys
            20

<210> SEQ ID NO 14
<211> LENGTH: 18
<212> TYPE: PRT
<213> ORGANISM: Homo sapiens

<400> SEQUENCE: 14

Tyr Asp Gly Ala Cys Val Asn Asn Asp Glu Thr Cys Glu Gln Arg Ala
1               5                   10                  15

Ala Arg

<210> SEQ ID NO 15
<211> LENGTH: 18
<212> TYPE: PRT
<213> ORGANISM: Homo sapiens

<400> SEQUENCE: 15

Cys Tyr Asp Gly Ala Cys Val Asn Asn Asp Glu Thr Cys Glu Gln Arg
1               5                   10                  15

Ala Ala

<210> SEQ ID NO 16
<211> LENGTH: 238
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 16

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Arg Ala Ser Glu Ser
            35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Asn Glu Asp Pro Tyr Thr Phe Gly Gly Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 17
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

```
Glu Asp Pro Tyr Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Val Leu Gln Thr Gln Val Phe Ile Ser Leu Leu Leu Trp Ile Ser
1               5                   10                  15

Gly Ala Tyr Gly
            20

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

<210> SEQ ID NO 20
<211> LENGTH: 15
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 20

Arg Ala Ser Glu Ser Val Asp Ser Tyr Gly Asn Ser Phe Met His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Asn Leu Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Ser Asn Glu Asp Pro Tyr Thr
1               5

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 24
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

-continued

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ser Met Asp Trp Val Arg Gln Ala Pro Gly Gln Gly Leu
    50                  55                  60

Glu Trp Met Gly Ala Ile Asn Pro Asn Ser Gly Thr Asn Tyr Asn
65                  70                  75                  80

Gln Lys Phe Lys Asp Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Gly Ser Tyr Asp Gly Tyr Tyr Ala Met Asp
        115                 120                 125

Tyr Trp Gly Gln Gly Thr Thr Val Thr Val Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ser Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
```

```
                420            425            430
Lys Ser Arg Trp Gln Gln Gly Asn Val Phe Ser Cys Ser Val Met His
            435                440                445
Glu Ala Leu His Asn His Tyr Thr Gln Lys Ser Leu Ser Leu Ser Pro
    450                455                460
Gly Lys
465

<210> SEQ ID NO 25
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
                20                  25                  30
Ser Met Asp Trp Val Arg Gln Ala Pro Gly Gln Gly Leu Glu Trp Met
            35                  40                  45
Gly Ala Ile Asn Pro Asn Ser Gly Gly Thr Asn Tyr Asn Gln Lys Phe
        50                  55                  60
Lys Asp Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Gly Ser Tyr Asp Gly Tyr Tyr Ala Met Asp Tyr Trp Gly
                100                 105                 110
Gln Gly Thr Thr Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
    290                 295                 300
```

```
Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ser Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Asp Trp Thr Trp Arg Val Phe Cys Leu Leu Ala Val Ala Pro Gly
1               5                   10                  15

Ala His Ser

<210> SEQ ID NO 27
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Met
        35                  40                  45

Gly Ala Ile Asn Pro Asn Ser Gly Gly Thr Asn Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Gly Ser Tyr Asp Gly Tyr Tyr Ala Met Asp Tyr Trp Gly
        100                 105                 110

Gln Gly Thr Thr Val Thr Val Ser Ser
    115                 120
```

```
<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Tyr Ser Met Asp
1               5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ile Asn Pro Asn Ser Gly Gly Thr Asn Tyr Asn Gln Lys Phe Lys
1               5                   10                  15

Asp

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Gly Ser Tyr Asp Gly Tyr Tyr Ala Met Asp Tyr
1               5                   10

<210> SEQ ID NO 31
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
```

-continued

```
                130                 135                 140
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 32
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Asp Tyr Ser Met Asp Trp Val Arg Gln Ala Pro Gly Gln Gly Leu
                50                  55                  60

Glu Trp Met Gly Ala Ile Asn Pro Asn Ser Gly Gly Thr Asn Tyr Asn
65                  70                  75                  80

Gln Lys Phe Lys Asp Arg Val Thr Met Thr Arg Asp Thr Ser Thr Ser
                85                  90                  95

Thr Val Tyr Met Glu Leu Ser Ser Leu Arg Ser Glu Asp Thr Ala Val
                100                 105                 110

Tyr Tyr Cys Ala Arg Ser Gly Ser Tyr Asp Gly Tyr Tyr Ala Met Asp
                115                 120                 125

Tyr Trp Gly Gln Gly Thr Thr Val Thr Val Ser Ser Ala Ser Thr Lys
                130                 135                 140

Gly Pro Ser Val Phe Pro Leu Ala Pro Cys Ser Arg Ser Thr Ser Glu
145                 150                 155                 160
```

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 33
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Met
        35                  40                  45

```
Gly Ala Ile Asn Pro Asn Ser Gly Gly Thr Asn Tyr Asn Gln Lys Phe
            50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Gly Ser Tyr Asp Gly Tyr Tyr Ala Met Asp Tyr Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 34
<211> LENGTH: 326
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 35
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 35

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Glu Ser
        35                  40                  45

Val Asp Ser Tyr Gly Asn Ser Phe Met His Trp Tyr Gln Gln Lys Pro
50                  55                  60

Gly Gln Pro Pro Lys Leu Leu Ile Tyr Trp Ala Ser Thr Arg Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Asn Glu Asp Pro Tyr Thr Phe Gly Gly Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 36
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

```
Thr Val Ala Ala Pro Ser Val Phe Ile Phe Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Ala Ser Thr Arg Glu Ser
1               5

<210> SEQ ID NO 39
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Glu Ser Val Asp Ser Tyr Gly Asn Ser Phe Met His Trp Tyr Gln Gln
    50                  55                  60

Lys Pro Gly Lys Ala Pro Lys Leu Leu Ile Tyr Arg Ala Ser Asn Leu
65                  70                  75                  80

Glu Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Asn Glu Asp Pro Tyr Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 40
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 41
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

```
Met Asp Met Arg Val Pro Ala Gln Leu Leu Gly Leu Leu Leu Leu Trp
1               5                   10                  15

Leu Arg Gly Ala Arg Cys
            20
```

<210> SEQ ID NO 42
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110
```

<210> SEQ ID NO 43
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Asp Tyr Ser Met Asp Trp Val Arg Gln Ala Pro Gly Gln Gly Leu
            50                  55                  60

Glu Trp Met Gly Ala Ile His Leu Asn Thr Gly Tyr Thr Asn Tyr Asn
65                  70                  75                  80

Gln Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Phe Tyr Asp Gly Tyr Ser Pro Met Asp Tyr
            115                 120                 125

Trp Gly Gln Gly Thr Thr Val Thr Val Ser Ser Ala Ser Thr Lys Gly
            130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Asn Phe Gly Thr Gln Thr Tyr Thr Cys Asn Val
            210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Gln Phe Asn Trp Tyr Val Asp Gly Val Glu Val His Asn
            290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
            325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
            370                 375                 380

Cys Leu Val Lys Gly Phe Tyr Pro Ser Asp Ile Ser Val Glu Trp Glu
385                 390                 395                 400

Ser Asn Gly Gln Pro Glu Asn Asn Tyr Lys Thr Thr Pro Pro Met Leu
            405                 410                 415

Asp Ser Asp Gly Ser Phe Phe Leu Tyr Ser Lys Leu Thr Val Asp Lys
```

```
                    420              425                430
Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Lys
465

<210> SEQ ID NO 44
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Met
        35                  40                  45

Gly Ala Ile His Leu Asn Thr Gly Tyr Thr Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300
```

```
Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ser Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Met
        35                  40                  45

Gly Ala Ile His Leu Asn Thr Gly Tyr Thr Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
            100                 105                 110

Gly Thr Thr Val Thr Val Ser Ser
        115                 120

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ile His Leu Asn Thr Gly Tyr Thr Asn Tyr Asn Gln Lys Phe Lys
1               5                   10                  15

Gly
```

-continued

```
<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Phe Tyr Asp Gly Tyr Ser Pro Met Asp Tyr
1               5                   10

<210> SEQ ID NO 48
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ser Met Asp Trp Val Arg Gln Ala Pro Gly Gln Gly Leu
    50                  55                  60

Glu Trp Met Gly Ala Ile His Leu Asn Thr Gly Tyr Thr Asn Tyr Asn
65                  70                  75                  80

Gln Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Phe Tyr Asp Gly Tyr Ser Pro Met Asp Tyr
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
```

```
                    290                 295                 300
Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465

<210> SEQ ID NO 49
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met Asp Trp Val Arg Gln Ala Pro Gly Gln Gly Leu Glu Trp Met
            35                  40                  45

Gly Ala Ile His Leu Asn Thr Gly Tyr Thr Asn Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      Flag tag

<400> SEQUENCE: 50

Asp Tyr Lys Asp Asp Asp Asp Lys
1               5

<210> SEQ ID NO 51
<211> LENGTH: 73
<212> TYPE: PRT
<213> ORGANISM: Mus sp.

<400> SEQUENCE: 51

Leu Arg Gln Lys Ile Glu Glu Gln Ala Ala Lys Tyr Lys His Ser Val
1               5                   10                  15

Pro Lys Lys Cys Cys Tyr Asp Gly Ala Arg Val Asn Phe Tyr Glu Thr
            20                  25                  30
```

```
Cys Glu Glu Arg Val Ala Arg Val Thr Ile Gly Pro Leu Cys Ile Arg
        35                  40                  45

Ala Phe Asn Glu Cys Cys Thr Ile Ala Asn Lys Ile Arg Lys Glu Ser
 50                  55                  60

Pro His Lys Pro Val Gln Leu Gly Arg
 65                  70
```

<210> SEQ ID NO 52
<211> LENGTH: 72
<212> TYPE: PRT
<213> ORGANISM: Mus sp.

<400> SEQUENCE: 52

```
Leu Arg Gln Lys Ile Glu Glu Gln Ala Ala Lys Tyr Lys His Ser Val
 1               5                  10                  15

Pro Lys Lys Cys Cys Tyr Asp Gly Ala Arg Val Asn Phe Tyr Glu Thr
            20                  25                  30

Cys Glu Glu Arg Val Ala Arg Val Thr Ile Gly Pro Leu Cys Ile Arg
        35                  40                  45

Ala Phe Asn Glu Cys Cys Thr Ile Ala Asn Lys Ile Arg Lys Glu Ser
 50                  55                  60

Pro His Lys Pro Val Gln Leu Gly
 65                  70
```

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Glu Ile Val Leu Thr Gln Ser Pro Ala Ile Met Ser Ala Ser Leu Gly
 1               5                  10                  15

Glu Lys Val Thr Met Ser Cys Arg Ala Ser Ser Ser Val Asn Tyr Ile
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
 50                  55                  60

Gly Ser Gly Asn Ser Tyr Ser Leu Thr Ile Ser Ser Met Glu Gly Glu
 65                  70                  75                  80

Asp Ala Ala Thr Tyr Tyr Cys Gln Gln Phe Thr Ser Ser Pro Leu Thr
             85                  90                  95

Phe Gly Val Gly Thr Lys Leu Glu Leu Lys Arg
            100                 105
```

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Arg Ala Ser Ser Ser Val Asn Tyr Ile Tyr
 1               5                  10
```

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Thr Ser Asn Leu Ala Pro
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Phe Thr Ser Ser Pro Leu Thr
1               5

<210> SEQ ID NO 57
<211> LENGTH: 106
<212> TYPE: PRT
<213> ORGANISM: Mus sp.

<400> SEQUENCE: 57

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met Gly Trp Ser Cys Ile Ile Leu Phe Leu Val Ala Thr Ala Thr Gly
1               5                   10                  15

Val His Ser

<210> SEQ ID NO 59
<211> LENGTH: 214
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 59

Arg Glu Ile Val Leu Thr Gln Ser Pro Ala Ile Met Ser Ala Ser Leu
1               5                   10                  15

Gly Glu Lys Val Thr Met Ser Cys Arg Ala Ser Ser Val Asn Tyr
            20                  25                  30

Ile Tyr Trp Tyr Gln Gln Lys Ser Asp Ala Ser Pro Lys Leu Trp Ile
        35                  40                  45

Tyr Tyr Thr Ser Asn Leu Ala Pro Gly Val Pro Ala Arg Phe Ser Gly
    50                  55                  60

Ser Gly Ser Gly Asn Ser Tyr Ser Leu Thr Ile Ser Ser Met Glu Gly
65                  70                  75                  80

Glu Asp Ala Ala Thr Tyr Tyr Cys Gln Gln Phe Thr Ser Ser Pro Leu
                85                  90                  95

Thr Phe Gly Val Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 60
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gly Trp Ser Cys Ile Ile Leu Phe Leu Val Ala Thr Ala Thr Gly
1               5                   10                  15

Val His Ser Arg Glu Ile Val Leu Thr Gln Ser Pro Ala Ile Met Ser
            20                  25                  30

Ala Ser Leu Gly Glu Lys Val Thr Met Ser Cys Arg Ala Ser Ser Ser
        35                  40                  45

Val Asn Tyr Ile Tyr Trp Tyr Gln Gln Lys Ser Asp Ala Ser Pro Lys
    50                  55                  60

Leu Trp Ile Tyr Tyr Thr Ser Asn Leu Ala Pro Gly Val Pro Ala Arg
65                  70                  75                  80

Phe Ser Gly Ser Gly Ser Gly Asn Ser Tyr Ser Leu Thr Ile Ser Ser
                85                  90                  95

Met Glu Gly Glu Asp Ala Ala Thr Tyr Tyr Cys Gln Gln Phe Thr Ser
            100                 105                 110

Ser Pro Leu Thr Phe Gly Val Gly Thr Lys Leu Glu Leu Lys Arg Ala

```
                 115                 120                 125
Asp Ala Ala Pro Thr Val Ser Ile Phe Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
                195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Leu Glu Val Gln Leu Gln Gln Ser Gly Pro Glu Leu Val Lys Pro Gly
1               5                   10                  15

Ala Ser Val Lys Ile Ser Cys Lys Ala Ser Gly Tyr Thr Phe Thr Asp
                20                  25                  30

Tyr Tyr Tyr Ile Asn Trp Val Lys Gln Ser His Gly Lys Ser Leu Glu
            35                  40                  45

Trp Ile Gly Tyr Ile Tyr Pro Asn Asp Gly Asp Thr Asn Tyr Asn Gln
        50                  55                  60

Lys Phe Lys Gly Lys Ala Thr Leu Thr Val Asp Lys Ser Ser Ser Thr
65                  70                  75                  80

Ala Tyr Met Glu Leu Arg Ser Leu Thr Ser Glu Asp Ser Ala Val Tyr
                85                  90                  95

Tyr Cys Ala Arg Pro Tyr Tyr Ser Asp Tyr Gly Met Asp Tyr Trp Gly
            100                 105                 110

Gln Gly Thr Ser Val Thr Val Ser Ser
        115                 120

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Tyr Tyr Tyr Ile Asn
1               5

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 63

Tyr Ile Tyr Pro Asn Asp Gly Asp Thr Asn Tyr Asn Gln Lys Phe Lys
1               5                   10                  15

Gly

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Tyr Tyr Ser Asp Tyr Gly Met Asp Tyr
1               5                   10

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Gly Trp Ser Cys Ile Ile Leu Phe Leu Val Ala Thr Ala Thr Gly
1               5                   10                  15

Val His Ser

<210> SEQ ID NO 66
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Leu Glu Val Gln Leu Gln Gln Ser Gly Pro Glu Leu Val Lys Pro Gly
1               5                   10                  15

Ala Ser Val Lys Ile Ser Cys Lys Ala Ser Gly Tyr Thr Phe Thr Asp
                20                  25                  30

Tyr Tyr Ile Asn Trp Val Lys Gln Ser His Gly Lys Ser Leu Glu
        35                  40                  45

Trp Ile Gly Tyr Ile Tyr Pro Asn Asp Gly Asp Thr Asn Tyr Asn Gln
    50                  55                  60

Lys Phe Lys Gly Lys Ala Thr Leu Thr Val Asp Lys Ser Ser Ser Thr
65                  70                  75                  80

Ala Tyr Met Glu Leu Arg Ser Leu Thr Ser Glu Asp Ser Ala Val Tyr
                85                  90                  95

Tyr Cys Ala Arg Pro Tyr Tyr Ser Asp Tyr Gly Met Asp Tyr Trp Gly
            100                 105                 110

Gln Gly Thr Ser Val Thr Val Ser Ser
        115                 120

<210> SEQ ID NO 67
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 67

Ala Ile Asn Pro Asn Ser Gly Gly Thr Asn Tyr Ser Gln Lys Phe Lys
1               5                   10                  15

Asp

<210> SEQ ID NO 68
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Trp Val Arg Gln Ala Pro Gly Gln Gly Leu Glu Trp Met Gly
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Val Arg Gln Ala Ser Gly Lys Gly Leu Glu Trp Val Gly
1               5                   10

<210> SEQ ID NO 72
<211> LENGTH: 32
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 72

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Arg Val Thr Ile Thr Arg Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
            20                  25                  30

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Gly Gln Gly Thr Thr Val Thr Val Ser Ser
1               5                   10

<210> SEQ ID NO 76
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Met
        35                  40                  45

Gly Ala Ile His Leu Asn Thr Gly Tyr Thr Asn Tyr Asn Gln Lys Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
                    100                 105                 110

Gly Thr Thr Val Thr Val Ser Ser
            115                 120

<210> SEQ ID NO 77
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met Asp Trp Val Arg Gln Ala Pro Gly Gln Gly Leu Glu Trp Val
            35                  40                  45

Gly Ala Ile His Leu Asn Thr Gly Tyr Thr Asn Tyr Asn Gln Lys Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
                    100                 105                 110

Gly Thr Thr Val Thr Val Ser Ser
            115                 120

<210> SEQ ID NO 78
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met Asp Trp Val Arg Gln Ala Ser Gly Lys Gly Leu Glu Trp Met
            35                  40                  45

Gly Ala Ile His Leu Asn Thr Gly Tyr Thr Asn Tyr Asn Gln Lys Phe
            50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

-continued

```
Ala Arg Gly Phe Tyr Asp Gly Tyr Ser Pro Met Asp Tyr Trp Gly Gln
            100                 105                 110

Gly Thr Thr Val Thr Val Ser Ser
        115                 120

<210> SEQ ID NO 79
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Ser Gly Lys Gly Leu Glu Trp Met
        35                  40                  45

Gly Ala Ile His Leu Asn Thr Gly Tyr Thr Asn Tyr Asn Gln Lys Phe
    50                  55                  60

Lys Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Phe Tyr Asp Gly Tyr Ser Pro Met Asp Tyr Trp Gly Gln
            100                 105                 110

Gly Thr Thr Val Thr Val Ser Ser
        115                 120

<210> SEQ ID NO 80
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met Asp Trp Val Arg Gln Ala Pro Gly Gln Gly Leu Glu Trp Val
        35                  40                  45

Gly Ala Ile Asn Pro Asn Ser Gly Gly Thr Asn Tyr Ser Gln Lys Phe
    50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Ser Tyr Asp Gly Tyr Tyr Ala Met Asp Tyr Trp Gly
            100                 105                 110

Gln Gly Thr Thr Val Thr Val Ser Ser
        115                 120

<210> SEQ ID NO 81
<211> LENGTH: 6
```

<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 81

His His His His His His
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      HA tag

<400> SEQUENCE: 82

Tyr Pro Tyr Asp Val Pro Asp Tyr Ala
1               5

<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Phe
                85                  90                  95

Thr Phe Gly Ser Gly Thr Lys Leu Glu Ile Lys Arg
            100                 105

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Ala Ser Gln Asn Val Gly Thr Asn Val Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Ala Ser Tyr Arg Tyr Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Gln Tyr Asn Ser Tyr Pro Phe Thr
1               5

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ala Ser Ser Ser Val Ser Tyr Met His
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Thr Ser Lys Leu Ala Ser
1               5

```
<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gln Trp Ser Ser Asn Pro Leu Thr
1               5

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
                20                  25                  30

His Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Pro Trp Thr
                85                  90                  95

Phe Gly Gly Gly Thr Lys Leu Glu Ile Lys Arg
            100                 105

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Ala Ser Ser Ser Ile Ser Tyr Met His
1               5                   10

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Gln Arg Ser Ser Tyr Pro Trp Thr
1               5

<210> SEQ ID NO 94
<211> LENGTH: 109
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 94

```
Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Thr Val Glu
65              70                  75                  80

Ala Glu Asp Ala Ala Ser Tyr Phe Cys His Gln Trp Ser Ser Tyr Pro
                85                  90                  95

Pro Thr Phe Gly Gly Gly Thr Lys Leu Glu Ile Lys Arg
            100                 105
```

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

```
Ser Ala Ser Ser Ser Val Ser Ser Ser Tyr Leu Tyr
1               5                   10
```

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

```
Ser Thr Ser Asn Leu Ala Ser
1               5
```

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
His Gln Trp Ser Ser Tyr Pro Pro Thr
1               5
```

<210> SEQ ID NO 98
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ala Pro Met Leu Ser Val Gly
1               5                   10                  15

Glu Thr Val Thr Ile Thr Cys Arg Gly Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Arg
                85                  90                  95

Thr Phe Gly Gly Gly Thr Lys Leu Glu Ile Lys Arg
            100                 105

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Gly Ser Glu Asn Ile Tyr Ser Asn Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ala Thr Asn Leu Ala Asp
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln His Phe Trp Gly Thr Pro Arg Thr
1               5

<210> SEQ ID NO 102
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Val Met Thr Gln Ser Gln Lys Phe Met Ser Thr Ser Val Gly
1               5                   10                  15

```
Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Trp
                85                  90                  95

Thr Phe Gly Gly Gly Thr Lys Leu Glu Ile Lys Arg
            100                 105
```

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Gln Gln Tyr Asn Ser Tyr Pro Trp Thr
1               5
```

<210> SEQ ID NO 104
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Ile Val Leu Thr Gln Ser Pro Val Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Ala Gly Thr Lys Leu Glu Leu Lys Arg
            100                 105
```

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Ser Ala Ser Ser Ser Val Ser Tyr Met Tyr
1               5                   10
```

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Asp Thr Ser Asn Leu Ala Ser
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Gln Gln Trp Ser Ser Tyr Pro Pro Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

His Gln Arg Arg Ser Tyr Pro Trp Thr
1               5

<210> SEQ ID NO 109
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Leu Thr Phe Gly Ala Gly Thr Lys Leu Glu Leu Lys Arg
            100                 105                 110

<210> SEQ ID NO 110
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 110

Leu Ala Ser Asn Leu Glu Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Asn Asn Glu Asp Pro Leu Thr
1               5

<210> SEQ ID NO 112
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Gln Ser Asn Glu Asp Pro Leu Thr
1               5

<210> SEQ ID NO 114
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Asp Tyr
            20                  25                  30

Tyr Tyr Met Asn Trp Val Lys Lys Ser His Gly Lys Ser Leu Glu Trp
        35                  40                  45

Ile Gly Tyr Ile Phe Pro Lys Thr Gly Gly Thr Asn Tyr Ser Gln Arg
50                  55                  60

Phe Lys Gly Lys Ala Thr Leu Thr Val Asp Lys Ser Ser Ser Thr Ala
65                  70                  75                  80

Tyr Met Glu Leu Arg Ser Leu Thr Ser Glu Asp Ser Ala Val Tyr Tyr
                85                  90                  95

Cys Ala Ser Gly Pro Phe Ala Tyr Trp Gly Gln Gly Thr Leu Val Thr
                100                 105                 110

Val Ser Ala
        115
```

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Asp Tyr Tyr Tyr Met Asn
1               5
```

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Tyr Ile Phe Pro Lys Thr Gly Gly Thr Asn Tyr Ser Gln Arg Phe Lys
1               5                   10                  15

Gly
```

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Gly Pro Phe Ala Tyr
1               5
```

<210> SEQ ID NO 118
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

-continued

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Ile Thr Phe Ser Ser Tyr
            20                  25                  30

Tyr Met Ala Trp Val Arg Gln Thr Pro Asp Lys Arg Leu Glu Trp Val
        35                  40                  45

Ala Thr Ile Ser Ser Gly Gly Ser Tyr Thr Tyr Pro Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Tyr Tyr Glu Asp Asp Ala Met Asp Tyr Trp Gly Gln Gly Thr
            100                 105                 110

Ser Val Thr Val Ser Ser
            115
```

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Ser Tyr Tyr Met Ala
1               5
```

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Thr Ile Ser Ser Gly Gly Ser Tyr Thr Tyr Pro Asp Asn Val Lys
1               5                   10                  15

Gly
```

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Tyr Tyr Glu Asp Asp Ala Met Asp Tyr
1               5
```

<210> SEQ ID NO 122
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Asp Tyr
            20                  25                  30

Tyr Tyr Met Asn Trp Val Lys Lys Ser His Gly Lys Ser Leu Glu Trp
        35                  40                  45

Ile Gly Tyr Ile Phe Pro Lys Thr Gly Gly Thr Asn Tyr Asn Gln Arg
50                  55                  60

Phe Lys Gly Lys Ala Thr Leu Thr Val Asp Lys Ser Ser Ser Thr Ala
65                  70                  75                  80

Tyr Met Glu Leu Arg Ser Leu Thr Ser Glu Asp Ser Ala Val Tyr Tyr
                85                  90                  95

Cys Ala Ser Gly Pro Phe Ala Tyr Trp Gly Gln Gly Thr Leu Val Thr
                100                 105                 110

Val Ser Ala
        115
```

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Tyr Ile Phe Pro Lys Thr Gly Gly Thr Asn Tyr Asn Gln Arg Phe Lys
1               5                   10                  15

Gly
```

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Tyr Ile Phe Pro Asn Thr Gly Gly Thr Thr Tyr Asn Gln Arg Phe Lys
1               5                   10                  15

Gly
```

<210> SEQ ID NO 125
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Tyr Thr Phe Ser Ser Tyr
            20                  25                  30

Tyr Met Ala Trp Val Arg Gln Thr Pro Asp Lys Arg Leu Glu Trp Val
        35                  40                  45

Ala Thr Ile Ser Ser Gly Gly Ser Tyr Thr Tyr Tyr Arg Asp Asn Val
50                  55                  60
```

```
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Thr Arg Tyr Phe Glu Asp Tyr Pro Met Asp Tyr Trp Gly Gln Gly Thr
            100                 105                 110

Ser Val Thr Val Ser Ser
            115

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Ile Ser Ser Gly Gly Ser Tyr Thr Tyr Tyr Arg Asp Asn Val Lys
1               5                   10                  15

Gly

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Tyr Phe Glu Asp Tyr Pro Met Asp Tyr
1               5

<210> SEQ ID NO 128
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Gln Gln Ser Gly Pro Glu Leu Gly Lys Pro Gly Ala
1               5                   10                  15

Ser Gly Lys Ile Ser Cys Lys Ala Ser Gly Tyr Thr Phe Thr Asp Tyr
                20                  25                  30

Tyr Tyr Met Asn Trp Val Lys Gln Ser His Gly Lys Ser Leu Glu Trp
            35                  40                  45

Ile Gly Tyr Ile Phe Pro Asn Thr Gly Gly Thr Ser Tyr Asn Gln Arg
        50                  55                  60

Phe Lys Asp Lys Ala Thr Leu Thr Val Asp Lys Ser Ser Ser Thr Ala
 65                 70                  75                  80

Tyr Met Glu Leu Arg Ser Leu Thr Ser Glu Asp Ser Ala Val Tyr Tyr
                85                  90                  95

Cys Ala Ser Gly Pro Phe Ala Tyr Trp Gly Gln Gly Thr Leu Val Thr
            100                 105                 110

Val Ser Ala
        115

<210> SEQ ID NO 129
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr Ile Phe Pro Asn Thr Gly Gly Thr Ser Tyr Asn Gln Arg Phe Lys
1               5                   10                  15

Asp

<210> SEQ ID NO 130
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Gln Gln Pro Gly Ser Val Leu Val Arg Pro Gly Ala
1               5                   10                  15

Thr Val Lys Leu Ser Cys Lys Ala Ser Gly Phe Thr Phe Thr Ser Ser
            20                  25                  30

Trp Met His Trp Ala Lys Gln Arg Pro Gly Gln Gly Leu Glu Trp Ile
        35                  40                  45

Gly Glu Ile His Thr Ser Gly His Thr Asn Tyr Asn Glu Lys Phe Lys
    50                  55                  60

Gly Lys Ala Thr Leu Thr Leu Asp Thr Ser Ser Ser Thr Ala Tyr Val
65                  70                  75                  80

Asp Ile Ser Ser Leu Thr Ser Glu Asp Ser Ala Val Tyr Tyr Cys Ala
                85                  90                  95

Arg Gly Gly Leu Arg Arg Gly Tyr Ala Met Asp Tyr Trp Gly Gln Gly
            100                 105                 110

Thr Ser Val Thr Val Ser Ser
        115

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Ser Trp Met His
1               5

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Glu Ile His Thr Ser Gly His Thr Asn Tyr Asn Glu Lys Phe Lys Gly
1               5                   10                  15

<210> SEQ ID NO 133
```

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Gly Leu Arg Arg Gly Tyr Ala Met Asp Tyr
1               5                   10

<210> SEQ ID NO 134
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Pro Gln Gln Ser Gly Pro Glu Leu Val Lys Pro Gly Ser
1               5                   10                  15

Ser Val Lys Ile Ser Cys Lys Ala Ser Gly Tyr Thr Phe Thr Asp Tyr
            20                  25                  30

Ser Met Asp Trp Val Lys Gln Ser His Gly Lys Ser Leu Glu Trp Ile
        35                  40                  45

Gly Ala Ile His Leu Asn Thr Gly Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Phe Tyr Asp Gly Tyr Ser Pro Met Asp Tyr Trp Gly Gln
            100                 105                 110

Gly Thr Ser Val Thr Val Ser Ser
        115                 120

<210> SEQ ID NO 135
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Gln Gln Ser Gly Ala Glu Leu Val Lys Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Tyr Ile
        35                  40                  45

Gly Glu Ile His Pro Ser Ser Gly His Thr Asn Tyr His Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Ser Leu Leu Arg Ala Tyr Ala Met Asp Tyr Trp Gly Gln
            100                 105                 110

```
Gly Thr Ser Val Thr Val Ser Ser
        115                 120
```

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

```
Ser Tyr Trp Met His
1               5
```

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

```
Glu Ile His Pro Ser Ser Gly His Thr Asn Tyr His Glu Lys Phe Lys
1               5                   10                  15

Ser
```

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Ala Ser Leu Leu Arg Ala Tyr Ala Met Asp Tyr
1               5                   10
```

<210> SEQ ID NO 139
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Glu Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys Arg
            100                 105
```

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Ala Ser Ser Ser Val Ser Ser Ser Tyr Leu His
1               5                   10

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Arg Ser Tyr Pro Trp Thr
                85                  90                  95

Phe Gly Gly Gly Thr Lys Leu Glu Ile Lys Arg
            100                 105

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Gln Tyr Ser Gly Tyr Pro Leu Thr
1               5

<210> SEQ ID NO 143
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Ser Asp Tyr
            20                  25                  30

Tyr Tyr Met Asn Trp Val Lys Lys Ser His Gly Lys Ser Leu Glu Trp
        35                  40                  45

Ile Gly Tyr Ile Phe Pro Lys Thr Gly Gly Thr His Tyr Asn Gln Arg
        50                  55                  60

Phe Lys Gly Lys Ala Thr Leu Thr Val Asp Lys Ser Ser Ser Thr Ala
 65                  70                  75                  80

Tyr Met Glu Leu Arg Ser Leu Thr Ser Glu Asp Ser Ala Val Tyr Tyr
                 85                  90                  95

Cys Ala Ser Gly Pro Phe Ala Tyr Trp Gly Gln Gly Thr Leu Val Thr
                100                 105                 110

Val Ser Ala
        115

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Tyr Ile Phe Pro Lys Thr Gly Gly Thr His Tyr Asn Gln Arg Phe Lys
 1               5                  10                  15

Gly

<210> SEQ ID NO 145
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
                20                  25                  30

Tyr Tyr Met Asn Trp Val Lys Gln Ser His Gly Lys Ser Leu Glu Trp
             35                  40                  45

Ile Gly Tyr Ile Phe Pro Asn Thr Gly Thr Thr Tyr Asn Gln Arg
        50                  55                  60

Phe Lys Gly Lys Ala Thr Leu Thr Val Asp Lys Ser Ser Ser Thr Ala
 65                  70                  75                  80

Tyr Met Glu Leu Arg Ser Leu Thr Ser Glu Asp Ser Ala Val Tyr Tyr
                 85                  90                  95

Cys Ala Ser Gly Pro Phe Ala Tyr Trp Gly Gln Gly Thr Leu Val Thr
                100                 105                 110

Val Ser Ala
        115

<210> SEQ ID NO 146
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Ile Val Leu Thr Gln Ser Pro Ala Ile Met Ser Ala Ser Pro Gly

```
                1               5                  10                  15
        Glu Lys Val Thr Met Thr Cys Ser Ala Ser Ser Ser Val Ser Tyr Met
                        20                  25                  30

Tyr Trp Tyr Gln Gln Lys Pro Gly Ser Ser Pro Arg Leu Leu Ile Tyr
                        35                  40                  45

Asp Thr Ser Asn Leu Ala Ser Gly Val Pro Val Arg Phe Ser Gly Ser
                50                  55                  60

Gly Ser Gly Thr Ser Tyr Ser Leu Thr Ile Ser Arg Met Glu Ala Glu
        65                  70                  75                  80

Asp Ala Ala Thr Tyr Tyr Cys Gln Gln Trp Ser Ser Tyr Pro Pro Thr
                        85                  90                  95

Phe Gly Gly Gly Thr Lys Leu Glu Ile Lys Arg
                        100                 105

<210> SEQ ID NO 147
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Gln Gln Ser Gly Pro Glu Leu Val Lys Pro Gly Ala
        1               5                   10                  15

Ser Val Arg Ile Ser Cys Lys Ala Ser Gly Tyr Thr Phe Asn Asp Tyr
                        20                  25                  30

Tyr Tyr Met Asn Trp Val Lys Gln Ser His Gly Lys Ser Leu Glu Trp
                        35                  40                  45

Ile Gly Tyr Ile Phe Pro Lys Thr Gly Thr His Tyr Asn Gln Arg
                50                  55                  60

Phe Lys Gly Lys Ala Thr Leu Thr Val Asp Lys Ser Ser Ser Thr Ala
        65                  70                  75                  80

Tyr Met Glu Leu Arg Ser Leu Thr Ser Glu Asp Ser Ala Val Tyr Tyr
                        85                  90                  95

Cys Ala Ser Gly Pro Phe Ala Tyr Trp Gly Gln Gly Thr Leu Val Thr
                        100                 105                 110

Val Ser Ala
                115

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Ile Val Leu Thr Gln Ser Pro Val Ile Met Ser Ala Ser Pro Gly
        1               5                   10                  15

Glu Lys Val Thr Met Ile Cys Ser Ala Ser Ser Ser Ile Ser Tyr Met
                        20                  25                  30

His Trp Tyr Gln Gln Lys Pro Gly Thr Ser Pro Lys Arg Trp Ile Tyr
                        35                  40                  45

Asp Thr Ser Lys Leu Ala Ser Gly Val Pro Ala Arg Phe Ser Gly Ser
                50                  55                  60

Gly Ser Gly Thr Ser Tyr Ser Leu Thr Ile Ser Ile Met Glu Ala Glu
```

```
                65                  70                  75                  80
Asp Ala Ala Thr Tyr Tyr Cys His Gln Arg Ser Ser Tyr Pro Trp Thr
                    85                  90                  95

Phe Gly Gly Gly Thr Lys Leu Glu Ile Lys Arg
                100                 105
```

<210> SEQ ID NO 149
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Glu Val Gln Met Gln Gln Ser Gly Pro Glu Leu Val Lys Pro Gly Ala
1               5                   10                  15

Ser Val Lys Ile Ser Cys Lys Ala Ser Gly Tyr Thr Phe Ser Asp Tyr
                20                  25                  30

Tyr Met Asn Trp Val Lys Lys Ser His Gly Lys Ser Leu Glu Trp
            35                  40                  45

Ile Gly Tyr Ile Phe Pro Lys Thr Gly Thr Asn Tyr Asn Gln Arg
    50                  55                  60

Phe Lys Gly Lys Ala Thr Leu Thr Val Asp Lys Ser Ser Thr Ala
65                  70                  75                  80

Tyr Met Glu Leu Arg Ser Leu Thr Ser Glu Asp Ser Ala Val Tyr Tyr
                85                  90                  95

Cys Ala Ser Gly Pro Phe Ala Tyr Trp Gly Gln Gly Thr Leu Val Thr
                100                 105                 110

Val Ser Ala
        115
```

<210> SEQ ID NO 150
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Glu Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Ser
                20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Pro Thr Phe Gly Gly Gly Thr Lys Leu Glu Ile Lys Arg
                100                 105
```

<210> SEQ ID NO 151
<211> LENGTH: 109
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 151

Glu Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Gly Gly Thr Lys Leu Glu Ile Lys Arg
            100                 105

<210> SEQ ID NO 152
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Val Arg Leu Gln Gln Ser Gly Pro Glu Leu Val Lys Pro Gly Ala
1               5                   10                  15

Ser Val Arg Ile Ser Cys Lys Ala Ser Gly Tyr Thr Phe Asn Asp Tyr
            20                  25                  30

Tyr Tyr Met Asn Trp Val Lys Gln Ser His Gly Lys Ser Leu Glu Trp
        35                  40                  45

Ile Gly Tyr Ile Phe Pro Lys Thr Gly Gly Thr His Tyr Asn Gln Arg
    50                  55                  60

Phe Lys Gly Lys Ala Thr Leu Thr Val Asp Lys Ser Ser Ser Thr Ala
65                  70                  75                  80

Tyr Met Glu Leu Arg Ser Leu Thr Ser Glu Asp Ser Ala Val Tyr Tyr
                85                  90                  95

Cys Ala Ser Gly Pro Phe Ala Tyr Trp Gly Gln Gly Thr Leu Val Thr
            100                 105                 110

Val Ser Ala
        115

<210> SEQ ID NO 153
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro
            35                  40                  45

Lys Leu Leu Ile Tyr Arg Ala Ser Asn Leu Glu Ser Gly Ile Pro Ala
 50                      55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Tyr Thr Phe Gly Gly Thr Lys Leu Glu Ile Lys Arg
            100                 105                 110

<210> SEQ ID NO 154
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Gln Gln Ser Gly Pro Glu Leu Val Lys Pro Gly Ser
 1               5                   10                  15

Ser Val Lys Ile Ser Cys Lys Ala Ser Gly Tyr Thr Phe Thr Asp Tyr
                 20                  25                  30

Ser Met Asp Trp Val Lys Gln Ser His Gly Lys Ser Leu Glu Trp Ile
             35                  40                  45

Gly Ala Ile Asn Pro Asn Ser Gly Gly Thr Asn Tyr Ser Gln Lys Phe
 50                  55                  60

Lys Asp Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Ser Ser Gly Ser Tyr Asp Gly Tyr Tyr Ala Met Asp Tyr Trp Gly
            100                 105                 110

Gln Gly Thr Ser Val Thr Val Ser Ser
        115                 120

<210> SEQ ID NO 155
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ala Ser Leu Ser Ala Ser Val Gly
 1               5                   10                  15

Glu Thr Val Thr Ile Thr Cys Arg Ala Ser Glu Asn Ile Tyr Ser Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Tyr
                 85                  90                  95

```
Thr Phe Gly Gly Gly Thr Lys Leu Glu Ile Lys Arg
            100                 105

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Arg Ala Ser Glu Asn Ile Tyr Ser Tyr Leu Ala
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Ala Lys Thr Leu Ala Glu
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln His His Tyr Gly Thr Pro Tyr Thr
1               5

<210> SEQ ID NO 159
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Gln Gln Pro Gly Ala Glu Ile Val Arg Pro Gly Ala
1               5                   10                  15

Ser Val Lys Leu Ser Cys Arg Ala Ser Gly Tyr Thr Phe Thr Asp Tyr
            20                  25                  30

Trp Met Asn Trp Val Lys Gln Arg Pro Gly Gln Gly Leu Glu Trp Ile
        35                  40                  45

Gly Thr Ile Asp Pro Ser Asp Ser Tyr Thr Ile Tyr Asn Gln Lys Phe
    50                  55                  60

Lys Gly Lys Ala Thr Leu Thr Val Asp Thr Ser Ser Thr Thr Ala Tyr
65                  70                  75                  80

Ile Gln Leu Ser Ser Leu Thr Ser Glu Asp Ser Ala Val Tyr Phe Cys
                85                  90                  95

Ala Arg Gly Glu Asp Tyr Asp Val Ser Ser Tyr Thr Met Asp Tyr Trp
            100                 105                 110

Gly Gln Gly Thr Ser Val Thr Val Ser Ser
```

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Tyr Trp Met Asn
1               5

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Ile Asp Pro Ser Asp Ser Tyr Thr Ile Tyr Asn Gln Lys Phe Lys
1               5                   10                  15

Gly

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Glu Asp Tyr Asp Val Ser Ser Tyr Thr Met Asp Tyr
1               5                   10

<210> SEQ ID NO 163
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Ile Val Leu Thr Gln Ser Pro Ala Ser Leu Ala Val Ser Leu Gly
1               5                   10                  15

Gln Arg Ala Thr Ile Ser Cys Ser Ala Ser Glu Ser Val Glu Tyr Phe
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Trp Thr Phe Gly Gly Gly Thr Lys Leu Glu Ile Lys Arg
            100                 105                 110

```
<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ala Ser Glu Ser Val Glu Tyr Phe Gly Thr Ser Leu Met Gln
1               5                   10                  15

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Ala Ser Asn Val Glu Ser
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Gln Ser Arg Lys Val Pro Trp Thr
1               5

<210> SEQ ID NO 167
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Val Lys Leu Val Glu Ser Gly Gly Leu Val Gln Pro Gly Gly
1               5                   10                  15

Ser Arg Lys Leu Ser Cys Ala Ala Ser Gly Phe Thr Phe Ser Asp Tyr
                20                  25                  30

Gly Met Val Trp Val Arg Gln Ala Pro Gly Lys Gly Leu Glu Trp Val
            35                  40                  45

Ala Phe Ile Ser Ser Gly Ser Ser Asn Ile Tyr Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Asn Ser Leu Arg Ser Glu Asp Thr Ala Ile Tyr Tyr Cys
                85                  90                  95

Gly Arg Ala Phe Ser Phe Tyr Tyr Gly Tyr Asp Tyr Trp Gly Gln Gly
            100                 105                 110

Thr Thr Leu Thr Val Ser Ser
        115

<210> SEQ ID NO 168
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Tyr Gly Met Val
1               5

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Phe Ile Ser Ser Gly Ser Ser Asn Ile Tyr Tyr Ala Asp Thr Val Lys
1               5                   10                  15

Gly

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Phe Ser Phe Tyr Tyr Gly Tyr Asp Tyr
1               5                   10

<210> SEQ ID NO 171
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
                100                 105                 110

Arg

<210> SEQ ID NO 172
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 172

Arg Ser Ser Gln Ser Leu Val His Ser Asn Gly Asn Thr Tyr Leu His
1               5                   10                  15

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Lys Val Ser Asn Arg Phe Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Gln Ser Thr His Val Pro Leu Thr
1               5

<210> SEQ ID NO 175
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Ser Tyr
                20                  25                  30

Leu Ile His Trp Val Lys Gln Lys Pro Gly Gln Gly Leu Glu Trp Ile
            35                  40                  45

Gly Tyr Ile Tyr Pro Phe Asn Asp Gly Thr Lys Asn Asn Glu Asn Phe
50                  55                  60

Lys Gly Lys Ala Thr Leu Thr Ser Asp Lys Ser Ser Thr Val Tyr
65                  70                  75                  80

Met Glu Val Ser Ser Leu Thr Ser Glu Asp Ser Ala Val Tyr Tyr Cys
                85                  90                  95

Ala Arg Ser His Gly Pro His Tyr Tyr Gly Gly Ser Tyr Gly Tyr His
                100                 105                 110

Phe Asp Tyr Trp Gly Gln Gly Thr Thr Leu Thr Val Ser Ser
            115                 120                 125

<210> SEQ ID NO 176
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 176

Ser Tyr Leu Ile His
1               5

<210> SEQ ID NO 177
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Tyr Ile Tyr Pro Phe Asn Asp Gly Thr Lys Asn Asn Glu Asn Phe Lys
1               5                   10                  15

Gly

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser His Gly Pro His Tyr Tyr Gly Gly Ser Tyr Gly Tyr His Phe Asp
1               5                   10                  15

Tyr

<210> SEQ ID NO 179
<211> LENGTH: 74
<212> TYPE: PRT
<213> ORGANISM: Macaca sp.

<400> SEQUENCE: 179

Met Leu Gln Glu Lys Ile Glu Glu Ile Ala Ala Lys Tyr Lys His Leu
1               5                   10                  15

Val Val Lys Lys Cys Cys Tyr Asp Gly Val Arg Ile Asn His Asp Glu
                20                  25                  30

Thr Cys Glu Gln Arg Ala Ala Arg Ile Ser Val Gly Pro Arg Cys Val
            35                  40                  45

Lys Ala Phe Thr Glu Cys Cys Val Val Ala Ser Gln Leu Arg Ala Asn
    50                  55                  60

Asn Ser His Lys Asp Leu Gln Leu Gly Arg
65                  70

<210> SEQ ID NO 180
<211> LENGTH: 73
<212> TYPE: PRT
<213> ORGANISM: Macaca sp.

<400> SEQUENCE: 180

Met Leu Gln Glu Lys Ile Glu Glu Ile Ala Ala Lys Tyr Lys His Leu
1               5                   10                  15

Val Val Lys Lys Cys Cys Tyr Asp Gly Val Arg Ile Asn His Asp Glu
                20                  25                  30

Thr Cys Glu Gln Arg Ala Ala Arg Ile Ser Val Gly Pro Arg Cys Val
            35                  40                  45
```

```
Lys Ala Phe Thr Glu Cys Cys Val Val Ala Ser Gln Leu Arg Ala Asn
        50              55                  60

Asn Ser His Lys Asp Leu Gln Leu Gly
65                  70

<210> SEQ ID NO 181
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Gly Trp Ser Cys Ile Ile Leu Phe Leu Val Ala Thr Ala Thr Gly
1               5                   10                  15

Val His Ser Leu Glu Val Gln Leu Gln Gln Ser Gly Pro Glu Leu Val
            20                  25                  30

Lys Pro Gly Ala Ser Val Lys Ile Ser Cys Lys Ala Ser Gly Tyr Thr
        35                  40                  45

Phe Thr Asp Tyr Tyr Ile Asn Trp Val Lys Gln Ser His Gly Lys
    50                  55                  60

Ser Leu Glu Trp Ile Gly Tyr Ile Tyr Pro Asn Asp Gly Asp Thr Asn
65                  70                  75                  80

Tyr Asn Gln Lys Phe Lys Gly Lys Ala Thr Leu Thr Val Asp Lys Ser
                85                  90                  95

Ser Ser Thr Ala Tyr Met Glu Leu Arg Ser Leu Thr Ser Glu Asp Ser
            100                 105                 110

Ala Val Tyr Tyr Cys Ala Arg Pro Tyr Tyr Ser Asp Tyr Gly Met Asp
        115                 120                 125

Tyr Trp Gly Gln Gly Thr Ser Val Thr Val Ser Ser
    130                 135                 140
```